United States Patent
Kalindjian et al.

(10) Patent No.: US 6,479,531 B1
(45) Date of Patent: Nov. 12, 2002

(54) GASTRIN AND CHOLECYSTOKININ RECEPTOR LIGANDS

(75) Inventors: Sarkis Barret Kalindjian, London (GB); Ildiko Maria Buck, London (GB); Ian Duncan Linney, London (GB); Paul Trevor Wright, London (GB); Iain Mair McDonald, London (GB); Katherine Isobel Mary Steel, London (GB); Robert Antony David Hull, London (GB); Sonia Patricia Roberts, London (GB); John David Gaffen, London (GB); Jeremy Gilbert Vinter, London (GB); Martin Keith Walker, London (GB); James Whyte Black, London (GB); Gillian Fairfull Watt, London (GB); Elaine Anne Harper, London (GB); Nigel Paul Shankley, London (GB); Matthew John Tozer, London (GB); David John Dunstone, London (GB); Michael John Pether, London (GB); Elliot James Lilley, London (GB); David Andrew Sykes, London (GB); Caroline Minli Rachel Low, London (GB); Eric Peter Griffin, London (GB); Laurence Wright, London (GB)

(73) Assignee: James Black Foundation Limited, London (GB)

( * ) Notice: Subject to any disclaimer, the term of this patent is extended or adjusted under 35 U.S.C. 154(b) by 0 days.

(21) Appl. No.: 09/831,385

(22) PCT Filed: Nov. 9, 1999

(86) PCT No.: PCT/GB99/03733
§ 371 (c)(1),
(2), (4) Date: Aug. 2, 2001

(87) PCT Pub. No.: WO00/27823
PCT Pub. Date: May 18, 2000

(30) Foreign Application Priority Data

Nov. 9, 1998 (GB) .............................. 9824536
Jul. 16, 1999 (GB) .............................. 9916786

(51) Int. Cl.$^7$ .................. C07D 403/06; A61K 31/4155
(52) U.S. Cl. ........................ 514/397; 514/398; 514/399; 548/314.7; 548/326.5; 548/331.1; 548/335.1
(58) Field of Search .............. 548/326.5, 331.1, 548/335.1, 314.7; 514/397, 398, 399

(56) References Cited

U.S. PATENT DOCUMENTS 5,939,437 A * 8/1999 Kalindjian et al. ......... 514/330

FOREIGN PATENT DOCUMENTS

| EP | 0 761 658 | 12/1997 |
| WO | 92/10476 | 6/1992 |
| WO | 93/16982 | 9/1993 |
| WO | 95/04720 | 2/1995 |
| WO | 95/30647 | 11/1995 |
| WO | 98/05637 | 2/1998 |

* cited by examiner

Primary Examiner—Floyd D. Higel
Assistant Examiner—Kamal Saeed
(74) Attorney, Agent, or Firm—Foley & Lardner

(57) ABSTRACT

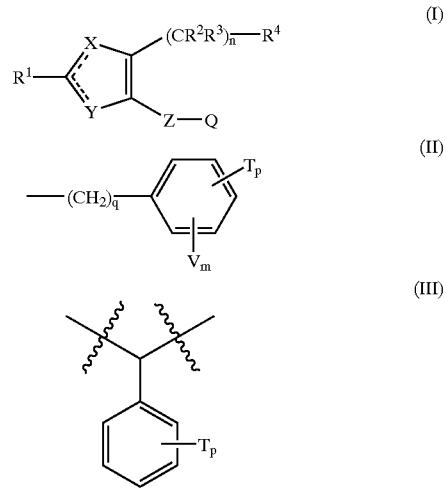

Compounds of formula (I) and their pharmaceutically acceptable salts are ligands at gastrin and/or cholecystokinin receptors. X and Y are independently $=N—$, $—N(R^5)—$ $=CH—$, $—S—$ or $—O—$. n is from 1 to 4; $R^1$ is H or $C_1$ to $C_{15}$ hydrocarbyl $R^2$ is selected from H, Me, Et, Pr and OH, $R_3$ is selected from H, Me, Et and Pr; or (when n is greater than 1) each $R^3$ is independently selected from H, Me, Et and Pr, or two $R^3$ groups on neighbouring carbon atoms are linked to form a $C_3$ to $C_6$ carbocyclic ring, or $R^2$ and $R^3$ on the same carbon atom together represent an $=O$ group; $R^4$ is $C_1$ to $C_{15}$ hydrocarbyl Z is $—(NR^7)_a—CO—$ $(NR^8)_b—$ (wherein a is 0 or 1, b is 0 or 1, $—CO—NR^7—$ $CH_2—CO—NR^8—$, $—CO—O—$, $—CH_2—CH_2—$, $—CH=CH—$, $—CH_2—NR^8—$ or a bond; Q is $—R^9V$, or (II), (wherein $R^9$ is $—CH_2—$; $—CH_2—CH_2—$; or (III), $R^9$ and $R^8$, together with the nitrogen atom to which $R^8$ is attached, form a piperidine or pyrrolidine ring which is substituted by V; V is $—CO—NH—SO_2—Ph$, $—SO_2—$ $NH—CO—Ph$, $—CH_2OH$, or a group of the formula $—R^{10}U$, (wherein U is $—COOH$, tetrazolyl, $—CONHOH—$ or $—SO_3H$; and $R^{10}$ is a bond; $C_1$ to $C_6$ hydrocarbylene, $—O—(C_1$ to $C_3$ alkylene)—; $—SO_2NR^{11}—CHR^{12}—$; $—CO—NR^{11}—CHR^{12}—$, or $—NH—(CO)_c—CH_2—$, c being 0 or 1).

23 Claims, No Drawings

GASTRIN AND CHOLECYSTOKININ RECEPTOR LIGANDS

This application is a 371 of Internation Application PCT/GB99/03733 filed Nov. 9, 1999

This invention relates to gastrin and cholecystokinin (CCK) receptor ligands. The invention also relates to methods for preparing such ligands and to compounds which are useful intermediates in such methods. The invention further relates to pharmaceutical compositions comprising such ligands and methods for preparing such pharmaceutical compositions.

Gastrin and the cholecystokinins are structurally related neuropeptides which exist in gastrointestinal tissue and the central nervous system (Mutt V., *Gastrointestinal Hormones*, Glass G. B. J., ed., Raven Press, New York, p. 169; Nisson G., ibid., p. 127).

Gastrin is one of the three primary stimulants of gastric acid secretion. Several forms of gastrin are found including 34-, 17- and 14-amino acid species with the minimum active fragment being the C-terminal tetrapeptide (TrpMetAspPhe-NH$_2$) which is reported in the literature to have full pharmacological activity (Tracey H. J. and Gregory R. A., *Nature* (London), 1964, 204, 935). Much effort has been devoted to the synthesis of analogues of this tetrapeptide (and the N-protected derivative Boc-TrpMetAspPhe-NH$_2$) in an attempt to elucidate the relationship between structure and activity.

Natural cholecystokinin is a 33 amino acid peptide (CCK-33), the C-terminal 5 amino acids of which are identical to those of gastrin. Also found naturally is the C-terminal octapeptide (CCK-8) of CCK-33.

The cholecystokinins are reported to be important in the regulation of appetite. They stimulate intestinal mobility, gall bladder contraction, pancreatic enzyme secretion and are known to have a trophic action on the pancreas. They also inhibit gastric emptying and have various effects in the central nervous system.

Compounds which bind to cholecystokinin and/or gastrin receptors are important because of their potential pharmaceutical use as antagonists or partial agonists of the natural peptides.

A number of gastrin antagonists have been proposed for various therapeutic applications, including the prevention of gastrin-related disorders, gastrointestinal ulcers, Zollinger-Ellison syndrome, antral G cell hyperplasia and other conditions in which lower gastrin activity or lower acid secretion is desirable. The hormone has also been shown to have a trophic action on cells and so an antagonist may be expected to be useful in the treatment of cancers, particularly in the stomach and the colon.

Possible therapeutic uses for cholecystokinin antagonists include the control of appetite disorders such as anorexia nervosa and the treatment of pancreatic inflammation, biliary tract disease and various psychiatric disorders. Other possible uses are in the potentiation of opiate (for example morphine) analgesia and in the treatment of cancers, especially of the pancreas. Moreover, ligands for cholecystokinin receptors in the brain (so-called CCK$_B$ receptors) have been claimed to possess anxiolytic activity.

According to the present invention, there are provided compounds of formula (I)

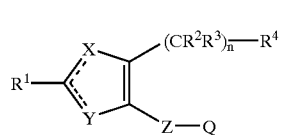

wherein

X and Y are independently =N—, —N(R$^5$)—(R$^5$ being selected from H, Me, Et, Pr, Bn, —OH and —CH$_2$COOR$^6$, wherein R$^6$ represents H, Me, Et, Pr or Bn), =CH—, —S— or —O—;

n is from 1 to 4;

R$^1$ is H or C$_1$ to C$_{15}$ hydrocarbyl wherein up to three C atoms may optionally be replaced by N, O and/or S atoms and up to three H atoms may optionally be replaced by halogen atoms;

R$^2$ is selected from H, Me, Et, Pr and OH, each R$^2$ being independently selected from H, Me, Et, Pr and OH when n is greater than 1;

R$^3$ (when n is 1) is selected from H, Me, Et and Pr; or (when n is greater than 1) each R$^3$ is independently selected from H, Me, Et and Pr, or two R$^3$ groups on neighbouring carbon atoms are linked to form a C$_3$ to C$_6$ carbocylic ring, or two R$^3$ groups are absent from neighbouring carbon atoms which are linked by a double bond; or R$^2$ and R$^3$ on the same carbon atom together represent an =O group;

R$^4$ is C$_1$ to C$_{15}$ hydrocarbyl wherein up to two C atoms may optionally be replaced by N, O and/or S atoms and up to two H atoms may optionally be replaced by halogen atoms;

Z is —(NR$^7$)$_a$—CO—(NR$^8$)$_b$— (wherein a is 0 or 1, b is 0 or 1, and R$^7$ and R$^8$ are independently selected from the groups recited above for R$^6$), —CO—NR$^7$—CH$_2$—CO—NR$^8$—, CO—O—, —CH$_2$—CH$_2$—, —CH=CH—, —CH$_2$—NR$^8$— or a bond;

Q is —R$^9$V, or

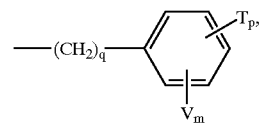

(wherein R$^9$ is —CH$_2$—; —CH$_2$—CH$_2$—; or

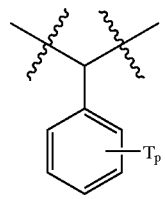

or R$^9$ and R$^8$, together with the nitrogen atom to which R$^8$ is attached, form a piperidine or pyrrolidine ring which is substituted by V;

V is —CO—NH—SO$_2$—Ph, —SO$_2$—NH—CO—Ph, —CH$_2$OH, or a group of the formula —R$^{10}$U, (wherein U is —COOH, tetrazolyl, —CONHOH or —SO$_3$H; and $R^{10}$ is a bond; $C_1$ to $C_6$ hydrocarbylene, optionally substituted by hydroxy, amino or acetamido; —O—($C_1$ to $C_3$ alkylene)—; —$SO_2NR^{11}$—$CHR^{12}$—; —CO—$NR^{11}$—$CHR^{12}$—, $R^{11}$ and $R^{12}$ being independently selected from H and methyl; or —NH—(CO)$_c$—$CH_2$—, c being 0 or 1);

T is $C_1$ to $C_6$ hydrocarbyl, —$NR^6R^7$ (wherein $R^6$ and $R^7$ are as defined above), —OMe, —OH, —$CH_2OH$, halogen or trihalomethyl;

m is 1 or 2;

p is from 0 to 3; and q is from 0 to 2, with the proviso that q is 1 or 2 when Z is a bond);

and pharmaceutically acceptable salts thereof.

In certain compounds according to the invention, $R^5$ is selected from H, Me, Et, Pr and Bn; Z is —$(NR^7)_a$—CO—$(NR^8)_b$—, —CO—NH—$CH_2$—CO—NH— or a bond; Q is

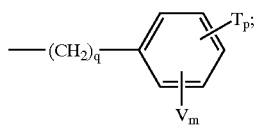

V is —CO—NH—$SO_2$—Ph, —$SO_2$—NH—CO—Ph, —$OCH_2COOH$, tetrazolyl or —$(CH_2)_s$COOH, wherein s is from 0 to 2; and T is $C_1$ to $C_6$ hydrocarbyl, —$NR^6R^7$, —OMe, —OH, —$CH_2OH$ or halogen. Such compounds are disclosed in U.K. patent application No. 9824536.8, the contents of which are hereby incorporated by reference.

A further group of compounds according to the invention are those in which $R^5$ is selected from H, Me, Et, Pr and Bn; Z is —$(NR^7)_a$—CO—$(NR^8)_b$—, Q is —$(CH_2)_r$COOH, wherein r is from 1 to 3; and T is $C_1$ to $C_6$ hydrocarbyl, —$NR^6R^7$, —OMe, —OH, —$CH_2OH$ or halogen.

A still further group of compounds according to the invention are those in which $R^5$ is selected from H, Me, Et, Pr and Bn; —Z—Q is

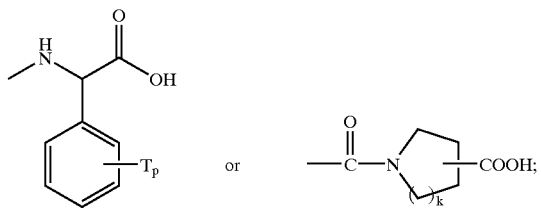

k is 1 or 2; and T is $C_1$ to $C_6$ hydrocarbyl, —$NR^6R^7$, —OMe, —OH, —$CH_2OH$ or halogen.

Preferably X and Y are independently =N—, =CH—, —NH—, —NOH—, —NMe— or —NBn—. Most preferably X is —NH— or —NOH— and Y is =CH— (or vice versa) or X is =N— and Y is —NH— or —NOH— (or vice versa).

Preferably $R^1$ is $C_1$ to $C_{12}$ hydrocarbyl wherein one C atom may optionally be replaced by N or O and up to three H atoms may optionally be replaced by F, Cl or Br. More preferably $R^1$ is $C_3$ to $C_{12}$ alicyclic; phenyl (optionally substituted with OMe, $NMe_2$, $CF_3$, Me, F, Cl, Br or I); or $C_1$ to $C_8$ alkyl. Alicyclic groups include $C_5$ to $C_8$ cycloalkyl, $C_7$ to $C_{10}$ polycycloalkyl, $C_5$ to $C_8$ cycloalkenyl and $C_7$ to $C_{10}$ polycycloalkenyl, all optionally substituted with methyl.

Preferably Z is —CO—NH—.

Preferably Q is

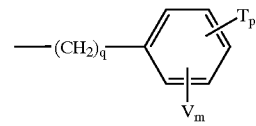

and more preferably

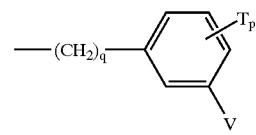

p is preferably 0 or 1, and q is preferably 0. If p is greater than 0, then T is preferably $C_1$ to $C_6$ hydrocarbyl or halo.

m is preferably 1, and V is preferably —$CO_2H$, —$CH_2CO_2H$ or tetrazolyl.

Preferably $R^2$ and $R^3$ are H; n is 1 to 3; and $R^4$ is $C_3$ to $C_{12}$ carbocyclic. More preferably, $R^4$ is adamantyl, cycloheptyl, cyclohexyl or phenyl. Alternatively, $R^4$ may be —NH—$R^{13}$ or —$OR^{13}$, wherein $R^{13}$ is $C_3$ to $C_{12}$ carbocyclic, preferably adamantyl, cycloheptyl, cyclohexyl or phenyl.

$R^{10}$ is preferably a bond, $C_1$ or $C_2$ alkylene (optionally substituted by hydroxy, amino or acetamido), —O—($C_1$ to $C_3$ alkylene)—; —$SO_2NR^{11}$—$CHR^{12}$—; —CO—$NR^{11}$—$CHR^{12}$—, —NH—(CO)$_c$—$CH_2$—, or a group of the formula

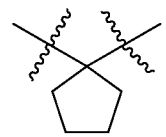

Certain compounds of the invention exist in various regioisomeric, enantiomeric, tautomeric and diastereomeric forms. It will be understood that the invention comprehends the different regioisomers, enantiomers, tautomers and diastereomers in isolations from each other as well as mixtures.

Compounds of the invention wherein (i) X is —NH—, (ii) Y is =CH—, and (iii) Z is —CO—NH— may conveniently be prepared by the route shown in Reaction Scheme A (in which PG represents a protecting group, and Q' represents Q or a suitably protected derivative of Q):

Reaction Scheme A

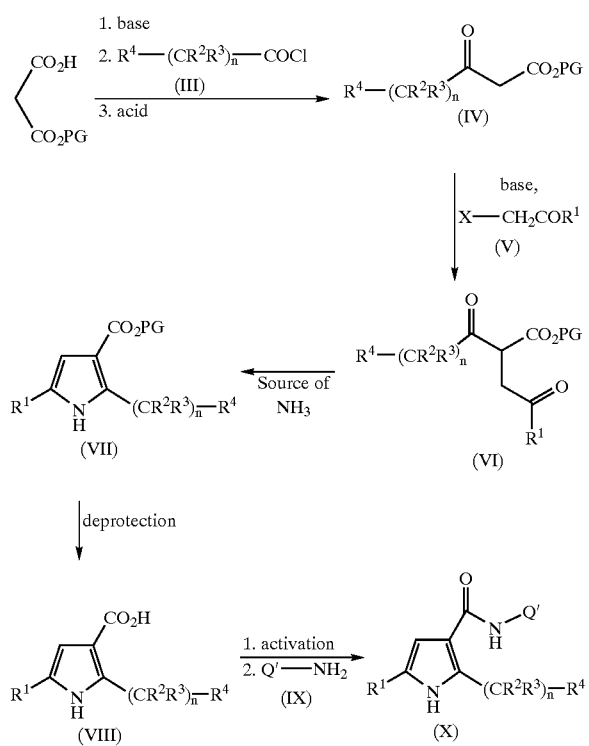

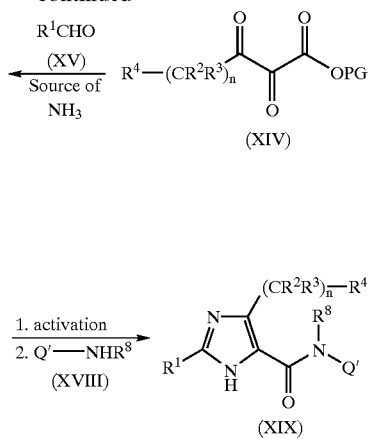

A suitably protected malonic acid derivative (II) is deprotonated and reacted with a suitably substituted acid chloride (III). The reaction product (IV) is deprotonated and reacted with a suitably substituted α-bromo carbonyl compound (V). The reaction product (VI) is cyclised, using for example AcOH and AcONH$_4$. The cyclisation product (VII) is deprotected to yield pyrrole (VIII). The free carboxylic acid of pyrrole (VIII) is activated, using for example SOCl$_2$, and reacted with a suitably substituted amine (IX) to yield compound (X). Any appropriate deprotection carried out on compounds (X) leads to compounds of the invention wherein X is —NH—, Y is =CH— and Z is —CO—NH—.

Compounds of the invention wherein (i) X is —NH— and Y is =N—, or X is =N— and Y is —NH—, and (ii) Z is —CO—NR$^8$— may conveniently be prepared by the route shown in reaction Scheme B (in which Q' and PG are as defined above):

Reaction Scheme B

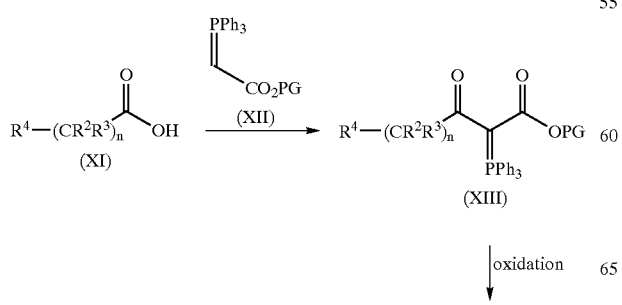

A suitably substituted carboxylic acid (XI) is reacted, using for example EDC or SOCl$_2$, with a suitably protected phosphorous ylid (XII). The product ylid (XIII) is oxidised, using for example oxone. The oxidation product (XIV) is cyclised with a suitably substituted aldehyde (XV), using for example AcOH and AcONH$_4$. The cyclisation product (XVI) is deprotected to yield imidazole (XVII). The free carboxylic acid of imidazole (XVII) is activated, using for example PyBrOP or EDC, and reacted with a suitably substituted amine (XVIII) to yield compound (XIX). Any appropriate deprotection carried out on compounds (XIX) leads to compounds of the invention wherein X is —NH— and Y is =N— or X is =N— and Y is —NH—, and Z is —CO—NH—.

Compounds in which X is —NR$^5$— (wherein R$^5$ is alkyl) may be made by treatment of compound (XVI) with sodium hydride, followed by quenching with R$^5$Br, activation, reaction with Q'NHR$^8$ and deprotection (if appropriate).

Hence another aspect of the present invention is a method of making a compound of formula (I). Preferably said method includes the step of cyclising a suitable precursor (VI) or (XIV) to yield a five membered ring, preferably a pyrrole (VII) or an imidazole (XVI). Preferably said cyclisation is effected using AcOH and AcONH$_4$. The invention further provides compounds which are useful intermediates in such methods.

Compounds of the invention wherein Z is —NH—CO—NH— or —NH—CO— may conveniently be prepared by the route shown in reaction Scheme C, in which Q' is as defined above. X' and Y' correspond to X and Y, except that when X (or Y) is —NH—, X' (or Y', as the case may be) is —N(PG)—, in which PG represents a protecting group.

Reaction Scheme C

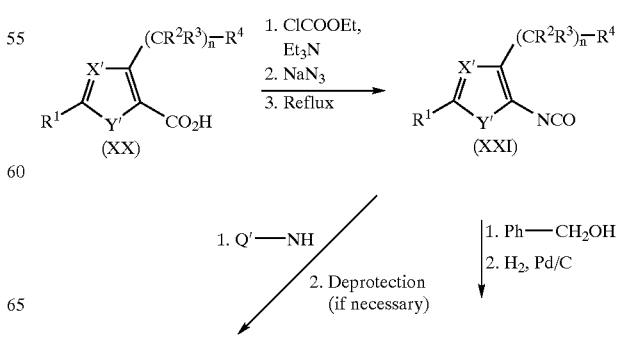

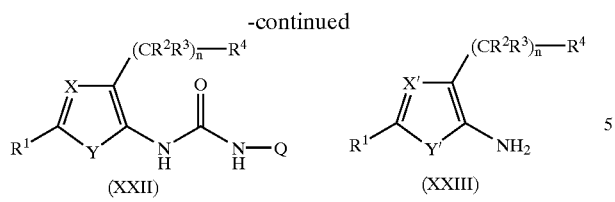

(XXII)  (XXIII)

1. Q'—COCl
2. Deprotection (if necessary)

(XXIV)

In this reaction scheme, the starting compound (XX) may be, for example, an N— protected derivative of compound (XVII) shown in Reaction Scheme B. Compound (XX) is first treated with ethylchloroformate and triethylamine, and sodium azide is then added. After heating under reflux, the compound (XXI) is obtained. Reaction of this compound with an amine of the formula Q'—NH, followed by appropriate deprotection, yields the urea derivative (XXII). Alternatively, compound (XXI) may be reacted with benzyl alcohol, followed by catalytic hydrogenation (using, for example, a Pd/C catalyst) to yield the corresponding amine (XXIII). This, in turn, may be reacted with an acid chloride of the formula Q'—COCl, followed by appropriate deprotection, to provide the "reverse" amide (XXIV).

Compounds wherein Z is —CH$_2$—CH$_2$— or —CH=CH— may conveniently be prepared by the method shown in Reaction Scheme D. In this scheme, compound (XXV) is an ester derived, for example, from compound (VII) shown in Reaction Scheme A or compound (XVI) shown in Reaction Scheme B. It is first reduced to the corresponding alcohol, such as by reaction with lithium aluminium hydride, followed by oxidation (e.g. using manganese(IV) oxide) to form the corresponding aldehyde (XXVI). The aldehyde, in turn, is reacted with a triphenylphosphonium compound of the formula Q'—CH$_2$—PPh$_3^+$Br$^-$, to yield compound (XXVII). This may be deprotected as required to yield the target compound (XVIII) in which Z is —CH=CH—, or it may first be reduced and then deprotected (as necessary) to provide the compound (XXIX) in which Z is —CH$_2$—CH$_2$—.

Reaction Scheme D

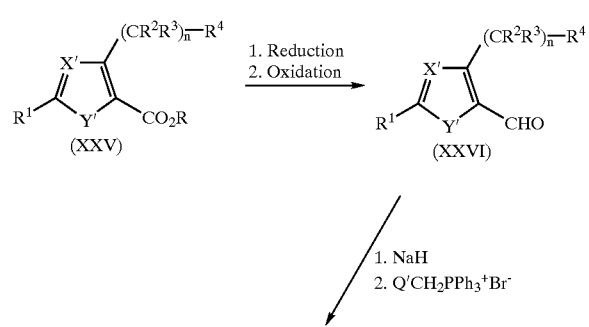

Compounds wherein X is =N— and Y is —S— may be prepared by the procedure outlined in Reaction Scheme E.

Reaction Scheme E

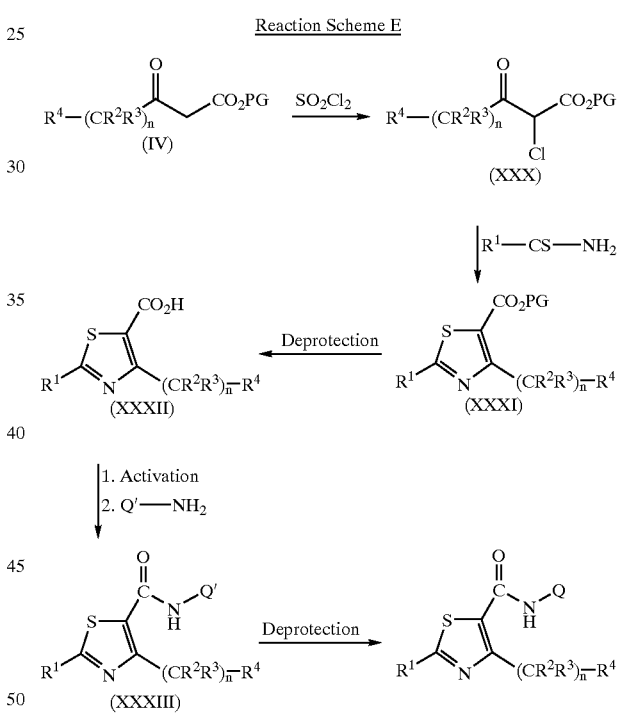

Compound (IV) (Reaction Scheme A) is first reacted with sulfonyl chloride to form compound (XXX), which is then refluxed in a suitable solvent (such as ethanol) with a compound of formula R$^1$—CS—NH$_2$, leading to formation of the thiazole derivative (XXXI). This is then deprotected to form the corresponding carboxylic acid (XXXII), the carboxyl group of which may then be elaborated as shown in Reaction Schemes A, B and C. For example, amidation with a suitably protected amine Q'—NH$_2$ leads to compound (XXXIII), which may then be deprotected to yield the target compound. The amidation reaction is preferably carried out using PyBrOP and N,N-diisopropylethylamine.

Compounds wherein X is —S— and Y is =N— may be prepared by the method illustrated in Reaction Scheme F.

Reaction Scheme F

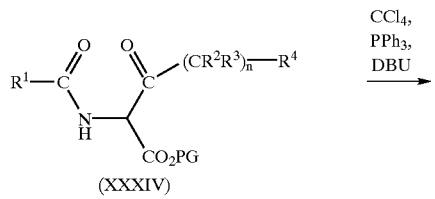

Compound (XXXIV), which may be prepared by the general methodology of Example 120, step a, is reacted with Lawesson's reagent to form the protected thiazole derivative (XXXV). This may then be deprotected, and the carboxyl group subsequently elaborated as described above.

Compound (XXXIV) may also be used in the preparation of compounds in which X is —O— and Y is =N—, as shown in Reaction Scheme G.

Reaction Scheme G

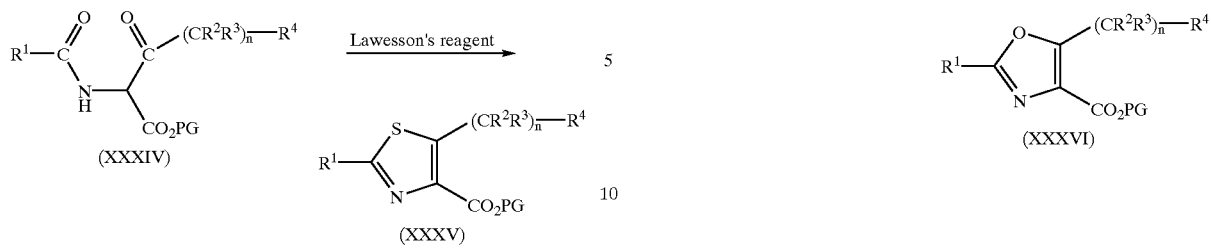

In this case, carbon tetrachloride, 1,8-diazabicyclo[5,4,0]undec-7-ene (DBU), and triphenylphosphine are sequentially added to a solution of compound (XXXIV) to form the protected oxazole derivative (XXXVI). This may then be deprotected, and the carboxyl group subsequently elaborated in the same way as for the corresponding imidazole, pyrrole and thiazole compounds.

Compounds of the invention wherein (i) X is —N=, (ii) Y is —N(OH)—, and (iii) Z is —CO—NR$^8$— may conveniently be prepared by the route shown in Reaction Scheme H

Reaction Scheme H

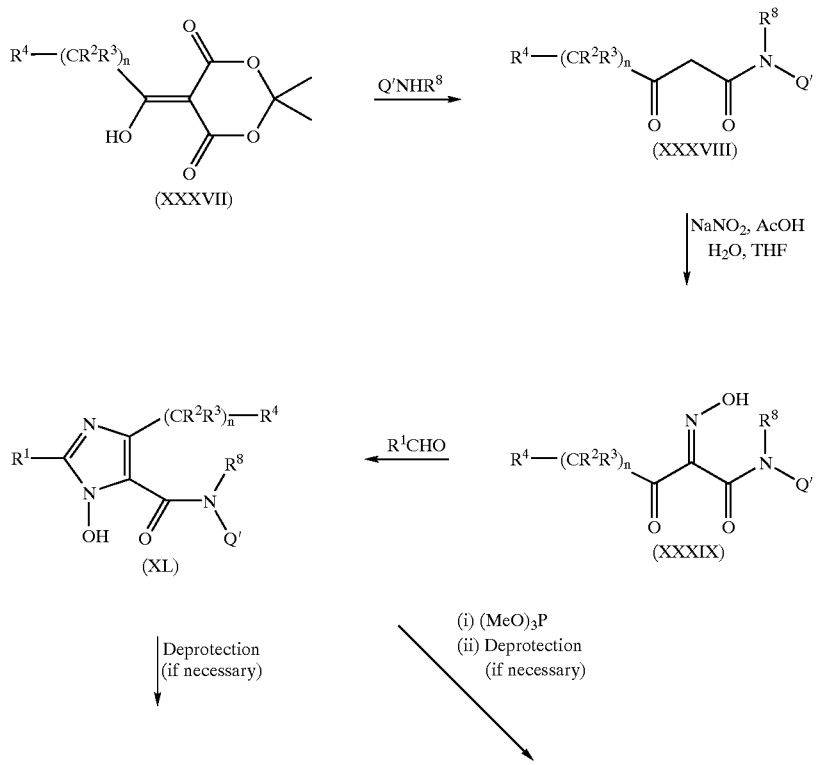

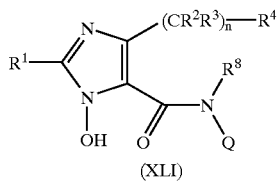

(XLI)

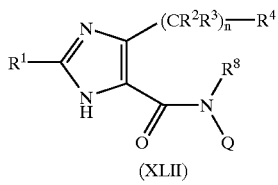

(XLII)

The dioxane-dione derivative (XXXVII) may be obtained by reaction of the corresponding acid $R^4—(CR^2R^3)_n—COOH$ with carbonyl di-imidazole, as illustrated in Example 308 below. Compound (XXXVII) is then reacted with amine $Q'NHR^8$, such as by heating in toluene in the presence of catalytic quantities of DMAP. The product (XXXVIII) is reacted with sodium nitrite to form the hydroxyimino derivative (XXXIX). This is then reacted with the aldehyde $R^1CHO$ to form the substituted hydroxyimidazole (XL), which is subsequently deprotected as appropriate.

The protected hydroxyimidazole (XL) provides a further route to the corresponding imidazole compound (XLII), by treatment with trimethylphosphite, and subsequent deprotection (if necessary).

An alternative way of making intermediates which may be elaborated to compounds of the invention in which X is —N= and Y is —NR$^5$ (or vice versa) is shown in Reaction Scheme I. The protected carboxyl group of compound (XLV) may be deprotected in conventional manner, and the free carboxyl group may then be elaborated in the ways discussed above. Alternatively, compound (XLV) may be converted to compound (XVI) by reaction with trimethylphosphite.

Reaction Scheme I

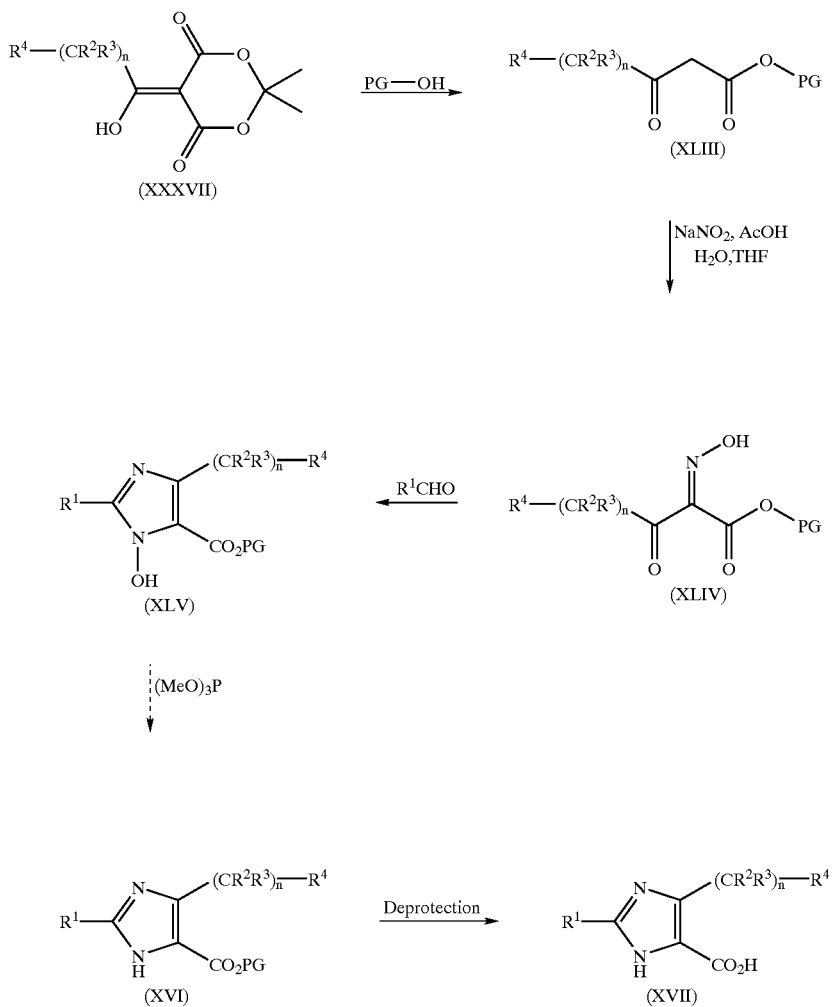

Still further routes to compound (XVI) are illustrated in Reaction Scheme J and Reaction Scheme K below.

Reaction Scheme J

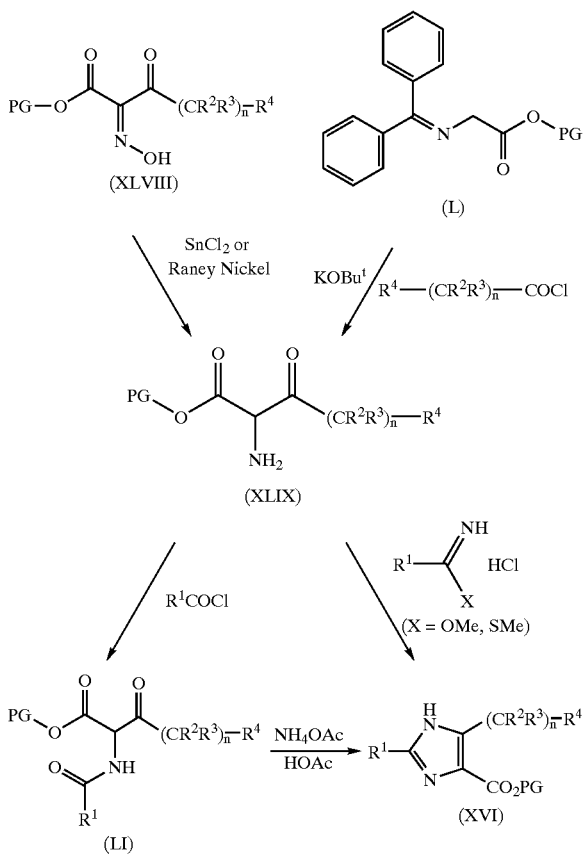

Reaction Scheme K

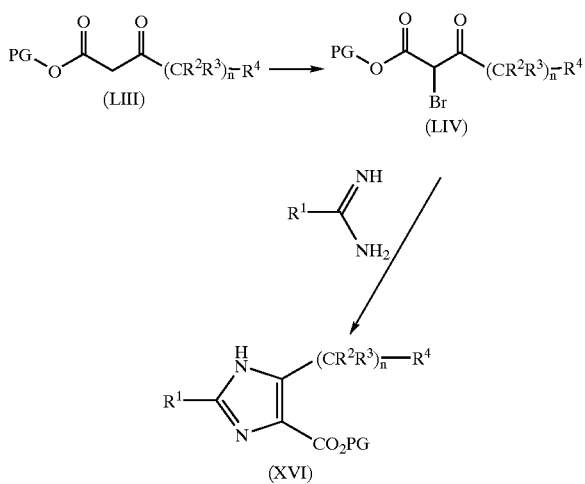

In these reaction schemes, the final product is the compound (XVI) having a protected carboxyl group. This may be deprotected and subsequently elaborated to provide compounds according to the invention, as discussed above.

The invention also comprehends derivative compounds ("pro-drugs") which are degraded in vivo to yield the species of formula (I). Pro-drugs are usually (but not always) of lower potency at the target receptor than the species to which they are degraded. Pro-drugs are particularly useful when the desired species has chemical or physical properties which make its administration difficult or inefficient. For example, the desired species may be only poorly soluble, it may be poorly transported across the mucosal epithelium, or it may have an undesirably short plasma half-life. Further discussion of pro-drugs may be found in Stella, V. J. et al., "Prodrugs", *Drug Delivery Systems,* 1985, pp. 112–176, and *Drugs,* 1985, 29, pp. 455–473.

Pro-drug forms of the pharmacologically-active compounds of the invention will generally be compounds according to formula (I) having an acid group which is esterified or amidated. Included in such esterified acid groups are groups of the form —COOR$^{14}$, wherein R$^{14}$ is C$_1$ to C$_5$ alkyl, phenyl, substituted phenyl, benzyl, substituted benzyl, or one of the following:

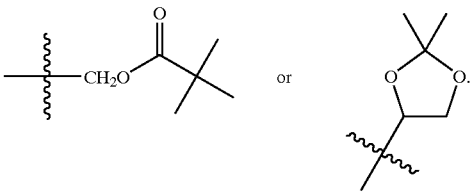

Amidated acid groups include groups of the formula —CONR$^{15}$R$^{16}$, wherein R$^{15}$ is H, C$_1$ to C$_5$ alkyl, phenyl, substituted phenyl, benzyl, or substituted benzyl, and R$^{16}$ is —OH or one of the groups just recited for R$^{15}$.

Compounds of formula (I) having an amino group may be derivatised with a ketone or an aldehyde such as formaldehyde to form a Mannich base. This will hydrolyse with first order kinetics in aqueous solution.

Another aspect of the present invention is a pharmaceutical composition comprising a compound of formula (I) substantially as described herein before with a pharmaceutically acceptable diluent or carrier.

Yet another aspect of the present invention is a method of making a pharmaceutical composition comprising a compound of formula (I) substantially as described herein before, comprising mixing said compound with a pharmaceutically acceptable diluent or carrier.

Pharmaceutically acceptable salts of the acidic or basic compounds of the invention can of course be made by conventional procedures, such as by reacting the free base or acid with at least a stoichiometric amount of the desired salt-forming acid or base.

Pharmaceutically acceptable salts of the acidic compounds of the invention include salts with inorganic cations such as sodium, potassium, calcium, magnesium, and zinc, and salts with organic bases. Suitable organic bases include N-methyl-D-glucamine, arginine, benzathine, diolamine, olamine, procaine and tromethamine.

Pharmaceutically acceptable salts of the basic compounds of the invention include salts derived from organic or inorganic acids. Suitable anions include acetate, adipate, besylate, bromide, camsylate, chloride, citrate, edisylate, estolate, fumarate, gluceptate, gluconate, glucuronate, hippurate, hyclate, hydrobromide, hydrochloride. iodide, isethionate, lactate, lactobionate, maleate, mesylate, methylbromide, methylsulfate, napsylate, nitrate, oleate, pamoate, phosphate, polygalacturonate, stearate, succinate, sulfate, sulfosalicylate, tannate, tartrate, terephthalate, tosylate and triethiodide.

It is anticipated that the compounds of the invention can be administered by oral or parenteral routes, including intravenous, intramuscular, intraperitoneal, subcutaneous, rectal and topical administration, and inhalation.

For oral administration, the compounds of the invention will generally be provided in the form of tablets or capsules or as an aqueous solution or suspension.

Tablets for oral use may include the active ingredient mixed with pharmaceutically acceptable excipients such as inert diluents, disintegrating agents, binding agents, lubricating agents, sweetening agents, flavouring agents, colouring agents and preservatives. Suitable inert diluents include sodium and calcium carbonate, sodium and calcium phosphate and lactose. Corn starch and alginic acid are suitable disintegrating agents. Binding agents may include starch and gelatine. The lubricating agent, if present, will generally be magnesium stearate, stearic acid or talc. If desired, the tablets may be coated with a material such as glyceryl monostearate or glyceryl distearate, to delay absorption in the gastrointestinal tract.

Capsules for oral use include hard gelatine capsules in which the active ingredient Is mixed with a solid diluent and soft gelatine capsules wherein the active ingredient is mixed with water or an oil such as peanut oil, liquid paraffin or olive oil.

For intramuscular, intraperitoneal, subcutaneous and intravenous use, the compounds of the invention will generally be provided in sterile aqueous solutions or suspensions, buffered to an appropriate pH and isotonicity. Suitable aqueous vehicles include Ringer's solution and isotonic sodium chloride. Aqueous suspensions according to the invention may include suspending agents such as cellulose derivatives, sodium alginate, polyvinyl-pyrrolidone and gum tragacanth, and a wetting agent such as lecithin. Suitable preservatives for aqueous suspensions include ethyl and n-propyl p-hydroxybenzoate.

Effective doses of the compounds of the present invention may be ascertained be conventional methods. The specific dosage level required for any particular patient will depend on a number of factors, including severity of the condition being treated, the route of administration and the weight of the patient. In general, however, it is anticipated that the daily dose (whether administered as a single dose or as divided doses) will be in the range 0.001 to 5000 mg per day, more usually from 1 to 1000 mg per day, and most usually from 10 to 200 mg per day. Expressed as dosage per unit body weight, a typical dose will be expected to be between 0.01 µg/kg and 50 mg/kg, especially between 10 µg/kg and 10 mg/kg, eg. between 100 µg/kg and 2 mg/kg.

The term "hydrocarbyl" is used herein to refer to monovalent groups consisting of carbon and hydrogen. Hydrocarbyl groups thus include alkyl, alkenyl and alkynyl groups (in both straight and branched chain forms), cycloalkyl (including polycycloalkyl), cycloalkenyl and aryl groups, and combinations of the foregoing, such as alkylcycloalkyl, alkylpolycycloalkyl, alkylaryl, alkenylaryl, alkynylaryl, cycloalkylaryl and cycloalkenylaryl groups.

A "carbocyclic" group, as the term is used herein, comprises one or more closed chains or rings, which consist entirely of carbon atoms. Carbocyclic groups thus include aryl groups (such as phenyl, naphthyl, indanyl, fluorenyl, (1,2,3,4)-tetrahydronaphthyl, indenyl and isoindenyl, and substituted derivatives thereof), and also alicyclic groups. The term "alicyclic group" refers to a carbocyclic group which does not contain an aromatic ring, and thus includes groups such as cyclopropyl, cyclobutyl, cyclopentyl, cyclohexyl, cyclohexenyl, adamantyl, norbornyl, bicyclo [2.2.2]octyl, norbornyl and bicyclo[2.2.2]octenyl, and also groups (such as adamantanemethyl and methylcyclohexyl) which contain both alkyl or alkenyl groups in addition to cycloalkyl or cycloalkenyl moieties.

The term "alkyl" is used herein to refer to both straight and branched chain forms.

A "heterocyclic" group comprises one or more closed chains or rings which have at least one atom other than carbon in the closed chain or ring. Examples include benzimidazolyl, thienyl, furanyl, pyrrolyl, imidazolyl, pyrazolyl, thiazolyl, isothiazolyl, oxazolyl, pyrrolidinyl, pyrrolinyl, imidazolidinyl, imidazolinyl, pyrazolidinyl, tetrahydrofuranyl, pyranyl, pyronyl, pyridyl, pyrazinyl, pyridazinyl, piperidyl, piperazinyl, morpholinyl, thionaphthyl, benzofuranyl, isobenzofuryl, indolyl, oxyindolyl, isoindolyl, indazolyl, indolinyl, 7-azaindolyl, isoindazolyl, benzopyranyl, coumarinyl, isocoumarinyl, quinolyl, isoquinolyl, naphthridinyl, cinnolinyl, quinazolinyl, pyridopyridyl, benzoxazinyl, quinoxadinyl, chromenyl, chromanyl, isochromanyl and carbolinyl.

When reference is made herein to a substituted carbocyclic group (such as substituted phenyl) or a substituted heterocyclic group, the substituents are preferably from 1 to 3 in number and selected from $C_1$ to $C_6$ alkyl, $C_1$ to $C_6$ alkoxy, thio, $C_1$ to $C_6$ alkylthio, carboxy, carboxy ($C_1$ to $C_6$)alkyl, formyl, $C_1$ to $C_6$ alkylcarbonyl, $C_1$ to $C_6$ alkylcarbonylalkoxy, nitro, trihalomethyl, hydroxy, $C_1$ to $C_6$ alkylhydroxy, hydroxy($C_1$ to $C_6$)alkyl, amino, $C_1$ to $C_6$ alkylamino, di($C_1$ to $C_6$ alkyl)amino, aminocarboxy, $C_1$ to $C_6$ alkylaminocarboxy, di($C_1$ to $C_6$ alkyl)aminocarboxy, aminocarboxy($C_1$ to $C_6$)alkyl, $C_1$ to $C_6$ alkylaminocarboxy ($C_1$ to $C_6$)alkyl, di($C_1$ to $C_6$ alkyl)aminocarboxy($C_1$ to $C_6$)alkyl, $C_1$ to $C_6$ alkylcarbonylamino, $C_5$ to $C_8$ cycloalkyl, $C_5$ to $C_8$ cycloalkyl($C_1$ to $C_6$)alkyl, $C_1$ to $C_6$ alkylcarbonyl ($C_1$ to $C_6$ alkyl)amino, aryl, aryl($C_1$ to $C_6$)alkyl, ($C_1$ to $C_6$ alkyl)aryl, halo, $C_1$ to $C_6$ alkylhalo, sulphamoyl, tetrazolyl and cyano.

The term "halogen" is used herein to refer to any of fluorine, chlorine, bromine and iodine. Most usually, however, halogen substituents in the compounds of the invention are chlorine and fluorine substituents.

The invention is now further illustrated by means of the following examples. All reactions were performed under an atmosphere of dry argon unless otherwise stated. Dichloromethane (DCM) was freshly distilled from calcium hydride. Anhydrous tetrahydrofuran (THF) and N,N-dimethylformamide (DMF) were used.

EXAMPLE 1

5-[(2-Adamantan-1-ylmethyl-5-phenyl-1H-pyrrole-3-carbonyl)-amino]-isophthalic Acid Step a. 4-Adamantan-1-yl-3-oxo-2-(2-oxo-2-phenyl-ethyl)-butyric Acid Ethyl Ester To a solution of 4-adamantan-1-yl-3-oxo-butyric acid ethyl ester, prepared by a modification of Wierenga and Skulnick's procedure (W. Wierenga and H. I. Skulnick, *J. Org. Chem.*, 1979, 44, 310)(3.00 g, 11.0 mmol) in acetone (30 ml) was added sodium iodide (0.55 g, 3.67 mmol) and anhydrous potassium carbonate (3.04 g, 22.0 mmol), then a solution of 2-bromo-1-phenyl-ethanone (2.38 g, 11.5 mmol) in acetone (10 ml). The mixture was stirred at reflux for 36 h, cooled to room temperature and filtered. The filtrate was evaporated, the residue was dissolved in diethyl ether (50 ml) and washed with water (2×20 ml). The organic phase was dried ($MgSO_4$) and the solvent was evaporated. The residue was purified by flash column chromatography (silica, hexane/ethyl acetate 4:1) to afford the product as pale yellow oil (1.92 g, 46%). $^1$H NMR (300 MHz, CDCl$_3$) 7.98 (2H, m), 7.65 (1H, m), 7.46 (2H, m), 4.19 (3H, m), 3.60 (1H, dd), 5.59 (1H, dd), 2.50 (2H, dd), 1.96 (3H, br s), 1.68 (12H, m), 1.29 (3H, t).

Step b. 2-Adamantan-1-ylmethyl-5-phenyl-1H-pyrrole-3-carboxylic Acid Ethyl Ester This compound was prepared by modification of Sammes's procedure (P.-K. Chiu and M. P. Sammes, *Tetrahedron*, 1990, 46, 3439). The product of step a (1.10 g, 2.88 mmol) and ammonium acetate (780 mg, 10.1 mmol) were stirred in acetic acid (1.4 ml) at 80° C. for 24 h. The reaction mixture was cooled, then partitioned between DCM and saturated sodium hydrogen carbonate. The organic layer was dried, the solvent was evaporated. The residue was crystallised from hexane/ethyl acetate 4:1 to afford the product as a white solid (750 mg, 71%). $^1$H NMR (300 MHz, CDCl$_3$) 8.21 (1H, br s), 7.21–7.48 (5H, m), 6.88 (1H, d), 4.30 (2H, q), 2.85 (2H, s), 1.96 (3H, br s), 1.60 (12H, m), 1.38 (3H, t).

Step c. 2-Adamantan-1-ylmethyl-5-phenyl-1H-pyrrole-3-carboxylic Acid

To a solution of the product of step b (750 mg, 2.06 mmol) in ethanol (45 ml) was added sodium hydroxide (5 ml of 6.0M solution). The mixture was heated at reflux for 48 h, it was allowed to cool to room temperature and concentrated to small volume under reduced pressure. The concentrated solution was diluted with 2M hydrochloric acid (40 ml), the precipitated solid was filtered, washed with water and dried to afford the acid (660 mg, 94%). $^1$H NMR (300 MHz, CDCl$_3$) 11.5 (1H, br s), 8.26 (1H, br s), 7.48 (2H, m), 7.40 (2H, m), 7.26 (1H, m), 6.94 (1H, d), 2.87 92H, s), 1.97 (3H, br s), 1.63 (12H, m).

Step d. 5-[(2-Adamantan-1-ylmethyl-5-phenyl-1H-pyrrole-3-carbonyl)-amino]-isophthalic Acid Dibenzyl Ester To a suspension of the product of step c above (290 mg, 0.91 mmol) in DCM (5 ml) was added thionyl chloride (200 µl, 2.74 mmol) and one drop of DMF. The mixture was stirred at room temperature for 30 min, the solvent was evaporated and the residue was coevaporated with DCM (2×5 ml). 5-Amino-isophthalic acid dibenzyl ester (361 mg, 1.00 mmol) was added to the residue followed by anhydrous pyridine (2 ml). The solution was kept at room temperature for 16 h and diluted with DCM (30 ml). The organic phase was washed with 2M hydrochloric acid (2×20 ml), brine (20 ml), dried (MgSO$_4$) and the solvent was evaporated. The residue was purified by flash column chromatography (silica, DCM/hexane/ethyl acetate 9:9:2) to afford the product as pale yellow solid (300 mg, 45%). $^1$H NMR (300 MHz, CDCl$_3$) 8.48 (3H, s), 8.30 (1H, br s), 7.69 (1H, s), 7.49–7.27 (15H, m), 6.66 (1H, d), 5.40 (4H, s), 2.91 (2H, s), 1.95 (3H, br s), 1.63 (12H, m).

Step e

A round bottom flask containing the product from the previous step (180 mg, 0.27 mmol), 10% palladium on charcoal (50 mg) and THF/methanol (1:1 mixture, 20 ml) was evacuated and flushed with hydrogen three times. The mixture was vigorously stirred overnight under an atmosphere of hydrogen. The catalyst was removed by filtration and the filtrate evaporated to afford the product as a white solid (130 mg, 98%). $^1$H NMR (300 MHz, d$_6$-DMSO) 13.17 (2H, br s), 11.22 (1H, s), 9.80 (1H, s), 8.64 (2H, s), 8.13 (1H, s), 7.66 (2H, m), 7.39 (2H, m), 7.19 (2H, m), 2.85 (2H, s), 1.88 (3H, br s), 1.53 (12H, m). The acid was converted to the di(N-methyl-D-glucamine) salt and lyophilised from water/dioxan. Found: C, 57.03; H, 7.64; N, 6.03%; C$_{44}$H$_{64}$N$_4$O$_{15}$·2.0 H$_2$O requires: C, 57.13; H, 7.41; N, 6.06%.

EXAMPLE 2

2-Adamantan-1-ylmethyl-5-phenyl-1H-pyrrole-3-carboxylic Acid [3,5-bis-(1H-tetrazol-5-yl)-phenyl]-amide

Step a. 2-Adamantan-1-ylmethyl-5-phenyl-1H-pyrrole-3-carboxylic Acid [3,5-bis-(1-pivaloyloxymethyl-1H-tetrazol-5-yl)-phenyl]-amide 2-Adamantan-1-yl-methyl-5-phenyl-1H-pyrrole-3-carboxylic acid (Example 1, step c) was reacted with 3,5-bis(1-pivaloyloxymethyl-1H-tetrazol-5-yl)-phenylamine according to the procedure given in Example 1, step d. $^1$H NMR (300 MHz, d$_6$-DMSO) 11.27 (1H, s), 9.95 (1H, s), 8.82 (2H, s), 8.44 (1H, s), 7.68 (2H, d), 7.40 (2H,t), 7.22 (2H,m), 6.70 (4H, s), 2.88 (2H, s), 1.88 (3H, br s), 1.56 (12H, m), 1.16 (18H, s).

Step b

The solution of the product of step a above (320 mg, 0.41 mmol) in saturated methanolic ammonia (20 ml) was stirred at room temperature for 2 h. The solvent was evaporated under reduced pressure, the residue was dissolved in water (10 ml) and the solution was acidified (pH=1, 1M HCl). The precipitate was collected by filtration, washed with water and dried to afford the title compound as a white solid (164 mg, 73%). $^1$H NMR (300 MHz, d$_6$-DMSO) 11.28 (1H, s), 9.99 (1H, s), 8.72 (2H, s), 8.40 (1H, s), 7.68 (2H, d), 7.40 (2H,t), 7.20 (2H, t), 2.89 (2H, s), 1.89 (3H, br s), 1.54 (12H, m). The product was converted to the di(N-methyl-D-glucamine) salt and lyophilised from water/dioxan. Found: C, 53.92; H, 6.94; N, 17.24%; C$_{45}$H$_{68}$N$_{12}$O$_{11}$·2.0 H$_2$O requires: C, 54.20; H, 7.24; N, 17.24%.

EXAMPLE 3

3-[(2-Adamantan-1-ylmethyl-5-phenyl-1H-pyrrole-3-carbonyl)-amino]-benzoic Acid The benzyl ester of the title compound was prepared by reacting 2-adamantan-1-ylmethyl-5-phenyl-1H-pyrrole-3-carboxylic acid (Example 1, step c) with 3-amino-benzoic acid benzyl ester according to the procedure of Example 1, step d. This was converted to the title compound using the procedure of Example 1, step e. $^1$H NMR (300 MHz, d$_6$-DMSO) 11.19 (1H, s), 9.62 (1H, s), 8.37 (1H, s), 7.97 (1H, d) 7.66 (2H, d), 7.58 (1H, d), 7.39 (3H, m), 7.16 (2H, m), 2.84 (2H, s), 1.88 (3H, br s), 1.54 (12H, m). The product was converted to the N-methyl-D-glucamine salt and lyophilised from water/dioxan. Found: C, 62.82; H, 7.38; N, 5.82%; C$_{36}$H$_{47}$N$_3$O$_8$·2.0 H$_2$O requires: C, 63.04; H, 7.50; N, 6.12%.

EXAMPLE 4

5-[(2-Adamantan-1-ylmethyl-5-naphthalen-2-yl-1H-pyrrole-3-carbonyl)-amino]-isophthalic Acid The title compound was prepared according to the procedure given in Example 1, using 2-bromo-1-naphtalen-2- yl-ethanone in step a instead of 2-bromo-1-phenyl-ethanone. $^1$H NMR (300 MHz, d$_6$-DMSO) 11.41 (1H, s), 9.84 (1H, s), 8.65 (2H, s), 8.15 (1H, d), 7.88 (4H, m), 7.47 (2H, m), 7.36 (1H, s), 2.90 (2H, s), 1.90 (3H, br s), 1.57 (12H, m). The acid was converted to the di(N-methyl-D-glucamine) salt and lyophilised from water/dioxan. Found: C, 58.96; H, 7.31; N, 5.83%; C$_{48}$H$_{66}$N$_4$O$_{15}$.2.0 H$_2$O requires: C, 59.12; H, 7.24; N, 5.75%.

EXAMPLE 5

2-Adamantan-1-ylmethyl-5-naphthalen-2-yl-1H-pyrrole-3-carboxylic Acid [3,5-bis-(1H-tetrazol-5-yl)-phenyl]-amide 2-Adamantan-1-ylmethyl-5-naphthalen-2-yl-1H-pyrrole-3-carboxylic acid was prepared according to the procedure of Example 1, steps a, b and c, using 2-bromo-1-naphthalen-2-yl-ethanone in step a instead of 2-bromo-1-phenyl-ethanone. This acid was then converted to the title compound using essentially the procedure of Example 2, steps a and b. $^1$H NMR (300 MHz, d$_6$-DMSO) 11.42 (1H, s), 9.87 (1H, s), 8.64 (2H, s), 8.38 (1H, s), 8.19 (1H, s), 7.88 (2H, d), 7.95 (1H, d), 7.86 (3H, m), 7.47 (3H, m), 2.93 (2H, s), 1.91 (3H, br s), 1.59 (12H, m). The product was converted to the di(N-methyl-D-glucamine) salt and lyophilised from water/dioxan.

EXAMPLE 6

2-[(2-Adamantan-1-ylmethyl-5-phenyl-1H-pyrrole-3-carbonyl)-amino]-benzoic Acid

Step a. 2-[(2-Adamantan-1-ylmethyl-5-phenyl-1H-pyrrole-3-carbonyl)-amino]-benzoic Acid Methyl Ester 2-Adamantan-1-ylmethyl-5-phenyl-1H-pyrrole-3-carboxylic acid (Example 1, step c) (335 mg, 1.00 mmol) was reacted with 2-amino-benzoic acid methyl ester (1.51 mg, 1.00 mmol) according to the procedure of Example 1, step d to afford the product as a pale yellow solid (155 mg, 33%). $^1$H NMR (300 MHz, d$_6$-DMSO) 11.32 (1H, s), 11.24 (1H, s), 8.67 (1H, d), 8.00 (1H, d) 7.60 (3H, m), 7.40 (2H, m), 7.25 (1H, t), 7.12 (1H, t), 6.83 (1H, s), 3.92 (3H, s), 2.86 (2H, s), 1.88 (3H, s), 1.55 (12H, m).

Step b

To a solution of the product from step a above (155 mg, 0.33 mmol) in THF (5 ml) and water (0.5 ml) was added lithium hydroxide monohydrate (42 mg, 1.00 mmol). The reaction mixture was stirred at room temperature for 24 h, the solvent was evaporated under reduced pressure and the residue was partitioned between ethyl acetate and 2M hydrochloric acid. The organic layer was washed with brine, dried and the solvent was evaporated to afford the title compound as a white solid (143 mg, 95%). $^1$H NMR (300 MHz, d$_6$-DMSO) 11.81 (1H, s), 11.30 (1H, s), 8.75 (1H, d), 8.01 (1H, d) 7.60 (3H, m), 7.40 (2H, m), 7.21 (1H, t), 7.09 (1H, t), 6.84 (1H, s), 2.86 (2H, s), 1.88 (3H, br s), 1.54 (12H, m). The product was converted to the N-methyl-D-glucamine salt and lyophilised from water/dioxan. Found: C, 63.88; H, 7.49; N, 6.18%; C$_{36}$H$_{47}$N$_3$O$_8$.1.5 H$_2$O requires: C, 63.89; H, 7.45; N, 6.21%.

EXAMPLE 7

4-[(2-Adamantan-1-ylmethyl-5-phenyl-1H-pyrrole-3-carbonyl)-amino]-benzoic Acid

The title compound was prepared according to the procedure of Example 6, steps a and b, using 4-amino-benzoic acid methyl ester in step a instead of 2-amino-benzoic acid methyl ester. $^1$H NMR (300 MHz, d$_6$-DMSO) 12.50 (1H, br s), 11.24 (1H, s), 9.77 (1H, s), 7.90 (4H, m), 7.68 (2H, d), 7.41 (2H, t), 7.21 (1H, t), 7.12 (1H, s), 2.86 (2H, s), 1.92 (3H, br s), 1.60 (12H, m). The product was converted to the N-methyl-D-glucamine salt and lyophilised from water/dioxan. Found: C, 61.67; H, 7.50; N, 5.97%; C$_{36}$H$_{47}$N$_3$O$_8$.3.0 H$_2$O requires: C, 61.47; H, 7.59; N, 5.97%.

EXAMPLE 8

5-[(2-Adamantan-1-ylmethyl-1-methyl-5-phenyl-1H-pyrrole-3-carbonyl)-amino]-isophthalic Acid Step a. 2-Adamantan-1-ylmethyl-1-methyl-5-phenyl-1H-pyrrole-3-carboxylic Acid Ethyl Ester To a solution of 2-adamantan-1-ylmethyl-5-phenyl-1H-pyrrole-3-carboxylic acid ethyl ester (Example 1, step b) (726 mg, 2.00 mmol) in DMF (3 ml) was added sodium hydride (60% dispersion in oil) (100 mg, 2.50 mmol) in small portions at 0° C. The mixture was stirred at room temperature for 30 min, then iodomethane (1.00 ml, 16.0 mmol) was added and the stirring was continued for 1 h. The reaction mixture was partitioned between ethyl acetate and 1M hydrochloric acid, the organic layer was washed with water, dried, and the solvent was evaporated to afford the product as a white solid (620 mg, 82%). $^1$H NMR (300 MHz, CDCl$_3$) 7.35 (5H, m), 6.64 (1H, s), 4.27 (2H, q), 3.51 (3H, s), 2.80 (2H, br s), 1.96 (3H, br s), 1.64 (12H, m), 1.35 (3H, t).

Step b. 2-Adamantan-1-ylmethyl-1-methyl-5-phenyl-1H-pyrrole-3-carboxylic Acid

To a solution of the product of step a (620 mg, 1.64 mmol) in dioxan/ethanol (30 ml of 1:1 mixture) was added sodium hydroxide (3.7 ml of 6M solution) and the mixture was stirred under reflux for 5 days. The mixture was cooled to room temperature, concentrated under reduced pressure, then 1M hydrochloric acid (20 ml) was added and the product was extracted with ethyl acetate (2×20 ml). The combined organic layers were washed with brine, dried (MgSO$_4$) and the solvent was evaporated. The crude product was heated at reflux in hexane/ethyl acetate 4:1 (20 ml), cooled to room temperature, the precipitate was filtered, washed with hexane and dried to afford the product as a white solid (290 mg, 51%). $^1$H NMR (300 MHz, CDCl$_3$) 11.80 (1H, br s), 7.40 (5H, m), 6.72 (1H, s), 3.52 (3H, s), 3.00 (2H, br s), 1.97 (3H, br s), 1.67 (12H, m).

Step c

The product of step b was converted to the title compound according to the procedure given in Example 1, steps d and e. $^1$H NMR (300 MHz, d$_6$-DMSO) 13.00 (2H, br s), 9.83 (1H, s), 8.60 (2H, s), 8.12 (1H, s), 7.40 (5H, m), 6.87 (1H, s), 3.52 (3H, s), 2.99 (2H, br s), 1.87 (3H, br s), 1.57 (12H, m). The acid was converted to the di(N-methyl-D-glucamine) salt and lyophilised from water/dioxan. Found: C, 57.77; H, 7.12; N, 5.83%; C$_{45}$H$_{66}$N$_4$O$_{15}$.2.0 H$_2$O requires: C, 58.09; H, 7.42; N, 5.89%.

EXAMPLE 9

5-[(2-Adamantan-1-ylmethyl-5-phenyl-1H-pyrrole-3-carbonyl)-amino-methyl]-isophthalic Acid 2-Adamantan-1-ylmethyl-5-phenyl-1H-pyrrole-3-carboxylic acid (Example 1, step c) was reacted with 5-methylamino-isophthalic acid dimethyl ester according to the procedure of Example 1, step c. The dimethyl ester was hydrolized according to the procedure described in Example 6, step b to afford the title compound as a pale yellow foam. $^1$H NMR (300 MHz, d$_6$-DMSO) 13.06 (2H, br s), 11.01 (1H, s), 8.36 (1H, t), 8.32 (1H, s), 8.12 (2H, s), 7.60 (2H, m), 7.35 (2H, m), 7.16 (1H, m), 6.87 (1H, s), 4.46 (2H, d), 2.76 (2H, s), 1.80 (3H, br s), 1.47 (12H, m). The acid was converted to the di(N-methyl-D-glucamine) salt and lyophilised from water/dioxan. Found: C, 59.61; H, 7.09; N, 6.04%; C$_{45}$H$_{66}$N$_4$O$_{15}$ requires: C, 59.85; H, 7.37; N, 6.20%.

EXAMPLE 10

3-[(2-Adamantan-1-ylmethyl-5-phenyl-1H-pyrrole-3-carbonyl)-amino]-propionic Acid The title compound was prepared according to the procedure of Example 1, using β-alanine benzyl ester in step d instead of 5-amino-isophthalic acid dibenzyl ester. $^1$H NMR (300 MHz, d$_6$-DMSO) 10.94 (1H, s), 7.60 (3H, m), 7.34 (2H, m), 7.15 (1H, m), 6.80 (1H, s), 3.35 (2H, m), 2.76 (2H, s), 2.46 (2H, t), 1.86 (3H, br s), 1.51 (12H, m).

The acid was converted to the di(N-methyl-D-glucamine) salt and lyophilised from water/dioxan. Found: C, 61.93; H, 7.73; N, 6.53%; C$_{32}$H$_{47}$N$_3$O$_8$.1.0 H$_2$O requires: C, 62.01; H, 7.97; N, 6.78%.

EXAMPLE 11

5-[(2-Cycloheptylmethyl-5-naphthalene-2-yl-1H-pyrrole-3-carbonyl)-amino]-isophthalic Acid The title compound was prepared according to the procedure of Example 1, using 4-cycloheptyl-3-oxo-butyric acid ethyl ester and 2-bromo-1-naphthalen-2-yl-ethanone instead of 4-adamantan-1-yl-3-oxo-butyric acid ethyl ester and 2-bromo-1-phenyl-ethanone in step a. $^1$H NMR (300 MHz, d$_6$-DMSO) 11.66 (1H, s), 9.79 (1H, s), 8.66 (2H, s), 8.15 (2H, s), 7.88 (4H, m), 7.44 (4H, m), 2.94 (2H, d), 2.00 (1H, br s), 1.68–1.23 (12H, m). The acid was converted to the di(N-methyl-D-glucamine) salt and lyophilised from water/dioxan. Found: C, 56.57; H, 7.39; N, 5.78%; C$_{45}$H$_{64}$N$_4$O$_{15}$.3.0 H$_2$O requires: C, 56.59; H, 7.38; N, 5.87%.

EXAMPLE 12

3-[(2-Cycloheptylmethyl-5-phenyl-1H-pyrrole-3-carbonyl)-amino]-benzoic Acid

The title compound was prepared according to the procedure of Example 1, using 4-cycloheptyl-3-oxo-butyric acid ethyl ester instead of 4-adamantan-1-yl-3-oxo-butyric acid ethyl ester in step a, and 3-amino-benzoic acid benzyl ester instead of 5-amino-isophthalic acid dibenzyl ester in step d. $^1$H NMR (300 MHz, d$_6$-DMSO) 11.42 (1H, s), 9.58 (1H, s), 8.38 (1H, s), 8.01 (1H, d), 7.62 (3H, m), 7.40 (3H, m), 7.20 (2H, m), 2.89 (2H, d), 1.93 (1H, br s), 1.61–1.19 (12H, m). The acid was converted to the N-methyl-D-glucamine salt and lyophilised from water/dioxan. Found: C, 60.99; H, 7.60; N, 6.28%; C$_{33}$H$_{45}$N$_3$O$_7$.2.0 H$_2$O requires: C, 61.20; H, 7.63; N, 6.49%.

EXAMPLE 13

5-[(2-Cycloheptylmethyl--phenyl-1H-pyrrole-3-carbonyl)-amino]-isophthalic Acid The title compound was prepared according to the procedure of Example 1, using 4-cycloheptyl-3-oxo-butyric acid ethyl ester instead of 4-adamantan-1-yl-3-oxo-butyric acid ethyl ester in step a. $^1$H NMR (300 MHz, d$_6$-DMSO) 11.46 (1H, s), 9.75 (1H, s), 8.65 (2H, s), 8.13 (1H, 3), 7.65 (2H, d), 7.39 (2H, t), 7.20 (2H, m), 2.89 (2H, d), 1.94 (1H, br s), 1.62–1.20 (12H, m). The acid was converted to the di(N-methyl-D-glucamine) salt and lyophilised from water/dioxan. Found: C, 55.51; H, 7.60; N, 6.32%; C$_{41}$H$_{61}$N$_4$O$_{14}$.2.0 H$_2$O requires: C, 55.52; H, 7.50; N, 6.28%.

EXAMPLE 14

3-[(2-Cycloheptylmethyl-5-naphthalen-2-yl-1H-pyrrole-3-carbonyl)-amino]-benzoic Acid The title compound was prepared according to the procedure of Example 1, using 4-cycloheptyl-3-oxo-butyric acid ethyl ester and 2-bromo-1-naphthalen-2-yl-ethanone instead of 4-adamantan-1-yl-3-oxo-butyric acid ethyl ester and 2-bromo-1-phenyl-ethanone in step a, and 3-amino-benzoic acid benzyl ester instead of 5-amino-isophthalic acid dibenzyl ester in step d. $^1$H NMR (300 MHz, d$_6$-DMSO) 11.62 (1H, s), 9.64 (1H, s), 8.41 (1H, s), 8.14 (1H, s), 8.03 (1H, d), 7.94 (1H, d), 7.84 (3H, m), 7.60 (1H, m), 7.44 (3H, m), 7.34 (1H, s), 2.93 (2H, d), 1.98 (1H, br s), 1.67–1.22 (12H, m). The acid was converted to the N-methyl-D-glucamine salt and lyophilised from water/dioxan. Found: C, 62.89; H, 7.51; N, 5.92%; C$_{37}$H$_{47}$N$_3$O$_8$.2.5 H$_2$O requires: C, 62.87; H, 7.41; N, 5.94%.

EXAMPLE 15

2-Cycloheptylmethyl-5-naphthalen-2-yl-1H-pyrrole-3-carboxylic Acid [3,5-bis-(1H-tetrazol-5-yl)-phenyl]-amide 2-Cycloheptylmethyl-5-naphthalen-2-yl-1H-pyrrole-3-carboxylic acid was prepared according to the procedure of Example 1, steps a, b and c, using 4-cycloheptyl-3-oxo-butyric acid ethyl ester and 2-bromo-1-naphthalen-2-yl-ethanone instead of 4-adamantan-1-yl-3-oxo-butyric acid ethyl ester and 2-bromo-1-phenyl-ethanone in step a. The acid was then converted to the title compound according to the procedure of Example 2. $^1$H NMR (300 MHz, d$_6$-DMSO) 11.69 (1H, s), 9.98 (1H, s), 8.75 (2H, s), 8.41 (1H, s), 8.16 (1H, s), 7.90 (4H, m), 7.50 (3H, m), 2.97 (2H, d), 2.02 (1H, br s), 1.70–1.21 (12H, m). The acid was converted to the di(N-methyl-D-glucamine) salt and lyophilised from water/dioxan. Found: C, 53.80; H, 6.88; N, 16.52%; C$_{45}$H$_{64}$N$_{12}$O$_{11}$.3.0 H$_2$O requires: C, 53.88; H, 7.03; N, 16.75%.

EXAMPLE 16

2-Cycloheptylmethyl-5-naphthalen-2-yl-1H-pyrrole-3-carboxylic Acid [3-(1H-tetrazol-5-yl)-phenyl]-amide 2-Cycloheptylmethyl-5-naphthalen-2-yl-1H-pyrrole-3-carboxylic acid was prepared according to the procedure of Example 1, steps a, b and c, using 4-cycloheptyl-3-oxo-butyric acid ethyl ester and 2-bromo-1-naphthalen-2-yl-ethanone instead of 4-adamantan-1-yl-3-oxo-butyric acid ethyl ester and 2-bromo-1-phenyl-ethanone in step a. The acid was then reacted with 3-(1-pivaloyloxymethyl-1H-tetrazol-5-yl)-phenylamine using essentially the same procedure as in Example 1, step d. Deprotection was performed following essentially the procedure of Example 2, step b, with the exception that after acidification the product was isolated by extraction with DCM. ¹H NMR (300 MHz, d₆-DMSO) 11.63 (1H, s), 9.72 (1H, s), 8.59 (1H, s), 8.15 (1H, s), 7.88 (5H, m), 7.67 (2H, d), 7.48 (3H, m), 7.34 (1H, s), 2.95 (2H, d), 1.99 (1H, br s), 1.68–1.23 (12H, m). The acid was converted to the N-methyl-D-glucamine salt and lyophilised from water/dioxan. Found: C, 63.03; H, 6.96; N, 13.71%; $C_{37}H_{47}N_7O_6 \cdot 1.0\ H_2O$ requires: C, 63.14; H, 7.02; N, 13.93%.

EXAMPLE 17

5-{[2-(2-Adamantan-1-yl-ethyl)-5-phenyl-1H-pyrrole-3-carbonyl]-amino}-isophthalic Acid The title compound was synthesised following the procedure of Example 1 with the modification that 5-adamantan-1-yl-3-oxo-pentanoic acid ethyl ester was used in step a instead of 4-adamantan-1-yl-3-oxo-butyric acid ethyl ester. 1H NMR (300 MHz, d₆-DMSO) 11.45 (1H, s), 9.53 (1H, s), 8.45 (2H, s), 8.16 (1H, s), 7.65 (2H, d), 7.37 (2H, m), 7.24 (1H, s), 7.17 (1H, m), 2.96 (2H, m), 1.94 (3H, s), 1.65 (6H, m), 1.55 (6H, s), 1.40 (2H, m). The acid was converted to the di(N-methyl-D-glucamine) salt and lyophilised from water/dioxan. Found: C, 56.39; H, 7.66; N, 5.92%; $C_{45}H_{66}N_{12}O_{11} \cdot 3.0\ H_2O$ requires: C, 56.47; H, 7.58; N, 5.85%.

EXAMPLE 18

2-(2-Adamantan-1-yl-ethyl)-5-phenyl-1H-pyrrole-3-carboxylic Acid [3,5-bis-(1H-tetrazol-5-yl)-phenyl]-amide 2-(2-Adamantan-1-yl-ethyl)-5-phenyl-1H-pyrrole-3-carboxylic acid was prepared following the procedure of Example 1, steps a, b and c, with the modification that 5adamantan-1-yl-3-oxo-pentanoic acid ethyl ester was used as the substrate in step a. The acid was then converted to the title compound according to the procedure of Example 2, steps a and b. ¹H NMR (300 MHz, d₆-DMSO) 11.49 (1H, s), 9.86 (1H, s), 8.69 (2H, s), 8.40 (1H, s), 7.66 (2H, d), 7.40 (2H, t), 7.22 (2H, m), 2.98 (2H, m), 1.95 (3H, s), 1.65 (6H, m), 1.55 (6H, s), 1.42 (2H, m). The acid was converted to the di(N-methyl-Dglucamine) salt and lyophilised from water/dioxan. Found: C, 47.87; H, 7.39; N, 14.59%; $C_{45}H_{66}N_{12}O_{11} \cdot 10.0\ H_2O$ requires: C, 47.82; H, 7.58; N, 14.87%.

EXAMPLE 19

3-{[2-(2-Adamantan-1-yl-ethyl)-5-phenyl-1H-pyrrole-3-carbonyl]-amino}-benzoic Acid The title compound was synthesised following the procedure of Example 1 with the modification that 5-adamantan-1-yl-3-oxo-pentanoic acid ethyl ester was used instead of 4-adamantan-1-yl-3-oxo-butyric acid ethyl ester in step a, and 3-amino-benzoic acid benzyl ester was used instead of 5-amino-isophthalic acid dibenzyl ester in step d. ¹H NMR (300 MHz, d₆-DMSO) 11.38 (1H, s), 9.42 (1H, s), 8.22 (1H, s), 7.91 (1H, d), 7.63 (2H, d), 7.56 (1H, d), 7.37 (2H, t), 7.28 (1H, t), 7.17 (2H, m), 2.96 (2H, m), 1.94 (3H, br s), 1.65 (6H, m), 1.54 (6H, s), 1.38 (2H, m). The acid was converted to the N-methyl-D-glucamine salt and lyophilised from water/dioxan.

EXAMPLE 20

5-[(5-Cycloheptylmethyl-2-naphthalen-2-yl-1H-imidazole-4-carbonyl)-amino]-isophthalic Acid

Step a. 4-Cycloheptyl-2,3-dioxo-butyric Acid Ethyl Ester Monohydrate

Cycloheptaneacetic acid was converted to 4-cycloheptyl-2,3-dioxo-butyric acid ethyl ester hydrate according to the procedure of H. H. Wasserman (H. H. Wasserman, D. S. Ennis, C. A. Blum and V. M. Rotello, *Tetrahedron Lett.*, 1992, 33, 6003). The tricarbonyl was isolated as pale yellow oil. ¹H NMR (300 MHz, CDCl₃) 4.99 (2H, br s), 4.30 (2H, q), 2.51 (2H, d), 2.14 (1H, m), 1.67–1.16 (15H, m).

Step b. 5-Cycloheptylmethyl-2-naphthalen-2-yl-1H-imidazole-4-carboxylic Acid Ethyl Ester This compound was prepared by modification of Brackeen's procedure (M. F. Brackeen, J. A. Stafford, P. L. Feldman and D. S. Karanewsky, *Tetrahedron Lett.*, 1994, 35, 1635). To a slurry of ammonium acetate (9.0 g, 116 mmol) in acetic acid (35 ml) was added the product of step a (3.00 g, 11.6 mmol) followed by 2-naphthaldehyde (3.60 g, 23.2 mmol). The mixture was stirred in an oil bath heated to 70° C. for 2 h. The solution was cooled to room temperature and the acetic acid was evaporated. The residue was dissolved in ethyl acetate (50 ml) and washed with saturated sodium hydrogen carbonate (2×50 ml), water (20 ml) and brine (20 ml). The organic phase was dried (MgSO₄), the solvent was evaporated. The crude product was purified by crystallisation from ethyl acetate to afford the imidazole derivative as a white solid (1.74 g, 40%). ¹H NMR (300 MHz, CDCl₃) 10.18 and 9.97 (1H, br s), 8.39 (1H, s), 7.90 (4H, m), 7.52 (2H, br s), 4.40 (2H, q), 2.89 (2H, m), 2.05–1.26 (16H, m).

Step c. 5-Cycloheptylmethyl-2-naphthalen-2-yl-1H-imidazole-4-carboxylic Acid To a suspension of the product of step b (1.73 g, 4.62 mmol) in ethanol (25 ml) was added the solution of sodium hydroxide (1.29 g, 32.3 mmol) in water (5 ml). The reaction mixture was heated under reflux for 48 h, allowed to cool to room temperature and concentrated under reduced pressure. The aqueous solution was diluted with water (30 ml) and acidified to pH=2 with 1M hydrochloric acid. The precipitate was collected by filtration, washed with water, and dried to afford the product as an off-white solid (1.53 g, 96%). ¹H NMR (300 MHz, d₆-DMSO) 8.77 (1H, s), 8.24–7.98 (4H, m), 7.64 (2H, m), 2.91 and 2.64 (2H, 2×d), 2.03 (1H, m), 1.69–1.24 (12H, m).

Step d. 5-[(5-Cycloheptylmethyl-2-naphthalen-2-yl-1H-imidazole-4-carbonyl)-amino]-isophthalic Acid Dibenzyl Ester To a solution of the product of step c above (500 mg, 1.44 mmol) and 5-amino-isophthalic acid dibenzyl ester (520 mg, 1.44 mmol) in DMF (3 ml) was added 1-hydroxybenzotriazole (HOBt) (195 mg, 1.44 mmol), 4-dimethylaminopyridine (DMAP) (cat.) and 1-(3-dimethylaminopropyl-3-ethylcarbodiimide hydrochloride (EDC) (280 mg, 1.44 mmol). The solution was kept at room temperature for 72 h, poured over 1M hydrochloric acid (20 ml) and the product was extracted with ethyl acetate (2×20 ml). The product crystallised from the ethyl acetate extracts. The crystals were collected by filtration, dried and triturated with methanol to afford a white solid (453 mg, 46%). ¹H NMR (300 MHz, d₆-DMSO) 13.00 (1H, br s), 10.50 (1H, s), 8.84 (2H, s), 8.61 (1H, s), 8.28 (2H, m), 8.00 (3H, m), 7.50 (12H, m), 5.41 (4H, s), 2.98 (2H, d), 2.00 (1H, m), 1.69–1.16 (12H, m).

Step e

The product of step d (450 mg, 0.65 mmol) was deprotected using the same procedure as in Example 1, step e to afford the title compound as a white solid (310 mg, 94%). ¹H NMR (300 MHz, d$_6$-DMSO) 10.75 (1H, s), 8.77 (3H, m), 8.40 (1H, d), 8.25 (1H, s), 8.13 (1H, d), 8.02 (2H, m), 7.65 (2H, m), 3.05 (2H, d), 2.11 (1H, m) 1.75–1.31 (12H, m). The acid was converted to the di(N-methyl-D-glucamine) salt and lyophilised from water/dioxan. Found: C, 53.27; H, 7.24; N, 7.09%; C$_{44}$H$_{63}$N$_5$O$_{15}$.4.8 H$_2$O requires: C, 53.44; H, 7.41; N, 7.08%.

EXAMPLE 21

3-[(5-Cycloheptylmethyl-2-naphthalen-2-yl-1H-imidazole-4-carbonyl)-amino]-benzoic Acid The title compound was prepared using essentially the procedure of Example 20 with the modification that 3-amino-benzoic acid benzyl ester was used in step d instead of 5-amino-isophthalic acid dibenzyl ester. $^1$H NMR (300 MHz, d$_6$-DMSO) 13.00 (1H, br s), 9.93 (1H, s), 8.54 (2H, d), 8.27 (1H, d), 8.00 (4H, m), 7.65–7.41 (4H, m), 2.98 (2H, d), 2.00 (1H, m), 1.70–1.22 (12H, m). The acid was converted to the N-methyl-D-glucamine salt and lyophilised from water/dioxan. Found: C, 64.88; H, 6.82; N, 8.21%; C$_{36}$H$_{46}$N$_4$O$_8$ requires: C, 65.24; H, 7.00; N, 8.45%.

EXAMPLE 22

5-Cycloheptylmethyl-2-naphthalen-2-yl-1H-imidazole-4-carboxylic Acid (3,5-bis-hydroxymethyl-phenyl)-amide Step a. 5-Cycloheptylmethyl-2-naphthalen-2-yl-1H-imidazole-4-carboxylic Acid (3,5-bis-methoxycarbonyloxymethyl-phenyl)-amide 5-Cycloheptylmethyl-2-naphthalen-2-yl-1H-imidazole-4-carboxylic acid (Example 20, step c) (605 mg, 1.75 mmol) was reacted with 3,5-bis-methoxycarbonyloxymethyl-aniline (492 mg, 1.75 mmol) according to the procedure of Example 20, step d to afford the product as a white solid (438 mg, 42%). $^1$H NMR (300 MHz, CDCl$_3$) 9.42 (1H, br s), 9.35 (1H, s), 8.27 (1H, s), 8.06–7.89 (4H, m), 7.79 (2H, s), 7.56 (2H, m), 7.14 (1H, s), 5.18 (4H, s), 3.83 (6H, s), 3.12 (2H, d), 2.00–1.29 (13H, m).

Step b

To the solution of the product of step a (438 mg, 0.72 mmol) in methanol (50 ml) was slowly added a 1% aqueous solution of potassium carbonate. The mixture was stirred at room temperature for 2 h, then heated at reflux for 1 h. The reaction mixture was allowed to cool to room temperature and the methanol was evaporated in vacuo. The precipitate was collected by filtration, washed with water and dried to afford the title compound as a white solid (290 mg, 83%). $^1$H NMR (300 MHz, d$_6$-DMSO) 13.88 (1H, br s), 9.62 (1H, s), 8.55 (1H, s), 8.27 (1H, d), 7.98 (3H, m), 7.67 (2H, s), 7.57 (2H, m), 6.99 (1H, s), 5.16 (2H, t), 4.49 (4H, d), 2.97 (2H, d), 2.01 (1H, m), 1.70–1.22 (12H, m). Found: C, 74.67; H, 6.74; N, 8.85%; C$_{30}$H$_{33}$N$_3$O$_3$ requires: C, 74.51; H, 6.88; N, 8.69%.

EXAMPLE 23

5-[(5-Cycloheptylmethyl-2-naphthalen-1-yl-1H-imidazole-4-carbonyl)-amino]-isophthalic Acid The title compound was prepared according to the procedure of Example 20, with the modification that 1-naphthaldehyde was used in step b instead of 2-naphthaldehyde. $^1$H NMR (300 MHz, d$_6$-DMSO) 13.25 (1H, br s), 12.86 (1H, br s), 10.17 (1H, s), 8.96 (1H, d), 8.68 (2H, s), 8.17 (1H, s), 8.01 (2H, m), 7.86 (1H, d), 7.60 (3H, m), 2.99 (2H, d), 2.03 (1H, m), 1.71–1.23 (12H, m). The acid was converted to the di(N-methyl-D-glucamine) salt and lyophilised from water/dioxan. Found: C, 4.33; H, 7.29; N, 7.18%; C$_{44}$H$_{63}$N$_5$O$_{15}$.2.4 H$_2$O requires: C, 54.12; H, 6.99; N, 7.17%.

EXAMPLE 24

5-[(5-Cycloheptylmethyl-2-phenyl-1H-imidazole-4-carbonyl)-amino]-isophthalic Acid The title compound was prepared according to the procedure of Example 20, with the modification that benzaldehyde was used in step b instead of 2-naphthaldehyde. $^1$H NMR (300 MHz, d$_6$-DMSO) 13.00 (1H, br s), 12.75 (1H, br s), 10.12 (1H, s), 8.70 (2H, s), 8.17 (1H, s), 8.09 (2H,d), 7.45 (3H, m), 2.94 (2H, d), 1.98 (1H, m), 1.67–1.15 (12H, m). The acid was converted to the di(N-methyl-D-glucamine) salt and lyophilised from water/dioxan. Found: C, 53.78; H, 7.34; N, 7.67%; C$_{40}$H$_{61}$N$_5$O$_{15}$.2.4 H$_2$O requires: C, 53.64; H, 7.41; N, 7.82%.

EXAMPLE 25

5-Cycloheptyimethyl-2-phenyl-1H-imidazole-4-carboxylic Acid [3,5-bis-(1H-tetrazol-5-yl)-phenyl]-amide 5-Cycloheptylmethyl-2-phenyl-1H-imidazole-4-carboxylic acid was prepared using essentially the same procedure as in Example 20, steps a, b and c, with the modification that benzaldehyde was used in step b instead of 2-naphthaidehyde. The acid was then reacted with 3,5-bis-(1-pivaloyloxymethyl-1H-tetrazol-5-yl)-phenylamine according to the procedure of Example 20, step d. Deprotection was carried out following the procedure of Example 2, step b to afford the title compound as a white solid. $^1$H NMR (300 MHz, d$_6$-DMSO) 11.10 (1H, s), 8.78 (2H, s), 8.51 (1H, s), 8.28 (2H, d), 7.61 (3H, m), 3.03 (2H, d), 2.06 (1H, m), 1.71–1.26 (12H, m). The acid was converted to the di(N-methyl-D-glucamine) salt and lyophilised from water/dioxan.

EXAMPLE 26

3-[(5-Cycloheptylmethyl-2-phenyl-1H-imidazole-4-carbonyl)-amino]-benzoic Acid

The title compound was prepared according to the procedure of Example 20, with the modification that benzaldehyde was used in step b instead of 2-naphthaldehyde and 3-amino-benzoic acid benzyl ester was used in step d instead of 5-amino-isophthalic acid dibenzyl ester. $^1$H NMR (300 MHz, d$_6$-DMSO) 13.00 (1H, br s), 9.86 (1H, s), 8.51 (1H, s), 8.07 (2H, d), 7.99 (1H, d), 7.63 (1H, d), 7.42 (4H, m), 2.94 (2H, d), 1.98 (1H, m), 1.66–1.22 (12H, m). The acid was converted to the N-methyl-D-glucamine salt and lyophilised from water/dioxan. Found: C, 59.97; H, 7.32; N, 8.72%; C$_{32}$H$_{44}$N$_4$O$_8$.1.5 H$_2$O requires: C, 60.04; H, 7.41; N, 8.75%.

EXAMPLE 27

5-[(5-Cycloheptylmethyl-2-(2-phenyl-ethyl)-1H-imidazole-4-carbonyl)-amino]-isophthalic Acid The title compound was prepared according to the procedure of Example 20, with the modification that transcinnamaldehyde was used in step b instead of 2-naphthaldehyde. $^1$H NMR (300 MHz, CDCl$_3$) 13.00 (2H, br s), 10.30 (1H, br s), 8.65 (2H, s), 8.17 (1H, s), 7.20 (5H, m), 3.36 (2H, br s), 2.86 (2H, d), 1.90 (1H, m), 1.60–1.15 (14H, m). The acid was converted to the di(N-methyl-D-glucamine) salt and lyophilised from water/dioxan.

EXAMPLE 28

5-[(5-Cycloheptylmethyl-2-(3-methoxy-phenyl)-1H-imidazole-4-carbonyl)-amino]-isophthalic Acid The title compound was prepared according to the procedure of Example 20, with the modification that m-anisaldehyde was used in step b instead of 2-naphthaldehyde. $^1$H NMR (300 MHz, d$_6$-DMSO) 13.20 (2H, br s), 12.82 (1H, br s), 10.16 (1H, s), 8.70 (2H, s), 8.16 (1H, s), 7.68 (2H, d), 7.39 (1H, t), 6.97 (1H, m), 3.84 (3H, s), 2.94 (2H, d), 1.97 (1H, m), 1.66–1.23 (12H, m). The acid was converted to the di(N-methyl-D-glucamine) salt and lyophilised from water/dioxan. Found: C, 52.42; H, 7.41; N, 7.61%; C$_{41}$H$_{63}$N$_5$O$_{16}$.3.1 H$_2$O requires: C, 52.55; H, 7.43; N, 7.47%.

EXAMPLE 29

5-[(5-Cycloheptylmethyl-2-(4-methoxy-phenyl)-1H-imidazole-4-carbonyl)-amino]-isophthalic Acid The title compound was prepared according to the procedure of Example 20, with the modification that p-anisaldehyde was used in step b instead of 2-naphthaldehyde. $^1$H NMR (300 MHz, d$_6$-DMSO) 12.66 (1H, br s), 10.09 (1H, s), 8.71 (2H, s), 8.22 (1H, s), 8.07 (2H, d), 7.09 (2H, d), 3.87 (3H, s), 2.98 (2H, d), 2.02 (1H, m), 1.70–1.28 (12H, m). The acid was converted to the di(N-methyl-D-glucamine) salt and lyophilised from water/dioxan. Found: C, 52.63; H, 7.42; N, 7.61%; C$_{41}$H$_{63}$N$_5$O$_{16}$.2.9 H$_2$O requires: C, 52.75; H, 7.42; N, 7.50%.

EXAMPLE 30

5-[(5-Cycloheptylmethyl-2-(1H-indol-5-yl)-1H-imidazole-4-carbonyl)-amino]-isophthalic Acid The title compound was prepared according to the procedure of Example 20, with the modification that indol-5-carboxaldehyde was used in step b instead of 2-naphthaldehyde. $^1$H NMR (300 MHz, d$_6$-DMSO) 13.21 (2H, br s), 12.64 (1H, br s), 11.27 (1H, s), 10.16 (1H, s), 8.73 (2H, s), 8.30 (1H, s), 8.19 (1H, s), 7.90 (1H, d), 7.50 (1H, d), 7.43 (1H, s), 6.54 (1H, s), 2.97 (2H, d), 2.02 (1H, m), 1.71–1.26 (12H, m). The acid was converted to the di(N-methyl-D-glucamine) salt and lyophilised from water/dioxan. Found: C, 53.22; H, 7.13; N, 9.01%; C$_{42}$H$_{62}$N$_6$O$_{15}$.3.0 H$_2$O requires: C, 53.34; H, 7.26; N, 8.89%.

EXAMPLE 31

5-[(5-Cycloheptylmethyl-2-(4-dimethylamino-phenyl)-1H-imidazole-4-carbonyl)-amino]-isophthalic Acid The title compound was prepared according to the procedure of Example 20, with the modification that 4-dimethylamino-benzaldehyde was used in step b instead of 2-naphthaldehyde. $^1$H NMR (300 MHz, d$_6$-DMSO) 13.00 (2H, br s), 10.50 (1H, br s), 8.68 (2H, s), 8.18 (1H, s), 7.97 (2H, d), 6.82 (2H, d), 2.99 (6H, s), 2.93 (2H, d) 1.97 (1H, m), 1.67–1.23 (12H, m). The acid was converted to the di(N-methyl-D-glucamine) salt and lyophilised from water/dioxan. Found: C, 52.04; H, 7.59; N, 8.39%; C$_{42}$H$_{66}$N$_6$O$_{15}$.4.3 H$_2$O requires: C, 51.85; H, 7.73; N, 8.64%.

EXAMPLE 32

5-[(5-Cycloheptylmethyl-2-pyridin-3-yl-1H-imidazole-4-carbonyl)-amino]-isophthalic Acid The title compound was prepared according to the procedure of Example 20, with the modification that 3-pyridinecarboxaldehyde was used in step b instead of 2-naphthaldehyde. $^1$H NMR (300 MHz, d$_6$-DMSO) 13.07 (3H, br s), 10.19 (1H, s), 9.33 (1H, s), 8.73 (2H, s), 8.59 (1H, d), 8.43 (1H, d), 8.19 (1H, s), 7.52 (1H, m), 2.97 (2H, d), 2.00 (1H, m) 1.82–1.21 (12H, m). The acid was converted to the di(N-methyl-D-glucamine) salt and lyophilised from water/dioxan. Found: C, 51.44; H, 7.17; N, 9.53%; C$_{39}$H$_{60}$N$_6$O$_{15}$.3.0 H$_2$O requires: C, 51.70; H, 7.33; N, 9.28%.

EXAMPLE 33

5-[(5-Cycloheptylmethyl-2-(1H-pyrrol-2-yl)-1H-imidazole-4-carbonyl)-amino]-isophthalic Acid The title compound was prepared according to the procedure of Example 20, with the modification that pyrrole-2-carboxaldehyde was used in step b instead of 2-naphthaldehyde. $^1$H NMR (300 MHz, d$_6$-DMSO) 13.22 (2H, br s), 12.42 (1H, s), 11.27 (1H, s), 9.91 (1H, s), 8.57 (2H, s), 8.16 (1H, s), 6.88 (1H, s), 6.62 (1H, s), 6.13 (1H, m), 2.90 (2H, d), 1.93 (1H, m), 1.67–1.22 (12H, m). The acid was converted to the di(N-methyl-D-glucamine) salt and lyophilised from water/dioxan. Found: C, 52.53; H, 7.47, N, 9.84%; C$_{38}$H$_{60}$N$_6$O$_{15}$.1.4 H$_2$O requires: C, 52.67; H, 7.31; N, 9.70%.

EXAMPLE 34

5-[(5-Cycloheptylmethyl-2-cyclohexyl-1H-imidazole-4-carbonyl)-amino]-isophthalic Acid The title compound was prepared according to the procedure of Example 20, with the modification that cyclohexanecarboxaldehyde was used in step b instead of 2-naphthaldehyde. $^1$H NMR (300 MHz, d$_6$-DMSO) 11.96 (1H, br s), 9.85 (1H, s), 8.61 (2H, s), 8.13 (1H, s), 2.82 (2H, d), 2.64 (1H, m), 1.95–1.17 (23H, m). The acid was converted to the di(N-methyl-D-glucamine) salt and lyophilised from water/dioxan. Found: C, 51.49; H, 7.85; N, 7.48%; C$_{40}$H$_{67}$N$_5$O$_{15}$.3.9 H$_2$O requires: C, 51.77; H, 8.12; N, 7.55%.

EXAMPLE 35

5-[(5-Cycloheptylmethyl-1H-imidazole-4-carbonyl)-amino]-isophthalic Acid

5-Cycloheptylmethyl-1H-imidazole-4-carboxylic acid ethyl ester was prepared according to the procedure of Example 20, steps a and b, with the modification that paraformaldehyde was used in step b instead of 2-naphthaldehyde. It was then converted to the title compound following the procedure of Example 20, steps c, d and e. $^1$H NMR (300 MHz, d$_6$-DMSO) 13.14 (2H, br s), 12.45 (1H, br s), 10.13 (1H, s), 8.64 (2H, s), 8.14 (1H, s), 7.68 (1H, s), 2.88 (2H, d), 1.88 (1H, m), 1.62–1.17 (12H, m). The acid was converted to the di(N-methyl-D-glucamine) salt and lyophilised from water/dioxan. Found: C, 50.06; H, 7.48; N, 8.78%; $C_{34}H_{57}N_5O_{15}$·2.1 $H_2O$ requires: C, 50.22; H, 7.58; N, 8.61%.

EXAMPLE 36

5-[(1-Benzyl-5-cycloheptylmethyl-1H-imidazole-4-carbonyl)-amino]-isophthalic Acid Step a. 1-Benzyl-5-cycloheptylmethyl-1H-imidazole-4-carboxylic Acid Ethyl Ester To a suspension of 5-cycloheptylmethyl-1H-imidazole-4-carboxylic acid ethyl ester (Example 35) (1.16 g, 4.63 mmol) in DMF (15 ml) was added sodium hydride (60% dispersion in oil) (200 mg, 5.10 mmol) in small portions. The resulting solution was stirred at room temperature for 1 h, then benzyl bromide (0.55 ml, 4.63 mmol) was added. The reaction mixture was stirred at room temperature for 2 h, the solvent was evaporated under reduced pressure and the residue was partitioned between saturated sodium hydrogen carbonate and ethyl acetate. The organic phase was washed with brine, dried ($MgSO_4$) and the solvent was evaporated. The residue was purified by flash column chromatography (silica, DCM/ethyl acetate 8:2). The major isomer (lower $R_f$) was isolated (855 mg, 54%). $^1H$ NMR (300 MHz, $CDCl_3$) 7.42 (1H, s), 7.34 (3H, m), 7.04 (2H, m), 5.09 (2H, s), 4.35 (2H, m), 2.81 (2H, d), 1.86–1.16 (16H, m).

Step b. 1-Benzyl-5-cycloheptylmethyl-1H-imidazole-4-carboxylic Acid

To a solution of the product of step a (1.13 g, 3.32 mmol) in ethanol (20 ml) was added the solution of sodium hydroxide (1.33 g, 33.2 mmol) in water (5 ml). The solution was heated under reflux for 16 h, allowed to cool to room temperature, and concentrated under reduced pressure. The aqueous solution was diluted with water (20 ml), then acidified (pH=5.0, 1M HCl). The precipitate was collected by filtration, washed with water and dried to afford the acid as a white solid (1.03 g, 99%). $^1H$ NMR (300 MHz, $d_6$-DMSO) 7.62 (1H, s), 7.28 (3H, m), 7.05 (2H, m), 5.17 (2H, s), 2.77 (2H, d), 1.50 (5H, m), 1.37 (4H, m), 1.12 (4H, m).

Step c. 5-[(1-Benzyl-5-cycloheptylmethyl-1H-imidazole-4-carbonyl)-amino]-isophthalic Acid Dimethyl Ester The product of step b above (310 mg, 1.00 mmol) was reacted with 5-amino-isophthalic acid dimethyl ester (210 mg, 1.00 mmol) using essentially the same procedure as in Example 20, step d. The crude product was purified by flash column chromatography (silica, DCM/ethyl acetate 92:8) to afford colourless foam (110 mg, 20%). $^1H$ NMR (300 MHz, $CDCl_3$) 9.36 (1H, s), 8.53 (2H, s), 8.40 (1H, s), 7.35 (4H, m), 7.08 (2H, m), 5.12 (2H, s), 3.94 (6H, s), 1.90–1.22 (13H, m).

Step d

To a solution of the product of step c above (110 mg, 0.22 mmol) in 1:1 THF/methanol (2 ml) was added the solution of lithium hydroxide monohydrate (30 mg, 0.66 mmol) in water (1 ml). The solution was stirred at room temperature for 16 h, concentrated under reduced pressure, diluted with water (1 ml) and acidified (pH=2.0, 1M HCl). The precipitate was collected by filtration, washed with water and dried to afford the title compound as a white solid (92 mg, 89%). $^1H$ NMR (300 MHz, $d_6$-DMSO) 13.00 (2H, br s), 10.23 (1H, s), 8.64 (2H, s), 8.15 (1H, s), 7.92 (1H, s), 7.32 (3H, m), 7.14 (2H, m), 5.28 (2H, s), 2.83 (2H, d), 1.51 (5H, m), 1.37 (4H, m), 1.14 (4H, m). The acid was converted to the di(N-methyl-D-glucamine) salt and lyophilised from water/dioxan. Found: C, 54.47; H, 7.63; N, 7.59%; $C_{41}H_{63}N_5O_{15}$·2.2 $H_2O$ requires: C, 54.35; H, 7.50; N, 7.73%.

EXAMPLE 37

5-[(5-Adamantan-1-ylmethyl-2-phenyl-1H-imidazole-4-carbonyl)-amino]-isophthalic Acid The title compound was prepared according to the procedure of Example 20, with the modification that adamantaneacetic acid was used instead of cycloheptaneacetic acid in step a, and benzaldehyde was used instead of 2-naphthaldehyde in step b. $^1H$ NMR (300 MHz, $d_6$-DMSO) 13.20 (2H, s), 12.55 (1H, s), 10.16 (1H, s), 8.71 (2H, s), 8.12 (3H, m), 7.45 (3H, m), 2.85 (2H, s), 1.91 (3H, s), 1.56 (12H, m). The acid was converted to the di(N-methyl-D-glucamine) salt and lyophilised from water/dioxan. Found: C, 57.80; H, 7.49; N, 7.55%; $C_{43}H_{63}N_5O_{15}$·0.4 $H_2O$ requires: C, 57.53; H, 7.17; N, 7.80%.

EXAMPLE 38

3-{[5-(2-Cycloheptyl-ethyl)-2-phenyl-1H-imidazole-4-carbonyl]-amino}-benzoic Acid 5-(2-Cycloheptyl-ethyl)-2-phenyl-1H-imidazole-4-carboxylic acid was prepared according to the procedure of Example 20, steps a, b and c, with the modification that cycloheptanepropionic acid was used in step a instead of cycloheptaneacetic acid, and 2-naphthaldehyde was replaced with benzaldehyde in step b. The acid was then converted to the title compound according to the procedure of Example 20, steps d and e, 3-amino-benzoic acid benzyl ester replacing 5-amino-isophthalic acid dibenzyl ester in step d. $^1H$ NMR (300 MHz, $d_6$-DMSO) 13.20 (1H, br s), 10.10 (1H, s), 8.50 (1H, s), 8.10 (2H, m), 8.00 (1H, m), 7.64 (1H, d), 7.45 (4H, m), 3.04 (2H, m), 1.72–1.21 (15H, m). The acid was converted to the N-methyl-D-glucamine salt and lyophilised from water/dioxan. Found: C, 58.92; H, 7.61; N, 8.48%; $C_{33}H_{46}N_4O_8$·2.5 $H_2O$ requires: C, 59.04; H, 7.65; N, 8.35%.

EXAMPLE 39

5-{[5-(2-Cycloheptyl-ethyl)-2-phenyl-1H-imidazole-4-carbonyl]-amino}-isophthalic Acid 5-(2-Cycloheptyl-ethyl)-2-phenyl-1H-imidazole-4-carboxylic acid was prepared according to the procedure of Example 20, steps a, b and c, with the modification that cycloheptanepropionic acid was used instead of cycloheptaneacetic acid in step a, and benzaldehyde replaced 2-naphthaldehyde was in step b. The acid was then converted to the title compound according to the procedure of Example 20, steps d and e. $^1H$ NMR (300 MHz, $d_6$-DMSO) 13.00 (3H, br s), 10.18 (1H, s), 8.70 (2H, s), 8.17 (1H, s), 8.09 (2H, m), 7.45 (3H, m), 3.03 (2H, m), 1.75–1.21(15H, m). The acid was converted to the di(N-methyl-D-glucamine) salt and lyophilised from water/dioxan. Found: C, 53.71; H, 7.61; N, 7.76%; $C_{41}H_{63}N_5O_{15}$·2.7 $H_2O$ requires: C, 53.81; H, 7.54; N, 7.65%.

EXAMPLE 40

3-{[5-(2-Cycloheptyl-ethyl)-2-(2-trifluoromethyl-phenyl)-1H-imidazole-4-carbonyl]-amino}-benzoic Acid 5-(2-Cycloheptyl-ethyl)-2-(2-trifluoromethyl-phenyl)-1H-imidazole-4-carboxylic acid was prepared according to the procedure of Example 20, steps a, b and c, with the modification that cycloheptanepropionic acid was used instead of cycloheptaneacetic acid in step a, and 2-naphthaldehyde was replaced with α,α,α-trifluoro-o-tolualdehyde in step b. The acid was then converted to the title compound according to the procedure of Example 20, steps d and e, 3-amino-benzoic acid benzyl ester replacing 5-amino-isophthalic acid dibenzyl ester in step d. $^1$H NMR (300 MHz, d$_6$-DMSO) 12.88 (1H, br s), 12.68 (1H, s), 9.74 (1H, s), 8.48 (1H, s), 7.90–7.60 (6H, m), 7.40 (1H, m), 3.03 (2H, m), 1.62–1.22 (15H, m). The acid was converted to the N-methyl-D-glucamine salt and lyophilised from water/dioxan. Found: C, 56.46; H, 6.67; N, 7.74%; $C_{34}H_{45}F_3N_4O_8$.1.5 H$_2$O requires: C, 56.51; H, 6.71; N, 7.75%.

EXAMPLE 41

5-{[5-(2-Cycloheptyl-ethyl)-2-(2-trifluoromethyl-phenyl)-1H-imidazole-4-carbonyl]-amino}-isophthalic Acid 5-(2-Cycloheptyl-ethyl)-2-(2-trifluoromethyl-phenyl)-1H-imidazole-4-carboxylic acid was prepared according to the procedure of Example 20, steps a, b and c, with the modification that cycloheptanepropionic acid was used instead of cycloheptaneacetic acid in step a, and 2-naphthaldehyde was replaced with α,α,α-trifluoro-o-tolualdehyde in step b. The acid was then converted to the title compound according to the procedure of Example 20, steps d and e. $^1$H NMR (300 MHz, d$_6$-DMSO) 13.16 (2H, br s), 12.68 (1H, s), 10.02 (1H, s), 8.61 (2H, s), 8.15 (1H, s), 7.90 (1H, d), 7.75 (3H, m), 3.03 (2H, t), 1.62–1.35 (15H, m). The acid was converted to the di(N-methyl-D-glucamine) salt and lyophilised from water/dioxan. Found: C, 52.44; H, 6.94; N, 7.19%; $C_{42}H_{62}F_3N_5O_{15}$.1.7 H$_2$O requires: C, 52.35; H, 6.83; N, 7.27%.

EXAMPLE 42

3-{[5-(2-Cycloheptyl-ethyl)-2-(3-methoxy-phenyl)-1H-imidazole-4-carbonyl]-amino}-benzoic Acid 5-(2-Cycloheptyl-ethyl)-2-(3-methoxy-phenyl)-1H-imidazole-4-carboxylic acid was prepared according to the procedure of Example 20, steps a, b and c, with the modification that cycloheptanepropionic acid was used instead of cycloheptaneacetic acid in step a, and 2-naphthaldehyde was replaced with m-anisaldehyde in step b. The acid was then converted to the title compound according to the procedure of Example 20, steps d and e, 3-amino-benzoic acid benzyl ester replacing 5-amino-isophthalic acid dibenzyl ester in step d. $^1$H NMR (300 MHz, d$_6$-DMSO) 12.91 (1H, s), 12.71 (1H, s), 9.86 (1H, s), 8.52 (1H, s), 8.02 (1H, d), 7.64 (3H, m), 7.42 (2H, m), 6.97 (1H, d), 3.85 (3H, s), 3.03 (2H, t), 1.78–1.21 (15H, m). The acid was converted to the N-methyl-D-glucamine salt and lyophilised from water/dioxan. Found: C, 60.63; H, 7.46; N, 8.26%; $C_{34}H_{48}N_4O_9$.0.9 H$_2$O requires: C, 60.63; H, 7.46; N, 8.31%.

EXAMPLE 43

3-{[5-(2-Cycloheptyl-ethyl)-2-(2-fluoro-phenyl)-1H-imidazole-4-carbonyl]-amino}-benzoic Acid 5-(2-Cycloheptyl-ethyl)-2-(2-fluoro-phenyl)-1H-imidazole-4-carboxylic acid was prepared according to the procedure of Example 20, steps a, b and c, with the modification that cycloheptanepropionic acid was used instead of cycloheptaneacetic acid in step a, and 2-naphthaldehyde was replaced with 2-fluoro-benzaldehyde in step b. The acid was then converted to the title compound according to the procedure of Example 20, steps d and e, 3-amino-benzoic acid benzyl ester replacing 5-amino-isophthalic acid dibenzyl ester in step d. $^1$H NMR (300 MHz, d$_6$-DMSO) 12.90 (1H, br s), 12.51 (1H, s), 9.87 (1H, s), 8.51 (1H, s), 8.13 (1H, m), 8.00 (1H, d), 7.63 (1H, d), 7.45 (4H, m), 3.04 (2H, t), 1.61–1.21 (15H, m). The acid was converted to the N-methyl-D-glucamine salt and lyophilised from water/dioxan. Found: C, 59.79; H, 7.13; N, 8.40%; $C_{33}H_{45}FN_4O_8$.1.0 H$_2$O requires: C, 59.74; H, 7.15; N, 8.45%.

EXAMPLE 44

5-{[5-(2-Adamantan-1-yl-ethyl)-2-naphthalene-2-yl-1H-imidazole-4-carbonyl]-amino}-isophthalic Acid 5-Adamantan-1-yl-2,3-dioxo-pentanoic acid ethyl ester monohydrate was prepared from 3-(adamantan-1-yl)-propionic acid (W. Oppolzer and R. Moretti, *Tetrahedron*, 1988, 44, 5541) according to the procedure of Example 20, step a. It was then reacted with 2-naphthaldehyde and the ethyl ester was hydrolized to produce 5-(2-adamantan-1-yl-ethyl)-2-naphthalen-2-yl-1H-imidazole-4-carboxylic acid according to the procedure of Example 20, step b and c. This was converted to the title compound using the procedure of Example 20, steps d and e. $^1$H NMR (300 MHz, d$_6$-DMSO) 8.72 (2H, s), 8.56 (1H, s), 8.30 (1H, d), 8.17 (1H, s), 8.02 (1H, d), 7.96 (2H, m), 7.56 (2H, m), 3.02 (2H, m), 1.98 (3H, br s), 1.68 (6H, m), 1.58 (6H, s), 1.45 (2H, m). The acid was converted to the di(N-methyl-D-glucamine) salt and lyophilised from water/dioxan. Found: C, 57.64; H, 7.62; N, 7.43%; $C_{48}H_{67}N_5O_{15}$.2.2 H$_2$O requires: C, 58.03; H, 7.24; N, 7.05%.

EXAMPLE 45

3-{[5-(2-Adamantan-1-yl-ethyl)-2-naphthalen-2-yl-1H-imidazole-4-carbonyl]-amino}-benzoic Acid 5-(2-Adamantan-1-yl-ethyl)-2-naphthalen-2-yl-1H-imidazole-4-carboxylic acid (Example 44) was reacted with 3-amino-benzoic acid benzyl ester according to the procedure of Example 20, step d. The benzyl ester was deprotected according to the procedure of Example 20, step e to afford the title compound. $^1$H NMR (300 MHz, d$_6$-DMSO) 12.91 (1H, br s), 9.90 (1H, br s), 8.54 (2H, d), 8.27 (1H, dd), 8.04–7.94 (4H, m), 7.65–7.44 (4H, m), 3.04 (2H, m), 1.98 (3H, br s), 1.66 (6H, m), 1.58 (6H, s), 1.45 (2H, m). The acid was converted to the N-methyl-D-glucamine salt and lyophilised from water/dioxan. Found: C, 63.85; H, 7.57; N, 7.80%; $C_{40}H_{50}N_4O_8$.1.9 H$_2$O requires: C, 64.12; H, 7.24; N, 7.48%.

EXAMPLE 46

5-{[5-(2-Adamantan-1-yl-ethyl)-2-phenyl-1H-imidazole-4-carbonyl]-amino}-isophthalic Acid 5-Adamantan-1-yl-2,3-dioxo-pentanoic acid ethyl ester monohydrate (Example 44) was reacted with benzaldehyde according to the procedure of Example 20, step b to produce 5-(2-adamantan-1-yl-ethyl)-2-phenyl-1H-imidazole-4-carboxylic acid ethyl ester. This was converted to the title compound following the procedure of Example 20, steps c, d and e. $^1$H NMR (300 MHz, d$_6$-DMSO) 12.74 (1H, s), 10.07 (1H, s), 8.67 (2H, s), 8.17 (1H, s), 8.08 (2H, d), 7.48 (2H, t), 7.39 (1H, t), 3.00 (2H, m), 1.96 (3H, br s), 1.66 (6H, m), 1.56 (6H, s), 1.45 (2H, m). The acid was converted to the di(N-methyl-D-glucamine) salt and lyophilised from water/dioxan. Found: C, 51.67; H, 7.29; N, 7.16%; C$_{44}$H$_{65}$N$_5$O$_{15}$.6.2 H$_2$O requires: C, 52.06; H, 7.68; N, 6.90%.

EXAMPLE 47

3-{[5-(2-Adamantan-1-yl-ethyl)-2-phenyl-1H-imidazole-4-carbonyl]-amino}-benzoic Acid 5-(2-Adamantan-1-yl-ethyl)-2-phenyl-1H-imidazole-4-carboxylic acid ethyl ester (Example 46) was converted to the title compound using essentially the same procedure as in Example 20, steps c, d and e, with the modification that 3-amino-benzoic acid benzyl ester replaced 5-amino-isophthalic acid dibenzyl ester in step d. $^1$H NMR (300 MHz, d$_6$-DMSO) 12.72 (1H, br s), 9.83 (1H, s), 8.50 (1H, s), 8.04 (3H, m), 7.63 (1H, d), 7.51–7.36 (4H, m), 2.99 (2H, m), 1.96 (3H, br s), 1.66 (6H, m), 1.55 (6H, s), 1.43 (2H, m). The acid was converted to the N-methyl-D-glucamine salt and lyophilised from water/dioxan. Found: C, 60.48; H, 7.84; N, 8.04%; C$_{36}$H$_{48}$N$_4$O$_8$.2.9 H$_2$O requires: C, 60.35; H, 7.56; N, 7.82%.

EXAMPLE 48

5-(2-Adamantan-1-yl-ethyl)-2-phenyl-1H-imidazole-4-carboxylic Acid (3-hydroxymethyl-phenyl)-amide 5-(2-Adamantan-1-yl-ethyl)-2-phenyl-1H-imidazole4-carboxylic acid ethyl ester (Example 46) was hydrolized according to the procedure of Example 20, step c. The acid was reacted with 3-methoxycarbonyloxymethyl-aniline using the procedure of Example 20, step d to produce 5-(2-adamantan-1-yl-ethyl)-2-phenyl-1H-imidazole-4-carboxylic acid (3-methoxycarbonyloxymethyl-phenyl)-amide, which was deprotected according to the procedure of Example 22, step b to afford the title compound as a white solid. $^1$H NMR (300 MHz, d$_6$-DMSO) 12.69 (1H, br s), 9.56 (1H, s), 8.08 (2H, d), 7.80 (1H, s), 7.65 (1H, d), 7.48 (2H, t), 7.39 (1H, t), 7.26 (1H, t), 7.00 (1H, d), 5.16 (1H, m), 4.49 (2H, d), 2.99 (2H, m), 1.96 (3H, br s), 1.67–1.55 (12H, m), 1.43 (2H, m). Found: C, 76.26; H, 7.38; N, 9.09%; C$_{29}$H$_{33}$N$_3$O$_2$ requires: C, 76.45; H, 7.30; N, 9.22%.

EXAMPLE 49

5-(2-Adamantan-1-yl-ethyl)-2-phenyl-1H-imidazole-4-carboxylic Acid [3-1H-tetrazol-5-yl)-phenyl]-amide 5-(2-Adamantan-1-yl-ethyl)-2-phenyl-1H-imidazole-4-carboxylic acid ethyl ester (Example 46) was hydrolized and then reacted with 3-(1-pivaloyloxymethyl-1H-tetrazol-5-yl)-phenylamine using the procedure of Example 20, steps c and d. Deprotection was performed following the procedure of Example 2, step b to afford the title compound as a white solid. $^1$H NMR (300 MHz, d$_6$-DMSO) 8.64 (1H, br s), 8.13 (2H, m), 7.98 (1H, d), 7.74 (1H, d), 7.52 (3H, m), 7.32 (1H, br s), 7.15 (1H, br s), 6.99 (1H, br s), 3.04 (2H, m), 1.96 (3H, br s), 1.72–1.43 (14H, m). The acid was converted to the N-methyl-D-glucamine salt and lyophilised from water/dioxan.

EXAMPLE 50

3-{[5-(2-Adamantan-1-yl-ethyl)-2-(2-fluoro-phenyl)-1H-imidazole-4-carbonyl]-amino}-benzoic Acid 5-Adamantan-1-yl-2,3-dioxo-pentanoic acid ethyl ester monohydrate (Example 44) was reacted with 2-fluorobenzaldehyde according to the procedure of Example 20, step b to produce 5-(2-adamantan-1-yl-ethyl)-2-(2-fluoro-phenyl)-1H-imidazole-4-carboxylic acid ethyl ester. The ester was hydrolyzed according to the procedure of Example 20, step c and the resulting 5-(2-adamantan-1-yl-ethyl)-2-(2-fluoro-phenyl)-1H-imidazole-4-carboxylic acid was reacted with 3-amino-benzoic acid benzyl ester using essentially the same procedure as in Example 20, step d. Deprotection was carried out according to the procedure of Example 20, step e to afford the title compound as a colourless foam.

$^1$H NMR (300 MHz, d$_6$-DMSO) 12.91 (1H, br s), 12.53 (1H, s), 9.86 (1H, s), 8.51 (1H, s), 8.12 (1H, t), 8.00 (1H, d), 7.63 (1H, d), 7.40 (4H, m), 3.01 (2H, m), 1.95 (3H, s), 1.71–1.39 (14H, m). The acid was converted to the N-methyl-D-glucamine salt and lyophilized from water/dioxan. Found: C, 61.15; H, 6.96; N, 7.80%; C$_{36}$H$_{47}$FN$_4$O$_8$.1.3 H$_2$O requires: C, 61.19; H, 7.08; N, 7.93%.

EXAMPLE 51

4-{[5-(2-Adamantan-1-yl-ethyl)-2-(2-fluoro-phenyl)-1H-imidazole-4-carbonyl]-amino}-benzoic Acid 5-(2-Adamantan-1-yl-ethyl)-2-(2-fluoro-phenyl)-1H-imidazole-4-carboxylic acid (Example 50) was reacted with 4-amino-benzoic acid methyl ester according to the procedure of Example 20, step d. Deprotection was carried out using essentially the same procedure as in Example 36, step d to afford the title compound as a white solid.

$^1$H NMR (300 MHz, d$_6$-DMSO) 12.58 (2H, br s), 9.92 (1H, s), 8.12 (1H, m), 7.94 (4H, m), 7.47 (1H, m), 7.35 (2H, m), 3.00 (2H, m), 1.96 (3H, s), 1.65 (6H, m), 1.55 (6H, s), 1.42 (2H, m). The acid was converted to the N-methyl-D-glucamine salt and lyophilised from water/dioxan. Found: C, 60.67; H, 6.95; N, 7.87%; C$_{36}$H$_{47}$FN$_4$O$_8$.1.6 H$_2$O requires C, 60.82; H, 7.11; N, 7.88%.

EXAMPLE 52

3-{[5-(2-Adamantan-1-yl-ethyl)-2-(2-fluoro-phenyl)-1H-imidazole-4-carbonyl]-amino}-propionic Acid Step a. 3-{[5-(2-Adamantan-1-yl-ethyl)-2-(2-fluoro-phenyl)-1H-imidazole-4-carbonyl]-amino}-propionic Acid Benzyl Ester To a solution of 5-(2-adamantan-1-yl-ethyl)-2-(2-fluoro-phenyl)-1H-imidazole-4-carboxylic acid (Example 50) (200 mg, 0.50 mmol) and β-alanine benzyl ester p-toluenesulfonate (175 mg, 0.50 mmol) in DCM (5 ml) was added N,N-diisopropylethylamine (0.26 ml, 1.50 mmol), 4-dimethylaminopyridine (cat.) and bromo-tris-pyrrolidino-phosphonium hexafluorophosphate (PyBrOP) (230 mg, 0.50 mmol). The solution was kept at room temperature for 16 h, diluted with DCM (10 ml), washed with 5% aqueous potassium hydrogen sulphate and with saturated sodium hydrogen carbonate. The organic phase was dried (MgSO$_4$) and the solvent was evaporated. The residue was purified by flash column chromatography (silica, DCM/ethyl acetate 9:1) to afford the product as colourless foam (153 mg, 58%). $^1$H NMR (300 MHz, CDCl$_3$) 9.72 (1H, br s), 8.23 (1H, m), 7.68 (1H, t), 7.37–7.15 (8H, m), 5.17 (2H, s), 3.73 (2H, m), 3.07 (2H, m), 2.72 (2H, m), 1.97 (3H, s), 1.73–1.41 (14H, m).

Step b

The product from the previous step was deprotected according to the procedure of Example 1, step e to afford the title compound as a colourless foam. $^1$H NMR (300 MHz, d$_6$-DMSO) 12.25 (1H, br s), 7.94–7.28 (5H, m), 3.40 (4H, m), 2.94 (2H, m), 1.94 (3H, s), 1.67 (6H, m), 1.39 (6H, s), 1.36 (2H, m). The acid was converted to the N-methyl-D-glucamine salt and lyophilised from water/dioxan. Found: C, 56.35; H, 7.85; N, 7.81%; C$_{32}$H$_{47}$FN$_4$O$_8$.2.8 H$_2$O requires: C, 56.03; H, 7.74; N, 8.17%.

EXAMPLE 53

2-{[5-(2-Adamantan-1-yl-ethyl)-2-(2-fluoro-phenyl)-1H-imidazole-4-carbonyl]-amino}-acetic Acid The title compound was prepared according to the procedure of Example 52, using glycine benzyl ester p-toluenesulfonate in step a instead of β-alanine benzyl ester p-toluenesulfonate. $^1$H NMR (300 MHz, d$_6$-DMSO) 12.60 (1H, br s), 12.42 (1H, s), 7.98 (2H, m), 7.45 (3H, m), 3.94 (2H, d), 2.98 (2H, m), 1.97 (3H, s), 1.69 (6H, m), 1.55 (6H, s), 1.39 (2H, m). The acid was converted to the N-methyl-D-glucamine salt and lyophilised from water/dioxan. Found: C, 56.42; H, 7.45; N, 8.65%; C$_{31}$H$_{45}$FN$_4$O$_8$.2.0 H$_2$O requires: C, 56.63; H, 7.52; N, 8.52%.

EXAMPLE 54

3-{[5-(2-Adamantan-1-yl-ethyl)-2-(4-fluoro-phenyl)-1H-imidazole-4-carbonyl]-amino}-benzoic Acid 5-Adamantan-1-yl-2,3-dioxo-pentanoic acid ethyl ester monohydrate (Example 44) was reacted with 4-fluorobenzaldehyde according to the procedure of Example 20, step b to produce 5-(2-adamantan-1-yl-ethyl)-2-(4-fluoro-phenyl)-1H-imidazole-4-carboxylic acid ethyl ester. This was converted to the title compound using the procedure of Example 20, steps c, d and e, with the modification that 3-amino-benzoic acid benzyl ester wags used in step d instead of 5-amino-isophthalic acid dibenzyl ester. $^1$H NMR (300 MHz, d$_6$-DMSO) 12.91 (1H, br s), 12.72 (1H, s), 9.85 (1H, s), 8.51 (1H, s), 8.11 (2H, m), 8.02 (1H, d), 7.63 (1H, d), 7.44 (1H, m), 7.34 (2H, m), 2.98 (2H, m), 1.96 (3H, s), 1.68 (6H, m), 1.56 (6H, s), 1.43 (2H, m). The acid was converted to the N-methyl-D-glucamine salt and lyophilised from water/dioxan. Found: C, 60.27; H, 6.98; N, 7.98%; C$_{36}$H$_{47}$FN$_4$O$_8$.1.8 H$_2$O requires: C, 60.43; H, 7.13; N, 7.83%.

EXAMPLE 55

3-{[5-(2-Adamantan-1-yl-ethyl)-2-(3-fluoro-phenyl)-1H-imidazole-4-carbonyl]-amino}-benzoic Acid 5-Adamantan-1-yl-2,3-dioxo-pentanoic acid ethyl ester monohydrate (Example 44) was reacted with 3-fluorobenzaldehyde according to the procedure of Example 20, step b to produce 5-(2-adamantan-1-yl-ethyl)-2-(3-fluoro-phenyl)-1H-imidazole-4-carboxylic acid ethyl ester. This was converted to the title compound using the procedure of Example 20, steps c, d and e, with the modification that 3-amino-benzoic acid benzyl ester was used in step d instead of 5-amino-isophthalic acid dibenzyl ester. $^1$H NMR (300 MHz, d$_6$-DMSO) 12.83 (2H, br s), 9.88 (1H, s), 8.51 (1H, s), 8.03 (1H, d), 7.90 (2H, m), 7.64 (1H, d), 7.55 (2H, m), 7.23 (1H, t), 3.02 (2H, m), 1.96 (3H, s) 1.67–1.45 (14H, m). The acid was converted to the N-methyl-D-glucamine salt and lyophilised from water/dioxan. Found: C, 61.16; H, 7.11; N, 8.05%; C$_{36}$H$_{47}$FN$_4$O$_8$.1.3 H$_2$O requires: C, 61.27; H, 7.08; N, 7.94%.

EXAMPLE 56

3-{[5-(2-Adamantan-1-yl-ethyl)-2-(2-trifluoromethyl-phenyl)-1H-imidazole-4-carbonyl]-amino}-benzoic Acid 5-Adamantan-1-yl-2,3-dioxo-pentanoic acid ethyl ester monohydrate (Example 44) was reacted with α,α,α,-trifluoro-o-tolualdehyde according to the procedure of Example 20, step b to produce 5-(2-adamantan-1-yl-ethyl)-2-(2-trifluoromethyl-phenyl)-1H-imidazole-4-carboxylic acid ethyl ester. This was converted to the title compound using the procedure of Example 20, steps c, d and e, with the modification that 3-amino-benzoic acid benzyl ester was used in step d instead of 5-amino-isophthalic acid dibenzyl ester. $^1$H NMR (300 MHz, d$_6$-DMSO) 13.00 (1H, br s), 12.71 (1H, s), 9.72 (1H, s), 8.48 (1H, s), 7.89 (2H, m), 7.75 (3H, m), 7.62 (1H, d), 7.41 (1H, t), 2.98 (2H, m), 1.95 (3H, s), 1.64 (6H, m), 1.53 (6H, s), 1.41 (2H, m). The acid was converted to the N-methyl-D-glucamine salt and lyophilised from water/dioxan. Found: C, 57.65; H, 6.58; N, 7.19%; C$_{37}$H$_{47}$F$_3$N$_4$O$_8$.2.0 H$_2$O requires: C, 57.76; H, 6.69; N, 7.28%.

EXAMPLE 57

3-{[5-(2-Adamantan-1-yl-ethyl)-2-o-tolyl-1H-imidazole-4-carbonyl]-amino}-benzoic Acid 5-Adamantan-1-yl-2,3-dioxo-pentanoic acid ethyl ester monohydrate (Example 44) was reacted with o-tolualdehyde according to the procedure of Example 20, step b to produce 5-(2-adamantan-1-yl-ethyl)-2-o-tolyl-1H-imidazole-4-carboxylic acid ethyl ester. This was converted to the title compound using the procedure of Example 20, steps c, d and e with the modification that 3-amino-benzoic acid benzyl ester was used in step d instead of 5-amino-isophthalic acid dibenzyl ester. $^1$H NMR (300 MHz, d$_6$-DMSO) 12.70 (1H, br s), 12.55 (1H, br s), 9.76 (1H, s), 8.49 (1H, s), 7.95 (1H, d), 7.61 (2H, m), 7.43 (1H, d), 7.30 (3H, m), 2.98 (2H, m), 2.55 (3H, s), 1.95 (3H, s), 1.71–1.41 (14H, m). The acid was converted to the N-methyl-D-glucamine salt and lyophilised from water/dioxan. Found: C, 61.98; H, 7.63; N, 7.82%; C$_{37}$H$_{50}$N$_4$O$_8$.2.1 H$_2$O requires: C, 61.98; H, 7.63; N, 7.81%.

EXAMPLE 58

3-{[5-(2-Adamantan-1-yl-ethyl)-2-(2-methoxy-phenyl)-1H-imidazole-4-carbonyl]-amino}-benzoic Acid 5-Adamantan-1-yl-2,3-dioxo-pentanoic acid ethyl ester monohydrate (Example 44) was reacted with o-anisaldehyde according to the procedure of Example 20, step b to produce 5-(2-adamantan-1-yl-ethyl)-2-(2-methoxy-phenyl)-1H-imidazole-4-carboxylic acid ethyl ester. This was converted to the title compound using the procedure of Example 20, steps c, d and e with the modification that 3-amino-benzoic acid benzyl ester was used in step d instead of 5-amino-isophthalic acid dibenzyl ester. $^1$H NMR (300 MHz, d$_6$-DMSO) 13.00 (1H, br s), 11.93 (1H, s), 9.86 (1H, s), 8.51 (1H, s), 8.17 (1H, d), 8.02 (1H, d), 7.62 (1H, d), 7.42 (2H, m), 7.16 (1H, d), 7.06 (1H, t), 3.94 (3H, s), 3.02 (2H, m),

EXAMPLE 59

3-{[5-(2-Adamantan-1-yl-ethyl)-2-(2-bromo-phenyl)-1H-imidazole-4-carbonyl]-amino}-benzoic Acid 5-Adamantan-1-yl-2,3-dioxo-pentanoic acid ethyl ester monohydrate (Example 44) was reacted with 2-bromobenzaldehyde according to the procedure of Example 20, step b to produce 5-(2-adamantan-1-yl-ethyl)-2-(2-bromo-phenyl)-1H-imidazole-4-carboxylic acid ethyl ester. This was converted to the title compound using the procedure of Example 20, steps c, d and e with the modification that 3-amino-benzoic acid benzyl ester was used in step d instead of 5-amino-isophthalic acid dibenzyl ester. $^1$H NMR (300 MHz, $d_6$-DMSO) 10.23 (1H, s), 8.42 (1H, s), 8.11 (2H, m), 8.01 (1H, d), 7.70–7.46 (6H, m), 3.00 (2H, m), 1.95 (3H, s), 1.70–1.43 (14H, m). The acid was converted to the N-methyl-D-glucamine salt and lyophilised from water/dioxan. Found: C, 57.86; H, 6.58; N, 7.30%; $C_{36}H_{47}BrN_4O_8$ requires: C, 58.14; H, 6.37; N, 7.53%.

EXAMPLE 60

3-{[5-(2-Adamantan-1-yl-ethyl)-2-(2, 4-difluoro-phenyl)-1H-imidazole-4-carbonyl]-amino}-benzoic Acid 5-Adamantan-1-yl-2,3-dioxo-pentanoic acid ethyl ester monohydrate (Example 44) was reacted with 2,4-difluorobenzaldehyde according to the procedure of Example 20, step b to produce 5-(2-adamantan-1-yl-ethyl)-2-(2,4-difluoro-phenyl)-1H-imidazole-4-carboxylic acid ethyl ester. This was converted to the title compound using the procedure of Example 20, steps c, d and e with the modification that 3-amino-benzoic acid benzyl ester was used in step d instead of 5-amino-isophthalic acid dibenzyl ester. $^1$H NMR (300 MHz, $d_6$-DMSO) 12.55 (1H, s), 9.85 (1H, s), 8.48 (1H, s), 8.13 (1H, m), 7.97 (1H, m), 7.62 (1H, m), 7.44 (2H, m), 7.25 (1H, m), 2.98 (2H, m), 1.95 (3H, s) 1.67 (6H, m), 1.54 (6H, s), 1.39 (2H, m). The acid was converted to the N-methyl-D-glucamine salt and lyophilised from water/dioxan. Found: C, 60.09; H, 6.77; N, 7.62%; $C_{36}H_{46}F_2N_4O_8 \cdot 1.1\ H_2O$ requires: C, 59.96; H, 6.74; N, 7.77%.

EXAMPLE 61

3-{[5-(2-Adamantan-1-yl-ethyl)-2-(2, 6-difluoro-phenyl)-1H-imidazole-4-carbonyl]-amino}-benzoic Acid 5-Adamantan-1-yl-2,3-dioxo-pentanoic acid ethyl ester monohydrate (Example 44) was reacted with 2,6-difluorobenzaldehyde according to the procedure of Example 20, step b to produce 5-(2-adamantan-1-yl-ethyl)-2-(2,6-difluoro-phenyl)-1H-imidazole-4-carboxylic acid ethyl ester. This was converted to the title compound using the procedure of Example 20, steps c, d and e with the modification that 3-amino-benzoic acid benzyl ester was used in step d instead of 5-amino-isophthalic acid dibenzyl ester. $^1$H NMR (300 MHz, $d_6$-DMSO) 12.85 (2H, s), 9.83 (1H, s), 8.52 (1H, s), 7.92 (1H, d), 7.60 (2H, m), 7.37 (1H, t), 7.25 (2H, m), 3.00 (2H, m), 1.95 (3H, s), 1.66 (6H, m), 1.53 (6H, s), 1.42 (2H, m). The acid was converted to the N-methyl-D-glucamine salt and lyophilised from water/dioxan. Found: C, 58.66; H, 6.94; N, 7.67%; $C_{36}H_{46}F_2N_4O_8 \cdot 2.0\ H_2O$ requires: C, 58.68; H, 6.84; N, 7.60%.

EXAMPLE 62

3-{[5-(2-Adamantan-1-yl-ethyl)-2-(3-hydroxy-phenyl)-1H-imidazole-4-carbonyl]-amino}-benzoic Acid 5-Adamantan-1-yl-2,3-dioxo-pentanoic acid ethyl ester monohydrate (Example 44) was reacted with 3-hydroxybenzaldehyde according to the procedure of Example 20, step b to produce 5-(2-adamantan-1-yl-ethyl)-2-(3-hydroxy-phenyl)-1H-imidazole-4-carboxylic acid ethyl ester. This was converted to the title compound using the procedure of Example 20, steps c, d and e with the modification that 3-amino-benzoic acid benzyl ester was used in step d instead of 5-amino-isophthalic acid dibenzyl ester, $^1$H NMR (300 MHz, $d_6$-DMSO) 12.75 (1H, br s), 9.86 (1H, s), 9.59 (1H, s), 8.48 (1H, s), 7.99 (1H, d), 7.63 (1H, d), 7.44 (3H, m), 7.27 (1H, t), 6.81 (1H, d), 2.97 (2H, m), 1.95 (3H, br s), 1.67 (6H, m), 1.54 (6H, s), 1.42 (2H, m). The acid was converted to the N-methyl-D-glucamine salt and lyophilised from water/dioxan. Found: C, 56.40; H, 7.42; N, 7.31%; $C_{36}H_{48}N_4O_9 \cdot 4.7\ H_2O$ requires: C, 56.53; H, 7.56; N, 7.32%.

EXAMPLE 63

3-{[5-(2-Adamantan-1-yl-ethyl)-2(4-hydroxy-phenyl)-1H-imidazole-4-carbonyl]-amino}-benzoic Acid 5-Adamantan-1-yl-2,3-dioxo-pentanoic acid ethyl ester monohydrate (Example 44) was reacted with 4-hydroxybenzaldehyde according to the procedure of Example 20, step b to produce 5-(2-adamantan-1-yl-ethyl)-2-(4-hydroxy-phenyl)-1H-imidazole-4-carboxylic acid ethyl ester. This was converted to the title compound using the procedure of Example 20, steps c, d and e with the modification that 3-amino-benzoic acid benzyl ester was used in step d instead of 5-amino-isophthalic acid dibenzyl ester. $^1$H NMR (300 MHz, $d_6$-DMSO) 12.95 (1H, br s), 12.55 (1H, br s), 9.83 (1H, s), 9.76 (1H, s), 8.48 (H, s), 7.98 (1H, t), 7.88 (2H, d), 7.60 (1H, d), 7.43 (1H, t), 6.86 (2H, d), 2.95 (2H, m), 1.95 (3H, br s), 1.64 (6H, m), 1.55 (6H, s), 1.42 (2H, m). The acid was converted to the N-methyl-D-glucamine salt and lyophilised from water/dioxan. Found: C, 59.98; H, 7.55; N, 7.92%; $C_{36}H_{48}N_4O_8 \cdot 2.3\ H_2O$ requires: C, 59.88, H, 7.34; N 7.76%

EXAMPLE 64

3-{[5-(2-Adamantan-1-yl-ethyl)-2-(2-hydroxy-phenyl)-1H-imidazole-4-carbonyl]-amino}-benzoic Acid 5-Adamantan-1-yl-2,3-dioxo-pentanoic acid ethyl ester monohydrate (Example 44) was reacted with 2-hydroxybenzaldehyde according to the procedure of Example 20, step b to produce 5-(2-adamantan-1-yl-ethyl)-2-(2-hydroxy-phenyl)-1H-imidazole-4-carboxylic acid ethyl ester. This was converted to the title compound using the procedure of Example 20, steps c, d and e with the modification that 3-amino-benzoic acid benzyl ester was used in step d instead of 5-amino-isophthalic acid dibenzyl ester. $^1$H NMR (300 MHz, $d_6$-DMSO) 13.00 (1H, br s), 11.50 (1H, br s), 10.15 (1H, s), 8.40 (1H, s), 8.02 (1H, d), 7.91 (1H, d), 7.64 (1H, d), 7.42 (1H, m), 7.27 (1H, m), 6.95 (2H, m), 3.02 (2H, m), 1.95 (3H, s), 1.64 (6H, m), 1.55 (6H, s), 1.43 (2H, m). converted to the N-methyl-D-glucamine salt and lyophilised from water/dioxan. Found: C, 59.89; H, 7.22; N, 7.66%; $C_{36}H_{48}N_4O_9 \cdot 2.2\ H_2O$ requires: C, 60.00; H, 7.33; N, 7.78%.

EXAMPLE 65

3-{[5-(2-Adamantan-1-yl-ethyl)-2-(2, 6-dimethyl-phenyl)-1H-imidazole-4-carbonyl]-amino}-benzoic Acid 5-Adamantan-1-yl-2,3-dioxo-pentanoic acid ethyl ester monohydrate (Example 44) was reacted with 2,6-dimethylbenzaldehyde (L. Xiang, H. Wu and V. Hruby, *Tetrahedron: Asymmetry*, 1995, 6, 83) according to the procedure of Example 20, step b to produce 5-(2-adamantan-1-yl-ethyl)-2-(2,6-dimethyl-phenyl)-1H-imidazole-4-carboxylic acid ethyl ester. This was converted to the title compound using the procedure of Example 20, steps c, d and e with the modification that 3-amino-benzoic acid benzyl ester was used in step d instead of 5-amino-isophthalic acid dibenzyl ester. $^1$H NMR (300 MHz, $d_6$-DMSO) 12.43 (1H, s), 9.82 (1H, s), 8.53 (1H, s), 7.92 (1H, d), 7.60 (1H, d), 7.38 (1H, m), 7.26 (1H, m), 7.14 (2H, d), 3.00 (2H, m), 2.11 (6H, s), 1.95 (3H, s), 1.65 (6H, m), 1.51 (6H, s), 1.43 (2H, m). The acid was converted to the N-methyl-D-glucamine salt and lyophilised from water/dioxan. Found: C, 61.03; H, 7.71; N, 7.40%; $C_{38}H_{52}N_4O_8 \cdot 3.0\ H_2O$ requires: C, 61.14; H, 7.83; N, 7.51%.

EXAMPLE 66

3-{[5-(2-Adamantan-1-yl-ethyl)-2-(2, 5-dimethyl-phenyl)-1H-imidazole-4-carbonyl]-amino}-benzoic Acid 5-Adamantan-1-yl-2,3-dioxo-pentanoic acid ethyl ester monohydrate (Example 44) was reacted with 2,5-dimethylbenzaldehyde according to the procedure of Example 20, step b to produce 5-(2-adamantan-1-yl-ethyl)-2-(2,5-dimethyl-phenyl)-1H-imidazole-4-carboxylic acid ethyl ester. This was converted to the title compound using the procedure of Example 20, steps c, d and e with the modification that 3-amino-benzoic acid benzyl ester was used in step d instead of 5-amino-isophthalic acid dibenzyl ester. $^1$H NMR (300 MHz, $d_6$-DMSO) 12.48 (1H, br s), 9.72 (1H, s), 8.47 (1H, s), 7.94 (1H, d), 7.62 (1H, d), 7.42 (2H, m), 7.20 (2H, m), 2.99 (2H, m), 2.50 (3H, s), 2.32 (3H, s), 1.95 (3H, br s), 1.64 (6H, m), 1.54 (6H, s), 1.42 (2H, m). The acid was converted to the N-methyl-D-glucamine salt and lyophilised from water/dioxan. Found: C, 61.03; H, 7.92; N, 7.47%; $C_{38}H_{52}N_4O_8 \cdot 3.0\ H_2O$ requires: C, 61.05; H, 7.83; N, 7.49%.

EXAMPLE 67

3-{[5-(2-Adamantan-1-yl-ethyl)-2-(2, 4-dimethyl-phenyl)-1H-imidazole-4-carbonyl]-amino}-benzoic Acid 5-Adamantan-1-yl-2,3-dioxo-pentanoic acid ethyl ester monohydrate (Example 44) was reacted with 2,4-dimethylbenzaldehyde according to the procedure of Example 20, step b to produce 5-(2-adamantan-1-yl-ethyl)-2-(2,4-dimethyl-phenyl)-1H-imidazole-4-carboxylic acid ethyl ester. This was converted to the title compound using the procedure of Example 20, steps c, d and e with the modification that 3-amino-benzoic acid benzyl ester was used in step d instead of 5-amino-isophthalic acid dibenzyl ester. $^1$H NMR (300 Hz, $d_6$-DMSO) 13.00 (1H, br s), 12.43 (1H, s), 9.71 (1H, s), 8.47 (1H, s), 7.94 (1H, d), 7.62 (1H, d), 7.44 (2H, m), 7.12 (2H, m), 2.97 (2H, m), 2.52 (3H, s), 2.31 (3H, s), 1.95 (3H, br s), 1.66 (6H, m), 1.54 (6H, s), 1.42 (2H, m). The acid was converted to the N-methyl-D-glucamine salt and lyophilised from water/dioxan. Found: C, 61.40; H, 7.88, N, 7.65%; $C_{38}H_{52}N_4O_8 \cdot 2.7\ H_2O$ requires: C, 61.51; H, 7.81; N, 7.55%.

EXAMPLE 68

3-{[5-(2-Adamantan-1-yl-ethyl)-2-(3,4-dichloro-phenyl)-1H-imidazole-4-carbonyl]-amino}-benzoic Acid 5-Adamantan-1-yl-2,3-dioxo-pentanoic acid ethyl ester monohydrate (Example 44) was reacted with 3,4-dichlorobenzaldehyde according to the procedure of Example 20, step b to produce 5-(2-adamantan-1-yl-ethyl)-2-(3,4-dichloro-phenyl)-1H-imidazole-4-carboxylic acid ethyl ester. The ester was hydrolyzed according to the procedure of Example 20, step c and the resulting 5-(2-adamantan-1-yl-ethyl)-2-(3,4-dichloro-phenyl)-1-H-imidazole-4-carboxylic acid was reacted with 3-amino-benzoic acid methyl ester using essentially the same procedure as in Example 52, step a. Deprotection was carried out following essentially the procedure of Example 36, step d to afford the title compound. $^1$H NMR (300 MHz, $d_6$-DMSO) 12.89 (2H, br s), 9.90 (1H, s), 8.50 (1H, s), 8.32 (1H, s), 8.03 (2H, m), 7.76 (1H, d), 7.63 (1H, d), 7.43 (1H, t), 2.98 (2H, m), 1.97 (3H, s), 1.70–1.39 (14H, m). The acid was converted to the N-methyl-D-glucamine salt and lyophilised from water/dioxan. Found: C, 56.90; H, 6.44; N, 7.08%; $C_{36}H_{46}Cl_2N_4O_8 \cdot 1.6\ H_2O$ requires: C, 56.72; H, 6.50; N, 7.35%.

EXAMPLE 69

3-{[5-(2-Adamantan-1-yl-ethyl)-2-(2, 3-dichloro-phenyl)-1H-imidazole-4-carbonyl]-amino}-benzoic Acid The title compound was prepared according to the procedure of Example 68, using 2,3-dichlorobenzaldehyde instead of 3,4-dichlorobenzaldehyde. $^1$H NMR (300 MHz, $d_6$-DMSO) 12.80 (1H, br s), 12.76 (1H, s), 9.85 (1H, s), 8.51 (1H, s), 7.93 (1H, m), 7.74 (2H, m), 7.62 (1H, d), 7.46 (2H, m), 3.00 (2H, m), 1.95 (3H, s), 1.66–1.40 (14H, m). The acid was converted to the N-methyl-D-glucamine salt and lyophilised from water/dioxan. Found: C, 56.14; H, 6.56; N, 7.26%; $C_{36}H_{46}Cl_2N_4O_8 \cdot 2.0\ H_2O$ requires: C, 56.15; H, 6.55; N, 7.28%.

EXAMPLE 70

3-{[5-(2-Adamantan-1-yl-ethyl)-2-(2-dimethylamino-phenyl)-1H-imidazole-4-carbonyl]-amino}-benzoic Acid Step a. 5-(2-Adamantan-1-yl-ethyl)-2-(2-dimethylamino-phenyl)-1H-imidazole-4-carboxylic Acid Benzyl Ester 5-Adamantan-1-yl-2,3-dioxo-pentanoic acid benzyl ester monohydrate (1.10 g, 3.00 mmol) (prepared from 3-(adamantan-1-yl)-propionic acid (W. Oppolzer and R.

Moretti, *Tetrahedron*, 1988, 44, 5541) according to the procedure of Example 20, step a) was reacted with 2-dimethylamino-benzaldehyde (900 mg, 6.00 mmol) using essentially the procedure of Example 20, step b. The crude product was purified by flash column chromatography (silica, DCM/ethyl acetate 98:2) to afford the benzyl ester as a pale yellow oil (690 mg, 48%). $^1$H NMR (300 MHz, CDCl$_3$) 12.25 and 12.10 (1H, 2×br s), 8.30 (1H, m), 7.35 (8H, m), 5.40 and 5.34 (2H, 2×s), 3.05 and 2.88 (2H, 2×m), 2.72 (6H, s), 1.93 (3H, br s), 1.65 (6H, m), 1.49 (8H, m).

Step b. 5-(2-Adamantan-1-yl-ethyl)-2-(2-dimethylamino-phenyl)-1H-imidazole-4-carboxylic Acid The product of step a (690 mg, 1.43 mmol) was deprotected using the same procedure as in Example 1, step e to afford the acid as a pale yellow solid (533 mg, 95%). $^1$H NMR (300 MHz, CDCl$_3$) 8.29 (1 H, d), 7.31 (3H, m), 3.02 (2H, m), 2.75 (6H, s), 1.98 (3H, br s), 1.69 (6H, m), 1.59 (6H, s), 1.48 (2H, m).

Step c. 3-{[5-(2-Adamantan-1-yl-ethyl)-2-(2-dimethylamino-phenyl)-1H-imidazole-4-carbonyl]-amino}-benzoic Acid Benzyl Ester The product of step b (310 mg, 0.80 mmol) was reacted with 3-amino-benzoic acid benzyl ester (220 mg, 0.95 mmol) according to the procedure given in Example 20, step d to afford a colourless foam after purification by flash column chromatography (silica, DCM/hexane/ethyl acetate 9:9:2) (278 mg, 58%). $^1$H NMR (300 MHz, CDCl$_3$) 12.10 (1H, br s), 9.33 (1H, s), 8.29 (2H, m), 8.17 (1H, s), 7.80 (1H, d), 7.49–7.26 (9H, m), 5.39 (2H, s), 3.14 (2H, m), 2.76 (6H, s), 2.00 (3H, br s), 1.76–1.60 (12H, m), 1.48 (2H, m).

Step d

The product of step c (278 mg, 0.46 mmol) was deprotected using the same procedure as in Example 1, step e to afford the title compound as a white solid (224 mg, 95%). $^1$H NMR (300 MHz, d$_6$-DMSO) 13.00 (1H, br s), 10.00 (1H, br s), 8.47 (1H, s), 7.97 (2H, m), 7.64 (1H, d), 7.44 (3H, m), 7.25 (1H, m), 3.02 (2H, m), 2.76 (6H, br s), 1.94 (3H, s), 1.65 (6H, m), 1.54 (6H, s), 1.42 (2H, m). The acid was converted to the N-D-glucamine salt and lyophilised from water/dioxan. Found: C, 59.99; H, 7.65; N, 8.81%; C$_{38}$H$_{53}$N$_5$O$_8$.3.2 H$_2$O requires: C, 59.69; H, 7.82; N, 9.16%.

EXAMPLE 71

3-{[5-(2-Adamantan-1-yl-ethyl)-2-(3-dimethylamino-phenyl)-1H-imidazole-4-carbonyl]-amino}-benzoic Acid The title compound was prepared using essentially the same procedure as in Example 70, with the modification that 3-dimethylamino-benzaldehyde was used in step a instead of 2-dimethylamino-benzaldehyde. $^1$H NMR (300 MHz, d$_6$-DMSO) 12.59 (1H, br s), 9.81 (1H, s), 8.49 (1H, s), 7.99 (1H, d), 7.62 (1H, d), 7.38 (3H, m), 7.25 (1H, t), 6.73 (1H, m), 2.97 (8H, m), 1.95 (3H, br s), 1.65 (6H, m), 1.55 (6H, s), 1.42 (2H, m). The acid was converted to the N-methyl-D-glucamine salt and lyophilised from water/dioxan. Found: C, 61.02; H, 8.00; N, 9.22%; C$_{38}$H$_{53}$N$_5$O$_8$.2.3 H$_2$O requires: C, 60.88; H, 7.75; N, 9.34%.

EXAMPLE 72

3-{[5-(2-Adamantan-1-yl-ethyl)-2-(4-dimethylamino-phenyl)-1H-imidazole-4-carbonyl]-amino}-benzoic Acid The title compound was prepared using essentially the same procedure as in Example 70, with the modification that 4-dimethylamino-benzaldehyde was used in step a instead of 2-dimethylamino-benzaldehyde. $^1$H NMR (300 MHz, d$_6$-DMSO) 13.00 (1H, br s), 12.50 (1H, br s), 9.92 (1H, br s), 8.55 (1H, s), 8.04 (1H, d), 7.94 (2H, d), 7.67 (1H, d), 7.48 (1H, t), 6.84 (2H, d), 3.01 (8H, m), 2.00 (3H, br s), 1.70 (6H, m), 1.59 (6H, s), 1.46 (2H, m). The acid was converted to the N-methyl-D-glucamine salt and lyophilised from water/dioxan. Found: C, 59.89; H, 8.07; N, 8.94%; C$_{38}$H$_{53}$N$_5$O$_8$.3.1 H$_2$O requires: C, 59.82; H, 7.81; N, 9.18%.

EXAMPLE 73

3-{[5-(2-Adamantan-1-yl-ethyl)-1-methyl-2-o-tolyl-1H-imidazole-4-carbonyl]-amino}-benzoic Acid Step a. 5-(2-Adamantan-1-yl-ethyl)-1-methyl-2-o-tolyl-1H-imidazole-4-carboxylic Acid Ethyl Ester and 5-(2-adamantan-1-yl-ethyl)-3-methyl-2-o-tolyl-3H-imidazole-4-carboxylic Acid Ethyl Ester To a solution of 5-(2-adamantan-1-yl-ethyl)-2-o-tolyl-1H-imidazole-4-carboxylic acid ethyl ester (Example 57) (784 mg, 2.00 mmol) in DMF (7.5 ml) was added sodium hydride (60% dispersion in oil) (100 mg, 2.50 mmol) in small portions at 0° C. The mixture was stirred at room temperature for 30 min, iodomethane (140 µl, 2.20 mmol) was added and the stirring was continued for 2 h. The reaction mixture was partitioned between diethyl ether and 1M sodium hydroxide, the organic phase was washed with water, dried and the solvent was evaporated. The products were separated by flash column chromatography (silica, DCM/ethyl acetate 9:1, then 1:1). The high R$_f$ product (257 mg, 32%) was identified as 5-(2-adamantan-1-yl-ethyl)-3-methyl-2-o-tolyl-3H-imidazole-4-carboxylic acid ethyl ester, whilst the low R$_f$ material (397 mg, 49%) was the isomeric 5-(2-adamantan-1-yl-ethyl)-1-methyl-2-o-tolyl-1H-imidazole-4-carboxylic acid ethyl ester. $^1$H NMR (300 MHz, CDCl$_3$) of the high R$_f$ material 7.34–7.24 (4H, m), 4.36 (2H, q), 3.62 (3H, s), 2.89 (2H, m), 2.17 (3H, s), 1.96 (3H, s), 1.74–1.57 (12H, m), 1.48 (2H, m), 1.42 (3H, t). $^1$H NMR (300 MHz, CDCl$_3$) of the low R$_f$ material 7.33–7.22 (4H, m), 4.36 (2H, q), 3.31 (3H, s), 2.98 (2H, m), 2.15 (3H, s), 1.99 (3H, s), 1.75–1.60 (12H. m), 1.34 (5H, m).

Step b. 5-(2-Adamantan-1-yl-ethyl)-1-methyl-2-o-tolyl-1H-imidazole-4-carboxylic Acid To a solution of 5-(2-adamantan-1-yl-ethyl)-1-methyl-2-o-tolyl-1H-imidazole-4-carboxylic acid ethyl ester (397 mg, 0.98 mmol) in ethanol (30 ml) was added 2.0M potassium hydroxide solution (3.4 ml). The solution was heated at reflux for 16 h, cooled to 50° C. and acidified (1M hydrochloric acid, pH=3–4). The ethanol was evaporated, the residue was diluted with water (30 ml) and the product was extracted with DCM. The organic layer was dried (MgSO$_4$) and the solvent was evaporated to afford the product as a white solid (351 mg, 95%). $^1$H NMR (300MHz, CDCl$_3$) 7.41–7.27 (4H, m), 6.00 (1H, br s), 3.38 (3H, s), 3.01 (2H, m), 2.20 (3H, s), 2.01 (3H, s), 1.70 (6H, m), 1.61 (6H, s), 1.37 (2H, m).

Step c. 3-{[5-(2-Adamantan-1-yl-ethyl)-1-methyl-2-o-tolyl-1H-imidazole-4-carbonyl]-amino}-benzoic Acid Benzyl Ester The product of step b above (351 mg, 0.93 mmol) was reacted with 3-amino-benzoic acid benzyl ester (211 mg, 0.93 mmol) using essentially the same procedure as in Example 70, step c to afford the benzyl ester as a white solid (388 mg, 71%). ¹H NMR (300 MHz, CDCl₃) 9.19 (1H, s), 8.15 (1H, d), 8.13 (1H, s), 7.78 (1H, d), 7.45–7.31 (9H, m), 5.36 (2H, s), 3.37 (3H, s), 3.11 (2H, m), 2.23 (3H, s), 2.02 (3H, s), 1.77–1.64 (12H, m), 1.30 (2H, m).

Step d

The product of step c (388 mg, 0.66 mmol) was deprotected using the same procedure as in Example 1, step e to afford the title compound as a white solid (292 mg, 89%). ¹H NMR (300 MHz, d₆-DMSO) 12.50 (1H, br s), 9.85 (1H, s), 8.53 (1H, s), 7.92 (1H, d), 7.60 (1H, m), 7.36 (5H, m), 3.35 (3H, s), 3.02 (2H, m), 2.16 (3H, s), 1.96 (3H, s), 1.71–1.58 (12H, m), 1.32 (2H, m). The acid was converted to the N-methyl-D-glucamine salt and lyophilised from water/dioxan. Found: C, 63.42; H, 8.00; N, 7.75%; $C_{38}H_{52}N_4O_8 \cdot 1.5 H_2O$ requires: C, 63.40; H, 7.70; N, 7.78%.

EXAMPLE 74

3-{[5-(2-Adamantan-1-yl-ethyl)-3-methyl-2-o-tolyl-3H-imidazole-4-carbonyl]-amino}-benzoic Acid 5-(2-Adamantan-1-yl-ethyl)-3-methyl-2-o-tolyl-3H-imidazole-4-carboxylic acid ethyl ester (Example 73, step a) was converted to the title compound according to the procedure of Example 73, steps b, c and d. ¹H NMR (300 MHz, d₆-DMSO) 13.00 (1H, br s), 9.84 (1H, s), 8.52 (1H, m), 7.91 (1H, m), 7.60 (1H, d), 7.36 (5H, m), 3.34 (3H, s), 3.03 (2H, m), 2.16 (3H, s), 1.96 (3H, s), 1.71–1.58 (12H, m), 1.32 (2H, m).

EXAMPLE 75

3-{3-[5-(2-Adamantan-1-yl-ethyl)-2-o-tolyl-1H-imidazol-4-yl]-ureido}-benzoic Acid Step a. 5-(2-Adamantan-1-yl-ethyl)-2-o-tolyl-1H-imidazole-4-carboxylic Acid Benzyl Ester 5-Adamantan-1-yl-2,3-dioxo-pentanoic acid benzyl ester monohydrate (8.44 g, 22.8 mmol) (prepared from 3-(adamantan-1-yl)-propionic acid (W. Oppolzer and R. Moretti, *Tetrahedron*, 1988, 44, 5541) according to the procedure of Example 20, step a) was reacted with o-tolualdehyde (5.47 g, 44.0 mmol) using essentially the procedure of Example 20, step b. The crude product was purified by flash column chromatography (silica, hexane/DCM/ethyl acetate 9:9:2) to afford the benzyl ester as a colourless foam (5.54 g, 54%). ¹H NMR (300 MHz, CDCl₃) 9.71 (1H, br s), 7.63 (1H, d), 7.49–7.27 (8H, m), 5.36 (2H, s), 2.92 (2H, m), 2.58 (3H, s), 1.97 (3H, br s), 1.67 (6H, m), 1.4 (8H, m).

Step b. 5-(2-Adamantan-1-yl-ethyl)-2-o-tolyl-imidazole-1,4-dicarboxylic acid 4-benzyl Ester 1-tert-butyl Ester To a solution of the product of step a above (454 mg, 1.00 mmol) in anhydrous dioxan (5 ml) was added di-tert-butyl dicarbonate (264 mg, 1.20 mmol) and 4-dimethylaminopyridine (20 mg). The solution was stirred at room temperature for 3 h, then the solvent was evaporated. The crude product was purified by flash column chromatography (silica, hexane/DCM/ethyl acetate 5:4:1). The major isomer (300 mg, 54%) (low R_f) was used in step c. ¹H NMR (300 MHz, CDCl₃) 7.51 (2H, d), 7.43–7.24 (8H, m), 5.44 (2H, s), 3.25 (2H, m), 2.23 (3H, s), 1.99 (3H, br s), 1.70 (6H, m), 1.52 (6H, s), 1.35 (2H, m), 1.22 (9H, s).

Step c. 5-(2-Adamantan-1-yl-ethyl)-2-o-tolyl-imidazole-1,4-dicarboxylic acid 1-tert-butyl Ester The benzyl ester of the product of step b (300 mg, 0.54 mmol) was hydrogenolyzed using the same procedure as in Example 1, step e to afford the acid as a colourless foam (237 mg, 95%). ¹H NMR (300 MHz, CDCl₃) 7.40 (1H, m), 7.30 (4H, m), 3.32 (2H, m), 2.24 (3H, s), 2.04 (3H, br s), 1.80–1.63 (12H, m), 1.44 (2H, m), 1.25 (9H, s).

Step d. 5-(2-Adamantan-1-yl-ethyl)-4-[3-(3-benzyloxycarbonyl-phenyl)-ureido]-2-o-tolyl-imidazole-1-carboxylic acid tert-butyl Ester To a solution of the product of step c above (464 mg, 1.00 mmol) and triethylamine (186 μl, 1.33 mmol) in anhydrous acetone (7 ml) was slowly added a solution of ethyl-chloroformate (186 ml, 2.00 mmol) in anhydrous acetone (2 ml) at 0° C. The reaction mixture was stirred at 0° C. for 30 min, then a solution of sodium azide (100 mg, 1.50 mmol) in water (1 ml) was added dropwise and the stirring was continued at room temperature for 30 min. The reaction mixture was diluted with water (20 ml) and the acetone was evaporated under reduced pressure. The aqueous layer was extracted with toluene (2×10 ml), and the combined toluene layers were dried (MgSO₄) and filtered. The filtrate was heated at reflux for 1 h, then 3-amino-benzoic acid benzyl ester was added and the mixture was heated at reflux for further 2 h. The reaction mixture was cooled; the solvent was evaporated in vacuo. The crude product was purified by flash column chromatography (silica, DCM/ethyl acetate 9:1) to afford the product as a white solid (237 mg, 34%). ¹H NMR (300 MHz, CDCl₃) 10.24 (1H, s), 8.03 (1H, s), 7.83 (1H, d), 7.74 (1H, d), 7.44–7.24 (10H, m), 6.48 (1H, s), 5.35 (2H, s), 2.77 (2H, m), 2.24 (3H, s), 1.98 (3H, br s), 1.65 (6H, m), 1.55 (6H, s), 1.29 (2H, m), 1.20 (9H, s).

Step e. 3-{3-[5-(2-Adamantan-1-yl-ethyl)-2-o-tolyl-1H-imidazol-4-yl]-ureido}-benzoic Acid Benzyl Ester The product of step d (237 mg, 0.34 mmol) was dissolved in trifluoroacetic acid (2 ml) and the solution was stirred at room temperature for 1 h. The trifluroracetic acid was removed in vacuo. The residue was parititioned between DCM and saturated aqueous sodium hydrogen carbonate. The organic layer was dried (MgSO₄) and the solvent was evaporated to afford the product as a white solid (190 mg, 94%). ¹H NMR (300 MHz, CDCl₃) 10.84 (1H, br s), 8.96 (1H, br s), 8.08 (1H, s), 7.75 (1H, d), 7.52 (1H, d), 7.47–7.27 (10H, m), 6.86 (1H, s), 5.36 (2H, s), 2.65 (3H, s), 2.57 (2H, m), 1.95 (3H, br s), 1.65 (6H, m), 1.51 (6H, s), 1.37 (2H, m).

Step f

The product of step e (190 mg, 0.32 mmol) was deprotected using the procedure of Example 1, step e to afford the title compound as a white solid. ¹H NMR (300 MHz, d₆-DMSO) 12.40 (1H, br s), 12.0 (1H, br s), 10.0(1H, br s), 8.20 (1H, br s), 8.11 (1H, s), 7.67–7.25 (7H, m), 2.59 (3H, s), 2.50 (2H, m), 1.92 (3H, s), 1.76–1.58 (12H, m), 1.38 (2H, m). The acid was converted to the N-methyl-D-glucamine salt and lyophilised from water/dioxan. Found: C, 60.21; H, 7.83; N, 9.26%; $C_{37}H_{51}N_5O_8 \cdot 1.5 H_2O$ requires: C, 60.01; H, 7.65; N, 9.46%.

EXAMPLE 76

3-{[5-(2-Adamantan-1-yl-ethyl)-2-cyclohexyl-1H-imidazole-4-carbonyl]-amino}-benzoic Acid The title compound was prepared using essentially the same procedure as in Example 70, with the modification that cyclohexanecarboxaldehyde was used in step a instead of 2-dimethylamino-benzaldehyde. ¹H NMR (300 MHz, $d_6$-DMSO) 13.00 (1H, br s), 11.94 (1H, br s), 9.57 (1H, s), 8.46 (1H, s), 7.88 (1H, d), 7.58 (1H, d), 7.39 (1H, t), 2.88 (2H, m), 2.60 (1H, m), 1.93–1.26 (27H, m). The acid was converted to the N-methyl-D-glucamine salt and lyophilised from water/dioxan. Found: C, 59.72; H, 8.33; N, 7.49%; $C_{36}H_{54}N_4O_8$.3.1 $H_2O$ requires: C, 59.50; H, 8.35,N, 7.71%.

EXAMPLE 77

3-{[5-(2-Adamantan-1-yl-ethyl)-1H-imidazole-4-carbonyl]-amino}-benzoic Acid

The title compound was prepared using essentially the same procedure as in Example 70, with the modification that paraformaldehyde was used in step a instead of 2-dimethylamino-benzaldehyde. $^1$H NMR (300 MHz, $d_6$-DMSO) 12.55 (1H, br s), 12.46 (1H, br s), 9.84 (1H, s), 8.52 (1H, s), 7.90 (1H, d), 7.60 (2H, m), 7.39 (1H, m), 2.93 (2H, m), 1.94 (3H, br s), 1.63 (6H, m), 1.52 (6H, s), 1.34 (2H, m). The acid was converted to the N-methyl-D-glucamine salt and lyophilised from water/dioxan. Found: C, 57.88; H, 8.04; N, 8.92%; $C_{30}H_{44}N_4O_8$.2.0 $H_2O$ requires: C, 57.74; H, 7.74; N, 8.98%.

EXAMPLE 78

3-{[5-(2-Adamantan-1-yl-ethyl)-2-isopropyl-1H-imidazole-4-carbonyl]-amino}-benzoic Acid The title compound was prepared using essentially the same procedure as in Example 70, with the modification that iso-butyraldehyde was used in step a instead of 2-dimethylamino-benzaldehyde. $^1$H NMR (300 MHz, $d_6$-DMSO) 13.20 (1H, br s), 12.25 (1H, br s), 9.77 (1H, br s), 8.45 (1H, s), 7.91 (1H, m), 7.61 (1H, d), 7.41 (1H, t), 3.10 (1H, m), 2.90 (2H, m), 1.94 (3H, br s), 1.63 (6H, m), 1.51 (6H, s), 1.36 (2H, m), 1.29 (3H, s), 1.27 (3H, s). The acid was converted to the N-methyl-D-glucamine salt and lyophilised from water/dioxan. Found: C, 57.52; H, 8.33; N, 8.04%; $C_{33}H_{50}N_4O_8$.3.2 $H_2O$ requires: C, 57.51; H, 8.26; N, 8.13%.

EXAMPLE 79

3-{[5-(2-Adamantan-1-yl-ethyl)-2-cycloheptyl-1H-imidazole-4-carbonyl]-amino}-benzoic Acid The title compound was prepared using essentially the same procedure as in Example 70, with the modification that cycloheptanecarboxaldehyde was used in step a instead of 2-dimethylamino-benzaldehyde. $^1$H NMR (300 MHz, $d_4$-MeOH) 8.36 (1H, t), 7.91 (1H, dt), 7.79 (1H, dt), 7.44 (1H, t), 2.97 (2H, m), 2.90 (1H, m), 1.97 (6H, m), 1.87–1.60 (23H, m), 1.41 (2H, m). The acid was converted to the N-methyl-D-glucamine salt and lyophilised from water/dioxan. Found: C, 61.04; H, 8.49; N, 7.89%; $C_{37}H_{56}N_4O_8$.2.2 $H_2O$ requires: C, 61.23; H, 8.41; N, 7.72%.

EXAMPLE 80

3-{[5-(2-Adamantan-1-yl-ethyl)-2-tert-butyl-1H-imidazole-4-carbonyl]-amino}-benzoic Acid The title compound was prepared using essentially the same procedure as in Example 70, with the modification that trimethylacetaldehyde was used in step a instead of 2-dimethylamino-benzaldehyde. $^1$H NMR (300 MHz, $d_4$-MeOH) 8.36 (1H, t), 7.93 (1H, dd), 7.76 (1H, dd), 7.45 (1H, t), 2.98 (2H, m), 1.96 (3H, s), 1.72 (6H, m), 1.60 (6H, m), 1.41 (11 H, m). The acid was converted to the N-methyl-D-glucamine salt and lyophilised from water/dioxan. Found: C, 59.69; H, 8.46; N, 8.17%; $C_{34}H_{52}N_4O_8$.2.3 $H_2O$ requires: C, 59.57; H, 8.31; N, 8.17%.

EXAMPLE 81

3-{[5-(2-Adamantan-1-yl-ethyl)-2-propyl-1H-imidazole-4-carbonyl]-amino}-benzoic Acid The title compound was prepared using essentially the same procedure as in Example 70, with the modification that butyraldehyde was used in step a instead of 2-dimethylamino-benzaldehyde. $^1$H NMR (300 MHz, $d_4$-MeOH) 8.35 (1H, m), 7.81 (1H, m), 7.48 (1H, t), 2.99 (2H, m), 2.83 (2H, t), 1.96 (3H, s), 1.79 (8H, m), 1.59 (6H, m),1.44 (2H, m), 1.02 (3H, t). The hydrochloride salt was formed by evaporating a solution of the title compound in dioxan/HCl. Found: C, 64.89; H, 7.41; N, 8.79%; $C_{26}H_{34}ClN_3O_3$.0.5 $H_2O$ requires: C, 64.96; H, 7.33; N, 8.74%.

EXAMPLE 82

(3-{[5-(2-Adamantan-1-yl-ethyl)-2-phenyl-1H-imidazole-4-carbonyl]-amino}-phenyl)-acetic Acid The title compound was prepared using essentially the same procedure as in Example 70, with the modification that benzaldehyde was used in step a instead of 2-dimethylamino-benzaldehyde and 3-amino-benzoic acid benzyl ester was replaced with (3-amino-phenyl)-acetic acid benzyl ester in step c. $^1$H NMR (300 MHz, $d_6$-DMSO) 12.72 (1H, s), 12.25 (1H, br s), 9.58 (1H, s), 8.05 (2H, m), 7.70 (2H, m), 7.48 (2H, m), 7.38 (1H, m), 7.25 (1H, t), 6.95 (1H, d), 3.55 (2H, s), 2.98 (2H, m), 1.95 (3H, br s), 1.65 (6H, m), 1.54 (6H, s), 1.42 (2H, m). The acid was converted to the N-methyl-D-glucamine salt and lyophilised from water/dioxan. Found: C, 60.45; H, 7.80; N, 7.47%; $C_{37}H_{50}N_4O_8$.3.2 $H_2O$ requires: C, 60.36; H, 7.72; N, 7.61%.

EXAMPLE 83

(3-{[5-(2-Adamantan-1-yl-ethyl)-2-o-tolyl-1H-imidazole-4-carbonyl]-amino}-phenyl)-acetic Acid The title compound was prepared using essentially the same procedure as in Example 70, with the modification that o-tolualdehyde was used in step a instead of 2-dimethylamino-benzaldehyde and 3-amino-benzoic acid benzyl ester was replaced with (3-amino-phenyl)-acetic acid benzyl ester in step c. $^1$H NMR (300 MHz, $d_6$-DMSO) 12.70 (1H, br s), 9.55 (1H, br s), 7.70 (1H, s), 7.61 (2H, m), 7.30 (4H, m), 6.94 (1H, d), 3.54 (2H, s), 2.98 (2H, m), 1.95 (3H, br s), 1.65 (6H, m), 1.54 (6H, s), 1.43 (2H, m). The acid was converted to the N-methyl-D-glucamine salt and lyophilised from water/dioxan. Found: C, 61.11; H, 8.17; N, 7.38%; $C_{38}H_{52}N_4O_8$.3.2 $H_2O$ requires: C, 60.87; H, 7.84; N, 7.47%.

EXAMPLE 84

(3-{[5-(2-Adamantan-1-yl-ethyl)-2-cyclohexyl-1H-imidazole-4-carbonyl]-amino}-phenyl)-acetic Acid The title compound was prepared using essentially the same procedure as in Example 70, with the modification that cyclohexanecarboxaldehyde was used in step a instead of 2-dimethylamino-benzaldehyde and 3-amino-benzoic acid benzyl ester was replaced with (3-amino-phenyl)-acetic acid benzyl ester in step c. $^1$H NMR (300 MHz, $d_6$-DMSO) 12.00 (1H, br s), 9.31 (1H, s), 7.67 (1H, s), 7.57 (1H, m), 7.21

(I1H, t), 6.90 (1H, d), 3.51 (2H, s), 2.87 (2H, m), 2.65 (1H, m), 1.93–1.30 (27H, m). The acid was converted to the N-methyl-D-glucamine salt and lyophilised from water/dioxan. Found: C, 61.71; H, 8.57; N, 7.71%; $C_{37}H_{56}N_4O_8 \cdot 2.0 H_2O$ requires: C, 61.63; H, 8.39; N, 7.77%.

EXAMPLE 85

3-({[5-(2-Adamantan-1-yl-ethyl)-2-phenyl-1H-imidazole-4-carbonyl]-amino}-methyl)-benzoic Acid 5-(2-Adamantan-1-yl-ethyl)-2-phenyl-1H-imidazole-4-carboxylic acid ethyl ester (Example 46) was converted to the title compound using essentially the same procedure as in Example 20, steps c, d and e, with the modification that 3-aminomethyl-benzoic acid benzyl ester replaced 5-amino-isophthalic acid dibenzyl ester in step d. $^1$H NMR (300 MHz, $d_6$-DMSO) 13.00 (1H, br s), 12.54 (1H, br s), 8.44 (1H, t), 7.95 (3H, m), 7.80 (1H, d), 7.56 (1H, d), 7.40 (4H, m), 4.48 (2H, d), 2.94 (2H, m), 1.93 (3H, s), 1.64 (6H, m), 1.51 (6H, s), 1.39 (2H, m). The acid was converted to the N-methyl-D-glucamine N-methyl-D-glucamine salt and lyophilised from water/dioxan. Found: C, 62.12; H, 7.72; N, 7.64%; $C_{37}H_{50}N_4O_8 \cdot 2.1 H_2O$ requires: C, 62.03; H, 7.62; N, 7.82%.

EXAMPLE 86

3-[(2-Adamantan-1-ylmethyl-5-phenethyl-1H-imidazole-4-carbonyl)-amino]-benzoic Acid 2-Adamantan-1-ylmethyl-5-phenethyl-1H-imidazole-4-carboxylic acid was prepared according to the procedure of Example 20, steps a, b and c with the modification that phenylpropionic acid was used in step a instead of cycloheptaneacetic acid and adamantan-1-yl-acetaldehyde replaced 2-naphthaldehyde in step b. The acid was then converted to the title compound according to the procedure of Example 20, steps d and e, 3-amino-benzoic acid benzyl ester was used in step d instead of 5-amino-isophthalic acid dibenzyl ester. $^1$H NMR (300 MHz, $d_6$-DMSO) 12.00 (1H, br s), 9.63 (1H, s), 8.41 (1H, s), 7.89 (1H, d), 7.60 (1H, d), 7.36 (1H, t), 7.18 (5H, m), 3.20 (2H, m), 2.94 (2H, t), 2.35 (2H, s), 1.90 (3H, s), 1.55 (6H, m), 1.46 (6H, s). The acid was converted to the N-methyl-D-glucamine salt and lyophilised from water/dioxan. Found: C, 60.43; H, 7.82, N, 7.57%; $C_{37}H_{50}N_4O_8 \cdot 3.1 H_2O$ requires: C, 60.51; H, 7.71; N, 7.63%.

EXAMPLE 87

3-[(5-Phenethyl-2-o-tolyl-1H-imidazole-4-carbonyl)-amino]-benzoic Acid

5-Phenethyl-2-o-tolyl-1H-imidazole-4-carboxylic acid was prepared according to the procedure of Example 20, steps a, b and c with the modification that phenylpropionic acid was used in step a instead of cycloheptaneacetic acid and o-tolualdehyde replaced 2-naphthaldehyde in step b. The acid was then converted to the title compound according to the procedure of Example 20, steps d and e, with the modification that 3-amino-benzoic acid benzyl ester was used in step d instead of 5-amino-isophthalic acid dibenzyl ester. $^1$H NMR (300 MHz, $d_6$-DMSO) 12.60 (1H, br s), 9.79 (1H, s), 8.51 (1H, s), 7.95 (1H, m), 7.60 (2H, m), 7.42 (1H, m), 7.32 (8H, m), 3.31 (2H, m), 2.99 (2H, m), 2.51 (3H, s). The acid was converted to the N-methyl-D-glucamine salt and lyophilised from water/dioxan. Found: C, 61.26; H, 6.86; N, 8.47%; $C_{33}H_{40}N_4O_8 \cdot 1.5 H_2O$ requires: 61.11; H, 6.70; N, 8.64%.

EXAMPLE 88

3-[(2-Cyclohexyl-5-phenethyl-1H-imidazole-4-carbonyl)-amino]-benzoic Acid

2-Cyclohexyl-5-phenethyl-1H-imidazole-4-carboxylic acid was prepared according to the procedure of Example 20, steps a, b and c with the modification that phenylpropionic acid was used in step a instead of cycloheptaneacetic acid and cyclohexanecarboxaldehyde replaced 2-naphthaldehyde in step b. The acid was then converted to the title compound according to the procedure of Example 20, steps d and e, with the modification that 3-amino-benzoic acid benzyl ester was used in step d instead of 5-amino-isophthalic acid dibenzyl ester. $^1$H NMR (300 MHz, $d_6$-DMSO) 13.00 (1H, br s), 12.10 (1H, br s), 9.68 (1H, s), 8.48 (1H, s), 7.92 (1H, dd), 7.61 (1H, d), 7.41 (1H, t), 7.30–7.15 (5H, m), 3.20 (2H, m), 2.90 (2H, m), 2.75 (1H, m), 1.94–1.35 (10H, m). The hydrochloride salt was formed with dioxan/HCl. Found: C, 57.85; H, 6.80, N, 7.84%; $C_{25}H_{28}ClN_3O_3 \cdot 3.71 H_2O$ requires: C, 57.66; H, 6.86; N, 8.07%.

EXAMPLE 89

3-{[5-(2-Cyclohexyl-ethyl)-2-o-tolyl-1H-imidazole-4-carbonyl]-amino}-benzoic Acid 5-Cyclohexyl-2,3-dioxo-pentanoic acid benzyl ester monohydrate (prepared from cyclohexanepropionic acid according to the procedure of Example 20, step a) was reacted with o-tolualdehyde according to the procedure of Example 20, step b to produce 5-(2cyclohexyl-ethyl)-2-o-tolyl-1H-imidazole-4-carboxylic acid benzyl ester. This derivative was then converted to the title compound following the procedure of Example 70, steps b, c and d. $^1$H NMR (300 MHz, $d_6$-DMSO) 12.50 (1H, br s), 9.76 (1H, s), 8.49 (1H, s), 7.94 (1H, m), 7.60 (2H, m), 7.41 (1H, t), 7.33 (3H, m), 3.03 (2H, m), 2.54 (3H, s), 1.78–1.53 (6H, m), 1.18 (5H, m), 0.93 (2H, m). The acid was converted to the N-methyl-D-glucamine salt and lyophilised from water/dioxan. Found: C, 60.17; H, 7.75; N, 8.68%; $C_{33}H_{46}N_4O_8 \cdot 1.67 H_2O$ requires: C, 60.34; H, 7.57; N, 8.53%.

EXAMPLE 90

3-{[5-(2-Methyl-butyl)-2-o-tolyl-1H-imidazole-4-carbonyl]-amino}-benzoic Acid

6-Methyl-2,3-dioxo-heptanoic acid benzyl ester monohydrate (prepared from 4-methyl-pentanoic acid according to the procedure of Example 20, step a) was reacted with o-tolualdehyde according to the procedure of Example 20, step b to produce 5-(2-methyl-butyl)-2-o-tolyl-1H-imidazole-4-carboxylic acid benzyl ester. This derivative was then converted to the title compound following the procedure of Example 70, steps b, c and d. $^1$H NMR (300 MHz, $d_6$-DMSO) 12.52 (1H, br s), 9.76 (1H, s), 8.49 (1H, s), 7.94 (1H m), 7.60 (2H, m), 7.41 (1H, t), 7.32 (3H, m), 3.03 (2H, m), 2.54 (3H, s), 1.57 (3H, m), 0.93 (6H, m). The acid was converted to the N-methyl-D-glucamine salt and lyophilised from water/dioxan. Found: C, 57.68; H, 7.60; N, 9.16%; $C_{30}H_{42}N_4O_8 \cdot 2.0 H_2O$ requires: C, 57.85; H, 7.45; N, 8.99%.

EXAMPLE 91

3-{[5-(3,3-Dimethyl-butyl)-2-o-tolyl-1H-imidazole-4-carbonyl]-amino}-benzoic Acid 6,6-Dimethyl-2,3-dioxo-heptanoic acid benzyl ester monohydrate (prepared from 4,4-dimethyl-pentanoic acid according to the procedure of Example 20, step a) was reacted with o-tolualdehyde according to the procedure of Example 20, step b to produce 5-(3,3-dimethyl-butyl)-2-o-tolyl-1H-imidazole-4-carboxylic acid benzyl ester. This derivative was then converted to the title compound following the procedure of Example 70, steps b, c and d. $^1$H NMR (300 MHz, d$_6$-DMSO) 12.53 (1H, br s), 9.74 (1H, s), 8.47 (1H, s), 7.94 (1H, m), 7.60 (2H, m), 7.41 (1H, t), 7.32 (3H, m), 3.01 (2H, m), 2.55 (3H, s), 1.56 (2H, m), 0.95 (9H, s). The acid was converted to the N-methyl-D-glucamine salt and lyophilised from water/dioxan. Found: C, 58.04; H, 8.51; N, 8.47%; C$_{31}$H$_{44}$N$_4$O$_8$.2.3 H$_2$O requires: C, 57.87; H, 7.64; N, 8.71%.

EXAMPLE 92

N-[5-(2-Adamantan-1-yl-ethyl)-2-o-tolyl-1H-imidazol-4-yl]-isophthalamic Acid

Step a. 5-(2-Adamantan-1-yl-ethyl)-4-benzyloxycarbonylamino-2-o-tolyl-imidazole-1-carboxylic Acid tert-butyl Ester 5-(2-Adamantan-1-yl-ethyl)-2-o-tolyl-imidazole-1,4-dicarboxylic acid 1-tert-butyl ester (Example 75, step c) was converted to the isocyanate and reacted with benzyl alcohol according to the procedure of Example 75, step d using benzyl alcohol in place of 3-amino-benzoic acid benzyl ester. The crude reaction mixture was purified by flash column chromatography (silica, hexane/ethyl acetate 3:2) to give the product. $^1$H NMR (300 MHz, CDCl$_3$) 7.39–7.19 (9H, m), 6.10 (1H, br s), 5.20 (2H, s), 2.79 (2H, m), 2.18 (3H, s), 1.96 (3H, s), 1.68 (6H, m), 1.50 (6H, s), 1.31 (2H, m), 1.19 (9H, s).

Step b. 5-(2-Adamantan-1-yl-ethyl)-4-amino-2-o-tolyl-imidazole-1-carboxylic Acid tert-butyl Ester The product from the previous step (340 mg, 0.57 mmol) was hydrogenolyzed using the same procedure as in Example 1, step e to afford the amine (175 mg, 71%). $^1$H NMR (300 MHz, CDCl$_3$) 7.25–7.18 (4H, m), 3.28 (2H, br s), 2.72 (2H, m), 2.18 (3H, s), 1.98 (3H, s), 1.69 (6H, m), 1.57 (6H, m), 1.32 (2H, m), 1.18 (9H, s).

Step c. 5-(2-Adamantan-1-yl-ethyl)-4-(3-methoxycarbonyl-benzoylamino)-2-o-tolyl-imidazole-1-carboxylic Acid tert-butyl Ester Isophthalic acid mono methyl ester (200 mg, 1.10 mmol) was heated at reflux for 15 min in the mixture of thionyl chloride (2 ml) and DMF (cat.). The solvent was evaporated in vacuo, the residue was dissolved in DCM (5mi) and the solvent was evaporated to afford 3-chlorocarbonyl-benzoic acid methyl ester. To a solution of the product of step b above (435 mg, 1.00 mmol) and triethylamine (280 µl, 2.00 mmol) in DCM (10 ml) was added a solution of the previously prepared 3-chlorocarbonyl-benzoic acid methyl ester in DCM (2 ml). The reaction mixture was stirred at room temperature for 1h. It was washed with 5% aqueous potassium hydrogen sulfate (10 ml) and water (10 ml), dried (MgSO$_4$) and the solvent was evaporated. The residue was purified by flash column chromatography (silica, DCM/ethyl acetate 4:1) to afford the product as a white solid (310mg, 52%). $^1$H NMR (300 MHz, CDCl$_3$) 8.53 (1H, s), 8.18 (2H, m), 8.07 (1H, d), 7.51 (1H, t), 7.30–7.21 (4H, m), 3.95 (3H, s), 2.91 (2H, m), 2.20 (3H, s), 1.94 (3H, br s), 1.66 (6H, m), 1.5 (6H, s), 1.38 (2H, m), 1.21 (9H, s).

Step d. N-[5-(2-Adamantan-1-yl-ethyl)-2-o-tolyl-1H-imidazol-4-yl]-isophthalamic Acid methyl Ester The product of step c above was deprotected according to the procedure of Example 75, step e. $^1$H NMR (300 MHz, d$_6$-DMSO) 11.95 (1H, s), 10.12 (1H, s), 8.55 (1H, s), 8.24 (1H, d), 8.13 (1H, d), 7.66 (1H, t), 7.58 (1H, m), 7.26 (3H, m), 3.89 (3H, s), 2.54 (3H, s), 2.50 (2H, m), 1.89 (3H, br s), 1.63 (6H, m), 1.42 (8H, m).

Step e

The methyl ester was hydrolyzed following essentially the procedure of Example 36, step d to afford the title compound as a beige solid. $^1$H NMR (300 MHz,d$_6$-DMSO) 13.00 (1H, br s), 11.96 (1H, br s), 10.09 (1H, s), 8.53 (1H, s), 8.20 (1H, d), 8.11 (1H, d), 7.62 (2H, m), 7.26 (3H, m), 2.54 (3H, s), 2.50 (2H, m), 1.89 (3H, br s), 1.62 (6H, m), 1.42 (8H, m). The acid was converted to the N-methyl-D-glucamine salt and lyophilised from water/dioxan. Found: C, 61.34; H, 7.72; N, 7.57%; C$_{37}$H$_{50}$N$_4$O$_8$.2.5 H$_2$O requires: C, 61.39; H, 7.66, N, 7.74%.

EXAMPLE 93

(±)-1-[5-(2-Adamantan-1-yl-ethyl)-2-o-tolyl-1H-imidazole-4-carbonyl]-piperidine-3-carboxylic Acid 5-(2-Adamantan-1-yl-ethyl)-2-o-tolyl-1H-imidazole-4-carboxylic acid was prepared according to the procedure of Example 70, steps a and b, with the modification that o-tolualdehyde was used in step a instead of 2-dimethylamino-benzaldehyde. The acid was converted to the title compound according to the procedure of Example 70, steps c and d, using (±)-piperidine-3-carboxylic acid benzyl ester in step c instead of 3-amino-benzoic acid benzyl ester. $^1$H NMR (300 MHz, d$_6$-DMSO) 12.30 (2H, br s), 7.59 (1H, m), 7.26 (3H, m), 5.20–4.30 (2H, br m), 3.60–3.00 (2H, br m), 2.77 (2H, m), 2.51 (3H, s), 2.48 (1H, m), 2.00–1.35 (21H, m). The acid was converted to the N-methyl-D-glucamine salt and lyophilised from water/dioxan. Found: C, 58.45; H, 7.75; N, 7.74%; C$_{36}$H$_{54}$N$_4$O$_8$.1.0 DCM requires: C, 58.75; H, 7.46; N, 7.40%.

EXAMPLE 94

(±)-1-[5-(2-Adamantan-1-yl-ethyl)-2-o-tolyl-1H-imidazole-4-carbonyl]-piperidine-4-carboxylic Acid 5-(2-Adamantan-1-yl-ethyl)-2-o-tolyl-1H-imidazole-4-carboxylic acid (Example 93) was converted to the title compound according to the procedure of Example 70, steps c and d, using (±)-piperidine-4-carboxylic acid benzyl ester in step c instead of 3-amino-benzoic acid benzyl ester. $^1$H NMR (300 MHz, d$_6$-DMSO) 12.29 (1H, br s), 12.19 (1H, s), 7.58 (1H, m), 7.26 (3H, m), 5.20–4.30 (2H, br m), 3.40–2.80 (2H, br m), 2.75 (2H, m), 2.52 (3H, s), 1.93–1.35 (22H, m). The acid was converted to the N-methyl-D-glucamine salt and lyophilised from water/dioxan. Found: C, 61.00; H, 8.33; N, 7.98%; C$_{36}$H$_{54}$N$_4$O$_8$.2.0 H$_2$O requires: C, 61.17; H, 8.27; N, 7.92%.

EXAMPLE 95

(2S)-1-[5-(2-Adamantan-1-yl-ethyl)-2-o-tolyl-1H-imidazole-4-carbonyl]-pyrrolidine-carboxylic Acid 5-(2-Adamantan-1-yl-ethyl)-2-o-tolyl-1H-imidazole-4-carboxylic acid (Example 93) was converted to the title compound according to the procedure of Example 70, steps c and d, using (2S)-pyrrolidine-carboxylic acid benzyl ester in step c instead of 3-amino benzoic acid benzyl ester. $^1$H NMR (300 MHz, d$_6$-DMSO) 12.30 (1H, br s), 12.20 (1H, s), 7.58 (1H, m), 7.29 (3H, m), 4.01 (1H, m), 3.60–3.30 (2H, br m), 2.88 (2H, m), 2.53 (3H, s), 2.25–1.35 (21H, m). The acid was converted to the N-methyl-D-glucamine salt and lyophilised from water/dioxan. Found: C, 60.61; H, 8.00; N, 7.88%; $C_{35}H_{52}N_4O_8 \cdot 2.0\ H_2O$ requires: C, 60.67; H, 8.14; N, 8.08%.

EXAMPLE 96

3-{[5-(2-Adamantan-1-yl-ethyl)-2-(4-fluoro-2-methyl-phenyl)-1H-imidazole-4-carbonyl]-amino}-benzoic Acid 5-(2-Adamantan-1-yl-ethyl)-2-(4-fluoro-2-methyl-phenyl)-1H-imidazole-4-carboxylic acid was prepared according to the procedure of Example 70, steps a and b, with the modification that 4-fluoro-2-methyl-benzaldehyde was used in step a instead of 2-dimethylamino-benzaldehyde. The acid was converted to the title compound according to the procedure of Example 70, steps c and d. $^1$H NMR (300 MHz, $d_6$-DMSO) 12.60 (1H, br s), 12.52 (1H, s), 9.74 (1H, s), 8.48 (1H, s), 7.94 (1H, d), 7.62 (2H, m), 7.41 (1H, t), 7.22–7.11 (2H, m), 2.97 (2H, m), 2.55 (3H, s), 1.95 (3H, s), 1.71–1.40 (14H, m). The acid was converted to the N-methyl-D-glucamine salt and lyophilised from water/dioxan. Found: C, 61.39; H, 7.29; N, 7.55%; $C_{37}H_{49}FN_4O_8 \cdot 1.5\ H_2O$ requires: C, 61.39; H, 7.24; N, 7.74%.

EXAMPLE 97

3-(3-{[5-(2-Adamantan-1-yl-ethyl)-2-o-tolyl-1H-imidazole-4-carbonyl]-amino}-phenyl)-propionic Acid Trifluoroacetic Acid Salt Step a. 3-(3-{[5-(2-Adamantan-1-yl-ethyl)-2-o-tolyl-1H-imidazole-4-carbonyl]-amino}-phenyl)-propionic acid tert-butyl ester 5-(2-Adamantan-1-yl-ethyl)-2-o-tolyl-1H-imidazole-4-carboxylic acid (Example 93) (364 mg, 1.00 mmol) was reacted with 3-(3-amino-phenyl)-propionic acid tert-butyl ester (243 mg, 1.10 mmol) according to the procedure of Example 70, step c to afford the product as a colourless foam (359 mg, 63%). $^1$H NMR (300 MHz, $CDCl_3$) 9.14 (1H, br s), 9.07 (1H, br s), 7.59–7.51 (3H, m), 7.35–7.22 (4H, m), 6.94 (1H, d), 3.16 (2H, m), 2.92 (2H, m), 2.60 (3H, s), 2.56 (2H, m), 1.99 (3H, s), 1.76–1.44 (23H, m).

Step b

The product of step b above (355 mg, 0.63 mmol) was dissolved in trifluoroacetic acid (5 ml) and the solution was stirred at room temperature for 16 h. The reaction mixture was diluted with toluene (50 ml) and the solvent was evaporated in vacuo. The residue was suspended in chloroform (2×40 ml) and the solvent was evaporated. The same process was repeated from methanol (2×30 ml). The residue was dried in vacuo to afford the title compound as a white solid (378 mg, 96%). $^1$H NMR (300 MHz, $d_6$-DMSO) 13.00 (1H, br s), 9.58 (1H, br s), 8.00–6.00 (2H, br s), 7.59 (3H, m), 7.41–7.30 (3H, m), 7.23 (1H, m), 6.94 (1H, m), 2.95 (2H, m), 2.79 (2H, m), 2.52 (5H, m), 1.95 (3H, s), 1.68–1.44 (14H, m). Found: C, 65.20; H, 6.31; N, 6.78%; $C_{34}H_{38}F_3N_3O_5$ requires: C, 65.27; H, 6.12; N, 6.72%.

EXAMPLE 98

(3-{[5-(2-Adamantan-1-yl-ethyl)-2-o-tolyl-1H-imidazole-4-carbonyl]-amino}-phenoxy)-acetic Acid 5-(2-Adamantan-1-yl-ethyl)-2-o-tolyl-1H-imidazole-4-carboxylic acid (Example 93) was converted to the title compound according to the procedure of Example 70, steps c and d, using (3-amino-phenoxy)-acetic acid benzyl ester in step c instead of 3-amino benzoic acid benzyl ester. $^1$H NMR (300 MHz, $d_6$-DMSO) 13.00 (1H, br s), 12.50 (1H, br s), 9.51 (1H, br s), 7.58–7.16 (7H, m), 6.59 (1H, m), 4.63 (2H, s), 2.96 (2H, m) 2.53 (3H, s), 1.95 (3H, s), 1.67–1.40 (14H, m). The acid was converted to the N-methyl-D-glucamine salt and lyophilised from water/dioxan. Found: C, 61.28; H, 7.62; N, 7.52%; $C_{38}H_{52}N_4O_9 \cdot 2.0\ H_2O$ requires: C, 61.27; H, 7.58; N, 7.52%.

EXAMPLE 99

(4-{[5-2-Adamantan-1-yl-ethyl)-2-o-tolyl-1H-imidazole-4-carbonyl]-amino}-phenyl)-acetic Acid 5-(2-Adamantan-1-yl-ethyl)-2-o-tolyl-1H-imidazole-4-carboxylic acid (Example 93) was converted to the title compound according to the procedure of Example 70, steps c and d, using (4-amino-phenyl)-acetic acid benzyl ester in step c instead of 3-amino benzoic acid benzyl ester. $^1$H NMR (300 MHz, $d_6$-DMSO) 12.48 (1H, br s), 12.20 (1H, br s), 9.49 (1H, br s), 7.71 (2H, d), 7.58 (1H, m), 7.30 (3H, m), 7.20 (2H, d), 3.51 (2H, s), 2.99 (2H, m), 2.53 (3H, s), 1.95 (3H, s), 1.67–1.40 (14H, m). The acid was converted to the N-methyl-D-glucamine salt and lyophilised from water/dioxan. Found: C, 61.19; H, 7.98; N, 7.66%; $C_{38}H_{52}N_4O_9 \cdot 3.0\ H_2O$ requires: C, 61.11; H, 7.83; N, 7.50%.

EXAMPLE 100

5-(2-Adamantan-1-yl-ethyl)-2-o-tolyl-1H-imidazole-4-carboxylic Acid (3-benzoylsulfamoyl-phenyl)-amide 5-(2-Adamantan-1-yl-ethyl)-2-o-tolyl-1H-imidazole-4-carboxylic acid (Example 93) was reacted with 3-amino-N-benzoyl-benzenesulfonamide using essentially the same procedure as in Example 20, step d. The crude product was purified by flash column chromatography (silica, ethyl acetate/hexane 2:1) to afford the title compound. $^1$H NMR 300 MHz, $d_6$-DMSO) 12.52 (1H, br s), 9.85 (1H, br s), 8.55 (1H, br s), 7.89 (3H, m), 7.62–7.29 (9H, m), 2.99 (2H, m), 2.54 (3H, s), 1.95 (3H, s), 1.66–1.40 (14H, m). Found: C, 67.51; H, 6.33; N, 8.63%; $C_{36}H_{38}N_4O_4S \cdot 1.0\ H_2O$ requires: C, 67.48; H, 6.29; N, 8.74%.

EXAMPLE 101

5-(2-Adamantan-1-yl-ethyl)-2-o-tolyl-1H-imidazole-4-carboxylic acid (3-benzenesulfonylaminocarbonyl-phenyl)-amide 5-(2-Adamantan-1-yl-ethyl)-2-o-tolyl-1H-imidazole-4-carboxylic acid (Example 93) was reacted with N-(3-amino-benzoyl)-benzenesulfonamide using essentially the same procedure as in Example 20, step d. The crude product was purified by flash column chromatography (silica, ethyl acetate/hexane 2:1) to afford the title compound. $^1$H NMR (300 MHz, $d_6$-DMSO) 12.52 (1H, br s), 9.70 (1H, br s), 8.29 (1H, s), 7.98 (3H, m), 7.68–7.52 (5H, m), 7.42–7.28 (4H, m), 2.98 (2H, m), 2.54 (3H, s), 1.95 (3H, s), 1.67–1.35 (14H, m). Found: C, 67.65; H, 6.34; N, 8.49%; $C_{36}H_{38}N_4O_4S \cdot 1.0\ H_2O$ requires: C, 67.48; H, 6.29; N, 8.74%.

EXAMPLE 102

{[5-(2-Adamantan-1-yl-ethyl)-2-o-tolyl-1H-imidazole-4-carbonyl]-amino}-phenyl-acetic Acid Step a. {[5-(2-Adamantan-1-yl-ethyl)-2-o-tolyl-1H-imidazole-4-carbonyl]-amino}-phenyl-acetic Acid Methyl Ester To a solution of 5-(2-adamantan-1-yl-ethyl)2-o-tolyl-1H-imidazole-4-carboxylic acid (Example 93) (389 mg, 1.07 mmol) and DL-α-phenylglycine methyl ester hydrochloride (258 mg, 1.28 mmol) in DMF (5 ml) was added triethylamine (196 μl, 1.41 mmol), 1-hydroxybenzotriazole (203 mg, 1.50 mmol) and 1-(3-dimethylaminopropyl-3-ethylcarbodiimide hydrochloride (288 mg, 1.50 mmol). The solution was kept at room temperature for 72 h, poured into 1 M hydrochloric acid (20 ml) and the product was extracted with ethyl acetate (2×20 ml). The solvent was evaporated and the residue was purified by flash column chromatography (silica, hexane/ethyl acetate 2:1) to afford the product as a colourless foam (447 mg, 82%). $^1$H NMR (300 MHz, CDCl$_3$) 9.11 (1H, br s),8.13 (1H, br d), 7.55–7.26 (9H, m), 5.80 (1H, d), 3.75 (3H, s), 3.07 (2H, m), 2.57 (3H, s), 1.96 (3H, s), 1.73–1.54 (12H, m), 1.42 (2H, m).

Step b

To a solution of the product of step a above (441 mg, 0.86 mmol) in water (4 ml) and THF (4 ml) was added lithium hydroxide monohydrate (1 81 mg, 4.31 mmol). The solution was stirred at room temperature for 16 h, acidified with 2M hydrochloric acid (pH=1), diluted with water (20 ml). The product was extracted with ethyl acetate (2×30 ml), the organic phase was dried (MgSO$_4$) and the solvent was evaporated to afford the title compound as a white solid (391 mg, 91%). $^1$H NMR (300 MHz, d$_6$-DMSO) 13.00 (1H, br s), 12.42 (1H, br s), 8.11 (1H, d), 7.56 (1H, m), 7.44–7.27 (8H, m), 5.51 (1H, d), 2.90 (2H, m), 2.51 (3H, s), 1.91 (3H, br s), 1.63 (6H, m), 1.49 (6H, s), 1.37 (2H, m). The acid was converted to the N-methyl-D-glucamine salt and lyophilised from water/dioxan. Found: C, 63.87; H, 7.64; N, 7.92%; C$_{38}$H$_{52}$N$_4$O$_8$.1.0 H$_2$O requires C, 64.21; H, 7.66; N, 7.88%.

EXAMPLE 103

3-(2-([5-(2-Adamantan-1-yl-ethyl)-2-o-tolyl-1H-imidazole-4-carbonyl]-amino-acetylamino)-benzoic Acid Step a. 3-(2-Benzyloxycarbonylamino-acetylamino)-benzoic Acid Methyl Ester 3-Amino-benzoic acid methyl ester hydrochloride (1.88 g, 10.0 mmol) was reacted with N-α-CBZ-glycine (3.14 g, 15.0 mmol) according to the procedure of Example 102, step a to afford the product (3.12 g, 91%). $^1$H NMR (300MHZ, CDCl$_3$) 10.18 (1H, br s), 8.26 (1H, m), 7.84 (1H, d), 7.65 (1H, d), 7.55 (1H, d), 7.48–7.22 (7H, m), 5.05 (2H, s), 3.85 (3H, s), 3.83 (2H, d).

Step b. 3-(2-Amino-acetylamino)-benzoic Acid Methyl Ester

The product of step a above (3.12 g, 9.12 mmol) was deprotected according to the procedure of Example 1, step e to afford the amine (1.95 g, 100%). $^1$H NMR (300 MHz, CDCl$_3$) 9.54 (1H, br s), 8.05 (2H, m), 7.79 (1H, m), 7.42 (1H, m), 3.92 (3H, s), 3.50 (2H, s), 1.61 (2H, br s). The amine was converted to the hydrochloride salt with 4M hydrogen chloride in dioxan.

Step c 5-(2-Adamantan-1-yl-ethyl)-2-o-tolyl-1H-imidazole-4-carboxylic acid (Example 93) was reacted with the product of step b above according to the procedure of Example 102, step a to afford 3-(2-{[5-(2-Adamantan-1-yl-ethyl)-2-o-tolyl-1H-imidazole-4-carbonyl]-amino}-acetylamino)-benzoic acid methyl ester. The methyl ester was hydrolyzed using the same procedure as in Example 102, step b to afford the title compound as a white solid. $^1$H NMR (300 MHz, d$_6$-DMSO) 13.00–12.50 (2H, br s), 10.26 (1H, s), 8.24 (1H, s), 8.15 (1H, br s), 7.85 (1H, d), 7.60 (2H, m), 7.45–7.29 (4H, m), 4.09 (2H, d), 2.93 (2H, m), 2.53 (3H, s), 1.90 (3H, br s), 1.65–1.40 (14H, m). The acid was converted to the N-methyl-D-glucamine salt and lyophilised from water/ dioxan. Found: C, 58.84; H, 7.58; N, 8.92%; C$_{39}$H$_{53}$N$_5$O$_8$.3.25 H$_2$O requires: C, 58.96; H, 7.55; N, 8.82%.

EXAMPLE 104

3-{[5-(2-Adamantan-1-yl-ethyl)-2-o-tolyl-1H-imidazole-4-carbonyl]-amino}-2-methyl-benzoic Acid 5-(2-Adamantan-1-yl-ethyl)-2-o-tolyl-1H-imidazole-4-carboxylic acid (Example 93) was converted to the title compound according to the procedure of Example 20, steps d and e, using 3-amino-2-methyl-benzoic acid benzyl ester in step d instead of 5-amino-isophthalic acid dibenzyl ester. $^1$H NMR (300 MHz, d$_6$-DMSO) 13.00 (1H, br s), 12.56 (1H, br s), 9.48 (1H, br s), 8.11 (1H, d), 7.63 (1H, m), 7.51 (1H, d), 7.33–7.25 (4H, m), 2.97 (2H, m), 2.59 (3H, s), 2.44 (3H, s), 1.94 (3H, s), 1.67–1.40 (14H, m). The acid was converted to the N-methyl-D-glucamine salt and lyophilised from water/dioxan. Found: C, 61.49; H, 7.84; N, 7.60%; C$_{38}$H$_{52}$N$_4$O$_9$.3.0 H$_2$O requires: C, 61.11; H, 7.83; N, 7.50%.

EXAMPLE 105

5-{[5-(2-Adamantan-1-yl-ethyl)-2-o-tolyl-1H-imidazole-4-carbonyl]-amino}-2-fluoro-benzoic Acid The title compound was prepared using essentialy the same procedure as in Example 102, with the modification that 5-amino-2-fluoro-benzoic acid methyl ester hydrochloride was used in step a instead of DL-α-phenylglycine methyl ester hydrochloride. $^1$H NMR (300 MHz, d$_6$-DMSO) 12.50 (1H, br s), 10.27 (1H, br s), 8.38 (1H, m), 7.98 (1H, m), 7.63 (1H, d), 7.45–7.25 (4H, m), 3.00 (2H, m), 2.52 (3H, s), 1.95 (3H, s), 1.65 (6H, m), 1.55 (6H, br s), 1.44 (2H, m). The acid was converted to the N-methyl-D-glucamine salt and lyophilised from water/dioxan. Found: C, 58.94; H, 7.31; N, 7.60%; C$_{37}$H$_{49}$FN$_4$O$_8$.3.0 H$_2$O requires: C, 59.17; H, 7.38; N, 7.46%.

EXAMPLE 106

5-{[5-(2-Adamantan-1-yl-ethyl)-2-o-tolyl-1H-imidazole-4-carbonyl]-amino}-2-methyl-benzoic Acid 5-(2-Adamantan-1-yl-ethyl)-2-o-tolyl-1H-imidazole-4-carboxylic acid (Example 93) was converted to the title compound according to the procedure of Example 20, steps d and e, using 5-amino-2-methyl-benzoic acid benzyl ester in step d instead of 5-amino-isophthalic acid dibenzyl ester. $^1$H NMR (300 MHz, d$_6$-DMSO) 12.80 (1H, br s), 12.49 (1H, br s), 9.62 (1H, br s), 8.31 (1H, m), 7.79 (1H, m), 7.58 (1H, m), 7.33–7.20 (4H, m), 2.98 (2H, m), 2.54 (3H, s), 2.46 (3H, s), 1.95 (3H, s), 1.67–1.40 (14H, m). The acid was converted to the N-methyl-D-glucamine salt and lyophilised from water/dioxan. Found: C, 61.60; H, 7.53; N, 7.81%; C$_{38}$H$_{52}$N$_4$O$_8$.2.5 H$_2$O requires: C, 61.85; H, 7.79, N, 7.59%.

EXAMPLE 107

5-{[5-(2-Adamantan-1-yl-ethyl)-2-cyclohexyl-1H-imidazole-4-carbonyl]-amino)-}-2-methyl-benzoic Acid 5-(2-Adamantan-1-yl-ethyl)-2-cyclohexyl-1H-imidazole-4-carboxylic acid was prepared according to the procedure of Example 70, steps a and b, using cyclohexanecarboxaldehyde in step a instead of 2-dimethylamino-benzaldehyde. The acid was converted to the title compound using essentially the same procedure as in Example 52, steps a and b, with the modification that 5-amino-2-methyl-benzoic acid benzyl ester replaced β-alanine benzyl ester β-toluenesulfonate in step a. $^1$H NMR (300 MHz, $d_6$-DMSO) 12.30 (1H, br s), 11.92 (1H, br s), 9.45 (1H, s), 8.29 (1H, s), 7.74 (1H, m), 7.19 (1H, d), 2.85 (2H, m), 2.62 (1H, m), 2.45 (3H, s), 1.93–1.31 (27H, m).

The acid was converted to the N-methyl-D-glucamine salt and lyophilised from water/dioxan. Found: C, 59.81; H, 8.49; N, 7.66%; $C_{37}H_{56}N_4O_8$.3.0 $H_2O$ requires: C, 60.14; H, 8.46; N, 7.58%.

EXAMPLE 108

3-{[5-(2-Adamantan-1-yl-ethyl)-2-methyl-1H-imidazole-4-carbonyl]-amino}-benzoic Acid The title compound was prepared using essentially the same procedure as in Example 70, with the modification that acetaldehyde was used in step a instead of 2-dimethylamino-benzaldehyde. $^1$H NMR (300 MHz, $d_6$-DMSO) 10.60 (1H, s), 8.40 (1H, s), 7.96 (1H, m), 7.69 (1H, m), 7.48 (1H, t), 2.92 (2H, m), 2.55 (3H, s), 1.94 (3H, br s), 1.64 (6H, m), 1.50 (6H, m), 1.38 (2H, m). The acid was converted to the N-methyl-D-glucamine salt and lyophilised from water/dioxan. Found: C, 53.10; H, 8.04; N, 8.39%; $C_{31}H_{46}N_4O_8$.5.2 $H_2O$ requires: C, 53.44; H, 8.17; N, 8.04%.

EXAMPLE 109

3-{[2-Adamantan-1-yl-5-(2-adamantan-1-yl-ethyl)-1H-imidazole-4-carbonyl]-amino}-benzoic Acid The title compound was prepared using essentially the same procedure as in Example 70, with the modification that adamantan-1-yl-carboxaldehyde was used in step a instead of 2-dimethylamino-benzaldehyde. $^1$H NMR (300 MHz, $d_6$-DMSO) 11.85 (1H, br s), 9.48 (1H, s), 8.40 (1H, s), 7.90 (1H, dd), 7.60 (1H, d), 7.39 (1H, t), 2.88 (2H, m), 2.04 (3H, s), 1.97 (9H, m), 1.66 (12H, m), 1.51 (6H, s), 1.34 (2H, m). The acid was converted to the N-methyl-D-glucamine salt and lyophilised from water/dioxan.

EXAMPLE 110

3-{[5-(2-Adamantan-1-yl-ethyl)-1H-3'H-[2,4']biimidazolyl-4-carbonyl]-amino}-benzoic Acid The title compound was prepared using essentially the same procedure as in Example 70, with the modification that 1-trityl-1H-imidazole-4-carbaldehyde was used in step a instead of 2-dimethylamino-benzaldehyde. $^1$H NMR (300 MHz, $d_6$-DMSO) 9.68 (1H, s), 8.44 (1H, s), 7.95 (1H, m), 7.78 (1H, d), 7.61 (2H, m), 7.42 (1H, t), 2.94 (2H, m), 1.95 (3H, s), 1.65 (6H, m), 1.53 (6H, s), 1.40 (2H, m). The acid was converted to the N-methyl-D-glucamine salt and lyophilised from water/dioxan. Found: C, 56.99; H, 7.18; N, 12.33%; $C_{33}H_{46}N_6O_8$.2.1 $H_2O$ requires: C, 57.20; H, 7.31; N, 12.13%.

EXAMPLE 111

3-{[5-(2-Adamantan-1-yl-ethyl)-2-(2,2-dimethyl-propyl)-1H-imidazole-4-carbonyl]-amino}-benzoic Acid The title compound was prepared using essentially the same procedure as in Example 70, with the modification that 3,3-dimethyl-butyraldehyde was used in step a instead of 2-dimethylamino-benzaldehyde. $^1$H NMR (300 MHz, $d_6$-DMSO) 8.43 (1H, s), 7.97 (1H, d), 7.68 (1H, d), 7.47 (1H, t), 2.96 (2H, m), 2.71 (2H, s), 1.93 (3H, br s), 1.63 (6H, m), 1.50 (6H, d), 1.38 (2H, m), 0.98 (9H, s). The acid was converted to the N-methyl-D-glucamine salt and lyophilised from water/dioxan. Found: C, 58.61; H, 8.25; N, 7.99%; $C_{35}H_{54}N_4O_8$.3.1 $H_2O$ requires: C, 58.85; H, 8.49; N, 7.84%.

EXAMPLE 112

3-{[5-(2-Adamantan-1-yl-ethyl)-2-(1-ethyl-propyl)-1H-imidazole-4-carbonyl]-amino}-benzoic Acid The title compound was prepared using essentially the same procedure as in Example 70, with the modification that 2-ethyl-butyraldehyde was used in step a instead of 2-dimethylamino-benzaldehyde. $^1$H NMR (300 MHz, $d_6$-DMSO) 9.68 (1H, br s), 8.47 (1H, s), 7.91 (1H, d), 7.60 (1H, d), 7.40 (1H, t), 2.91 (2H, m), 2.56 (1H, m), 1.93 (3H, br s), 1.66 (10H, m), 1.51 (6H, d), 1.36 (2H, m), 0.77 (6H, t). The acid was converted to the N-methyl-D-glucamine salt and lyophilised from water/dioxan. Found: C, 60.25; H, 8.34; N, 8.27%; $C_{35}H_{54}N_4O_8$.2.0 $H_2O$ requires: C, 60.47; H, 8.42; N, 8.06%.

EXAMPLE 113

5{-[5-(2-Adamantan-1-yl-ethyl)-2-(1-ethyl-propyl)-1H-imidazole-4-carbonyl]-amino}-2-methyl-benzoic Acid 5-(2-Adamantan-1-yl-ethyl)-2-(1-ethyl-propyl)-1H-imidazole-4-carboxylic acid was prepared using essentially the same procedure as in Example 70, steps a and b, with the modification that 2-ethyl-butyraldehyde was used in step a instead of 2-dimethylamino-benzaldehyde. The acid was converted to the title compound according to the procedure of Example 20, steps d and e, using 5-amino-2-methyl-benzoic acid benzyl ester in step d instead of 5-amino-isophthalic acid dibenzyl ester. $^1$H NMR (300 MHz, $d_6$-DMSO) 12.50 (1H, br s), 11.90 (1H, br s), 9.48 (1H, s), 8.30 (1H, m), 7.76 (1H, m), 7.20 (1H, d), 2.89 (2H, m), 2.50 (1H, m), 2.45 (3H, s), 1.92 (3H, s), 1.69–1.33 (18H, m), 0.76 (6H, m). The acid was converted to the N-methyl-D-glucamine salt and lyophilised from water/dioxan. Found: C, 61.62; H, 8.60; N, 8.05%; $C_{36}H_{56}N_4O_8$.1.5 $H_2O$ requires: C, 61.78; H, 8.50; N, 8.01%.

EXAMPLE 114

(±)-endo-3-{[5-(2-Adamantan-1-yl-ethyl)-2-bicyclo[2.2.1]hept-2-yl-1H-imidazole-4-carbonyl]-amino}-benzoic Acid Step a. (±)-endo-5-(2-Adamantan-1-yl-ethyl)-2-bicyclo[2.2.1]hept-5-en-2-yl-1H-imidazole-4-carboxylic Acid Benzyl Ester 5-Adamantan-1-yl-2,3-dioxo-pentanoic acid benzyl ester monohydrate (Example 70, step a) (1.43 g, 3.85 mmol) was reacted with (±)-5-norbornene-2-carboxaldehyde (693 μl 5.78 mmol) using essentially the same procedure as in Example 20, step b. The crude product was purified by flash column chromatography (silica, DCM/ethyl acetate 92:8). Two isomers were obtained as white solids: endo (low $R_f$, 468 mg, 27%) and exo (high $R_f$, 118 mg, 7%). endo: $^1$H NMR (300 MHz, CDCl$_3$) 7.38 (5H, m), 6.41 (1H, m), 5.97 (1H, m), 5.28 (2H, s), 3.54 (1H, m), 3.21 (1H, s), 3.02 (1H, s), 2.74 (2H, m), 2.26 (1H, ddd), 1.90 (3H, br s), 1.58 (8H, m), 1.43 (6H, m), 1.36 (2H, m), 1.18 (1H, m). exo: $^1$H NMR (300 MHz, CDCl$_3$) 7.38 (5H, m), 6.17 (2H, s), 5.31 (2H, s), 3.02 (2H, s), 2.78 (2H, m), 2.69 (1H, dd), 2.01 (1H, m), 1.90 (3H, br s), 1.60 (8H, m), 1.43 (9H, m).

Step b

The endo isomer of step a above was converted to the title compound using essentially the same procedure as in Example 70, steps b, c and d to afford the acid as a white solid. $^1$H NMR (300 MHz, d$_6$-DMSO) 11.92 (1H, br s), 9.54 (1H, s), 8.43 (1H, s), 7.92 (1H, m), 7.60 (1H, m), 7.40 (1H, t), 3.10 (1H, m), 2.90 (2H, m), 2.52 (1H, m), 2.27 (1H, m), 1.93 (3H, s), 1.82 (1H, m), 1.64 (6H, m), 1.50 (8H, m), 1.35 (6H, m) 1.01 (1H, m). The acid was converted to the N-methyl-D-glucamine salt and lyophilised from water/dioxan. Found: C, 64.42; H, 7.94; N, 8.18%; C$_{37}$H$_{52}$N$_4$O$_8$.0.4 H$_2$O requires: C, 64.48; H, 8.00; N, 8.13%.

EXAMPLE 115

(±)-exo-3-{[5-(2-Adamantan-1-yl-ethyl)-2-bicyclo [2.2.1]hept-2-yl-1H-imidazole-4-carbonyl]-amino}-benzoic Acid The exo isomer of Example 114, step a was converted to the title compound using essentially the same procedure as in Example 70, steps b, c and d to afford the acid as a white solid. $^1$H NMR (300 MHz, d$_6$-DMSO) 12.88 (1H, br s), 11.96 (1H, s), 9.55 (1H, s), 8.44 (1H, s), 7.92 (1H, m), 7.60 (1H, m), 7.40 (1H, t), 2.87 (2H, m), 2.72 (1H, m), 2.38 (1H, m), 2.31 (1H, m), 2.21 (1H, m), 1.94 (3H, s), 1.63 (6H, m), 1.50 (8H, m), 1.30 (6H, m), 1.09 (1H, m). The acid was converted to the N-methyl-D-glucamine salt and lyophilised from water/dioxan. Found: C, 61.43; H, 8.01; N, 7.99%; C$_{37}$H$_{54}$N$_4$O$_8$.2.1 H$_2$O requires: C, 61.65; H, 8.14; N, 7.77%.

EXAMPLE 116

(±)-endo-3-{[5-(2-Adamantan-1-yl-ethyl)-2-bicyclo [2.2.1]hept-5-ene-2-yl-1H-imidazole-4-carbonyl]-amino}-benzoic Acid Step a. (±)-endo-5-(2-Adamantan-1-yl-ethyl)-2-bicyclo[2.2.1]hept-5-en-2-yl-1H-imidazole-4-carboxylic Acid Ethyl Ester 5-Adamantan-1-yl-2,3-dioxo-pentanoic acid ethyl ester monohydrate (Example 44) (1.96 g, 6.32 mmol) was reacted with (±)-5-norbornene-2-carboxaldehyde (1.20 ml, 9.48 mmol) using essentially the same procedure as in Example 20, step b. The crude product was purified by flash column chromatography (silica, DCM/ethyl acetate 85:15). Two isomers were obtained as white solids: endo (low R$_f$, 683 mg, 27%) and exo (high R$_f$, 280 mg, 11%). endo: $^1$H NMR (300 MHz, CDCl$_3$) 6.42 (1H, m), 5.98 (1H, m), 4.33 (2H, m), 3.56 (1H, m), 3.22 (1H, 3.02 (1H, s), 2.81 (2H, m), 2.28 (1H, m), 1.97 (3H, br s), 1.74–1.35 (19H, m), 1.18 (1H, m). exo: $^1$H NMR (300 MHz, CDCl$_3$) 6.18 (2H, s), 4.34 (2H, m), 3.02 (2H, m), 2.81 (2H, m), 2.69 (1H, m), 2.05 (1H, m), 1.97 (3H, br s), 1.70–1.35 (20H, m).

Step b

The endo isomer of step a above was hydrolyzed according to the procedure of Example 20, step c and the resulting (±)-5-(2-adamantan-1-yl-ethyl)-2-bicyclo[2.2.1]hept-5-en-2-yl-1H-imidazole-4-carboxylic acid was reacted with 3-amino-benzoic acid methyl ester using essentially the same procedure as in Example 52, step a. Deprotection was carried out following the procedure of Example 36, step d to afford the title compound as a white solid. $^1$H NMR (300 MHz, d$_6$-DMSO) 11.75 (2H, br s), 9.49 (1H, s), 8.43 (1H, s), 7.89 (1H, d), 7.60 (1H, d), 7.39 (1H, t), 6.19 (1H, br s), (1H, m), 3.31 (2H, m), 2.91 (3H, m), 2.05 (1H, m), 1.93 (3H, s), 1.70–1.59 (7H, m), 1.51 (6H, s), 1.35 (4H, m). The acid was converted to the N-methyl-D-glucamine salt and lyophilised from water/dioxan. Found: C, 59.61; H, 8.07; N, 7.79%; C$_{37}$H$_{52}$N$_4$O$_8$.3.5 H$_2$O requires: C, 59.74; H, 8.00; N, 7.53%.

EXAMPLE 117

(±)-exo-3-{[5-(2-Adamantan-1-yl-ethyl)-2-bicyclo [2.2.1]hept-5-ene-2-yl-1H-imidazole-4-carbonyl]-amino}-benzoic Acid The exo isomer of Example 116, step a was converted to the title compound according to the same procedure as in Example 116, step b. $^1$H NMR (300 MHz, d$_6$-DMSO) 12.00 (1H, s), 1.90 (1H, br s), 9.58 (1H, s), 8.44 (1H, s), 7.92 (1H, m), 7.60 (1H, d), 7.40 (1H, t), 6.21 (2H, s), 2.95 (2H, s), 2.90 (2H, m), 2.60 (1H, m), 2.10 (1H, m), 1.94 (3H, s), 1.70–1.59 (6H, m), 1.51 (6H, s), 1.42–1.30 (5H, m). The acid was converted to the N-methyl-D-glucamine salt and lyophilised from water/dioxan. Found: C, 59.89; H, 7.97; N, 7.70%; C$_{37}$H$_{52}$N$_4$O$_8$.3.5 H$_2$O requires: C, 59.74; H, 8.00; N, 7.53%.

EXAMPLE 118

3-{2-[5(Adamantan-1-ylcarbamoyl)-2-o-tolyl-1H-imidazole-4-yl]-ethyl}-benzoic Acid Step a. 5-[2-(3-Methoxycarbonyl-phenyl)-ethyl]-2-o-tolyl-1H-imidazole-4-carboxylic Acid Benzyl Ester 3-(4-Benzyloxycarbonyl-3,4-dioxo-butyl)-benzoic acid methyl ester monohydrate (3.70 g, 10 mmol) (prepared from 3-(2-carboxy-ethyl)-benzoic acid methyl ester according to the procedure of Example 20, step a) was reacted with o-tolualdehyde (2.40 g, 20 mmol) using essentially the procedure of Example 20, step b. The crude product was purified by flash column chromatography (silica, DCM/ethyl acetate 9:1) to afford the benzyl ester (2.42 g, 53%). $^1$H NMR (300 MHz, CDCl$_3$) 10.00 (1H, br s), 7.85 (2H, m), 7.55 (1H, m), 7.37–7.28 (10H, m), 5.28 (2H, m), 3.89 (3H, s), 3.26 (2H, m), 3.09 (2H, m) 2.51 (3H, s).

Step b. 5-[2-(3-Methoxycarbonyl-phenyl)-ethyl]-2-o-tolyl-1H-imidazole-4-carboxylic Acid The product of step a (2.42 g, 5.33 mmol) was deprotected using the same procedure as in Example 1, step e, to afford the acid (1.81 g, 93%). $^1$H NMR (300 MHz, d$_6$-DMSO) 12.20 (1H, br d), 7.94–7.26 (8H, m), 3.82 (3H, s), 3.16 (2H, m), 3.02 (2H, m), 2.43 (3H, s).

Step c. 3-{2-[5-(Adamantan-1-ylcarbamoyl)-2-o-tolyl-1H-imidazole-4-yl]-ethyl}-benzoic Acid Methyl Ester The product of step b was reacted with 1-adamantanamine using essentially the same procedure as in Example 70, step c. $^1$H NMR (300 MHz, CDCl$_3$) 8.60 (1H br s), 7.88 (2H, m), 7.39–7.20 (6H, m), 7.09 (1H, m), 3.89 (3H, s), 3.46 (2H, t), 3.10 (2H, t), 2.35 (3H, s), 2.17 (6H, s), 2.12 (3H, s), 1.73 (6H, m).

Step d

To a solution of the product of step c (232 mg, 0.65 mmol) in ethanol (13 ml) was added 1M sodium hydroxide (1.3 ml, 1.3 mmol). The solution was refluxed for 2 h, diluted with water (10 ml), then acidified (pH=5, 0.01M HCl). The resulting precipitate was collected by filtration, washed with water and dried to give the title compound (271 mg, 86%). $^1$H NMR (300 MHz, d$_6$-DMSO) 12.40 (1H, br s), 12.2 (1H, br s), 7.80–7.29 (8H, m), 6.98 (1H, br s), 3.23 (2H, m), 3.00 (2H, m), 2.44 (3H, s) 2.03 (9H, s), 1.65 (6H, s). The acid was converted to the N-methyl-D-glucamine salt and lyophilised from water/dioxan. Found: C, 58.98; H, 7.83; N, 7.40% C$_{37}$H$_{50}$N$_4$O$_8$.4H$_2$O requires: C, 59.18 H, 7.79; N, 7.46%.

EXAMPLE 119

3-{2-[5-(Adamantan-1-ylmethylcarbamoyl)-2-o-tolyl-1H-imidazol-4-yl]-ethyl}-benzoic Acid The title compound was prepared using essentially the same procedure as in Example 118, with the modification that 1-adamantanemethylamine was used in step c instead of 1-adamantanamine. $^1$H NMR (300 MHz, d$_6$-DMSO) 12.60 (1H, br s), 12.38 (1H, s), 7.79–7.26 (9H, m), 3.26 (2H, t), 3.01 (2H, t), 2.96 (2H, d), 2.48 (3H, s), 1.92 (3H, s), 1.63 (6H, m), 1.55 (6H, s). The acid was converted to the N-methyl-D-glucamine salt and lyophilised from water/dioxan. Found: C, 62.41; H, 8.00; N, 7.48%. C$_{38}$H$_{52}$N$_4$O. 2H$_2$O requires: C, 62.62; H, 7.74; N, 7.69%.

EXAMPLE 120

3-{[5-(2-Adamanatan-1-yl-ethyl)-2-o-tolyl-oxazole-4-carbonyl]-amino}-benzoic Acid

Step a. 5-Adamantan-1-yl-2-(2-methyl-benzoylamino)-3-oxo-pentanoic Acid Ethyl Ester 5-Adamantan-1-yl-2-amino-3-oxo-pentanoic acid ethyl ester hydrochloride (prepared using the method of T. W. von Geldem & C. Hutchins et al, J. Med. Chem. 1996, 39, 957) (3.30 g, 10.0 mmol) was suspended in DMF (15 ml) and a solution of 2-methylbenzoyl chloride (1.55 g 10.0 mmol) in THF (15 ml) was added. The mixture was stirred at room temperature and a solution of N,N-diisopropylethylamine (3.48 ml 20.0 mmol) in THF (10 ml) was added dropwise over 30 min. After stirring for 2 h the THF was evaporated and the residue was partitioned between ethyl acetate and saturated sodium bicarbonate. The organic layer was separated, washed with water, 2M HCl, brine, dried (MgSO$_4$), and the solvent was evaporated. The residue was purified by flash column chromatography (silica, DCM/hexane/ethyl acetate 9:9:2) to afford the product as a pale yellow oil. (2.08 g, 60%). $^1$NMR (300 MHz, CDCl$_3$) 7.49–7.23 (4H, m), 6.97 (1H, d), 5.45 (1H, d), 4.30 (2H, m), 2.77 (2H, m), 2.47 (3H, s), 1.97 (3H, s) 1.67 (6H, m), 1.47 (8H, m), 1.34 (3H, t).

Step b. 5-(2-Adamantan-1-yl-ethyl)-2-o-tolyl-oxazole-4-carboxylic Acid Ethyl Ester To a solution of the product from step a (1.00 g, 2.43 mmol) in acetonitrile (4 ml) and pyridine (4 ml) was added sequentially carbon tetrachloride (486 µl 4.88 mmol) 1,8-diazabicyclo[5,4,0]undec-7-ene (1.22 ml, 8.13 mmol), and triphenylphosphine (693 mg, 2.64 mmol). The mixture was left to stand at room temperature for 16 h. The solvent was evaporated and the residue was dissolved in DCM. The solution was washed with saturated sodium bicarbonate, brine, 1M phosphoric acid, brine, dried (MgSO$_4$), and the solvent was evaporated. The residue was purified by flash column chromatography (silica, DCM/hexane/ethyl acetate 9:9:2) to afford the product as a pale yellow oil (540 mg, 57%). $^1$H NMR (300 MHz, CDCl$_3$) 7.98 (1H, d), 7.32 (3H, m), 4.42 (2H, q), 3.08 (2H, m), 2.68 (3H, s), 2.00 (3H s), 1.76–1.40 (14H, m), 1.26 (3H, t).

Step c. 5-(2-Adamantan-1-yl-ethyl)-2-o-tolyl-oxazole-4-carboxylic Acid

A solution of the product from step b (540 mg, 1.37 mmol) in ethanol (48m1) and 2M sodium hydroxide (4.8 ml, 9.60 mmol) were refluxed for 16 h. The resulting hot suspension was acidified (pH=3, 1M H$_3$PO$_4$), the ethanol was evaporated, the residue was diluted with water and extracted with ethyl acetate. The organic layer was washed with water, dried (MgSO$_4$), and the solvent was evaporated to afford the product as a white solid (460 mg, 92%). $^1$H NMR (300 MHz, CDCl$_3$) 8.00 (1H, d), 7.33 (3H, m), 3.11 (2H, m), 2.70 (3H, s), 2.00 (3H, s), 1.77–1.49 (14H, m).

Step d. 3-{[5-(2-Adamanatan-1-yl-ethyl)-2-o-tolyl-oxazole-4-carbonyl]-amino}-benzoic Acid Benzyl Ester The acid from step c was coupled to 3-amino-benzoic acid benzyl ester using essentially the procedure of Example 52, step a to afford the product as a white solid (328 mg, 45%). $^1$H NMR (300 MHz, CDCl$_3$) 8.96 (1H, s), 8.20 (1H, d), 8.14 (1H, s), 7.98 (1H, d), 7.83 (1H, d), 7.49–7.33 (9H, m), 5.4 (2H, s), 3.19 (2H, m), 2.73 (3H, s), 2.00 (3H, s), 1.76–1.54 (14H, m).

Step e

The product of step d (328 mg, 0.57 mmol) was deprotected using the same procedure as in Example 1, step e to afford the title compound as a white solid (273 mg, 99%). $^1$H NMR (300 Hz, d$_6$-DMSO) 12.96 (1H, s), 10.04 (1H, s), 8.48 (1H, s), 7.99 (2H, m), 7.68 (1H, d), 7.49–7.37 (4H, m), 3.12 (2H, m), 2.68 (3H, s), 1.94 (3H, s), 1.75–1.46 (14H, m). The acid was converted to the N-methyl-D-glucamine salt and lyophilised from water/dioxan. Found: C, 63.50; H, 7.46; N, 5.96%. C$_{37}$H$_{49}$N$_3$O$_9$ H$_2$O requires: C, 63.68; H, 7.37; N, 6.02%.

EXAMPLE 121

3-{[5-(2-Adamanatan-1-yl-ethyl)-2-o-tolyl-thiazole-4-carbonyl]-amino}-benzoic Acid

Step a. 5-(2-Adamantan-1-yl-ethyl)-2-o-tolyl-thiazole-4-carboxylic Acid Ethyl Ester A solution of the product from Example 120, step a (1.00 g, 2.43 mmol) and Lawesson's reagent (1.23 g, 3.00 mmol) in THF (16 ml) was refluxed for 4 hrs. The solvent was evaporated and the residue was taken up in DCM. The solution was washed with saturated sodium bicarbonate, brine, 1M phosphoric acid, then dried (MgSO$_4$), and the solvent was evaporated. The residue was purified by flash column chromatography (silica, DCM/hexane/ethyl acetate 9:9:2) to afford the product as a white solid (400 mg, 40%). $^1$H NMR (300 MHz, CDCl$_3$) 7.64 (2H, d), 7.29 (3H, m), 4.44 (2H, q), 3.26 (2H, m), 2.57 (3H, s), 2.01 (3H, s), 1.77–1.49 (14H, m), 1.43 (3H, t).

Step b. 5-(2-Adamantan-1-yl-ethyl)-2-o-tolyl-thiazole-4-carboxylic Acid

The ethyl ester from step a (400 mg, 0.98 mmol) was hydrolysed using essentially the same procedure as in Example 120, step c to afford the product as a white solid (351 mg, 94%). $^1$H NMR (300 MHz, CDCl$_3$) 7.65 (1H, d), 7.35 (3H, m), 3.31 (2H, m), 2.60 (3H, s), 2.00 (3H, s), 1.76–1.50 (14H, m).

Step c. 3-{[5-(2-Adamanatan-1-yl-ethyl)-2-o-tolyl-thiazole-4-carbonyl]-amino}-benzoic Acid Methyl Ester The acid from step b was reacted with 3-amino-benzoic acid methyl ester using essentially the same procedure as in Example 52, step a to afford the product as a white solid. $^1$H NMR (300 MHz, CDCl$_3$) 9.55 (1H, s), 8.17 (1H, s), 8.11 (1H, d), 7.79 (1H, d), 7.70 (1H, d), 7.48–7.32 (4H, m), 3.94 (3H, s), 3.43 (2H, m), 2.65 (3H, s), 2.01 (3H, s), 1.73–1.54 (14H, m).

Step d

The product of step c (351 mg, 0.68 mmol) was hydrolysed using essentially the same procedure as in Example 118, step d, to afford the title compound as a white solid (315 mg, 93%). $^1$H NMR (300 MHz, d$_6$-DMSO) 12.94 (1H, s), 10.24 (1H, s), 8.46 (1H, s), 8.00 (1H, d), 7.90 (1H, d), 7.68 (1H, d), 7.49–7.34 (4H, m), 3.34 (2H, m), 2.60 (3H, s), 1.95 (3H, s), 1.70–1.45 (14H, m). The acid was converted to the N-methyl-D-glucamine salt and lyophilised from water/dioxan. Found: C, 61.40; H, 7.52; N, 5.85%. C$_{37}$H$_{49}$N$_3$O$_8$S. 1.5 H$_2$O requires: C, 61.47; H, 7.25; N, 5.81%.

EXAMPLE 122

3-{[4-(Adamantan-1-yl-ethyl)-2-cyclohexyl-thiazole-5-carbonyl]-amino}-benzoic Acid Step a. 4-Adamanatan-1-yl-2-chloro-3-oxo-butyric Acid Ethyl Ester To a solution of 4-adamantan-1-yl-3-oxo-butyric acid ethyl ester (prepared by the method of W. Wierenga & H. I. Skulnick, *J. Org. Chem.* 1979, 44, 310) (2.78 g, 10.0 mmol) in DCM (10 ml) was added dropwise a solution of sulfuryl chloride (0.843 ml, 10.5 mmol) in DCM (10 ml) over 10 min. The solution was stirred at room temperature for 1 h, then it was washed with water, brine, dried (MgSO$_4$), and the solvent was evaporated to afford the product as an orange oil (2.39 g, 73%). $^1$H NMR (300 MHz, CDCl$_3$) 5.30 (1H, s), 4.27 (2H, m), 2.65 (2H, m), 1.96 (3H, s), 1.74–1.32 (14H, m), 1.30 (3H, t).

Step b. 4-(2-Adamantan-1-yl-ethyl)-2-cyclohexyl-thiazole-5-carboxylic Acid Ethyl Ester A solution of the product from step a (2.39 g, 7.65 mmol) and cyclohexanethiocarboxamide (1.19 g 7.65 mmol) in ethanol (30 ml) was refluxed for 2 h. The solvent was evaporated and the residue was taken up in ether. The solution was washed with saturated sodium bicarbonate, brine, dried (MgSO$_4$), and the solvent was evaporated. The residue was purified by flash column chromatography (silica, hexane/ethyl acetate 9:1) to afford the product as a colourless oil. (2.91 g, 95%). $^1$H NMR (300 MHz, CDCl$_3$) 4.32 (2H, q), 3.08 (2H, m), 2.96 (1H, m), 2.14–1.22 (30H, m).

Step c. 4-(2-Adamantan-1-yl-ethyl)-2-cyclohexyl-thiazole-5-carboxylic Acid

The product from step b (2.90 g, 7.35 mmol) was hydrolysed using essentially the procedure of Example 120, step c to afford the product as a white solid (1.80 g, 66%). $^1$H NMR (300 MHz, d$_6$-DMSO) 13.00 (1H, br s), 2.95 (3H, m), 1.99–1.32 (27H, m).

Step d. 3-{[4-(2-Adamantan-1-yl-ethyl)-2-cyclohexyl-thiazole-5-carbonyl]-amino}-benzoic Acid Methyl Ester The product from step c was reacted with 3-amino-benzoic acid methyl ester using essentially the same method as in Example 52, step a. The product was obtained as a white solid in 59% yield. $^1$H NMR (300 MHz, CDCl$_3$) 8.00 (2H, m), 7.82 (1H, d), 7.47 (2H, m), 3.93 (3H, s), 3.06 (3H, m), 2.18–1.27 (27H, m).

Step e

The product from step d (300 mg, 0.59 mmol) was hydrolysed using essentially the same method as in Example 118, step d, to afford the title compound as a white solid (246 mg, 90%). $^1$H NMR (300 MHz, d$_6$-DMSO) 13.0 (1H, br s), 10.27 (1H, s), 8.28 (1H, s), 7.85 (1H, d), 7.66 (1H, d), 7.45 (1H, t), 2.90 (3H, m), 2.18–1.36 (27H, m). The acid was converted to the N-methyl-D-glucamine salt and lyophilised from water/dioxan. Found: C, 60.27; H, 8.01; N, 5.93% C$_{36}$H$_{53}$N$_3$O$_8$S. 1.5 H$_2$O requires: C, 60.48; H, 7.90; N, 5.88%.

EXAMPLE 123

3-{[2-(2-Adamantan-1-yl-ethyl)-5-o-tolyl-1H-pyrrole-3-carbonyl]-amino}-benzoic Acid The title compound was synthesised following the procedure of Example 1, with the modification that 5-adamantan-1-yl-3-oxo-pentanoic acid ethyl ester was used instead of 4-adamantan-1-yl-3-oxo-butyric acid ethyl ester, and o-methyl-2-bromo-1-phenyl-ethanone was used instead of 2-bromo-1-phenyl-ethanone in step a, and 3-amino-benzoic acid benzyl ester replaced 5-amino-isophthalic acid dibenzyl ester in step d. $^1$H NMR (300 MHz, d$_6$-DMSO) 13.0 (1H, br s), 11.22 (1H, s), 9.51 (1H, s), 8.32 (1H, s), 8.02 (1H, d), 7.60 (1H, d), 7.40 (2H, m), 7.25 (3H, m), 6.88 (1H, s), 2.95 (2H, m), 2.45 (3H, s), 1.94 (3H, s), 1.64 (6H, m), 1.53 (6H, s), 1.36 (2H, m). The acid was converted to the N-methyl-D-glucamine salt and lyophilised from water/ dioxan. Found: C, 64.72; H, 7.77; N, 5.87%. C$_{38}$H$_{51}$N$_3$O$_8$.1.5 H$_2$O requires: C, 64.72; H, 7.72, N, 5.96%.

EXAMPLE 124

3-{[5-(2-Adamantan-1-yl-ethyl)-2-(1-ethyl-pentyl)-1H-imidazole-4-carbonyl]-amino}-benzoic Acid The title compound was prepared according to the procedure of Example 70, using 2-ethyl-hexanal instead of 2-dimethylamino-benzaldehyde in step a. $^1$H NMR (300 MHz, d$_6$-DMSO) 12.00 (1H, s), 9.60 (1H, s), 8.39 (1H, s), 7.85 (1H, d), 7.59 (1H, d), 7.34 (1H, t), 2.88 (2H, m), 2.60 (1H, m), 1.92 (3H, s), 1.64–1.22 (22H, m), 0.79 (6H, m). The acid was converted to the N-methyl-D-glucamine salt and lyophilised from water/dioxan. Found: C, 61.31; N, 8.80; N, 7.61%. C$_{37}$H$_{58}$N$_4$O$_8$.2H$_2$O requires: C, 61.47; H, 8.65; N, 7.75%.

EXAMPLE 125

3-{[5-(2-Adamantan-1-yl-ethyl)-2-(1-propyl-butyl)-1H-imidazole-4-carbonyl]-amino}-benzoic Acid The title compound was prepared according to the procedure of Example 70, using 2-propyl-pentanal instead of 2-dimethylamino-benzaldehyde in step a. $^1$H NMR (300 MHz, d$_6$-DMSO) 12.00 (1H, br s), 9.60 (1H, s), 8.45 (1H, s), 7.88 (1H, d), 7.59 (1H, d), 7.38 (1H, t), 2.87 (2H, m), 2.60 (1H, m), 1.92 (3H, s), 1.65–1.12 (22H, m), 0.82 (6H, t). The acid was converted to the N-methyl-D-glucamine salt and lyophilised from water/dioxan. Found: C, 60.70; H, 8.83; N, 7.49%. C$_{37}$H$_{58}$N$_4$O$_8$·2.5 H$_2$O requires: C, 60.72; H, 8.68; N, 7.66%.

EXAMPLE 126

5-{[5-(2-Adamantan-1-yl-ethyl)-2-(1-propyl-butyl)-1H-imidazole-4-carbonyl]-amino}-2-methyl-benzoic Acid The title compound was prepared according to the procedure of Example 70, with the modification that 2-propyl-pentanal was used instead of 2-dimethylamino-benzaldehyde in step a, and 5-amino-2-methyl-benzoic acid benzyl ester replaced 3-amino benzoic acid benzyl ester in step c. $^1$H NMR (300 MHz, d$_6$-DMSO) 12.50 (1H, br s),11.90 (1H, br s), 9.46 (1H, s), 8.28 (1H, s), 7.75 (1H, d), 7.19 (1H, d), 2.86 (2H, m), 2.60 (1H, m), 2.45 (3H, s), 1.92 (3H, s), 1.65–1.12 (22H, m), 0.82 (6H, t). The acid was converted to the N-methyl-D-glucamine salt and lyophilised from water/dioxan. Found: C, 61.05; H, 8.96; N, 7.68%. C$_{38}$H$_{60}$N$_4$O$_8$·2.5 H$_2$O requires C, 61.19; H, 8.78; N, 7.51%.

EXAMPLE 127

3-{[5-(2-Adamantan-1-yl-ethyl)-2-cyclododecyl-1H-imidazole-4-carbonyl]-amino}-benzoic Acid The title compound was prepared according to the procedure of Example 70, using cylododecanecarboxaldehyde instead of 2-dimethylamino-benzaldehyde in step a. $^1$H NMR (300 MHz, d$_6$-DMSO) 12.50 (1H, br s), 12.00 (1H, s), 9.58 (1H, s), 8.45 (1H, s), 7.89 (1H, d), 7.59 (1H, d), 7.38 (1H, t), 2.88 (3H, m), 1.93 (3H, s), 1.70–1.30 (36H, m). The acid was converted to the N-methyl-D-glucamine salt and lyophilised from water/dioxan. Found: C, 63.15; H, 9.15; N, 6.81%. C$_{42}$H$_{66}$N$_4$O$_8$·2.5 H$_2$O requires: C, 63.05; H, 8.96; N, 7.00%.

EXAMPLE 128

3-{[5-(2-Adamanatan-1-yl-ethyl)-2-dicyclohexylmethyl-1H-imidazole-4-carbonyl]-amino}-benzoic Acid The title compound was prepared according to the procedure of Example 70 using dicyclohexylacetaldehyde instead of 2-dimethylamino-benzaldehyde in step a. $^1$H NMR (300 MHz, d$_6$-DMSO). 12.00 (1H, br s), 9.30 (1H, br s), 8.31 (1H, s), 7.86 (1H, d), 7.66 (1H, d), 7.32 (1H, t), 2.87 (2H, m), 2.36 (1H, m), 1.89 (3H, s), 1.74–0.94 (36H, m). The acid was converted to the N-methyl-D-glucamine salt and lyophilised from water/dioxan. Found: C, 61.38; N, 9.00; N, 6.77%. C$_{43}$H$_{66}$N$_4$O$_8$·4H$_2$O requires: C, 61.55; H, 8.89; N, 6.68%.

EXAMPLE 129

5-{[5-(2-Adamantan-1-yl-ethyl)-2-cyclohexyl-1H-imidazole-4-carbonyl]-amino}-isophthalic Acid The title compound was prepared using essentially the same procedure as in Example 70 with the modification that cyclohexanecarboxaldehyde was used in step a instead of 2-dimethylamino-benzaldehyde and 5-amino-isophthalic acid dibenzyl ester was used instead of 3-amino-benzoic acid benzyl ester in step c. $^1$H NMR (300 MHz, d$_6$-DMSO) 12.0 (1H, br s), 9.83 (1H, s), 8.60 (2H, s), 8.14 (1H, s), 2.88 (2H, m), 2.60 (1H, m), 1.94–1.27 (27H, m). The acid was converted to the di(N-methyl-D-glucamine) salt and lyophilised from water/dioxan. Found: C, 54.83; H, 8.06; N, 7.29%. C$_{44}$H$_{71}$N$_5$O$_{15}$·3H$_2$O requires: C, 54.82; H, 8.05; N, 7.26%.

EXAMPLE 130

5-(2-Adamantan-1-yl-ethyl)-2-cyclohexyl-1H-imidazole-4-carboxylic Acid[{3-(1H-tetrazol-5-yl)-phenyl]-amide 5-(2-Adamantan-1-yl-ethyl)-2-cyclohexyl-1H-imidazole-4-carboxylic acid[{3-(1-pivaloyloxymethyl-1H-tetrazol-5-yl)-phenyl]-amide was prepared using essentially the same procedure as in Example 70, steps a, b and c, with the modification that cyclohexanecarboxaldehyde was used in step a instead of 2-dimethylamino-benzaldehyde and 3-(1-pivalyloxymethyl-1H-tetrazol-5-yl)-phenylamine was used instead of 3-amino-benzoic acid benzyl ester in step c. Deprotection was carried out following essentially the same procedure as in Example 2, step b to afford the title compound. $^1$H NMR (300 MHz, d$_6$-DMSO). 14.0 (1H, br s), 10.40 (1H, br s), 8.59 (1H, s), 7.90 (1H, d), 7.77 (1H, d), 7.59 (1H, t), 2.95 (3H, m), 1.99–1.36 (27H, m). The tetrazole was converted to the N-methyl-D-glucamine salt and lyophilised from water/dioxan. Found: C, 56.55; H, 8.17; N, 14.32%. C$_{36}$H$_{54}$N$_8$O$_6$·4H$_2$O requires: C, 56.38; H, 8.15; N, 14.61%.

EXAMPLE 131

3-{[5-(2-Adamantan-1-yl-ethyl)-2-cyclohexyl-1H-imidazole-4-carbonyl]-amino}-4-amino-benzoic Acid 3-{[5-(2-Adamantan-1-yl-ethyl)-2-cyclohexyl-1H-imidazole-4-carbonyl]-amino}-4-amino-benzoic acid was prepared using essentially the same procedure as in Example 70, steps a, b and c, with the modification that cyclohexanecarboxaldehyde was used in step a instead of 2-dimethylamino-benzaldehyde and 3,4-diamino-benzoic acid methyl ester was used instead of 3-amino-benzoic acid benzyl ester in step c. Deprotection was carried out following essentially the procedure of Example 36, step d. The title compound was isolated as the dihydrochloride salt. $^1$H NMR (300 MHz, d$_6$-DMSO). 7.73 (1H, s), 7.56 (1H, d), 6.76 (1H, d), 6.0–4.00 (4H, br s), 2.90 (3H, m), 1.99–1.28 (27H, m). Found: C, 59.02; H, 7.38; N, 9.33%. C$_{29}$H$_{40}$Cl$_2$N$_4$O$_3$·1.5 H$_2$O requires: C, 58.98; H, 7.34; N, 9.49%.

EXAMPLE 132

(±)-3-{[5-(2-Adamantan-1-yl-propyl)-2-cyclohexyl-1H-imidazole-4-carbonyl]-amino}-benzoic Acid The title compound was prepared according to the procedure given in Example 70, with the modification that (±)-5-adamantan-1-yl-2,3-dioxo-hexanoic acid benzyl ester monohydrate was used instead of 5-adamantan-1-yl-2,3-dioxo-pentanoic acid benzyl ester monohydrate, and cyclohexylcarboxaldehyde was used instead of 2-dimethylamino-benzaldehyde in step a. $^1$H NMR (300 MHz, d$_6$-DMSO) 12.50 (1H, br s), 12.10 (1H, br s), 9.90 (1H, br s), 8.43 (1H, s), 7.90 (1H, d), 7.60 (1H, d), 7.41 (1H, t), 3.00 (1H, m), 2.71 (2H, m), 1.96–1.28 (26H, m), 0.61 (3H, d). The acid was converted to the N-methyl-D-glucamine salt and lyophilised from water/dioxan. Found: C, 61.28; H, 8.70; N, 7.55%. $C_{37}H_{56}N_4O_8\cdot2.3\ H_2O$ requires C, 61.19; H, 8.41; N, 7.77%.

EXAMPLE 133

3-({2-Cyclohexyl-5-[2-(1-methyl-cyclohexyl)-ethyl]-1H-imidazole-4-carbonyl}-amino)-benzoic Acid The title compound was prepared according to the procedure of Example 70, with the modification that 5-(1-methyl-cyclohexyl)-2,3-dioxo-pentanoic acid benzyl ester monohydrate and cyclohexylcarboxaldehyde were used in step a instead of 5-adamantan-1-yl-2,3-dioxo pentanoic acid benzyl ester monohydrate and 2-dimethylamino-benzaldehyde. $^1$H NMR (300 MHz, $d_6$-DMSO) 12.80 (1H, br s), 12.00 (1H, br s), 9.58 (1H, s), 8.45 (1H, s), 7.90 (1H, d), 7.59 (1H, d), 7.39 (1H, t), 2.85 (2H, m), 2.60 (1H, m), 1.89–1.25 (22H, m), 0.91 (3H, s). The acid was converted to the N-methyl-D-glucamine salt and lyophilised from water/dioxan. Found: C, 60.90; H, 8.52; N, 8.51%. $C_{33}H_{52}N_4O_8\cdot H_2O$ requires: C, 60.90; H, 8.36; N, 8.61%.

EXAMPLE 134

3-{[2-Cyclohexyl-5-(2-oxepan-2-yl-ethyl)-1H-imidazole-4-carbonyl]-amino}-benzoic Acid The title compound was prepared according to the procedure given in Example 70, with the modification that 5-oxepan-2-yl-2,3-dioxo-pentanoic acid benzyl ester monohydrate and cyclohexylcarboxaldehyde were used instead of 5-adamantan-1-yl-2,3-dioxo-pentanoic acid benzyl ester monohydrate and 2-dimethylamino-benzaldehyde in step a. $^1$H NMR (300 MHz, $d_6$-DMSO). 12.68 (1H, br s), 12.10 (1H, br s), 9.69 (1H, s), 8.47 (1H, s), 7.91 (1H, d), 7.60 (1H, d), 7.40 (1H, t), 3.75 (1H, m), 3.40 (2H, m), 2.94 (2H, m), 2.60 (1H, m), 1.90–1.27 (20H, m). The acid was converted to the N-methyl-D-glucamine salt and lyophilised from water/dioxan. Found: C, 58.14; H, 8.09; N, 8.41%. $C_{32}H_{50}N_4O_9\cdot1.5\ H_2O$ requires: C, 58.08; H, 8.07; N, 8.47%

EXAMPLE 135

5-{[5-(2-Adamantan-1-yl-ethyl)-2-cyclohexyl-1H-imidazole-4-carbonyl]-amino}-2-methyl-benzoic Acid The title compound was prepared using essentially the same procedure as in Example 70, with the modification that cyclohexanecarboxaldehyde was used in step a instead of 2-dimethylamino-benzaldehyde, and 5-amino-2-methyl-benzoic acid benzyl ester replaced 3-amino-benzoic acid benzyl ester in step c. $^1$H NMR (300 MHz, $d_6$-DMSO) 12.30 (1H, br s), 11.92 (1H, br s), 9.45 (1H, s), 8.29 (1H, s), 7.73 (1H, d), 7.19 (1H, d), 2.84(2H, m), 2.65 (1H, m), 2.45 (3H, s), 1.93–1.31 (27H, m). The acid was converted to the N-methyl-D-glucamine salt and lyophilised from water/dioxan. Found: 59.81; H, 8.49; N, 7.66%. $C_{37}H_{56}N_4O_8\cdot31H_2O$ requires: C, 60.14; H, 8.46; N, 7.58%.

EXAMPLE 136

(S)-3-{[5-(2-Adamantan-1-yl-ethyl)-2-pyrrolidin-2-yl-1H-imidazole-4-carbonyl]-amino}-benzoic Acid Step a. (S)-5-(2-Adamantan-1-yl-ethyl)-2-[1(9H-fluoren-9-ylmethoxycarbonyl)-pyrrolidin-2-yl]-1H-imidazole-4-carboxylic acid benzyl ester 5-Adamantan-1-yl-2,3-dioxo-pentanoic acid benzyl ester monohydrate (Example 70, step a ) (2.89 g, 7.77 mmol) was reacted with (S)-FMOC-pyrrolidine-2-carboxaldehyde (5.06 g, 15.54 mmol) using essentially the procedure of Example 20, step b. The crude product was purified by flash column chromatography (silica, DCM/ethyl acetate 4:1) to afford colourless oil (3.85 g, 76%). $^1$H NMR (300 MHz, CDCl$_3$) (Signals are broad and complex due to restricted rotation.) 10.37 (1H, br d), 7.79–7.30 (13H, m), 5.30 (2H, m), 4.90 (1H, m), 4.45 (2H, m), 4.26 (1H, m), 3.50 (2H, m), 2.79 (2H, m, 2.20–1.35 (21H, m).

Step b. (S)-5-(2-Adamantan-1-yl-ethyl)-2-[-(9H-fluoren-9-ylmethoxycarbonyl)-pyrrolidin-2-yl]-1H-imidazole-4-carboxylic Acid The product of step a (3.85 g, 5.88 mmol) was deprotected using the same procedure as in Example 1, step e to afford the acid as a white solid (3.05 g, 92%). $^1$H NMR (300 MHz, $d_6$-DMSO) (Signals are broad and complex due to restricted rotation.) 12.40–11.90 (2H, br m), 7.87–7.06 (8H, m), 5.00–4.79 (1H, m), 4.25–4.03 (3H, m), 3.61 (1H, br s), 3.40 (1H, br s), 2.2–1.27 (21H, m).

Step c. (S)-3-{[5-(2-Adamantan-1-yl-ethyl)-2-[(1-(9H-fluoren-9-ylmethoxycarbonyl)-pyrrolidin-2-yl]-1H-imidazole-4-carbonyl-amino}-benzoic Acid Benzyl Ester The product from step b (565 mg, 1 mmol) was reacted with 3-amino-benzoic acid benzyl ester (227 mg, 1 mmol) using essentially the procedure of Example 70, step c. The crude material was purified by flash column chromatography (silica, DCM/hexane/ethyl acetate, 2:2:1) to afford the product as a white solid (554 mg, 72%). $^1$H NMR (300 MHz, CDCl$_3$) 10.33 (1H, s), 9.13 (1H, s), 8.24 (1H, d), 8.07 (1H, s), 7.78 (3H, d), 7.60 (2H, d), 7.50–7.30 (10H, m), 5.39 (2H, s), 4.94 (1H, m), 4.48 (2H, m), 4.28 (1H, t), 3.53 (2H, m), 2.96 (2H, m), 2.2–1.54 (19H, m), 1.38 (2H, m).

Step d. (S)-3-{[5-(2-Adamantan-1-yl-ethyl)-2-pyrrolidin-2-yl-1H-imidazole-4-carbonyl]-amino}-benzoic Acid Benzyl Ester To a solution of the product from step c (554 mg, 0.72 mmol) in DCM (4 ml) was added piperidine (1 ml). After standing for 30 min at room temperature the solution was diluted with DCM (20 ml) and washed with water (3×20 ml). The solution was dried (MgSO$_4$), and the solvent was evaporated. The residue was purified by flash column chromatography (silica, DCM/MeOH, 9:1) to afford the product as a white solid (280 mg, 71%). $^1$H NMR (300 MHz, CDCl$_3$) 10.00 (1H, br s), 9.09 (1H, s), 8.20 (1H, d), 8.11 (1H, s), 7.77 (1H, d), 7.45–7.34 (6H, m), 5.38 (2H, s), 4.39 (1H, t), 3.06 (4H, m), 2.24–1.70 (19H, m), 1.40 (2H, t).

Step e

The product from step d (100 mg, 0.18 mmol) was deprotected using essentially the same procedure as in Example 1, step e, with the modification that the hydrogenation was carried out for 2 h. The title compound was isolated as a white solid (72 mg, 87%). $^1$H NMR (300 MHz, $d_6$-DMSO) 9.67 (1H, s), 8.40 (1H, s), 7.93 (1H, d), 7.62 (1H, d), 7.36 (1H, t), 4.40 (1H, t), 3.14 (2H, m), 2.90 (2H, m), 2.10–1.57 (19H, m), 1.38 (2H, m). The acid was converted to the N-methyl-D-glucamine salt and lyophilised from water/dioxan. Found: C, 58.77; H, 8.07; N, 10.03%. $C_{34}H_{51}N_5O_8\cdot2H_2O$ requires: C, 58.85; H, 7.99; N, 10.09%.

EXAMPLE 137

(S)-3-{[5-(2-Adamantan-1-yl-ethyl)-2-(1-methyl-pyrrolidin-2-yl)-1H-imidazole-4-carbonyl]-amino}-benzoic Acid Step a. (S)-3-{[5-(2-adamantan-1-yl-ethyl)-2-(1-methyl-pyrrolidin-2-yl)-1H-imidazole-4-carbonyl]-amino}-benzoic Acid Benzyl Ester To a rapidly stirred solution of (S)-3-{[5-(2-adamantan-1-yl-ethyl)-2-pyrrolidin-2-yl-1H-imidazole-4-carbonyl]- amino}-benzoic acid benzyl ester (Example 136, step d) (180 mg, 0.33 mmol) and formaldehyde (100 µl, 37% aqueous) in dichloroethane (5 ml) was added sodium triacetoxyborohydride (100 mg, 0.47 mmol). After stirring for 1 h at room temperature the reaction mixture was diluted with DCM and the solution was washed with saturated sodium bicarbonate. The organic layer was dried ($MgSO_4$) and the solvent was evaporated. The residue was purified by flash column chromatography (silica, DCM/hexane/IPA, 9:9:2) to afford the product as a white solid (130 mg, 71%). $^1$H NMR (300 MHz, $CDCl_3$) 9.70 (1H, br s), 9.12 (1H, s), 8.17 (1H, d), 8.12 (1H, s), 7.77 (1H, d), 7.47–7.35 (6H, m), 5.37 (2H, s), 3.41 (1H, m), 3.20 (1H, m), 3.06 (2H, m), 2.30 (4H, s+m),1.96–1.55 (19H, m), 1.42 (2H, m).

Step b

The product from step a (130 mg, 0.236 mmol) was deprotected using the same procedure as in Example 136, step e, to afford the title compound as a white solid (107 mg, 98%). $^1$H NMR (300 MHz, $d_6$-DMSO) 12.30 (1H, br s), 9.72 (1H, s), 8.48 (1H, s), 7.92 (1H, d), 7.60 (1H, d), 7.40 (1H, t), 3.80 (1H, m), 3.25 (2H, m), 2.90 (2H, m), 2.34 (3H, s), 2.2–1.3 (21H, m). The acid was converted to the N-methyl-D-glucamine salt and lyophilised from water/dioxan. Found: C, 58.08; H, 8.34; N, 9.88%. $C_{35}H_{53}N_5O_8 \cdot 3H_2O$ requires: C, 57.91; H, 8.19; N, 9.65 %.

EXAMPLE 138

(S)-5-{[5-(2-Adamantan-1-yl-ethyl)-2-(1-methyl-pyrrolidin-2-yl)-1H-imidazole-4-carbonyl]-amino}-2-methyl-benzoic Acid (S)-5-{[5-(2-Adamantan-1-yl-ethyl)-2-pyrrolidin-2-yl-1H-imidazole-4-carbonyl]-amino}-2-methyl-benzoic acid benzyl ester was prepared using essentially the same procedure as in Example 136, steps a, b, c, d, with the modification that 5-amino-2-methyl-benzoic acid benzyl ester was used in step c instead of 3-amino-benzoic acid benzyl ester. The product was converted to the title compound following the procedure given in Example 137, steps a and b. $^1$H NMR (300 MHz, $d_6$-DMSO) 12.10 (1H, br s), 9.56 (1H, s), 8.31 (1H, s), 7.75 (1H, d), 7.17 (1H, d), 3.28 (1H, t), 3.09 (1H, t), 2.88 (2H, m), 2.44 (3H, s), 2.15 (3H, s), 2.2–1.50 (20H, m), 1.36 (2H, m). The acid was converted to the N-methyl-D-glucamine salt and lyophilised from water/dioxan. Found: C, 59.98; H, 8.20; N, 9.55%. $C_{36}H_{55}N_5O_8 \cdot 2H_2O$ requires: C, 59.90; H, 8.24; N, 9.70%.

EXAMPLE 139

(±)-3-{[5-(2-Adamantan-1-yl-ethyl)-2-(1-methyl-piperidin-2-yl)-1H-imidazole-4-carbonyl]-amino}-benzoic Acid (±)-3-{[5-(2-Adamantan-1-yl-ethyl)-2-piperidin-2-yl-1H-imidazole-4-carbonyl]-amino}-benzoic acid benzyl ester was prepared using essentially the same procedure as in Example 136, steps a, b, c, d, with the modification that that (±)-FMOC-piperidine-2-carboxaldehyde was used in step a instead of (S)-FMOC-pyrrolidine-2-carboxaldehyde. The product was converted to the title compound following the procedure given in Example 137, steps a and b. $^1$H NMR (300 MHz, $d_6$-DMSO) 12.20 (1H, br s), 9.65 (1H, s), 8.49 (1H, s), 7.87 (1H, d), 7.60 (1H, d), 7.38 (1H, t), 3.06 (1H, t), 2.94 (3H, m), 2.01 (1H, m), 1.94 (3H, s), 1.90–1.57 (21H, m), 1.36 (2H, m). The acid was converted to the N-methyl-D-glucamine salt and lyophilised from water/dioxan. Found: C, 60.07; H, 8.51; N, 9.88%. $C_{36}H_{55}N_5O_8 \cdot 2H_2O$ requires: C, 59.90; H, 8.24; N, 9.70%.

EXAMPLE 140

(±)-3-{[5-(2-Adamantan-1-yl-ethyl)-2-[1-(2-methyl-propyl)-piperidin-2-yl])-1H-imidazole-4-carbonyl]-amino}-benzoic Acid (±)-3-{[5-(2-Adamantan-1-yl-ethyl)-2-piperidin-2-yl-1H-imidazole-4-carbonyl]-amino}-benzoic acid benzyl was prepared using essentially the same procedure as in Example 136, steps a, b, c, d, with the modification that that (±)-FMOC-piperidine-2-carboxaldehyde was used in step a instead of (S)-FMOC-pyrrolidine-2-carboxaldehyde. The product was converted to the title compound following the procedure given in Example 137, steps a and b, with the modification that 2-methyl propanal was used in step a instead of formaldehyde. $^1$H NMR (300 MHz, $d_6$-DMSO) 12.00 (1H, br s), 9.64 (1H, s), 8.48 (1H, s), 7.88 (1H, d), 7.59 (1H, d), 7.38 (1H, t), 3.19 (1H, m), 3.05 (2H, m), 2.80 (1H, m), 1.93–1.50 (24H, m), 1.34 (2H, m), 0.90–0.66 (7H, m). The acid was converted to the N-methyl-D-glucamine salt and lyophilised from water/dioxan. Found: C, 61.26; N, 8.64; N, 9.02%. $C_{39}H_{61}N_5O_8 \cdot 2H_2O$ requires: C, 61.32; H, 8.58; N, 9.17%.

EXAMPLE 141

(±)-5-{[5-(2-Adamantan-1-yl-ethyl)-2-[1-methyl-piperidin-2-yl])-1H-imidazole-4-carbonyl]-amino}-2-methyl-benzoic Acid (±)-5-{[5-(2-Adamantan-1-yl-ethyl)-2-piperidin-2-yl-1H-imidazole-4-carbonyl]-amino}-2-methyl-benzoic acid benzyl was prepared using essentially the same procedure as in Example 136, steps a, b, c, d, with the modification that that (±)-FMOC-piperidine-2-carboxaldehyde was used instead of (S)-FMOC-pyrrolidine-2-carboxaldehyde in step a, and 5-amino-2-methyl-benzoic acid benzyl ester replaced 3-amino-benzoic acid benzyl ester in step c. The product was converted to the title compound following the procedure given in Example 137, steps a and b. $^1$H NMR (300 MHz, $d_6$-DMSO) 12.20 (1H, br s), 9.53 (1H, s), 8.30 (1H, s), 7.76 (1H, d), 7.18 (1H, d), 3.2–2.88 (4H, m), 2.48 (3H, s), 2.45 (3H, s), 2.00–1.33 (24H, m). The acid was converted to the N-methyl-D-glucamine salt and lyophilised from water/dioxan. Found: C, 59.67; H, 8.51; N, 9.68%. $C_{37}H_{57}N_5O_8 \cdot 2H_2O$ requires: C, 61.32; H, 8.58; N, 9.17%.

EXAMPLE 142

5-{[5-(2-Adamantan-1-yl-ethyl)-2-[1-(2-methyl-propyl)-piperidin-2-yl])-1H-imidazole-4-carbonyl]-amino}-2-methyl-benzoic Acid 5-{[5-(2-Adamantan-1-yl-ethyl)-2-piperidin-2-yl-1H-imidazole-4-carbonyl]-amino}-2-methyl-benzoic acid benzyl was prepared using essentially the same procedure as in Example 136, steps a, b, c, d, with the modification that that FMOC-piperidine-2-carboxaldehyde was used instead of (S)-FMOC-pyrrolidine-2-carboxaldehyde in step a, and 5-amino-2-methyl-benzoic acid benzyl ester replaced 3-amino-benzoic acid benzyl ester in step c. The product was converted to the title compound following the procedure given in Example 137, steps a and b, with the modification that 2-methyl propanal was used in step a instead of formaldehyde. $^1$H NMR (300 MHz, $d_6$-DMSO) 12.00 (1H, br s), 9.52 (1H, s), 8.30 (1H, s), 7.34 (1H, d), 7.19 (1H, d), 3.00–2.60 (4H, m, 2.45 (3H, s), 2.00–1.34 (26H, m), 0.88–0.67 (7H, m). The acid was converted to the N-methyl-D-glucamine salt and lyophilised from water/dioxan. Found: C, 60.09; H, 8.72; N, 8.92%. $C_{40}H_{63}N_5O_8 \cdot 2.5\, H_2O$ requires: C, 61.05; H, 8.71; N, 8.92%.

EXAMPLE 143

(R)-3-{[5-(2-Adamantan-1-yl-ethyl)-2-(]-methyl-pyrrolidin-2-yl)-1H-imidazole-4-carbonyl]-amino}-benzoic Acid (R)-3-{[5-(2-Adamantan-1-yl-ethyl)-2-pyrrolidin-2-yl-1H-imidazole-4-carbonyl]-amino}-benzoic acid benzyl ester was prepared using essentially the same procedure as in Example 136, steps a, b, c, d, with the modification that that (R)-FMOC-pyrrolidin-2-carboxaldehyde was used in step a instead of (S)-FMOC-pyrrolidine-2-carboxaldehyde. The product was converted to the title compound following the procedure given in Example 137, steps a and b. $^1$H NMR (300 MHz, $d_6$-DMSO) 12.30 (1H, br s), 9.72 (1H, s), 8.48 (1H, s), 7.92 (1H, d), 7.60 (1H, d), 7.40 (1H, t), 3.80 (1H, m), 3.25 (2H, m), 2.90 (2H, m), 2.34 (3H, s), 2.20–1.30 (21H, m). The acid was converted to the N-methyl-D-glucamine salt and lyophilised from water/dioxan. Found: C, 60.79; H, 8.29; N, 9.89%. $C_{35}H_{53}N_5O_8 \cdot H_2O$ requires: C, 60.94; H, 8.04; N, 10.15%.

EXAMPLE 144

(R)-3-{[5-(2-Adamantan-1-yl-ethyl)-2-[1-(2-methyl-propyl)-pyrrolidin-2-yl]-1H-imidazole-4-carbonyl]-amino}-benzoic Acid (R)-3-{[5-(2-Adamantan-1-yl-ethyl)-2-pyrrolidin-2-yl-1H-imidazole-4-carbonyl]-amino)}-benzoic acid benzyl ester was prepared using essentially the same procedure as in Example 136, steps a, b, c, d, with the modification that that (R)-FMOC-pyrrolidin-2-carboxaldehyde was used in step a instead of (S)-FMOC-pyrrolidine-2-carboxaldehyde. The product was converted to the title compound following the procedure given in Example 137, steps a and b, with the modification that 2-methyl propanal was used in step a instead of formaldehyde. $^1$H NMR (300 MHz, $d_6$-DMSO) 12.00 (1H, br s), 9.68 (1H, s), 8.49 (1H, s), 7.90 (1H, d), 7.58 (1H, d), 7.38 (1H, t), 3.41 (2H, m), 3.20 (2H, m), 3.00 (1H, m), 2.80 (1H, m), 2.10–1.49 (21H, m), 1.35 (2H, m), 0.89–0.73 (7H, m). The acid was converted to the N-methyl-D-glucamine salt and lyophilised from water/dioxan. Found: C, 61.77; H, 8.60; N, 9.55%. $C_{38}H_{59}N_5O_8 \cdot 1.5\, H_2O$ requires: C, 61.60; H, 8.44; N, 9.45%.

EXAMPLE 145

3-{[5-(2-Adamantan-1-yl-ethyl)-2-naphthalen-1-yl-1H-imidazole-4-carbonyl]-amino}-benzoic Acid The title compound was prepared according to the procedure of Example 70, with the modofication that 1-naphthaldehyde was used in step a instead of 2-dimethylamino-benzaldehyde. $^1$H NMR (300 MHz, $d_6$-DMSO) 12.83 (1H, br s), 9.87 (1H, s), 8.88 (1H, d), 8.51 (1H, s), 8.00 (3H, m), 7.84 (1H, d), 7.61 (4H, m), 7.42 (1H, t), 3.05 (2H, m), 1.96 (3H, s), 1.71–1.46 (14H, m). The acid was converted to the N-methyl-D-glucamine salt and lyophilised from water/dioxan. Found: C, 62.38; H, 7.49; N, 7.26%. $C_{40}H_{50}N_4O_8 \cdot 3.1H_2O$ requires: C, 62.34; H, 7.35; N, 7.27%.

EXAMPLE 146

3-{[5-(2-Adamantan-1-yl-ethyl)-2-(2,4-dichlorophenyl)-1H-imidazole-4-carbonyl]-amino}-benzoic Acid The title compound was prepared according to the procedure of Example 68, using 2,4-dichlorobenzaldehyde instead of 3,4-dichlorobenzaldehyde. $^1$H NMR (300 MHz, $d_6$-DMSO) 12.90 (1H, br s), 12.70 (1H, br s), 9.84 (1H, s), 8.49 (1H, s), 7.95 (1H, d), 7.81 (2H, m), 7.59 (2H, m), 7.41 (1H, t), 3.00 (2H, m), 1.95 (3H, s), 1.64 (6H, m), 1.54 (6H, s), 1.42 (2H, m). The acid was converted to the N-methyl-D-glucamine salt and lyophilised from water/dioxan. Found: C, 56.95; H, 6.68; N, 7.53%. $C_{36}H_{46}Cl_2N_4O_8 \cdot 1.5$ mol $H_2O$ requires: C, 56.87; H, 6.49; N, 7.37%.

EXAMPLE 147

3-{[5-(2-Adamantan-1-yl-ethyl)-2-(3,5-dichlorophenyl)-1H-imidazole-4-carbonyl]-amino}-benzoic Acid The title compound was prepared according to the procedure of Example 68, using 3,5-dichlorobenzaldehyde instead of 3,4-dichlorobenzaldehyde. $^1$H NMR (300 MHz, $d_6$-DMSO) 12.92 (2H, br s), 9.94 (1H, s), 8.50 (1H, s), 8.14 (2H, m), 8.04 (1H, d), 7.63 (2H, m), 7.43 (1H, t), 2.97 (2H, m), 1.95 (3H, s), 1.64 (6H, m), 1.54 (6H, s), 1.43 (2H, m). The acid was converted to the N-methyl-D-glucamine salt and lyophilised from water/dioxan. Found: C, 56.95; H, 6.68; N, 7.53%. $C_{36}H_{46}Cl_2N_4O_8 \cdot 1.5$ mol $H_2O$ requires: C, 56.87; H, 6.49; N, 7.37%.

EXAMPLE 148

3-{[5-(2-Adamantan-1-yl-ethyl)-2-(2,6-dichlorophenyl)-1H-imidazole-4-carbonyl]-amino}-benzoic Acid The title compound was prepared according to the procedure of Example 68, using 2,6-dichlorobenzaldehyde instead of 3,4-dichlorobenzaldehyde. $^1$H NMR (300 MHz, $d_6$-DMSO) 12.84 (1H, br s), 12.77 (1H, s), 9.88 (1H, s), 8.56 (1H, s), 7.92 (1H, m), 7.60 (4H, m), 7.39 (1H, t), 3.01 (2H, m), 1.94 (3H br s), 1.65 (6H, m), 1.52 (6H, s), 1.43 (2H, m). The acid was converted to the N-methyl-D-glucamine salt and lyophilised from water/dioxan. Found: C, 56.55; H, 6.57; N, 7.15%. $C_{36}H_{46}Cl_2N_4O_8 \cdot 1.8$ mol $H_2O$ requires: C, 56.41; H, 6.53; N, 7.31%.

EXAMPLE 149

5-{[5-(2-Adamantan-1-yl-ethyl)-2-(2,6-dichlorophenyl)-1H-imidazole-4-carbonyl]-amino}-2-methyl-benzoic Acid The title compound was prepared according to the procedure of Example 68, using 2,6-dichlorobenzaldehyde instead of 3,4-dichlorobenzaldehyde and 5-amino-2-methyl-benzoic acid methyl ester instead of 3-amino-benzoic acid methyl ester. $^1$H NMR (300 MHz, $d_6$-DMSO) 12.74 (2H, br s), 9.75 (1H, s), 8.39 (1H, s), 7.77 (1H, d), 7.60 (3H, m), 7.19 (1H, d), 3.00 (2H, m), 2.45 (3H, s), 1.93 (3H, br s), 1.64 (6H, m), 1.51 (6H, s), 1.43 (2H, m). The acid was converted to the N-methyl-D-glucamine salt and lyophilised from water/dioxan. Found: C, 57.53; H, 6.70; N, 7.12%. $C_{37}H_{48}Cl_2N_4O_8 \cdot 1.5$ mol $H_2O$ requires: C, 57.42; H, 6.63; N, 7.24%.

EXAMPLE 150

5-{[5-(2-Adamantan-1-yl-ethyl)-2-(2,3-dichlorophenyl)-1H-imidazole-4-carbonyl]-amino}-2-methyl-benzoic Acid The title compound was prepared according to the procedure of Example 68, using 2,3-dichlorobenzaldehyde instead of 3,4-dichlorobenzaldehyde and 5-amino-2-methyl-benzoic acid methyl ester instead of 3-amino-benzoic acid methyl ester. $^1$H NMR (300 MHz, d$_6$-DMSO) 12.73 (2H, s), 9.72 (1H, s), 8.33 (1H, s), 7.74 (3H, m), 7.50 (1H, m), 7.20 (1H, d), 2.99 (2H, m), 2.46 (3H, s), 1.94 (3H, s), 1.65 (6H, m), 1.53 (6H, s), 1.42 (2H, m). The acid was converted to the N-methyl-D-glucamine salt and lyophilised from water/dioxan. Found: C, 56.31; H, 6.62; N, 7.07%. $C_{37}H_{48}Cl_2N_4O$.2.2 mols $H_2O$ requires: C, 56.40; H, 6.71; N, 7.11%.

EXAMPLE 151

5-{[5-(2-Adamantan-1-yl-ethyl)-2-(2,4-dimethyl-phenyl)-1H-imidazole-4-carbonyl]-amino}-2-methyl-benzoic Acid The title compound was prepared according to the procedure of Example 70, with the modification that 2,4-dimethylbenzaldehyde was used instead of 2-dimethylamino-benzaldehyde in step a, and 5-amino-2-methyl-benzoic acid benzyl ester replaced 3-amino-benzoic acid benzyl ester in step c. $^1$H NMR (300 MHz, d$_6$-DMSO) 12.45 (1H, br s), 9.59 (1H, s), 8.29 (1H, s), 7.78 (1H, dd), 7.48 (1H, d), 7.20 (1H, d), 7.10 (2H, m), 2.96 (2H, m), 2.52 (3H, s), 2.46 (3H, s), 2.31 (3H, s), 1.95 (3H, s), 1.65 (6H, m), 1.53 (6H, s), 1.42 (2H, m). The acid was converted to the N-methyl-D-glucamine salt and lyophilised from water/dioxan. Found: C, 63.12; H, 7.77; N, 7.40%. $C_{39}H_{54}N_4O_8$.2.0 mols $H_2O$ requires: C, 63.04; H, 7.87; N, 7.54%.

EXAMPLE 152

5-{[5-(2-Adamantan-1-yl-ethyl)-2-(2,4-difluoro-phenyl)-1H-imidazole-4-carbonyl]-amino}-2-methyl-benzoic Acid The title compound was prepared according to the procedure of Example 70, with the modification that 2,4-difluoro-benzaldehyde was used instead of 2-dimethylamino-benzaldehyde in step a, and 5-amino-2-methyl-benzoic acid benzyl ester replaced 3-amino-benzoic acid benzyl ester in step c. $^1$H NMR (300 MHz, d$_6$-DMSO) 12.80 (1H, br s), 12.52 (1H, br s), 9.74 (1H, s), 8.32 (1H, s), 8.13 (1H, m), 7.83 (1H, dd), 7.43 (1H, m), 7.24 (2H, m), 2.98 (2H, m), 2.46 (3H, s), 1.95 (3H, s), 1.65 (6H, m), 1.53 (6H, s), 1.40 (2H, m). The acid was converted to the N-methyl-D-glucamine salt and lyophilised from water/dioxan. Found: C, 60.55; H, 6.92; N, 7.40%. $C_{37}H_{48}F_2N_4O_8$.1.2 mols $H_2O$ requires: C, 60.36; H, 6.90; N, 7.61%.

EXAMPLE 153

5-{[5-(2-Adamantan-1-yl-ethyl)-2-(2,6-dimethyl-phenyl)-1H-imidazole-4-carbonyl]-amino}-2-methyl-benzoic Acid The title compound was prepared according to the procedure of Example 70, with the modification that 2,6-dimethylbenzaldehyde (L. Xiang, H. Wu and V. Hruby, Tetrahedron: Asymmetry, 1995, 6, 83) was used instead of 2-dimethylamino-benzaldehyde in step a, and 5-amino-2-methyl-benzoic acid benzyl ester replaced 3-amino-benzoic acid benzyl ester in step c. $^1$H NMR (300 MHz, d$_6$-DMSO) 12.70 (1H, br s), 12.40 (1H, br s), 9.70 (1H, s), 8.36 (1H, s), 7.78 (1H, dd), 7.28–7.12 (4H, m), 2.99 (2H, m), 2.45 (3H, s), 2.10 (6H, s), 1.93 (3H, s), 1.64 (6H, m), 1.51 (6H, s), 1.43 (2H, m). The acid was converted to the N-methyl-D-glucamine salt and lyophilised from water/dioxan. Found: C, 63.80; H, 7.77; N, 7.67%. $C_{39}H_{54}N_4O_8$.1.5 mols $H_2O$ requires: C, 63.86; H, 7.83; N, 7.64%.

EXAMPLE 154

3-{[5-(2-Adamantan-1-yl-ethyl)-2-(2,4,6-trimethyl-phenyl)-1H-imidazole-4-carbonyl]-amino}-benzoic Acid The title compound was prepared according to the procedure of Example 70, with the modification that 2,4,6-trimethylbenzaldehyde was used instead of 2-dimethylamino-benzaldehyde in step a. $^1$H NMR (300 MHz, d$_6$-DMSO) 12.36 (1H, br s), 9.80 (1H, s), 8.52 (1H, s), 7.92 (1H, d), 7.60 (1H, d), 7.38 (1H, t), 6.95 (2H, s), 2.99 (2H, m), 2.88 (3H, s), 2.07 (6H, s), 1.93 (3H, s), 1.63 (6H, m), 1.51 (6H, s), 1.43 (2H, m). The acid was converted to the N-methyl-D-glucamine salt and lyophilised from water/dioxan. Found: C, 62.32; H, 8.06; N, 7.31%. $C_{39}H_{54}N_4O_8$.2.5 mols $H_2O$ requires: C, 62.28; H, 7.91; N, 7.45%.

EXAMPLE 155

5-{[5-(2-Adamantan-1-yl-ethyl)-2-(2,4,6-trimethyl-phenyl)-1H-imidazole-4-carbonyl]-amino}-2-methyl-benzoic Acid The title compound was prepared according to the procedure of Example 70, with the modification that 2,4,6-trimethylbenzaldehyde was used instead of 2-dimethylamino-benzaldehyde in step a, and 5-amino-2-methyl-benzoic acid benzyl ester replaced 3-amino-benzoic acid benzyl ester in step c. $^1$H NMR (300 MHz, d$_6$-DMSO) 12.75 (1H, br s), 12.33 (1H, br s), 9.68 (1H, s), 8.35 (1H, d), 7.77 (1H, dd), 7.18 (1H, d), 6.95 (2H, s), 2.98 (2H, m), 2.45 (3H, s), 2.28 (3H, s), 2.06 (6H, s), 1.93 (3H, s), 1.63 (6H, m), 1.51 (6H, s), 1.42 (2H, m). The acid was converted to the N-methyl-D-glucamine salt and lyophilised from water/dioxan. Found: C, 62.94; H, 7.90; N, 7.51%. $C_{40}H_{56}N_4O_8$.2.3 mols $H_2O$ requires: C, 63.10; H, 8.01; N, 7.36%.

EXAMPLE 156

5-{[5-(2-Adamantan-1-yl-ethyl)-2-(2,4,6-trimethyl-phenyl)-1H-imidazole-4-carbonyl]-amino}-2-fluoro-benzoic Acid 5-{[5-(2-Adamantan-1-yl-ethyl)-2-(2,4,6-trimethyl-phenyl)-1H-imidazole4-carbonyl]-amino}-2-fluoro-benzoic acid methyl ester was prepared according to the procedure of Example 70, steps a,b, and c, with the modification that 2,4,6-trimethylbenzaldehyde was used instead of 2-dimethylamino-benzaldehyde in step a, and 5-amino-2-fluoro-benzoic acid methyl ester replaced 3-amino-benzoic acid benzyl ester in step c. Deprotection was carried out following essentially the procedure of Example 36, step d to afford the title compound. $^1$H NMR (300 MHz, d$_6$-DMSO) 12.35 (1H, br s), 9.88 (1H, s), 8.44 (1H, dd), 7.95 (1H, m), 7.21 (1H, t), 6.95 (2H, s), 2.98 (2H, m), 2.28 (3H, s), 2.06 (6H, s), 1.93 (3H, s), 1.62 (6H, m), 1.51 (6H, s), 1.42 (2H, m). The acid converted to the N-methyl-D-glucamine salt and lyophilised from water/dioxan. Found: C, 61.85; H, 7.80; N, 7.14%. $C_{39}H_{53}FN_4O_8$.1.9 mols $H_2O$ requires: C, 61.74; H, 7.54; N, 7.38%.

EXAMPLE 157

(3-{[5-(2-Adamantan-1-yl-ethyl)-2-(2,4,6-trimethyl-phenyl)-1H-imidazole-4-carbonyl]-amino}-phenyl)-acetic Acid The title compound was prepared according to the procedure of Example 70, with the modification that 2,4,6- trimethylbenzaldehyde was used instead of 2-dimethylamino-benzaldehyde in step a, and (3-aminophenyl)-acetic acid benzyl ester replaced 3-amino-benzoic acid benzyl ester in step c. $^1$H NMR (300 MHz, d$_6$-DMSO) 12.30 (1H, br s), 9.53 (1H, s), 7.73 (1H, s), 7.60 (1H, d), 7.20 (1H, t), 6.92 (3H, m), 3.56 (2H, s), 2.98 (2H, m), 2.28 (3H, s), 2.06 (6H, s), 1.92 (3H, s), 1.63 (6H, m), 1.50 (6H, s), 1.42 (2H, m). The acid was converted to the N-methyl-D-glucamine salt and lyophilised from water/dioxan. Found: C, 62.98; H, 8.04; N, 7.27%. C$_{40}$H$_{56}$N$_4$O$_8$.2.4 mols H$_2$O requires: C, 62.93; H, 8.02; N, 7.34%.

EXAMPLE 158

3-{[5-(2-Adamantan-1-yl-ethyl)-2-(2-ethyl-phenyl)-1H-imidazole-4-carbonyl]-amino}-benzoic Acid The title compound was prepared according to the procedure of Example 70, with the modification that 2-ethylbenzaldehyde was used instead of 2-dimethylamino-benzaldehyde in step a. $^1$H NMR (300 MHz, d$_6$-DMSO) 13.00 (1H, br s), 12.56 (1H, br s), 9.70 (1H, s), 8.47 (1H, s), 7.90 (1H, d), 7.62 (1H, d), 7.51 (1H, d), 7.44–7.29 (4H, m), 2.95 (4H, m), 1.94 (3H, br s), 1.64 (6H, m), 1.53 (6H, s), 1.44 (2H, m), 1.11 (3H, t). The acid was converted to the N-methyl-D-glucamine salt and lyophilised from water/dioxan. Found: C, 62.90; H, 7.75; N, 7.66%. C$_{38}$H$_{52}$N$_4$O$_8$.1.8 mols H$_2$O requires: C, 62.88; H, 7.73; N, 7.72%.

EXAMPLE 159

5-{[5-(2-Adamantan-1-yl-ethyl)-2-(2-ethyl-phenyl)-1H-imidazole-4-carbonyl]-amino}-2-methyl-benzoic Acid The title compound was prepared according to the procedure of Example 70, with the modification that 2-ethylbenzaldehyde was used instead of 2-dimethylamino-benzaldehyde in step a, and 5-amino-2-methyl-benzoic acid benzyl ester replaced 3-amino-benzoic acid benzyl ester in step c. $^1$H NMR (300 MHz, d$_6$-DMSO) 12.80 (1H, br s), 12.53 (1H, br s), 9.58 (1H, s), 8.30 (1H, d), 7.76 (1H, dd), 7.50 (1H, d), 7.30 (3H, m), 7.21 (1H, d), 2.95 (4H, m), 2.46 (3H, s), 1.94 (3H, s), 1.65 (6H, m), 1.53 (6H, s), 1.43 (2H, m), 1.10 (3H, t). The acid was converted to the N-methyl-D-glucamine salt and lyophilised from water/dioxan. Found: C, 64.56; H, 7.88; N, 7.54%. C$_{40}$H$_{56}$N$_4$O$_8$.1.0 mol H$_2$O requires: C, 64.46; H, 7.80; N, 7.71%.

EXAMPLE 160

3-{[5-(2-Adamantan-1-yl-ethyl)-2-(2,4,6-trimethoxy-phenyl)-1H-imidazole-4-carbonyl]-amino}-benzoic Acid The title compound was prepared according to the procedure of Example 70, with the modification that 2,4,6-trimethoxybenzaldehyde was used instead of 2-dimethylamino-benzaldehyde in step a. $^1$H NMR (300 MHz, d$_6$-DMSO) 12.85 (1H, br s), 12.16 (1H, br s), 9.73 (1H, s), 8.55 (1H, s), 7.89 (1H, d), 7.59 (1H, d), 7.38 (1H, t), 6.29 (2H, s), 3.83 (3H, s), 3.68 (6H, s), 2.92 (2H, m), 1.94 (3H, br s), 1.64 (6H, m), 1.52 (6H, br s), 1.40 (2H, m). The acid was converted to the N-methyl-D-glucamine salt and lyophilised from water/dioxan. Found: C, 57.87; H, 7.65; N, 7.42%. C$_{39}$H$_{54}$N$_4$O$_{11}$.3.0 mols H$_2$O requires: C, 57.91; H, 7.48; N, 6.93%.

EXAMPLE 161

5-{[5-(2-Adamantan-1-yl-ethyl)-1-methyl-2-o-tolyl-1H-imidazole-4-carbonyl]-amino}-2-methyl-benzoic Acid The title compound was prepared according to the procedure of Example 73, with the modification that 5-amino-2-methyl-benzoic acid benzyl ester replaced 3-amino-benzoic acid benzyl ester in step c. $^1$H NMR (300 MHz, d$_6$-DMSO) 12.73 (1H, br s), 9.72 (1H, s), 8.36 (1H, d), 7.78 (1H, m), 7.45–7.29 (4H, m), 7.20 (1H, d), 3.34 (3H, s), 3.02 (2H, m), 2.45 (3H, s), 2.16 (3H, s), 1.96 (3H, s), 1.72–1.58 (12H, m), 1.32 (2H, m), The acid was converted to the N-methyl-D-glucamine salt and lyophilised from water/dioxan. Found: C, 62.28; H, 7.99; N, 7.37%. C$_{39}$H$_{54}$N$_4$O$_8$.2.5 mols H$_2$O requires: C, 62.30; H, 7.91; N, 7.45%.

EXAMPLE 162

5-{[5-(2-Adamantan-1-yl-ethyl)-3-methyl-2-o-tolyl-3H-imidazole-4-carbonyl]-amino}-2-methyl-benzoic Acid 5-(2-Adamantan-1-yl-ethyl)-3-methyl-2-o-tolyl-3H-imidazole-4-carboxylic acid ethyl ester (Example 73, step a) was converted to the title compound according to the procedure of Example 73, steps b, c and d, with the modification that 5-amino-2-methyl-benzoic acid benzyl ester replaced 3-amino-benzoic acid benzyl ester in step c. $^1$H NMR (300 MHz, d$_6$-DMSO) 10.11 (1H, br s), 8.18 (1H, d), 7.72 (1H, dd), 7.44–7.24 (5H, m), 3.46 (3H, s), 2.71 (2H, m), 2.47 (3H, s), 2.17 (3H, s), 1.85 (3H, br s), 1.65–1.52 (6H, m), 1.42–1.34 (8H, m). The acid was converted to the N-methyl-D-glucamine salt and lyophilised from water/dioxan. Found: C, 63.17; H, 7.70; N, 7.36%. C$_{39}$H$_{54}$N$_4$O$_8$.2.0 mols H$_2$O requires: C, 63.05; H, 7.87; N, 7.54%.

EXAMPLE 163

(3-{[5-(2-Adamantan-1-yl-ethyl)-1-methyl-2-(2,4,6-trimethyl-phenyl)-1H-imidazole-4-carbonyl]-amino}-phenyl)-acetic Acid Step a. 5-(2-Adamantan-1-yl-ethyl)-1-methyl-2-(2,4,6-trimethyl-phenyl)-1H-imidazole-4-carboxylic Acid Benzyl Ester and 5-(2-adamantan-1-yl-ethyl)-3-methyl-2-(2,4,6-trimethyl-phenyl)-3H-imidazole-4-carboxylic Acid Benzyl Ester 5-(2-Adamantan-1-yl-ethyl)-2-(2,4,6-trimethyl-phenyl)-1H-imidazole-4-carboxylic acid benzyl ester (prepared according to the procedure of Example 70, step a using 2,4,6-trimethylbenzaldehyde instead of 2-dimethylamino-benzaldehyde) was converted to the two isomeric N-methyl derivatives according to the procedure of Example 73, step a.

Step b 5-(2-Adamantan-1-yl-ethyl)-1-methyl-2-(2,4,6-trimethyl-phenyl)-1H-imidazole-4-carboxylic acid benzyl ester (the low R$_f$ material isolated in step a) was converted to the title compound according to the procedure given in Example 73, steps b, c and d, with the modification that (3-aminophenyl)-acetic acid benzyl ester replaced 3-amino-benzoic acid benzyl ester in step c. $^1$H NMR (300 MHz, d$_6$-DMSO) 9.56 (1H, s), 7.74 (1H, s), 7.62 (1H, d), 7.21 (1H, t), 6.99 (2H, s), 6.92 (1H, d), 3.50 (2H, s), 3.23 (3H, s), 3.03 (2H, m), 2.30 (3H, s), 1.95 (9H, br s), 1.71–1.57 (12H, m), 1.32 (2H, m). The acid was converted to the N-methyl-D-glucamine salt and lyophilised from water/dioxan. Found: C, 63.77; H, 8.40; N, 7.09%. C$_{41}$H$_{58}$N$_4$O.2.2 mols H$_2$O requires: C, 63.58; H, 8.12; N, 7.23%.

EXAMPLE 164

(3-{[5-(2-Adamantan-1-yl-ethyl)-3-methyl-2-(2,4,6-trimethyl-phenyl)-3H-imidazole-4-carbonyl]-amino}-phenyl)-acetic Acid 5-(2-Adamantan-1-yl-ethyl)-3-methyl-2-(2,4,6-trimethyl-phenyl)-3H-imidazole-4-carboxylic acid benzyl ester (Example 163, step a, high $R_f$ material) was converted to the title compound according to the procedure given in Example 73, steps b, c and d, with the modification that (3-aminophenyl)-acetic acid benzyl ester replaced 3-amino-benzoic acid benzyl ester in step c. $^1$H NMR (300 MHz, $d_6$-DMSO) 10.00 (1H, s), 7.63 (1H, s), 7.53 (1H, d), 7.27 (1H, t), 6.97 (3H, m), 3.53 (2H, s), 3.33 (3H, s), 2.73 (2H, m), 2.29 (3H, s), 1.95 (6H, s), 1.86 (3H, br s), 1.56 (6H, m), 1.38 (8H, m). The acid was converted to the N-methyl-D-glucamine salt and lyophilised from water/dioxan. Found: C, 63.66; H, 8.29; N, 7.00%. $C_{41}H_{58}N_4O_8$.2.3 mols $H_2O$ requires: C, 63.44; H, 8.13; N, 7.22%.

EXAMPLE 165

3-[(5-Cycloheptylmethyl-2-o-tolyl-1H-imidazole-4-carbonyl)-amino]-benzoic Acid The title compound was prepared according to the procedure of Example 20, with the modification that o-tolualdehyde was used instead of 2-naphthaldehyde in step b, and 3-amino-benzoic acid benzyl ester replaced 5-amino-isophthalic acid dibenzyl ester in step d. $^1$H NMR (300 MHz, $d_6$-DMSO) 13.00 (1H, br s), 12.52 (1H, br s), 9.78 (1H, s), 8.51 (1H, s), 7.93 (1H, m), 7.60 (2H, m), 7.41 (1H, t), 7.32 (3H, m), 2.93 (2H, d), 2.54 (3H, s), 2.00 (1H, m), 1.66–1.22 (12H, m). The acid was converted to the N-methyl-D-glucamine salt and lyophilised from water/dioxan. Found: C, 60.05; H, 7.70; N, 8.46%. $C_{33}H_{46}N_4O_8$.1.9 mols $H_2O$ requires: C, 60.03; H, 7.59; N, 8.49%.

EXAMPLE 166

3-{[5-(2-Cycloheptyl-ethyl)-2-cyclohexyl-1H-imidazole-4-carbonyl]-amino}-benzoic Acid 5-(2-Cycloheptyl-ethyl)-2-cyclohexyl-1H-imidazole-4-carboxylic acid was prepared according to the procedure of Example 20, steps a, b and c, with the modification that cycloheptanepropionic acid was used instead of cycloheptaneacetic acid in step a, and cyclohexanecarboxaldehyde replaced 2-naphthaldehyde in step b. The acid was then converted to the title compound according to the procedure of Example 20, steps d and e, with the modification that 3-amino-benzoic acid benzyl ester replaced 5-amino-isophthalic acid dibenzyl ester in step d. $^1$H NMR (300 MHz, $d_6$-DMSO) 12.00 (1H, br s), 9.58 (1H, s), 8.45 (1H, s), 7.88 (1H, m), 7.59 (1H, d), 7.38 (1H, t), 2.89 (2H, m), 2.70 (1H, m), 2.00 (2H, m), 1.75–1.35 (23H, m). The acid was converted to the N-methyl-D-glucamine salt and lyophilised from water/dioxan. Found: C, 60.15; H, 8.43; N, 8.58%. $C_{33}H_{52}N_4O_8$.1.4 mols $H_2O$ requires: C, 60.22; H, 8.40; N, 8.51%.

EXAMPLE 167

5-{[5-(2-Cycloheptyl-ethyl)-2-cyclohexyl-1H-imidazole-4-carbonyl]-amino}-2-methyl-benzoic Acid 5-(2-Cycloheptyl-ethyl)-2-cyclohexyl-1H-imidazole-4-carboxylic acid was prepared according to the procedure of Example 20, steps a, b and c, with the modification that cycloheptanepropionic acid was used instead of cycloheptaneacetic acid in step a, and cyclohexanecarboxaldehyde replaced 2-naphthaldehyde in step b. The acid was then converted to the title compound according to the procedure of Example 20, steps d and e, with the modification that 5-amino-2-methyl-benzoic acid benzyl ester replaced 5-amino-isophthalic acid dibenzyl ester in step d. $^1$H NMR (300 MHz, $d_6$-DMSO) 11.90 (1H, br s), 9.46 (1H, s), 8.29 (1H, d), 7.74 (1H, dd), 7.19 (1H, d), 2.92 (2H, m), 2.70 (1H, m), 2.45 (3H, s), 1.90 (2H, m), 1.75–1.35 (23H, m). The acid was converted to the N-methyl-D-glucamine salt and lyophilised from water/dioxan. Found: C, 60.04; H, 8.78; N, 8.44%. $C_{34}H_{54}N_4O_8$.1.8 mols $H_2O$ requires: C, 60.05; H, 8.55; N, 8.24%.

EXAMPLE 168

3-{[2-Cyclohexyl-5-(2-cyclohexyl-ethyl)-1H-imidazole-4-carbonyl]-amino}-benzoic Acid 5-Cyclohexyl-2,3-dioxo-pentanoic acid benzyl ester monohydrate (prepared from cyclohexanepropionic acid according to the procedure of Example 20, step a) was reacted with cyclohexanecarboxaldehyde according to the procedure of Example 20, step b to produce 2-cyclohexyl-5-(2-cyclohexyl-ethyl)-1H-imidazole-4-carboxylic acid benzyl ester. This derivative was then converted to the title compound following the procedure of Example 70, steps b, c and d. $^1$H NMR (300 MHz, $d_6$-DMSO) 12.00 (1H, br s), 9.58 (1H, s), 8.46 (1H, s), 7.88 (1H, m), 7.59 (1H, m), 7.39 (1H, t), 2.92 (2H, m), 2.70 (1H, m), 1.89 (2H, m), 1.75–1.13 (19H, m), 0.91 (2H, m). The acid was converted to the N-methyl-D-glucamine salt and lyophilised from water/dioxan. Found: C, 60.10; H, 7.98; N, 8.77%. $C_{32}H_{50}N_4O_8$.1.0 mol $H_2O$ requires: C, 60.36; H, 8.23; N, 8.80%.

EXAMPLE 169

5-{[5-(2-Cyclohexyl-ethyl)-2-o-tolyl-1H-imidazole-4-carbonyl]-amino}-2-methyl-benzoic Acid 5-(2-Cyclohexyl-ethyl)-2-o-tolyl-1H-imidazole-4-carboxylic acid benzyl ester (Example 89) was converted to the title compound according to the procedure of Example 70, steps b, c and d, with the modification that 5-amino-2-methyl-benzoic acid benzyl ester replaced 3-amino-benzoic acid benzyl ester in step c. $^1$H NMR (300 MHz, $d_6$-DMSO) 12.60 (1H, br s), 9.64 (1H, s), 8.32 (1H, d), 7.78 (1H, m), 7.58 (1H, d), 7.30 (3H, m), 7.21 (1H, d), 3.02 (2H, m), 2.54 (3H, s), 2.46 (3H, s), 1.78–1.55 (7H, m), 1.17 (4H, M), 0.91 (2H, m). The acid was converted to the N-methyl-D-glucamine salt and lyophilised from water/dioxan. Found: C, 60.23; H, 7.73; N, 8.25%. $C_{34}H_{48}N_4O_8$.2.1 mols $H_2O$ requires: C, 60.26; H, 7.75; N, 8.27%.

EXAMPLE 170

3-[(5-Adamantan-1-ylmethyl-2-o-tolyl-1H-imidazole-4-carbonyl)-amino]-benzoic Acid 4-Adamantyl-2,3-dioxo-butyric acid benzyl ester monohydrate (prepared from adamantaneacetic acid according to the procedure of Example 20, step a) was reacted with o-tolualdehyde according to the procedure of Example 20, step b to produce 5-adamantan-1-ylmethyl-2-o-tolyl-1H-imidazole-4-carboxylic acid benzyl ester. This derivative was then converted to the title compound following the procedure of Example 70, steps b, c and d. $^1$H NMR (300 MHz, $d_6$-DMSO) 12.36 (1H, br s), 9.81 (1H, s), 8.51 (1H, s), 7.91 (1H, d), 7.60 (2H, m), 7.40 (1H, t), 7.32 (3H, m), 2.84 (2H, s), 2.53 (3H, s), 1.91 (3H, br s), 1.65–1.56 (12H, m). The acid was converted to the N-methyl-D-glucamine salt and lyophilised from water/dioxan. Found: C, 61.88; H, 7.42; N, 8.05%. $C_{36}H_{48}N_4O_8$.1.9 mols $H_2O$ requires: C, 61.92; H, 7.47; N, 8.02%.

EXAMPLE 171

3-{[5-(3-Adamantan-1-yl-propyl)-2-cyclohexyl-1H-imidazole-4-carbonyl]-amino}-benzoic Acid 6-Adamantan-1-yl-2,3-dioxo-hexanoic acid benzyl ester monohydrate was prepared from 4-(adamantan-1-yl)-butanoic acid (synthesized from 3-(adamantan-1-yl)-propionic acid in four steps using standard homologation techniques) according to the procedure of Example 20, step a. This was reacted with cyclohexanecarboxaldehyde according to the procedure of Example 20, step b to produce 5-(3-adamantan-1-yl-propyl)-2-cyclohexyl-1H-imidazole-4-carboxylic acid benzyl ester. This derivative was then converted to the title compound following the procedure of Example 70, steps b, c and d. $^1$H NMR (300 MHz, $d_6$-DMSO) 12.00 (1H, br s), 9.59 (1H, s), 8.47 (1H, s), 7.89 (1H, m), 7.59 (1H, d), 7.39 (1H, t), 2.85 (2H, t), 2.70 (1H, m), 1.89 (5H, m), 1.76 (2H, m), 1.66–1.27 (20H, m), 1.05 (2H, m). The acid was converted to the N-methyl-D-glucamine salt and lyophilised from water/dioxan. Found: C, 61.59; H, 8.66; N, 7.52%. $C_{37}H_{56}N_4O_8$.2.2 mols $H_2O$ requires: C, 61.40; H, 8.40; N, 7.74%.

EXAMPLE 172

3-{[5-(2-Adamantan-2-yl-ethyl)-2-cyclohexyl-1H-imidazole-4-carbonyl]-amino}-benzoic Acid 3-(Adamanta-2-yl)-propionic acid was synthesized in two steps by reacting 2-bromoadamantane with methyl acrylate according to the procedure of Eguchi (S. Eguchi et al. *J.Org.Chem.*, 1988, 53, 1285) and then hydrolysing the methyl ester. The acid was converted to 5-adamantan-2-yl-2,3-dioxo-pentanoic acid benzyl ester monohydrate according to the procedure of Example 20, step a, which was reacted with cyclohexanecarboxaldehyde according to the procedure of Example 20, step b to produce 5-(2-adamantan-2-yl-ethyl)-2-cyclohexyl-1H-imidazole-4-carboxylic acid benzyl ester. This derivative was then converted to the title compound following the procedure of Example 70, steps b, c and d. $^1$H NMR (300 MHz, $d_6$-DMSO) 13.00 (1H, br s), 12.00 (1H, br s), 9.59 (1H, s), 8.46 (1H, s), 7.90 (1H, dd), 7.60 (1H, d), 7.39 (1H, t), 2.88 (2H, m), 2.60 (1H, m), 1.90–1.20 (27H, m). The acid was converted to the N-methyl-D-glucamine salt and lyophilised from water/dioxan. Found: C, 61.78; H, 8.47; N, 7.99%. $C_{36}H_{54}N_4O_8$.1.5 mols $H_2O$ requires: C, 61.96; H, 8.23; N, 8.03%.

EXAMPLE 173

5-{[5-(2-Adamantan-2-yl-ethyl)-2-cyclohexyl-1H-imidazole-4-carbonyl]-amino}-2-methyl-benzoic Acid 5-(2-Adamantan-2-yl-ethyl)-2-cyclohexyl-1H-imidazole-4-carboxylic acid benzyl ester (Example 172) was converted to the title compound following the procedure of Example 70, steps b, c and d, with the modification that 5-amino-2-methyl-benzoic acid benzyl ester replaced 3-amino-benzoic acid benzyl ester in step c. $^1$H NMR (300 MHz, $d_6$-DMSO) 12.80 (1H, br s), 11.94 (1H, br s), 9.46 (1H, s), 8.29 (1H, s), 7.74 (1H, dd), 7.19 (1H, d), 2.88 (2H, m), 2.60 (1H, m), 2.45 (3H, s), 1.93–1.27 (27H, m). The acid was converted to the N-methyl-D-glucamine salt and lyophilised from water/dioxan. Found: C, 60.65; H, 8.53; N, 7.58%. $C_{37}H_{56}N_4O_8$.2.5 mols $H_2O$ requires: C, 60.89; H, 8.42; N, 7.68%.

EXAMPLE 174

3-({2-Cyclohexyl-5-[2-(3,5-dimethyl-adamantan-1-yl)-ethyl]-1H-imidazole-4-carbonyl}-amino)-benzoic Acid 5-(3,5-Dimethyl-adamantan-1-yl)-2,3-dioxo-pentanoic acid benzyl ester monohydrate (prepared from 3-(3,5-dimethyl-adamantan-1-yl)-propionic acid according to the procedure of Example 20, step a) was reacted with cyclohexanecarboxaldehyde according to the procedure of Example 20, step b to produce 2-cyclohexyl-5-[2-(3,5-dimethyl-adamantan-1-yl)-ethyl]-1H-imidazole-4-carboxylic acid benzyl ester. This derivative was then converted to the title compound following the procedure of Example 70, steps b, c and d. $^1$H NMR (300 MHz, $d_6$-DMSO) 11.94 (1H, br s), 9.56 (1H, s), 8.44 (1H, s), 7.88 (1H, dd), 7.58 (1H, d), 7.38 (1H, t), 2.85 (2H, m), 2.70 (1H, m), 1.88–1.07 (25H, m), 0.79 (6H, s). The acid was converted to the N-methyl-D-glucamine salt and lyophilised from water/dioxan. Found: C, 62.69; H, 8.52; N, 7.53%. $C_{38}H_{58}N_4O_8$.1.9 mols $H_2O$ requires: C, 62.55; H, 8.48; N, 7.68%.

EXAMPLE 175

3-{[5-(2-Bicyclo[2.2.2]oct-1-yl-ethyl)-2-cyclohexyl-1H-imidazole-4-carbonyl]-amino}-benzoic Acid 3-(Bicyclo[2.2.2]oct-1-yl)-propionic acid was prepared from bicyclo[2.2.2]oct-1-yl-methanol (C. A. Grob, M. Ohta, E. Renk and A. Weiss, *Helv. Chim. Acta* 1958, 41, 1191) using the same procedure as for the preparation of 3-(adamantan-1-yl)-propionic acid (W. Oppolzer and R. Moretti, *Tetrahedron*, 1988, 44, 5541). 3-(Bicyclo[2.2.2]oct-1-yl)-propionic acid was converted to 5-bicyclo[2.2.2]oct-1-yl-2,3-dioxo-pentanoic acid benzyl ester monohydrate according to the procedure of Example 20, step a, which was reacted with cyclohexanecarboxaldehyde according to the procedure of Example 20, step b to produce 5-(2-bicyclo[2.2.2]oct-1-yl-ethyl)-2-cyclohexyl-1H-imidazole-4-carboxylic acid benzyl ester. This derivative was converted to the title compound following the procedure of Example 70, steps b, c and d. $^1$H NMR (300 MHz, $d_6$-DMSO) 13.00 (1H, br s), 11.95 (1H, br s), 9.57 (1H, s), 8.46 (1H, s), 7.90 (1H, m), 7.60 (1H, m), 7.39 (1H, t), 2.82 (2H, m), 2.60 (1H, m), 1.90–1.20 (25H, m). The acid was converted to the N-methyl-D-glucamine salt and lyophilised from water/dioxan. Found: C, 59.06; H, 8.42; N, 8.02%. $C_{34}H_{52}N_4O_8$.2.5 mols $H_2O$ requires: C, 59.20; H, 8.33; N, 8.12%.

EXAMPLE 176

5-{[5-(2-Bicyclo[2.2.2]oct-1-yl-ethyl)-2-cyclohexyl-1H-imidazole-4-carbonyl]-amino}-2-methyl-benzoic Acid 5-(2-Bicyclo[2.2.2]oct-1-yl-ethyl)-2-cyclohexyl-1H-imidazole-4-carboxylic acid benzyl ester (Example 175) was converted to the title compound following the procedure of Example 70, steps b, c and d, with the modification that 5-amino-2-methyl-benzoic acid benzyl ester replaced 3-amino-benzoic acid benzyl ester in step c. $^1$H NMR (300 MHz, $d_6$-DMSO) 11.95 (1H, br s), 9.46 (1H, s), 8.29 (1H, s), 7.73 (1H, m), 7.20 (1H, d), 2.81 (2H, m), 2.60 (1H, m), 2.45 (3H, s), 1.90–1.20 (25H, m). The acid was converted to the N-methyl-D-glucamine salt and lyophilised from water/dioxan. Found: C, 60.23; H, 8.32; N, 7.87%. $C_{35}H_{54}N_4O_8$·2.0 mols $H_2O$ requires: C, 60.50; H, 8.41; N, 8.06%.

EXAMPLE 177

3-{[5-(2-Adamantan-1-yl-ethyl)-2-pyridine-3-yl-1H-imidazole-4-carbonyl]-amino}-benzoic Acid Step a. 3-{[5-(2-Adamantan-1-yl-ethyl)-2-pyridine-3-yl-1H-imidazole-4-carbonyl]-amino}-benzoic Acid Benzyl Ester 5-(2-Adamantan-1-yl-ethyl)-2-pyridine-3-yl-1H-imidazole-4-carboxylic acid was prepared according to the procedure of Example 70, steps a and b, with the modification that pyridine-3-carboxaldehyde was used instead of 2-dimethylamino-benzaldehyde in step a. This was used in the following procedure: oxalyl chloride(115 µl, 1.32 mmol) was added to a suspension of 5-(2-adamantan-1-yl-ethyl)-2-pyridine-3-yl-1H-imidazole-4-carboxylic acid (310 mg, 0.88 mmol) in DCM (10 ml) containing 1 drop of DMF. The resulting solution was stirred at ambient temperature for 1 h, then the excess reagent and the solvent were evaporated under reduced pressure. The residue was dissolved in THF (10 ml), N,N-diisopropylethylamine (310 µl, 1.76 mmol), and the solution of 3-amino-benzoic acid benzyl ester (400 mg, 1.76 mmol) in THF (5 ml) were added. The reaction mixture was stirred at ambient temperature for 16 h, then the solvent was evaporated. The residue was dissolved in DCM (30 ml) and the solution was washed with saturated sodium bicarbonate (1×20 ml), dried ($MgSO_4$) and the solvent was evaporated. The crude material was purified by flash colunm chromatography (DCM/methanol 97:3) to afford the product as a colourless foam (372 mg, 75%). $^1$H NMR (300 MHz, $CDCl_3$) 10.80 (1H, br s), 9.26 (1H, s), 9.20 (1H, s), 8.60 (1H, dd), 8.32 (1H, dt), 8.16 (2H, m), 7.81 (1H, d), 7.47–7.34 (6H, m), 5.37 (2H, s), 3.06 (2H, m), 1.91 (3H, br s), 1.61 (6H, m), 1.44 (8H, m).

Step b

The product of step a was deprotected using the same procedure as in Example 1, step e, to afford the title compound as a white solid. $^1$H NMR (300 MHz, $d_6$-DMSO) 13.10 (1H, br s), 9.85 (1H, br s), 9.26 (1H, s), 8.57 (1H, dd), 8.41 (2H, m), 7.92 (1H, d), 7.63 (1H, d), 7.50 (1H, dd), 7.35 (1H, t), 3.01 (2H, m), 1.95 (3H, br s), 1.65 (6H, m), 1.55–1.35 (8H, m). The acid was converted to the N-methyl-D-glucamine salt and lyophilised from water/dioxan. Found: C, 56.16; H, 7.57; N, 9.59%. $C_{35}H_{47}N_5O_8$·4.5 mols $H_2O$ requires: C, 56.29; H, 7.56; N, 9.38%.

EXAMPLE 178

3-{[5-(2-Adamantan-1-yl-ethyl)-2-pyridine-2-yl-1H-imidazole-4-carbonyl]-amino}-benzoic Acid 5-(2-Adamantan-1-yl-ethyl)-2-pyridine-2-yl-1H-imidazole-4-carboxylic acid (prepared according to the procedure of Example 70, steps a and b, with the modification that pyridine-2-carboxaldehyde was used instead of 2-dimethylamino-benzaldehyde in step a) was reacted with 3-amino-benzoic acid benzyl ester according to the procedure of Example 177, step a to afford 3-{[5-(2-adamantan-1-yl-ethyl)-2-pyridine-2-yl-1H-imidazole-4-carbonyl]-amino}-benzoic acid benzyl ester. The benzyl group was removed following the procedure of Example 1, step e, to afford the title compound as a white solid. $^1$H NMR (300 MHz, $d_6$-DMSO) 13.18 (1H, br s), 9.84 (1H, br s), 8.63 (1H, d), 8.48 (1H, s), 8.23 (1H, d), 8.00 (1H, d), 7.93 (1H, td), 7.63 (1H, d), 7.42 (2H, m), 2.99 (2H, m), 1.95 (3H, br s), 1.65 (6H, m), 1.54 (6H, s), 1.42 (2H, m). The product was converted to the L-tartaric acid salt and lyophilised from water/dioxan. Found: C, 58.35; H, 6.11; N, 8.80%. $C_{32}H_{36}N_4O_9$·2.0 mols $H_2O$ requires: C, 58.23; H, 6.14; N, 8.53%.

EXAMPLE 179

5-{[5-(2-Adamantan-1-yl-ethyl)-2-pyridine-2-yl-1H-imidazole-4-carbonyl]-amino}-2methyl-benzoic Acid 5-(2-Adamantan-1-yl-ethyl)-2-pyridine-2-yl-1H-imidazole-4-carboxylic acid (prepared according to the procedure of Example 70, steps a and b, with the modification that pyridine-2-carboxaldehyde was used instead of 2-dimethylamino-benzaldehyde in step a) was reacted with 5-amino-2-methyl-benzoic acid benzyl ester according to the procedure of Example 177, step a to afford 5-{[5-(2-adamantan-1-yl-ethyl)-2-pyridine-2-yl-1H-imidazole-4-carbonyl]-amino}-2-methyl-benzoic acid benzyl ester. The benzyl group was removed following the procedure of Example 1, step e, to afford the title compound as a white solid. $^1$H NMR (300 MHz, $d_6$-DMSO) 13.18 (1H, br s), 9.71 (1H, br s), 8.66 (1H, d), 8.32 (1H, s), 8.25 (1H, d), 7.96 (1H, td), 7.86 (1H, dd), 7.44 (1H, m), 7.24 (1H, d), 2.98 (2H, m), 2.48 (3H, s),1.94 (3H, br s), 1.63 (6H, m), 1.53 (6H, m), 1.42 (2H, m). The product was converted to the L-tartaric acid salt and lyophilised from water/dioxan. Found: C, 59.07; H, 6.40; N, 8.28%. $C_{33}H_{38}N_4O_8$·2.0 mols $H_2O$ requires: C, 59.10; H, 6.31; N, 8.35%.

EXAMPLE 180

3-{[5-(2-Adamantan-1-yl-ethyl)-2-pyridine-4-yl-1H-imidazole-4-carbonyl]-amino}-benzoic Acid 5-(2-Adamantan-1-yl-ethyl)-2-pyridine-4-yl-1H-imidazole-4-carboxylic acid (prepared according to the procedure of Example 70, steps a and b, with the modification that pyridine-4-carboxaldehyde was used instead of 2-dimethylamino-benzaldehyde in step a) was reacted with 3-amino-benzoic acid benzyl ester according to the procedure of Example 177, step a to afford 3-{[5-(2-adamantan-1-yl-ethyl)-2-pyridine-4-yl-1H-imidazole-4-carbonyl]-amino}-benzoic acid benzyl ester. The benzyl group was removed following the procedure of Example 1, step e, to afford the title compound as a white solid. $^1$H NMR (300 MHz, $d_6$-DMSO) 13.20 (1H, br s), 9.88 (1H, s), 8.67 (2H, dd), 8.47 (1H, s), 8.00 (3H, m), 7.64 (1H, d), 7.41 (1H, t), 3.01 (2H, m), 1.95 (3H, br s), 1.65 (6H, m), 1.55 (6H, s), 1.44 (2H, m). The product was converted to the maleic acid salt and lyophilised from water/dioxan. Found: C, 60.81; H, 6.48; N, 8.95%. $C_{32}H_{34}N_4O_7$·2.5 mols $H_2O$ requires: C, 60.85; H, 6.22; N, 8.87%.

EXAMPLE 181

3-{[5-(2-Adamantan-1-yl-ethyl)-2-(2-methyl-pyridine-3-yl)-1H-imidazole-4-carbonyl]-amino}-benzoic Acid 5-(2-Adamantan-1-yl-ethyl)-2-(2-methyl-pyridine-3-yl)-1H-imidazole-4-carboxylic acid was prepared according to the procedure of Example 70, steps a and b, with the modification that 2-methyl-pyridine-3-carboxaldehyde (prepared from ethyl 2-methylnicotinate in two steps) was used in step a instead of 2-dimethylamino-benzaldehyde. It was reacted with 3-amino-benzoic acid benzyl ester according to the procedure of Example 20, step d to afford 3-{[5-(2-adamantan-1-yl-ethyl)-2-(2-methyl-pyridine-3-yl)-1H-imidazole-4-carbonyl]-amino}-benzoic acid benzyl ester. The benzyl group was removed following the procedure of Example 1, step e, to afford the title compound as a white solid. $^1$H NMR (300 MHz, d$_6$-DMSO) 12.70 (1H, br s), 9.77 (1H, s), 8.49 (2H, m), 7.97 (2H, m), 7.62 (1H, d), 7.41 (1H, t), 7.35 (1H, dd), 2.87 (2H, m), 2.76 (3H, s), 1.95 (3H, br s), 1.69 (6H, m), 1.54 (6H, m), 1.44 (2H, m). The acid was converted to the N-methyl-D-glucamine salt and lyophilised from water/dioxan. Found: C, 58.93; H, 7.55; N, 9.80%. $C_{36}H_{49}N_5O_8$.3.0 mols $H_2O$ requires: C, 58.92; H, 7.55; N, 9.54%.

EXAMPLE 182

3-{[5-(2-Adamantan-1-yl-ethyl)-2-(2,4,6-trimethyl-pyridine-3-yl)-1H-imidazole-4-carbonyl]-amino}-benzoic Acid 5-(2-Adamantan-1-yl-ethyl)-2-(2,4,6-trimethyl-pyridine-3-yl)-1H-imidazole-4-carboxylic acid was prepared according to the procedure of Example 70, steps a and b, with the modification that 2,4,6-trimethyl-pyridine-3-carboxaldehyde (P. Beak et al *J. Org. Chem.* 1980, 45, 1354) was used in step a instead of 2-dimethylamino-benzaldehyde. It was reacted with 3-amino-benzoic acid benzyl ester according to the procedure of Example 20, step d to afford 3-{[5-(2-adamantan-1-yl-ethyl)-2-(2,4,6-trimethyl-pyridine-3-yl)-1H-imidazole-4-carbonyl]-amino}-benzoic acid benzyl ester. The benzyl group was removed following the procedure of Example 1, step e, to afford the title compound as a white solid. $^1$H NMR (300 MHz, d$_6$-DMSO) 12.49 (1H, br s), 9.83 (1H, s), 8.51 (1H, s), 8.30 (1H, s), 7.93 (1H, d), 7.60 (1H, d), 7.38 (1H, t), 7.05 (1H, s), 3.00 (2H, t), 2.43 (3H, s), 2.26 (3H, s), 2.10 (3H, s), 1.93 (3H, br s), 1.64 (6H, m), 1.52 (6H, m), 1.43 (2H, t). The acid was converted to the N-methyl-D-glucamine salt and lyophilised from water/dioxan. Found: C, 60.48; H, 7.78; N, 9.05%. $C_{38}H_{53}N_5O_8$.2.5 mols $H_2O$ requires: C, 60.62; H, 7.77; N, 9.30%.

EXAMPLE 183

5-{[5-(2-Adamantan-1-yl-ethyl)-2-(2,4,6-trimethyl-pyridine-3-yl)-1H-imidazole-4-carbonyl]-amino}-2-methyl-benzoic Acid 5-(2-Adamantan-1-yl-ethyl)-2-(2,4,6-trimethyl-pyridine-3-yl)-1H-imidazole-4-carboxylic acid (Example 182) was reacted with 5-amino-2-methyl-benzoic acid benzyl ester according to the procedure of Example 20, step d to afford 5-{[5-(2-adamantan-1-yl-ethyl)-2-(2,4,6-trimethyl-pyridine-3-yl)-1H-imidazole-4-carbonyl]-amino }-2-methyl-benzoic acid benzyl ester. The benzyl group was removed following the procedure of Example 1, step e, to afford the title compound as a white solid. $^1$H NMR (300 MHz, d$_6$-DMSO) 12.40 (1H, br s), 9.69 (1H, s), 8.30 (1H, d), 7.76 (1H, d), 7.17 (1H, d), 7.05 (1H, s), 2.99 (2H, m), 2.44 (3H, s), 2.43 (3H, s), 2.25 (3H, s), 2.09 (3H, s), 1.92 (3H, br s), 1.64 (6H, m), 1.51 (6H, br s), 1.42 (2H, m). The acid was converted to the N-methyl-D-glucamine salt and lyophilised from water/dioxan. Found: C, 54.92; H, 8.21; N, 8.30%. $C_{39}H_{55}N_5O_8$.7.0 mols $H_2O$ requires: C, 55.24; H, 8.20; N, 8.26%.

EXAMPLE 184

5-{[5-(2-Adamantan-1-yl-ethyl)-2-(2,4,6-trimethyl-pyridine-3-yl)-1H-imidazole-4-carbonyl]-amino}-2-fluoro-benzoic Acid 5-(2-Adamantan-1-yl-ethyl)-2-(2,4,6-trimethyl-pyridine-3-yl)-1H-imidazole-4-carboxylic acid (Example 182) was reacted with 5-amino-2-fluoro-benzoic acid methyl ester according to the procedure of Example 20, step d to afford 5-{[5-(2-adamantan-1-yl-ethyl)-2-(2,4,6-trimethyl-pyridine-3-yl)-1H-imidazole-4-carbonyl]-amino}-2-fluoro-benzoic acid methyl ester. The ester was hydrolysed following the procedure of Example 36, step d, to afford the title compound as a white solid. $^1$H NMR (300 MHz, d$_6$-DMSO) 12.50 (1H, br s), 9.67 (1H, s), 8.15 (1H, d), 7.71 (1H, m), 7.03 (2H, m), 2.99 (2H, m), 2.42 (3H, s), 2.25 (3H, s), 2.09 (3H, s), 1.92 (3H, br s), 1.60 (6H, m), 1.50 (6H, br s), 1.42 (2H, m). The acid was converted to the N-methyl-D-glucamine salt and lyophilised from water/dioxan. Found: C, 53.44; H, 7.81; N, 8.03%. $C_{38}H_{52}FN_5O_8$.7.0 mols $H_2O$ requires: C, 53.57; H, 7.81; N, 8.22%.

EXAMPLE 185

3-{[5-(2-Adamantan-1-yl-ethyl)-2-furan-2-yl-1H-imidazole-4-carbonyl]-amino}benzoic Acid The title compound was prepared according to the procedure of Example 70, with the modification that 2-furaldehyde was used in step a instead of 2-dimethylamino-benzaldehyde, and the reaction times in steps b and d were 2 h and 1 h respectively. $^1$H NMR (300 MHz, d$_6$-DMSO) 12.86 (1H, br s), 9.79 (1H, s), 8.51 (1H, s), 7.95 (1H, d), 7.81 (1H, s), 7.62 (1H, d), 7.42 (1H, t), 6.95 (1H, d), 6.65 (1H, dd), 2.96 (2H, m), 1.95 (3H, br s), 1.65 (6H, m), 1.54–1.38 (8H, m). The acid was converted to the N-methyl-D-glucamine salt and lyophilised from water/dioxan. Found: C, 58.92; H, 7.44; N, 8.03%. $C_{34}H_{46}N_4O_9$.2.0 $H_2O$ requires: C, 59.12; H, 7.30; N, 8.11%.

EXAMPLE 186

3-{[5-(2-Adamantan-1-yl-ethyl)-2-(tetrahydro-furan-2-yl)-1H-imidazole-4-carbonyl]-amino}-benzoic Acid The title compound was prepared according to the procedure of Example 70, with the modification that 2-furaldehyde was used in step a instead of 2-dimethylamino-benzaldehyde, and the reaction times in steps b and d were 2 h and 72 h respectively. $^1$H NMR (300 MHz, d$_4$-MeOH) 8.39 (1H, s), 7.95 (1H, d), 7.79 (1H, d), 7.47 (1H, t), 4.96 (1H, t), 4.11 (1H, dt), 3.94 (1H, dt), 3.02 (2H, m), 2.38 (1H, m), 2.25–2.05 (3H, m), 2.01 (3H, br s), 1.76 (6H, m), 1.64–1.42 (8H, m). The acid was converted to the N-methyl-D-glucamine salt and lyophilised from water/dioxan. Found: C, 57.22; H, 8.11; N, 7.87%. $C_{34}H_{50}N_4O_9$.3.0 $H_2O$ requires: C, 57.29; H, 7.92; N, 7.86%.

EXAMPLE 187

5-{[5-(2-Adamantan-1-yl-ethyl)-2-furan-2-yl-1H-imidazole-4-carbonyl]-amino}-2-methyl-benzoic Acid The title compound was prepared according to the procedure of Example 70, with the modification that 2-furaldehyde was used in step a instead of 2-dimethylamino-benzaldehyde, and 5-amino-2-methylbenzoic acid benzyl ester replaced 3-amino-benzoic acid benzyl ester in step c. The reaction times in steps b and d were 2 h and 1 h respectively. $^1$H NMR (300 MHz, d$_6$-DMSO) 12.83 (1H, br s), 12.75 (1H, br s), 9.66 (1H, s), 8.34 (1H, d), 7.80 (2H, m), 7.22 (1H, d), 6.94 (1H, d), 6.64 (1H, m), 2.96 (2H, m), 2.46 (3H, s), 1.95 (3H, br s), 1.65 (6H, m), 1.53 (6H, br s), 1.40 (2H, m). The acid was converted to the N-methyl-D-glucamine salt and lyophilised from water/dioxan. Found: C, 59.69; H, 7.64; N, 7.89%. C$_{35}$H$_{48}$N$_4$O$_9$.2.0 H$_2$O requires: C, 59.64; H, 7.44; N, 7.95%.

EXAMPLE 188

5-{[5-(2-Adamantan-1-yl-ethyl)-2-(tetrahydro-furan-2-yl)-1H-imidazole-4-carbonyl]-amino}-2-methyl-benzoic Acid The title compound was prepared according to the procedure of Example 70, with the modification that 2-furaldehyde was used in step a instead of 2-dimethylamino-benzaldehyde, and 5-amino-2-methyl-benzoic acid benzyl ester replaced 3-amino-benzoic acid benzyl ester in step c. The reaction times in steps b and d were 2 h and 72 h respectively. $^1$H NMR (300 MHz, d$_6$-DMSO) 12.75 (1H, br s), 12.27 (1H, br s), 9.55 (1H, s), 8.30 (1H, s), 7.76 (1H, d), 7.19 (1H, d), 4.84 (1H, t), 3.92 (1H, dt), 3.77 (1H, dt), 2.89 (2H, m), 2.45 (3H, s), 2.17 (2H, m), 2.02–1.94 (5H, m), 1.65 (6H, m), 1.51 (6H, m), 1.35 (2H, m). The acid was converted to the N-methyl-D-glucamine salt and lyophilised from water/dioxan. Found: C, 58.77; H, 8.43; N, 7.94%. C$_{35}$H$_{52}$N$_4$O$_9$.2.5H$_2$O requires: C, 58.56; H, 8.00; N, 7.80%.

EXAMPLE 189

3-{[5-(2-Adamantan-1-yl-ethyl)-2-(2-methoxy-1-methoxymethyl-ethyl)-1H-imidazole-4-carbonyl]-amino}-benzoic Acid Step a. 3-Methoxy-2-methoxymethyl-propane-1-ol Sodium hydride (60% dispersion in oil) (2.93 g, 73.2 mmol) was added to an ice-cooled solution of 2-hydroxymethyl-propane-1,3-diol (M. R. Harnden et al. *J. Med. Chem.* 1990, 33, 187) (3.53 g, 33.3 mmol) in DMF (100 ml) and the mixture was stirred at room temperature for 40 min. The reaction mixture was cooled with ice and iodomethane (4.56 ml, 73.2 mmol) was added, the stirring was continued allowing the mixture to reach room temperature over 24 h. The mixture was poured into ethyl acetate (300 ml) and washed with brine (150 ml). The organic phase was dried (MgSO$_4$), and the solvent was evaporated. The crude product was purified by flash column chromatography (silica, ethyl acetate) to afford colourless oil. $^1$H NMR (300 MHz, CDCl$_3$) 3.72 (2H, d), 3.47 (2H, d), 3.45 (2H, d), 3.32 (6H, s), 2.07(1H, m).

Step b. 3-Methoxy-2-methoxymethyl-propionaldehyde

A solution of oxalyl chloride (838 μl, 9.61 mmol) in DCM (30 ml) was cooled to −65° C and dimethyl sulfoxide (1.36 ml, 19.17 mmol) in DCM (5 ml) was added dropwise. The solution was stirred at −65° C. for 30 min, then the product of step a (1.03 g, 7.68 mmol) was added in DCM (5 ml). After stirring at −65° C. for further 45 min, triethylamine (5.35 ml, 38.4 mmol) was added and the mixture was stirred at room temperature for 3 h. Water (40 ml) was added and the layers were separated. The aqueous layer was extracted with DCM (2×20 ml), the combined organic layers were dried (MgSO$_4$) and the solvent was evaporated. The crude product was purified by flash column chromatography (silica, hexane/ethyl acetate 1:1) to afford colourless oil (760 mg, 75%). $^1$H NMR (300 MHz, CDCl$_3$) 9.76 (1H, s), 3.76–3.64 (4H, m), 3.35 (6H, s), 2.77 (1H, m).

Step c

The title compound was prepared using essentially the same procedure as in Example 70, with the modification that 3-methoxy-2-methoxymethyl-propionaldehyde was used in step a instead of 3-dimethylamino-benzaldehyde. $^1$H NMR (300 MHz, d$_6$-DMSO) 12.10 (1H, br s), 9.58 (1H, s), 8.43 (1H, s), 7.90 (1H, d), 7.59 (1H, d), 7.35 (1H, t), 3.77 (1H, m), 3.63 (2H, d), 3.61 (2H, d), 3.23 (6H, s), 2.89 (2H, m), 1.94 (3H, br s), 1.65 (6H, m), 1.51 (6H, br s), 1.35 (2H, m). The acid was converted to the N-methyl-D-glucamine salt and lyophilised from water/dioxan. Found: C, 56.22; H, 8.05; N, 7.84%. C$_{35}$H$_{54}$N$_4$O$_{10}$.3.0 H$_2$O requires: C, 56.44; H, 8.12; N, 7.52%.

EXAMPLE 190

3-{[5-(2-Adamantan-1-yl-ethyl)-2-(6,6-dimethyl-bicyclo[3.1.1]hept-2-yl)-1H-imidazole-4-carbonyl]-amino}-benzoic Acid The title compound was prepared according to the procedure of Example 70, with the modification that (1R)-(−)-myrtenal was used in step a instead of 2-dimethylamino-benzaldehyde. $^1$H NMR (300 MHz, d$_4$-MeOH) 8.36 (1H, t), 7.89 (1H, ddd), 7.75 (1H, dt), 7.43 (1H, t), 3.42 (1H, m), 2.98 (2H, m), 2.59 (2H, m), 2.50 (1H, m), 2.30–1.98 (7H, m), 1.73 (6H, m), 1.61 (6H, d), 1.41 (2H, m), 1.31 (1H, d), 1.25 (3H, s), 0.71 (3H, s). The acid was converted to the N-methyl-D-glucamine salt and lyophilised from water/dioxan. Found: C, 62.18; H, 8.40; N, 7.59%. C$_{39}$H$_{58}$N$_4$O.2.3 H$_2$O requires: C, 62.31; H, 8.39; N, 7.45%.

EXAMPLE 191

5-{[5-(2-Adamantan-1-yl-ethyl)-2-(6,6-dimethyl-bicyclo[3.1.1]hept-2-yl)-1H-imidazole-4-carbonyl]-amino}-2-methyl-benzoic Acid The title compound was prepared according to the procedure of Example 70, with the modification that (1R)-(−)-myrtenal was used in step a instead of 2-dimethylamino-benzaldehyde and 5-amino-2-methyl-benzoic acid benzyl ester replaced 3-amino-benzoic acid benzyl ester in step c. $^1$H NMR (300 MHz, d$_4$-MeOH) 8.20 (1H, d), 7.75 (1H, dd), 7.25 (1H, d), 3.42 (1H, m), 2.97 (2H, m), 2.58 (2H, m), 2.54 (3H, s), 2.44 (1H, m), 2.25–1.96 (7H, m), 1.72 (6H, m), 1.60 (6H, d), 1.41 (2H, m), 1.30 (1H, d) 1.25 (3H, s), 0.70 (3H, s). The acid was converted to the N-methyl-D-glucamine salt and lyophilised from water/dioxan. Found: C, 63.08; H, 8.48; N, 7.36%. C$_{40}$H$_{60}$N$_4$O$_8$.2.0 H$_2$O requires: C, 63.08; H, 8.63; N, 7.41%.

EXAMPLE 192

3-{[5-(2-Adamantan-1-yl-ethyl)-2-(6,6-dimethyl-bicyclo[3.1.1]hept-2-en-2-yl)-1H-imidazole-4-carbonyl]-amino}-benzoic Acid 5-(2-Adamantan-1-yl-ethyl)-2-(6,6-dimethyl-bicyclo[3.1.1]hept-2-en-2-yl)-1H-imidazole-4-carboxylic acid benzyl ester was prepared according to the procedure of Example 70, step a, with the modification that (1R)-(−)- myrtenal was used in instead of 2-dimethylamino-benzaldehyde. The benzyl ester was hydrolysed according to the procedure of Example 20, step c and the resulting 5-(2-adamantan-1-yl-ethyl)-2-(6,6-dimethyl-bicyclo[3.1.1]hept-2-en-2-yl)-1H-imidazole-4-carboxylic acid was reacted with 3-amino-benzoic acid methyl ester hydrochloride using essentially the same procedure as in Example 52, step a. Deprotection was carried out following essentially the procedure of Example 36, step d to afford the title compound. $^1$H NMR (300 MHz, d$_4$-MeOH) 8.36 (1H, t), 7.90 (1H, ddd), 7.75 (1H, dt), 7.42 (1H, t), 6.30 (1H, m), 3.02 (1H, dt), 2.99 (2H, m), 2.57 (1H, m), 2.49 (2H, dd), 2.19 (1H, m), 1.95 (3H, s), 1.71 (6H, m), 1.60 (6H, d), 1.42 (2H, m), 1.40 (3H, s), 1.26 (1H, d), 0.90 (3H, s) was converted to the N-methyl-D-glucamine salt and lyophilised from water/dioxan. Found: C, 62.39; H, 7.98; N, 7.58%. $C_{39}H_{56}N_4O_8$.2.2 $H_2O$ requires: C, 62.55; H, 8.14; N, 7.48%.

EXAMPLE 193

3-{[5-(2-Adamantan-1-yl-ethyl)-2-cyclohexylmethyl-1H-imidazole-4-carbonyl]-amino}-benzoic Acid The title compound was prepared according to the procedure of Example 70, with the modification that cyclohexyl-acetaldehyde was used in step a instead of 2-dimethylamino-benzaldehyde. $^1$H NMR (300 MHz, d$_6$-DMSO) 12.00 (1H, br s), 9.64 (1H, s), 8.49 (1H, s), 7.88 (1H, d), 7.59 (1H, d), 7.39 (1H, t), 2.89 (2H, m), 2.47 (2H, d), 1.93 (3H, br s), 1.64 (12H, m), 1.50 (6H, s), 1.35 (2H, m), 1.15 (3H, m), 0.95 (2H, m).

The acid was converted to the N-methyl-D-glucamine salt and lyophilised from water/dioxan. Found: C, 61.53; H, 8.59; N, 7.71%. $C_{37}H_{56}N_4O_8$.3.0 $H_2O$ requires: C, 61.40; H, 8.40; N, 7.74%.

EXAMPLE 194

3-{[5-(2-Adamantan-1-yl-ethyl)-2-(4-isopropyl-cyclohexyl)-1H-imidazole-4-carbonyl]-amino}-benzoic Acid The title compound was prepared according to the procedure of Example 70, with the modification that 4-isopropyl-cyclohexanecarboxaldehyde (prepared as a mixture of diastereoisomers by catalytic hydrogenation of (S)-perillaldehyde) was used in step a instead of 2-dimethylamino-benzaldehyde. $^1$H NMR (300 MHz, d$_6$-DMSO) 9.59 (1H, s), 8.46 (1H, s), 7.91 (1H, d), 7.59 (1H, d), 7.39 (1H, t), 2.88 (2H, m), 2.56 (1H, tt), 2.01 (1H, br s), 1.94 (4H, br s), 1.77 (2H, m), 1.64 (6H, m), 1.50 (8H, m), 1.34 (2H, m), 1.07 (4H, m), 0.87 (6H, d). The acid was converted to the N-methyl-D-glucamine salt and lyophilised from water/dioxan. Found: C, 62.64; H, 8.79; N, 7.51%. $C_{39}H_{60}N_4O$.2.0 $H_2O$ requires: C, 62.61; H, 8.61; N, 7.50%.

EXAMPLE 195

3-{[5-(2-Adamantan-1-yl-ethyl)-2-cyclohex-3-enyl-1H-imidazole-4-carbonyl]-amino}-benzoic Acid The title compound was prepared according to the procedure of Example 68, with the modification that 1,2,3,6-tetrahydro-benzaldehyde was used instead of 3,4-dichlorobenzaldehyde. $^1$H NMR (300 MHz, d$_6$-DMSO) 12.00 (1H, br s), 9.60 (1H, s), 8.46 (1H, s), 7.90 (1H, m), 7.59 (1H, m), 7.39 (1H, t), 5.73 (2H, d), 2.90 (3H, m), 2.32 (2H, m), 2.12 (2H, m), 1.94 (4H, m), 1.66 (7H, m), 1.51 (6H, s), 1.36 (2H, m). The acid was converted to the N-methyl-D-glucamine salt and lyophilised from water/dioxan. Found: C, 61.34; H, 8.12; N, 7.90%. $C_{36}H_{52}N_4O_8$.2.0 $H_2O$ requires: C, 61.31; H, 8.11; N, 7.94%.

EXAMPLE 196

3-{[5-(2-Adamantan-1-ethyl)-2-cyclopentyl-1H-imidazole-4-carbonyl]-amino}-benzoic Acid The title compound was prepared according to the procedure of Example 70, with the modification that cyclopentanecarboxaldehyde was used in step a instead of 2-dimethylamino-benzaldehyde. $^1$H NMR (300 MHz, d$_6$-DMSO) 12.00 (1H, br s), 9.59 (1H, s), 8.45 (1H, s), 7.89 (1H, dd), 7.59 (1H, d), 7.38 (1H, t), 3.02 (1H, m), 2.87 (2H, m), 1.94 (5H, m), 1.77–1.58 (12H, m), 1.50 (6H, s), 1.34 (2H, m). The acid was converted to the N-methyl-D-glucamine salt and lyophilised from water/dioxan. Found: C, 62.64; H, 8.79; N, 7.51%. $C_{39}H_{52}N_4O_8$.2.0 $H_2O$ requires: C, 62.61; H, 8.61; N, 7.50%.

EXAMPLE 197

3-{[5-(2-Adamantan-1-yl-ethyl)-2-cyclopropyl-1H-imidazole-4-carbonyl]-amino}-benzoic Acid The title compound was prepared according to the procedure of Example 68, with the modification that cyclopropylcarboxaldehyde was used instead of 3,4-dichlorobenzaldehyde. $^1$H NMR (300 MHz, d$_6$-DMSO) 9.51 (1H, s), 8.39 (1H, s), 7.85 (1H, d), 7.60 (1H, d), 7.34 (1H, t), 2.86 (2H, m), 1.94 (4H, m), 1.64 (6H, m), 1.50 (6H, m), 1.33 (2H, m), 0.89 (4H, m). The acid was converted to the N-methyl-D-glucamine salt and lyophilised from water/dioxan. Found: C, 60.32; H, 8.01; N, 8.25%. $C_{33}H_{48}N_4O_8$.1.7 $H_2O$ requires: C, 60.13; H, 7.86; N, 8.50%.

EXAMPLE 198

5-{[5-(2-Adamantan-1-yl-ethyl)-2-tert-butyl-1H-imidazole-4-carbonyl]-amino}-2-methyl-benzoic Acid The title compound was prepared according to the procedure of Example 70, with the modification that trimethylacetaldehyde was used in step a instead of 2-dimethylamino-benzaldehyde and 5-amino-2-methyl-benzoic acid benzyl ester replaced 3-amino-benzoic acid benzyl ester in step c. $^1$H NMR (300 MHz, d$_6$-DMSO) 12.75 (1H, br s), 11.85 (1H, br s), 9.38 (1H, s), 8.25 (1H, s), 7.76 (1H, d), 7.21 (1H, d), 2.88 (2H, m), 2.45 (3H, s), 1.94 (3H, br s), 1.70–1.59 (6H, m), 1.510 (6H, br s), 1.34 (11H, m). The acid was converted to the N-methyl-D-glucamine salt and lyophilised from water/dioxan. Found: C, 61.52; H, 8.39; N, 7.91%. $C_{35}H_{54}N_4O_8$.1.5 $H_2O$ requires: C, 61.29; H, 8.38; N, 8.17%.

EXAMPLE 199

3-{[5-(2-Adamantan-1-yl-ethyl)-2-(1-methyl-cyclohexyl)-1H-imidazole-4-carbonyl]-amino}-benzoic Acid The title compound was prepared according to the procedure of Example 70, with the modification that 1-methyl-cyclohexanecarboxaldehyde (prepared in two steps from 1-methyl-1-cyclohexanecarboxylic acid) was used in step a instead of 2-dimethylamino-benzaldehyde. $^1$H NMR (300 MHz, d$_6$-DMSO) 13.00 (1H, br s), 11.85 (1H, br s), 9.54

(1H, br s), 8.40 (1H, s), 7.92 (1H, d), 7.61 (1H, d), 7.42 (1H, t), 2.90 (2H, m), 2.12 (2H, m), 1.93 (3H, br s), 1.63 (6H, m), 1.51–1.33 (16H, m), 1.22 (3H, s). The acid was converted to the N-methyl-D-glucamine salt and lyophilised from water/dioxan. Found: C, 61.69; H, 8.56; N, 7.65%. $C_{37}H_{56}N_4O_8 \cdot 2.0\ H_2O$ requires: C, 61.63; H, 8.39; N, 7.77%.

EXAMPLE 200

5-{[5-(2-Adamantan-1-yl-ethyl)-2-(1-methyl-cyclohexyl)-1H-imidazole-4-carbonyl}-amino)-2-methyl-benzoic Acid The title compound was prepared according to the procedure of Example 70, with the modification that 1-methyl-cyclohexanecarboxaldehyde (prepared in two steps from 1-methyl-1-cyclohexanecarboxylic acid) was used in step a instead of 2-dimethylamino-benzaldehyde and 5-amino-2-methyl-benzoic acid benzyl ester replaced 3-amino-benzoic acid benzyl ester in step c. $^1$H NMR (300 MHz, $d_6$-DMSO) 11.80 (1H, br s), 9.36 (1H, s), 8.21 (1H, d), 7.75 (1H, dd), 7.19 (1H, d), 2.87 (2H, m), 2.45 (3H, s), 2.11 (2H, m), 1.93 (3H, br s), 1.62 (6H, m), 1.50–1.32 (16H, m), 1.20 (3H, s). The acid converted to the N-methyl-D-glucamine salt and lyophilised from water/dioxan. Found: C, 63.64; H, 8.72; N, 7.87%. $C_{38}H_{38}N_4O \cdot 1.1\ H_2O$ requires: C, 63.57; H, 8.44; N, 7.80%.

EXAMPLE 201

5-{[5-(2-Adamantan-1-yl-ethyl)-2-(1-methyl-cyclohexyl)-1H-imidazole-4-carbonyl]-amino]-2-fluoro-benzoic Acid 5-{[5-(2-Adamantan-1-yl-ethyl)-2-(1-methyl-cyclohexyl)-1H-imidazole4-carbonyl]-amino}-2-fluoro-benzoic acid methyl ester was prepared according to the procedure of Example 70, steps a, b, and c, with the modification that 1-methyl-cyclohexanecarboxaldehyde (prepared in two steps from 1-methyl-1-cyclohexanecarboxylic acid) was used instead of 2-dimethylamino-benzaldehyde in step a, and 5-amino-2-fluoro-benzoic acid methyl ester replaced 3-amino-benzoic acid benzyl ester in step c. Deprotection was carried out following essentially the procedure of Example 36, step d to afford the title compound. $^1$H NMR (300 MHz, $d_6$-DMSO) 13.00 (1H, br s), 12.00 (1H, br s), 9.70 (1H, br s), 8.33 (1H, m), 7.95 (1H, m), 7.23 (1H, m), 2.89 (2H, m), 2.14 (2H, m), 1.93 (3H, br s), 1.83–1.37 (22H, m), 1.22 (3H, s). The acid was converted to the N-methyl-D-glucamine salt and lyophilised from water/dioxan. Found: C, 57.76; H, 8.24; N, 7.14%. $C_{37}H_{55}FN_4O_8 \cdot 3.8\ H_2O$ requires: C 57.66; H, 8.18; N, 7.27%.

EXAMPLE 202

3-{[5-(2-Adamantan-1-yl-ethyl)-2-(2,6,6-trimethyl-cyclohex-1-enylmethyl)-1H-imidazole-4-carbonyl]-amino)-benzoic Acid The title compound was prepared according to the procedure of Example 68, with the modification that 2,6,6-trimethyl-1-cyclohexene-1-acetaldehyde was used instead of 3,4-dichlorobenzaldehyde. $^1$H NMR (300 MHz, $d_6$-DMSO) 13.00 (1H, br s), 11.80 (1H, br s), 9.80 (1H, br s), 8.43 (1H, s), 7.89 (1H, d), 7.61 (1H, d), 7.41 (1H, t), 3.46 (2H, s), 2.88 (2H, m), 2.01 (2H, m), 1.93 (3H, br s), 1.65–1.45 (19H, m), 1.32 (2H, m), 0.91 (6H, s). The acid was converted to the N-methyl-D-glucamine salt and lyophilised from water/dioxan. Found: C, 62.21; H, 8.62; N, 7.25%. $C_{40}H_{60}N_4O_8 \cdot 2.7\ H_2O$ requires: C, 62.13; H, 8.52; N, 7.25%.

EXAMPLE 203

3-{[5-(2-Adamantan-1-yl-ethyl)-2-(1-methoxymethyl-cyclohexyl)-1H-imidazole-4-carbonyl]-amino}-benzoic Acid The title compound was prepared according to the procedure of Example 70, with the modification that 1-methoxymethyl-cyclohexanecarboxaldehyde (prepared by alkylating methyl cyclohexanecarboxylate at −78° C. with chloromethyl methyl ether, then converting resulting 1-methoxymethyl-cyclohexanecarboxylic acid methyl ester to the aldehyde) was used in step a instead of 2-dimethylamino-benzaldehyde. $^1$H NMR (300 MHz, $d_6$-DMSO) 12.80 (1H, br s), 11.79 (1H, s), 9.47 (1H, s), 8.40 (1H, s), 7.92 (1H, d), 7.61 (1H, d), 7.41 (1H, t), 3.33 (2H, s), 3.14 (3H, s), 2.90 (2H, m), 2.19 (2H, m), 1.93 (3H, br s), 1.66 (6H, m), 1.51 (11H, m), 1.35 (5H, m). The acid was converted to the N-methyl-D-glucamine salt and lyophilised from water/dioxan. Found: C, 61.97; H, 8.46; N, 7.61%. $C_{38}H_{58}N_4O_9 \cdot 1.3\ H_2O$ requires: C, 61.88; H, 8.27; N, 7.60%.

EXAMPLE 204

3-{[5-(2-Adamantan-1-yl-ethyl)-2-(1-hydroxymethyl-cyclohexyl)-1H-imidazole-4-carbonyl]-amino}-benzoic Acid To a suspension of 3-{[5-(2-adamantan-1-yl-ethyl)-2-(1-methoxymethyl-cyclohexyl)-1H-imidazole-4-carbonyl]-amino}-benzoic acid (Example 203) (300 mg, 0.58 mmol) in DCM (10 ml) was added 1 M solution of boron tribromide in DCM (1.72 ml, 1.72 mmol) at 0° C. The mixture was stirred at room temperature for 16 h, cooled to 0° C., and water (20 ml) was added slowly. The product was extracted with DCM/MeOH (3×20 ml of 9:1 mixture), the organic phase was dried (MgSO$_4$) and the solvent was evaporated. The crude product was purified by flash column chromatography (silica, DCM/MeOH, 95:5) to afford the title compound as a white solid (40.5 mg, 14%). $^1$H NMR (300 MHz, $d_6$-DMSO) 9.51 (1H, s), 8.38 (1H, s), 7.92 (1H, d), 7.60 (1H, d), 7.40 (1H, t), 3.41 (2H, s), 2.87 (2H, m), 2.05 (2H, m), 1.94 (3H, br s), 1.65 (6H, m), 1.52 (11H, m), 1.34 (5H, m). The acid was converted to the N-methyl-D-glucamine salt and lyophilised from water/dioxan. Found: C, 60.86; H, 8.33; N, 7.76%. $C_{37}H_{56}N_4O_9 \cdot 1.6\ H_2O$ requires: C, 60.86; H, 8.18; N, 7.67%.

EXAMPLE 205

3-{[5-(2-Adamantan-1-yl-ethyl)-2-[(1R,2RS)-1,7,7-trimethyl-bicyclo[2.2.1]hept-2-yl]-1H-imidazole-4-carbonyl}-amino}-benzoic Acid Step a. 1,7,7-Trimethyl-bicyclo[2.2.1]heptane-2-carbonitrile (1R)-(+)-Camphor was converted to the nitrile using tosylmethyl isocyanide according to the procedure of O. H. Oldenziel (O. H. Oldenziel, D. van Leusen, and A. M. van Leusen *J.Org.Chem.* 1977, 42, 3114).

Step b. 1,7,7-Trimethyl-bicyclo[2.2.1]heptane-2-carbaldehyde

A solution of diisobutyl aluminium hydride (1.5M solution in toluene) (22.5 ml, 33.8 mmol) was added to an ice cooled solution of the product of step a (2.93 g, 17.9 mmol) in THF (30 ml). The mixture was stirred at room temperature for 1.5 h, then cooled with ice and MeOH (15 ml) was added. Hydrochloric acid (2M, 50 ml) was added and the product was extracted with diethyl ether (3×25 ml). The combined organic extracts were washed with brine (25 ml), dried (MgSO$_4$) and the solvent was evaporated. The crude product was purified by flash chromatography (silica, diethyl ether/hexane 3:7) to afford colourless oil (2.16 g, 72%).

$^1$H NMR (300 MHz, CDCl$_3$) 9.85 (1H, s), 2.54 (1H, m), 1.75 (4H, m), 1.40 (2H, m), 1.23 (1H, m), 1.08 (3H, s), 0.91 (3H, s), 0.88 (3H, s).

Step c

The title compound was prepared according to the procedure of Example 70, with the modification that 1,7,7-trimethyl-bicyclo[2.2.1]heptane-2-carbaldehyde (step b of this Example) was used in step a instead of 2-dimethylamino-benzaldehyde. $^1$H NMR (300 MHz, CDCl$_3$) 9.36 (1H, s), 8.34 (1H, d), 8.16 (1H, s), 7.82 (1H, d), 7.41 (1H, t), 6.98 (1H, s), 3.27 (1H, m), 3.05 (2H, m), 2.28 (2H, s), 1.94 (3H, br, s), 1.79–1.26 (17H, m), 1.01 (3H, s), 0.98 (3H, s), 0.94 (3H, s). The acid was converted to the N-methyl-D-glucamine salt and lyophilised from water/dioxan. Found: C, 61.79; H, 8.52; N, 7.33%. C$_{40}$H$_{60}$N$_4$O$_8$.3.0 H$_2$O requires: C, 61.68; H, 8.54; N, 7.19%.

EXAMPLE 206

3-{[5-(2-Adamantan-1-yl-ethyl)-2-[(1S,2RS)-1,7,7-trimethyl-bicyclo[2.2.1]hept-2-yl]-1H-imidazole-4-carbonyl]-amino}-benzoic Acid The title compound was prepared according to the procedure of Example 205, with the modification that (1S)-(–)-camphor was used in step a instead of (1R)-(+)-camphor. $^1$H NMR (300 MHz, CDCl$_3$) 9.36 (1H, s), 8.34 (1H, d), 8.16 (1H, s), 7.82 (1H, d), 7.41 (1H, t), 6.98 (1H, s), 3.27 (1H, m), 3.05 (2H, m), 2.28 (2H, s), 1.94 (3H, br s), 1.79–1.26 (17H, m), 1.01 (3H, s), 0.98 (3H, s), 0.94 (3H, s). The acid was converted to the N-methyl-D-glucamine salt and lyophilised from water/dioxan. Found: C, 63.99; H, 8.62; N, 7.67%. C$_{40}$H$_{60}$N$_4$O$_8$.1.5 H$_2$O requires: C, 63.89; H, 8.45; N, 7.45%.

EXAMPLE 207

3-{[2-Adamantan-2-yl-5-(2-adamantan-1-yl-ethyl)-1H-imidazole-4-carbonyl]-amino}benzoic Acid The title compound was prepared according to the procedure of Example 205, with the modification that adamantan-2-one was used in step a instead of (1R)-(+)-camphor. $^1$H NMR (300 MHz, d$_6$-DMSO) 12.90 (1H, br s), 11.86 (1H, br s), 9.49 (1H, s), 8.41 (1H, s), 7.91 (1H, d), 7.60 (1H, d), 7.40 (1H, t), 2.96 (1H, br s), 2.88 (2H, m), 2.45 (2H, s), 1.98–1.88 (10H, m), 1.77–1.51 (17H, m), 1.36 (2H, m). The acid was converted to the N-methyl-D-glucamine salt and lyophilised from water/dioxan. Found: C, 60.93; H, 8.48; N, 7.19%. C$_{40}$H$_{58}$N$_4$O$_8$.3.0 H$_2$O requires: C, 61.13; H, 8.34; N, 7.13%.

EXAMPLE 208

3-({[5-(2-Adamantan-1-yl-ethyl)-2-bicyclo[3.3.1]non-9-yl-1H-imidazole-4-carbonyl]-amino}-benzoic Acid The title compound was prepared according to the procedure of Example 205, with the modification that bicyclo[3.3.1]non-9-one was used in step a instead of (1R)-(+)-camphor. $^1$H NMR (300 MHz, d$_6$-DMSO) 12.88 (1H, br s), 11.87 (1H, br s), 9.50 (1H, s), 8.41 (1H, s), 7.91 (1H, d), 7.60 (1H, d), 7.41 (1H, t), 2.89 (2H, m), 2.72 (1H, s), 2.44 (2H, br s), 1.93–1.84 (10H, m), 1.70–1.59 (7H, m), 1.51 (8H, m), 1.35 (4H, m). The acid was converted to the N-methyl-D-glucamine salt and lyophilised from water/dioxan. Found: C, 60.97; H, 8.65; N, 7.29%. C$_{39}$H$_{58}$N$_4$O$_8$.3.0 H$_2$O requires: C, 61.08; H, 8.44; N, 7.31%.

EXAMPLE 209

(±)-endo-5-{[5-(2-Adamantan-1-yl-ethyl)-2-bicyclo[2.2.1]hept-2-yl-1H-imidazole-4-carbonyl]-amino}-2-methyl-benzoic Acid (±)-endo-5-(2-Adamantan-1-yl-ethyl)-2-bicyclo[2.2.1]hept-5-en-2-yl-1H-imidazole-4-carboxylic acid benzyl ester (Example 114, step a) was converted to the title compound using essentially the same procedure as in Example 70, steps b, c and d, with the modification the 5-amino-2-methyl-benzoic acid benzyl ester was used in step c instead of 3-amino-benzoic acid benzyl ester. $^1$H NMR (300 MHz, d$_6$-DMSO) 12.80 (1H, br s), 9.75 (1H, br s), 8.26 (1H, d), 7.79 (1H, dd), 7.23 (1H, d), 2.90 (2H, m), 2.57 (1H, br m), 2.46 (3H, s), 2.29 (1H, br m), 1.93 (5H, m), 1.65 (6H, m), 1.50 (8H, m), 1.33 (6H, m), 0.97 (1H, m). The acid was converted to the N-methyl-D-glucamine salt and lyophilised from water/dioxan. Found: C, 61.98; H, 8.39; N, 7.48%. C$_{38}$H$_{56}$N$_4$O$_8$.2.3 H$_2$O requires: C, 61.89; H, 8.27; N, 7.60%.

EXAMPLE 210

(±)-exo-(3-{[5-(2-Adamantan-1-yl-ethyl)-2-bicyclo[2.2.1]hept-2-yl-1H-imidazole-4-carbonyl]-amino}-phenyl)-acetic Acid (±)-exo-5-(2-Adamantan-1-yl-ethyl)-2-bicyclo[2.2.1]hept-5-en-2-yl-1H-imidazole-4-carboxylic acid benzyl ester (Example 114, step a) was converted to the title compound using essentially the same procedure as in Example 70, steps b, c and d, with the modification that (3-amino-phenyl)-acetic acid benzyl ester was used in step c instead of 3-amino-benzoic acid benzyl ester. $^1$H NMR (300 MHz, d$_6$-DMSO) 11.95 (1H, br s), 9.29 (1H, br s), 7.62 (2H, m), 7.21 (1H, t), 6.91 (1H, d), 3.16 (2H, s), 2.87 (2H, m), 2.70 (1H, dd), 2.37 (1H, br m), 2.31 (1H, br m), 2.13 (1H, m), 1.94 (3H, br s), 1.64 (6H, m), 1.50 (10H, m), 1.33 (3H, m), 1.23 (1H, m), 1.09 (1H, br d). The acid was converted to the N-methyl-D-glucamine salt and lyophilised from water/dioxan. Found: C, 65.20; H, 8.26; N, 7.83%. C$_{38}$H$_{56}$N$_4$O$_8$ requires: C, 65.49; H, 8.10; N, 8.04%.

EXAMPLE 211

(±)-endo-5-{[5-(2-Adamantan-1-yl-ethyl)-2-bicyclo[2.2.1]hept-5-en-2-yl-1H-imidazole-4-carbonyl]-amino}-2-methyl-benzoic Acid Step a. (±)-endo-5-{[5-(2-Adamantan-1-yl-ethyl)-2-bicyclo[2.2.1]hept-5-en-2-yl-1H-imidazole-4-carbonyl]-amino}-2-methyl-benzoic Acid Benzyl Ester (±)-endo-5-(2-Adamantan-1-yl-ethyl)-2-bicyclo[2.2.1]hept-5-en-2-yl-1H-imidazole4-carboxylic acid ethyl ester (Example 116, step a) was hydrolysed according to the procedure of Example 20, step c and the resulting (±)-endo-5-(2-adamantan-1-yl-ethyl)-2-bicyclo[2.2.1]hept-5-en-2-yl- 1H-imidazole4-carboxylic acid was reacted with 5-amino-2-methyl-benzoic acid benzyl ester according to the procedure of Example 70, step c. $^1$H NMR (300 MHz CDCl$_3$) 9.01 (1H, s), 8.65 (1H, br s), 8.00 (2H, m), 7.39 (5H, m), 7.20 (1H, d), 6.42 (1H, dd), 5.98 (1H, dd), 5.35 (2H, s), 3.45 (1H, m), 3.20 (1H, br m), 2.99 (3H, m), 2.26 (1H, m), 1.96 (3H, br m), 1.66 (6H, m), 1.57 (1H, m), 1.52 (6H, m), 1.45 (1H, m), 1.34 (3H, m).

Step b

To a solution of the product of step a (921 mg, 1.56 mmol) in ethanol (16 ml) was added a solution of potassium hydroxide (350 mg, 6.24 mmol) in water (4 ml). The mixture was heated at reflux for 1 h, then water (20 ml) was added. Hydrochloric acid (1M) was added until pH=3 was reached. The aqueous layer was extracted with chloroform (3×25 ml). The organic layers were combined and the product absorbed onto silica. Flash column chromatography (silica, DCM/MeOH, 9:1) afforded the product as a white solid (545 mg, 70%). $^1$H NMR (300 MHz, d$_6$-DMSO) 9.37 (1H, s), 7.74 (1H, dd), 7.19 (1H, d), 6.18 (1H, dd), 5.74 (1H, dd), 3.30 (2H, m), 2.91 (1H, m), 2.85 (2H, m), 2.45 (3H, s), 2.06 (1H, m), 1.93 (3H, m), 1.64 (7H, m), 1.50 (6H, m), 1.38 (2H, m), 1.32 (2H, m). The acid was converted to the N-methyl-D-glucamine salt and lyophilised from water/dioxan. Found: C, 62.54; H, 7.86; N, 7.40%. C$_{38}$H$_{54}$N$_4$O$_8$.2.1 H$_2$O requires: C, 62.31; H, 8.01; N, 7.65%.

EXAMPLE 212

3-{[5-(2-Adamantan-1-yl-ethyl)-2-bicyclo[2.2.2]oct-1-yl-1H-imidazole-4-carbonyl]-amino}-benzoic Acid The title compound was prepared according to the procedure of Example 70, with the modification that bicyclo[2.2.2]oct-1-yl-carbaldehyde (prepared by pyridinium chlorochromate oxidation of bicyclo[2.2.2]oct-1-yl-methanol (C. A. Grob, M. Ohta, E. Renk and A. Weiss, *Helv. Chim. Acta* 1958, 41, 1191)) was used in step a instead of 3-dimethylamino benzaldehyde. $^1$H NMR (300 MHz, d$_6$-DMSO) 11.86 (1H, br s), 9.49 (1H, br s), 8.43 (1H, s), 7.89 (1H, d), 7.59 (1H, d), 7.40 (1H, t), 2.86 (2H, m), 1.93 (3H, s), 1.80 (6H, m), 1.64 (13H, m), 1.50 (6H, s), 1.32 (2H, m). The acid was converted to the N-methyl-D-glucamine salt and lyophilised from water/dioxan. Found: C, 60.54; H, 8.53; N, 7.48%. C$_{38}$H$_{56}$N$_4$O$_8$.3.0 H$_2$O requires: C, 60.78; H, 8.32; N, 7.46%.

EXAMPLE 213

5-{[5-(2-Adamantan-1-yl-ethyl)-2-bicyclo[2.2.2]oct-1-yl-1H-imidazole-4-carbonyl]-amino}-2-fluoro-benzoic Acid 5-{[5-(2-Adamantan-1-yl-ethyl)-2-bicyclo[2.2.2]oct-1-yl-1H-imidazole-4carbonyl]-amino}-2-fluoro-benzoic acid methyl ester was prepared according to the procedure of Example 70, steps a, b, and c, with the modification that bicyclo[2.2.2]oct-1-yl-carbaldehyde (prepared by pyridinium chlorochromate oxidation of bicyclo[2.2.2]oct-1-yl-methanol (C. A. Grob, M. Ohta, E. Renk and A. Weiss, *Helv. Chim. Acta* 1958, 41, 1191)) was used instead of 2-dimethylamino-benzaldehyde in step a, and 5-amino-2-fluoro-benzoic acid methyl ester replaced 3-amino-benzoic acid benzyl ester in step c. Deprotection was carried out following essentially the procedure of Example 36, step d to afford the title compound. $^1$H NMR (300 MHz, d$_6$-DMSO) 8.30 (1H, d), 7.94 (1H, m), 7.28 (1H, t), 2.88 (2H, m), 1.98–1.75 (9H, m), 1.65 (13H, m), 1.49 (6 H, s), 1.34 (2H, m). The acid was converted to the N-methyl-D-glucamine salt and lyophilised from water/dioxan. Found: C, 57.85; H, 8.12; N, 7.18%. C$_{38}$H$_{55}$FN$_4$O$_8$.4.0 H$_2$O requires: C, 58.00; H, 8.07; N, 7.12%.

EXAMPLE 214

3-{[5-(2-Adamantan-1-yl-ethyl)-2-cyclohexyl-1-methyl-1H-imidazole-4-carbonyl]-amino}-benzoic Acid Step a. 5-(2-Adamantan-1-yl-ethyl)-2-cyclohexyl-1-methyl-1H-imidazole-4-carboxylic Acid Benzyl Ester and 5-(2-adamantan-1-yl-ethyl)-2-cyclohexyl-3-methyl-3H-imidazole-4-carboxylic Acid Benzyl Ester 5-(2-Adamantan-1-yl-ethyl)-2-cyclohexyl-1H-imidazole-4-carboxylic acid benzyl ester (prepared according to the procedure of Example 70, step a using cyclohexanecarboxaldehyde instead of 2-dimethylamino-benzaldehyde) was converted to the two isomeric N-methyl derivatives according to the procedure of Example 73, step a.

Step b 5-(2-Adamantan-1-yl-ethyl)-2-cyclohexyl-1-methyl-1H-imidazole-4-carboxylic acid benzyl ester (low R$_f$ material from step a) was converted to the title compound according to the procedure given in Example 70, steps b, c and d. $^1$H NMR (300 MHz, d$_6$-DMSO) 13.00 (1H, br s), 9.54 (1H, s), 8.43 (1H, s), 7.92 (1H, m), 7.62 (1H, d), 7.40 (1H, m), 3.49 (3H, s), 2.93 (2H, m), 2.76 (1H, m), 1.95–1.19 (27H, m). The acid was converted to the N-methyl-D-glucamine salt and lyophilised from water/dioxan. Found: C, 62.44; H, 8.49; N, 7.88%. C$_{37}$H$_{56}$N$_4$O$_8$.1.5 mols H$_2$O requires: C, 62.43; H, 8.35; N, 7.87%.

EXAMPLE 215

(3-{[5-(2-Adamantan-1-yl-ethyl)-2-cyclohexyl-1-methyl-1H-imidazole-4-carbonyl]-amino}-phenyl)-acetic Acid 5-(2-Adamantan-1-yl-ethyl)-2-cyclohexyl-1-methyl-1H-imidazole4-carboxylic acid benzyl ester (Example 214, step a) was converted to the title compound according to the procedure given in Example 70, steps b, c and d, with the modification that (3-amino-phenyl)-acetic acid benzyl ester replaced 3-amino-benzoic acid benzyl ester in step c. $^1$H NMR (300 MHz, d$_6$-DMSO) 9.27 (1H, br s), 7.62 (2H, m), 7.22 (1H, m), 6.93 (1H, d), 3.51 (2H, s), 3.48 (3H, s), 2.93 (2H, m), 2.73 (1H, m), 1.95–1.18 (27H, m). The acid was converted to the N-methyl-D-glucamine salt and lyophilised from water/dioxan. Found: C, 61.19; H, 8.66; N, 7.61%. C$_{38}$H$_{58}$N$_4$O$_8$.2.5 mols H$_2$O requires: C, 61.35; H, 8.54; N, 7.53%.

EXAMPLE 216

3-{[5-(Adamantan-1-yloxymethyl)-2-cyclohexyl-1H-imidazole-4-carbonyl]-amino}-benzoic Acid Step a. (Adamantan-1-yloxy)-acetic Acid A mixture of (adamantan-1-yloxy)-acetic acid ethyl ester (A. F. Noels et al. *Tetrahedron,* 1982, 38, 2733) (7.29 g, 29 mmol) and potassium hydroxide (2.60 g, 46 mmol) in water-ethanol (1:2 mixture, 180 ml) was heated at reflux for 2 h. The mixture was cooled, then concentrated in vacuum and acidified with concentrated hydrochloric acid. The resultant white precipitate was dissolved in ethyl acetate (200 ml). The solution was washed with brine (2×200 ml), dried (MgSO$_4$) and the solvent was evaporated to afford white crystalline solid (5.85 g 92%). $^1$H NMR (300 MHz, CDCl$_3$) 4.08 (2H, s), 2.20–1.58 (15H, m).

Step b. 4-(Adamantan-1-yloxy)-3-oxo-2-(triphenyl-1$^5$-phosphanylidene)-butyric Acid Benzyl Ester Oxalyl chloride (18.6 ml, 0.214 mol) was added to a solution of the product of step a (39.13 g, 0.178 mol) in DCM (800 ml) containing catalytic amount of DMF at room temperature. The mixture was stirred at room temperature for 1 h, then the solvent was evaporated. The residue was dissolved in benzene (100 ml) and added dropwise to a solution of benzyl (triphenylphosphoranylidene)acetate (72.9 g, 0.178 mol) and N,O-bis(trimethylsilyl)acetamide (53.2 ml, 0.215 mol) in benzene (300 ml) at 0° C. The mixture was allowed to warm to room temperature, and stirred for 16 h. The reaction mixture was diluted with ethyl acetate (500 ml), washed with 5% aqueous potassium hydrogen sulfate (500 ml), 10% sodium carbonate (500 ml), brine (300 ml), dried (MgSO$_4$) and the solvent was evaporated. The residue was triturated with diethyl ether to afford white solid (93.83 g, 98%). $^1$H NMR (300 MHz, CDCl$_3$) 7.64–6.94 (20H, m), 4.74 (2H, s), 4.72 (2H, s), 2.08–1.57 (15H, m).

Step c. 4-(Adamantan-1-yloxy)-2,3-dioxo-butyric Acid Benzyl Ester Monohydrate

To a vigorously stirred solution of the product of step b (12.0 g, 20.0 mmol) in DCM/water (1:1 mixture, 320 ml) were added tetrabutylammonium bromide (645 mg, 2.00 mmol) and potassium peroxymonosufate (OXONE) (24.7 g, 40.0 mmol) at 0° C. The mixture was stirred at room temperature for 48 h, the organic layer was separated, washed with water (3×100 ml), brine (100 ml), dried (MgSO$_4$) and the solvent was evaporated in vacuum. The residue was purified by flash chromatography (silica, hexane/ethyl acetate 1:1) to afford the product as pale yellow oil (6.1 g, 81%). $^1$H NMR (300 MHz, CDCl$_3$) 7.33 (5H, m), 5.26 (2H, s), 4.98 (2H, br s), 4.30 (2H, s), 2.14 (3H, br s), 1.72–1.54 (12H, m).

Step d. 5-(Adamantan-1-yloxymethyl)-2-cyclohexyl-1H-imidazole-4-carboxylic Acid Benzyl Ester To a slurry of the product of step c (1.70 g, 4.54 mmol) and ammonium acetate (3.40 g, 45.4 mmol) in acetic acid (20 ml) was added cyclohexanecarboxaldehyde (1.10 ml 9.08 mmol). The mixture was stirred in an oil bath heated at 70° C. for 2 h. The solution was cooled to room temperature and the acetic acid was evaporated in vacuum. The residue was dissolved in ethyl acetate (30 ml), saturated sodium bicarbonate (100 ml) was slowly added and the mixture was stirred for 30 min. The organic layer was separated, washed with sodium bicarbonate (30 ml), brine (30 ml), dried (MgSO$_4$) and the solvent was evaporated. The crude product was purified by flash column chromatography (silica, DCM/ethyl acetate 4:1) to afford colourless foam (1.0 g, 49%).

$^1$H NMR (CDCl$_3$) 7.40 (5H, m), 5.30 (2H, s), 4.76 (2H, br s), 2.79 (1H, m), 2.14 (3H, br s), 2.05 (2H, m), 1.85–1.26 (20H, m).

Step e. 5-(Adamantan-1-yloxymethyl)-2-cyclohexyl-1H-imidazole-4-carboxylic Acid

The product of step c (1.00 g, 2.23 mmol) was deprotected using the same procedure as in Example 1, step e to afford the acid as a white solid (0.76 g, 96%). $^1$H NMR (300 MHz, d$_6$-DMSO) 12.00 (1H, br s), 4.60 (2H, br s), 2.63 (1H, m), 2.09 (3H, br s), 2.02–1.23 (22H, m).

Step f. 3-{[5-(Adamantan-1-yloxymethyl)-2-cyclohexyl-1H-imidazole-4-carbonyl]-amino}-benzoic Acid Benzyl Ester The product of step d (0.76 g, 2.122 mmol) was reacted with 3-amino-benzoic acid benzyl ester (0.48 g, 2.12 mmol) according to the procedure of Example 20, step d. The crude material was purified by flash chromatography (silica, DCM/ethyl acetate 98:2, then 95:5) to afford colourless foam (786 mg, 65.5%). $^1$H NMR (300 MHz, CDCl$_3$) 9.50 and 8.90 (1H, 2× br s), 8.15 (2H, m), 7.81 (1H, d), 7.40 (6H, m), 5.38 (2H, s), 4.98 (2H, br s), 2.71 (1H, m), 2.16 (3H, br s), 2.00 (2H, m), 1.85–1.24 (20H, m).

Step g

The product of step c (780 mg, 1.37 mmol) was deprotected using the same procedure as in Example 1, step e to afford white solid (636 mg, 98%). $^1$H NMR (300 MHz, d$_6$-DMSO) 12.50 (1H, br s), 12.00 (1H, br s), 9.70 (1H, br s), 8.45 (1H, s), 7.92 (1H, dd), 7.62 (1H, d), 7.41 (1H, t), 4.79 (2H, s), 2.70 (1H, m), 2.11 (3H, br s), 1.89 (2H, m), 1.76 (6H, m), 1.60 (10H, m), 1.30 (4H, m). The acid was converted to the N-methyl-D-glucamine salt and lyophilised from water/dioxan. Found: C, 58.06; H, 8.12; N, 7.62%. C$_{35}$H$_{52}$N$_4$O$_9$.3.0 mols H$_2$O requires: C, 57.84; H, 8.04; N, 7.71%.

EXAMPLE 217

5-{[5-(Adamantan-1-yloxymethyl)-2-cyclohexyl-1H-imidazole-4-carbonyl]-amino}-2-methyl-benzoic Acid The title compound was prepared according to the procedure of Example 216, with the modification that 5-amino-2-methyl-benzoic acid benzyl ester was used in step f instead of 3-amino-benzoic acid benzyl ester. $^1$H NMR (300 MHz, d$_6$-DMSO) 9.57 (1H, br s), 8.31 (1H, brs), 7.77 (1H, dd), 7.21 (1H, d), 4.78 (2H, s), 2.72 (1H, m), 2.46 (3H, s), 2.11 (3H, br s), 1.88 (2H, m), 1.79–1.54 (16H, m), 1.30 (4H, m). The acid was converted to the N-methyl-D-glucamine salt and lyophilised from water/dioxan. Found: C, 56.95; H, 8.38; N, 7.41%. C$_{36}$H$_{54}$N$_4$O$_9$.4.0 mols H$_2$O requires: C, 56.98; H, 8.24; N, 7.38%.

EXAMPLE 218

3-{[5-(Adamantan-1-yloxymethyl)-2-cyclohexyl-1H-imidazole-4-carbonyl]-amino}-2-methyl-benzoic Acid The title compound was prepared according to the procedure of Example 216, with the modification that 3-amino-2-methyl-benzoic acid benzyl ester was used in step f instead of 3-amino-benzoic acid benzyl ester. $^1$H NMR (300 MHz, d$_6$-DMSO) 12.20 (1H, br s), 9.38 (1H, br s), 7.90 (1H, br d), 7.50 (1H, d), 7.26 (1H, t), 4.78 (2H, s), 2.69 (1H, m), 2.39 (3H, s), 2.09 (3H, br s), 1.90 (2H, m), 1.79–1.52 (17H, m), 1.31 (3H, m), was converted to the N-methyl-D-glucamine salt and lyophilised from water/dioxan. Found: C, 59.75; H, 8.26; N, 7.62%. C$_{36}$H$_{54}$N$_4$O$_9$.2.0 mols H$_2$O requires: C, 59.82; H, 8.08; N, 7.75%.

EXAMPLE 219

(3-{[5-(Adamantan-1-yloxymethyl)-2-cyclohexyl-1H-imidazole-4-carbonyl]-amino}-phenyl)-acetic Acid The title compound was prepared according to the procedure of Example 216, with the modification that (3-aminophenyl)-acetic acid benzyl ester was used in step f instead of 3-amino-benzoic acid benzyl ester. $^1$H NMR (300 MHz, d$_6$-DMSO) 12.14 (1H, br s), (1H, d), 9.40 (1H, br s), 7.68 (1H, br s), 7.61 (1H, d), 7.23 (1H, t), 6.93 (1H, 4.78 (2H, br s), 3.52 (2H, s), 2.69 (1H, m), 2.11 (3H, br s), 1.89 (2H, m), 1.75 (6H, m), 1.57 (10H, m), 1.28 (4H, m). The acid was converted to the N-methyl-D-glucamine salt and lyophilised from water/dioxan. Found: C, 61.21; H, 8.28; N, 7.87%. C$_{36}$H$_{54}$N$_4$O$_9$.1.2 mols H$_2$O requires: C, 61.11; H, 8.02; N, 7.92%.

EXAMPLE 220

5-([5-(Adamantan-1-yloxymethyl)-2-(1-methyl-cyclohexyl)-1H-imidazole-4-carbonyl]-amino}-2-methyl-benzoic Acid The title compound was prepared according to the procedure of Example 216, with the modification that 1-methyl-cyclohexanecarboxaldehyde (prepared in two steps from 1-methyl-1-cyclohexanecarboxylic acid) was used in step d instead of cyclohexanecarboxaldehyde and 5-amino-2-methyl-benzoic acid benzyl ester replaced 3-amino-benzoic acid benzyl ester in step f. $^1$H NMR (300 MHz, d$_6$-DMSO) 12.70 (1H, br s), 12.09 (1H, br s), 9.48 (1H, s), 8.25 (1H, s), 7.79 (1H, dd), 7.23 (1H, d), 4.79 (2H, s), 2.46 (3H, s), 2.15 (5H, m), 1.75 (6H, s), 1.62–1.35 (14H, m), 1.22 (3H, s). The acid was converted to the N-methyl-D-glucamine salt and lyophilised from water/dioxan. Found: C, 58.66; H, 8.44; N, 7.30%. C$_{37}$H$_{56}$N$_4$O$_9$.3.0 mols H$_2$O requires: C, 58.87; H, 8.28; N, 7.42%.

EXAMPLE 221

3-{[5-(Adamantan-1-yloxymethyl)-2-bicyclo[2.2.2]oct-1-yl-1H-imidazole-4-carbonyl]-amino}-benzoic Acid The title compound was prepared according to the procedure of Example 216, with the modification that bicyclo[2.2.2]oct-1-yl-carbaldehyde (prepared by pyridinium chlorochromate oxidation of bicyclo[2.2.2]oct-1-yl-methanol (C. A. Grob, M. Ohta, E. Renk and A. Weiss, *Helv. Chim. Acta* 1958, 41, 1191)) was used in step d instead of cyclohexanecarboxaldehyde. $^1$H NMR (300 MHz, d$_6$-DMSO) 12.80 (1H, br s), 12.06 (1H, br s), 9.59 (1H, s), 8.42 (1H, s), 7.92 (1H, d), 7.60 (1H, d), 7.41 (1H, t), 4.77 (2H, s), 2.10 (3H, br s), 1.84 (6H, m), 1.76 (6H, m), 1.64–1.53 (13H, m). The acid was converted to the N-methyl-D-glucamine salt and lyophilised from water/dioxan. Found: C, 60.50; H, 7.94; N, 7.49%. C$_{37}$H$_{54}$N$_4$O$_9$.2.0 mols H$_2$O requires: C, 60.47; H, 7.96; N, 7.62%.

EXAMPLE 222

3-{[5-(Adamantan-1-yloxymethyl)-2-bicyclo[2.2.2]oct-1-yl-1H-imidazole-4-carbonyl]-amino}-2-methyl-benzoic Acid The title compound was prepared according to the procedure of Example 216, with the modification that bicyclo[2.2.2]oct-1-yl-carbaldehyde (prepared by pyridinium chlorochromate oxidation of bicyclo[2.2.2]oct-1-yl-methanol (C. A. Grob, M. Ohta, E. Renk and A. Weiss, *Helv. Chim. Acta* 1958, 41, 1191)) was used in step d instead of cyclohexanecarboxaldehyde and 3-amino-2-methyl-benzoic acid benzyl ester replaced 3-amino-benzoic acid benzyl ester in step f. $^1$H NMR (300 MHz, d$_6$-DMSO) 12.90 (1H, br s), 12.11 (1H, br s), 9.38 (1H, s), 8.01 (1H, d), 7.51 (1H, d), 7.28 (1H, t), 4.76 (2H, s), 2.40 (3H, s), 2.09 (3H, br s), 1.85–1.73 (12H, m), 1.64–1.52 (13H, m). The acid was converted to the N-methyl-D-glucamine salt and lyophilised from water/dioxan. Found: C, 60.74; H, 7.99; N, 7.18%. C$_{38}$H$_{56}$N$_4$O$_9$.2.0 mols H$_2$O requires: C, 60.94; H, 8.08; N, 7.48%.

EXAMPLE 223

5-{[5-(Adamantan-1-yloxymethyl)-2-bicyclo[2.2.2]oct-1-yl-1H-imidazole-4-carbonyl]-amino}-2-fluoro-benzoic Acid 5-{[5-(Adamantan-1-yloxymethyl)-2-bicyclo[2.2.2]oct-1-yl-1H-imidazole-4-carbonyl]-amino}-2-fluoro-benzoic acid methyl ester was prepared according to the procedure of Example 216, steps a, b, c, d, e and f with the modification that bicyclo[2.2.2]oct-1-yl-carbaldehyde (prepared by pyridinium chlorochromate oxidation of bicyclo[2.2.2]oct-1-yl-methanol (C. A. Grob, M. Ohta, E. Renk and A. Weiss, *Helv. Chim. Acta* 1958, 41, 1191)) was used in step d instead of cyclohexanecarboxaldehyde, and 5-amino-2-fluoro-benzoic acid methyl ester replaced 3-amino-benzoic acid benzyl ester in step f. Deprotection was carried out following essentially the procedure of Example 36, step d to afford the title compound. $^1$H NMR (300 MHz, d$_6$-DMSO) 13.20 (1H, br s), 12.05 (1H, br s), 9.63 (1H, s), 8.33 (1H, d), 7.94 (1H, m), 7.24 (1H, t), 4.76 (2H, br s), 2.10 (3H, br s), 1.90–1.74 (12H, m), 1.64–1.53 (13H, m). The acid was converted to the N-methyl-D-glucamine salt and lyophilised from water/dioxan. Found: C, 59.14; H, 7.66; N, 7.43%.C$_{37}$H$_{53}$FN$_4$O$_9$.2.0 mols H$_2$O requires: C, 59.03; H, 7.63; N, 7.44%.

EXAMPLE 224

(3-{[5-(Adamantan-1-yloxymethyl)-2-bicyclo[2.2.2]oct-1-yl-1H-imidazole-4-carbonyl]-amino}-phenyl)-acetic Acid The title compound was prepared according to the procedure of Example 216, with the modification that bicyclo[2.2.2]oct-1-yl-carbaldehyde (prepared by pyridinium chlorochromate oxidation of bicyclo[2.2.2]oct-1-yl-methanol (C. A. Grob, M. Ohta, E. Renk and A. Weiss, *Helv. Chim. Acta* 1958, 41, 1191)) was used in step d instead of cyclohexanecarboxaldehyde and (3-amino-phenyl)-acetic acid benzyl ester replaced 3-amino-benzoic acid benzyl ester in step f. $^1$H NMR (300 MHz, d$_6$-DMSO) 12.05 (1H, br s), 9.34 (1H, br s), 7.62 (2H, m), 7.24 (1H, t), 6.94 (1H, d), 4.76 (2H, s), 3.52 (2H, s), 2.10 (3H, br s), 1.89–1.76 (12H, m), 1.64–1.58 (13H, m). The acid was converted to the N-methyl-D-glucamine salt and lyophilised from water/dioxan. Found: C, 60.94; H, 8.28; N, 7.31%. C$_{38}$H$_{56}$N$_4$O$_9$.2.0 mols H$_2$O requires: C, 60.94; H, 8.08; N, 7.48%.

EXAMPLE 225

3-{[5-(Adamantan-1-yloxymethyl)-2-bicyclo[2.2.2]oct-2-en-1-yl-1H-imidazole-4-carbonyl]-amino}-benzoic Acid 5-(Adamantan-1-yloxymethyl)-2-bicyclo[2.2.2]oct-2-en-1-yl-1H-imidazole-4-carboxylic acid benzyl ester was prepared according to the procedure of Example 216, steps a, b, c and d with the modification that bicyclo[2.2.2]oct-2-en-1-yl-carbaldehyde (prepared by reduction and then pyridinium chlorochromate oxidation of bicyclo[2.2.2]oct-2-en-1-ylcarboxylic acid ethyl ester (C. A. Grob, M. Ohta, E. Renk and A. Weiss, *Helv. Chim. Acta* 1958, 41, 1191)) was used in step d instead of cyclohexanecarboxaldehyde. The benzyl ester was hydrolysed according to the procedure of Example 211, step b and the resulting 5-(adamantan-1-yloxymethyl)-2-bicyclo[2.2.2]oct-2-en-1-yl-1H-imidazole4-carboxylic acid was reacted with 3-amino-benzoic acid benzyl ester according to the procedure of Example 177, step a to afford 3-{[5-(adamantan-1-yloxymethyl)-2-bicyclo[2.2.2]oct-2-en-1-yl-1H-imidazole4-carbonyl]-amino}-benzoic acid benzyl ester. The benzyl ester was hydrolysed according to the procedure of Example 211, step b to afford the title compound. $^1$H NMR (300 MHz, d$_6$-DMSO) 12.35 (1H, br s), 9.69 (1H, s), 8.44 (1H, br s), 7.95 (1H, d), 7.62 (1H, d), 7.41 (1H, t), 6.73 (1H, d), 6.38 (1H, dd), 4.81 (2H, s), 2.63 (1H, br s), 2.11 (3H, br s), 1.97 (2H, td), 1.76 (6H, s), 1.67–1.53 (8H, m), 1.44 (2H, t), 1.30 (2H, t). The acid was converted to the N-methyl-D-glucamine salt and lyophilised from water/dioxan. Found: C, 56.61; H, 7.99; N, 7.35%. $C_{37}H_{52}N_4O_9$.5.0 mols H$_2$O requires: C, 56.47; H, 7.94; N, 7.12%.

EXAMPLE 226

3-{[5-(Adamantan-1-yloxymethyl)-2-(2,4,6-trimethyl-phenyl)-1H-imidazole-4-carbonyl]-amino}-benzoic Acid The title compound was prepared according to the procedure of Example 216, with the modification that 2,4,6-trimethylbenzaldehyde was used in step d instead of cyclohexanecarboxaldehyde. $^1$H NMR (300 MHz, d$_6$-DMSO) 12.50 (1H, br s), 9.92 (1H, s), 8.53 (1H, s), 7.94 (1H, m), 7.62 (1H, d), 7.40 (1H, t), 6.95 (2H, s), 4.91 (2H, s), 2.28 (3H, s), 2.10 (3H, s), 2.07 (6H, s), 1.77 (6H, s), 1.57 (6H, m). The acid was converted to the N-methyl-D-glucamine salt and lyophilised from water/dioxan. Found: C, 62.29; H, 7.61; N, 7.45%. $C_{38}H_{52}N_4O_9$.1.2 mols H$_2$O requires: C, 62.56; H, 7.50; N, 7.68%.

EXAMPLE 227

(3-{[5-(Adamantan-1-yloxymethyl)-2-(2,4,6-trimethyl-phenyl)-1H-imidazole-4-carbonyl]-amino}-phenyl)-acetic Acid The title compound was prepared according to the procedure of Example 216, with the modification that 2,4,6-trimethylbenzaldehyde was used in step d instead of cyclohexanecarboxaldehyde and (3-amino-phenyl)-acetic acid benzyl ester replaced 3-amino-benzoic acid benzyl ester in step f. $^1$H NMR (300 MHz, d$_6$-DMSO) 12.53 (1H, br s), 9.63 (1H, br s), 7.75 (1H, s), 7.62 (1H, d), 7.22 (1H, t), 6.95 (3H, m), 4.89 (2H, s), 3.50 (2H, s), 2.28 (3H, s), 2.10 (3H, s), 2.07 (6H, s), 1.77 (6H, s), 1.58 (6H, m). The acid was converted to the N-methyl-D-glucamine salt and lyophilised from water/dioxan. Found: C, 61.64; H, 7.80; N, 7.28%. $C_{39}H_{54}N_4O_9$.2.1 mols H$_2$O requires: C, 61.61; H, 7.71; N, 7.37%.

EXAMPLE 228

3-{[5-(Adamantan-1-yloxymethyl)-2-cycloheptyl-1H-imidazole-4-carbonyl]-amino}-benzoic Acid The title compound was prepared according to the procedure of Example 216, with the modification that cycloheptanecarboxaldehyde was used in step d instead of cyclohexanecarboxaldehyde. $^1$H NMR (300 MHz, d$_4$-MeOH) 8.33 (1H, t), 7.96 (1H, m), 7.79 (1H, m), 7.47 (1H, t), 4.89 (2H, s), 3.03 (1H, m), 2.18 (3H, br s), 2.04 (2H, m), 1.86 (9H, m), 1.69 (13H, m). The acid was converted to the N-methyl-D-glucamine salt and lyophilised from water/dioxan. Found: C, 59.61; H, 8.26; N, 7.56%. $C_{36}H_{54}N_4O_9$.2.2 mols H$_2$O requires: C, 59.58; H, 8.18; N, 7.72%.

EXAMPLE 229

(3-{[5-(Adamantan-1-yloxymethyl)-2-cycloheptyl-1H-imidazole-4-carbonyl]-amino}-phenyl)-acetic Acid The title compound was prepared according to the procedure of Example 216, with the modification that cycloheptanecarboxaldehyde was used in step d instead of cyclohexanecarboxaldehyde and (3-amino-phenyl)-acetic acid benzyl ester replaced 3-amino-benzoic acid benzyl ester in step f. $^1$H NMR (300 MHz, d$_4$-MeOH) 7.60 (2H, m), 7.31 (1H, t), 7.06 (1H, d), 4.88 (2H, s), 3.62 (2H, s), 2.96 (1H, m), 2.17 (3H, br s), 2.01 (2H, m), 1.85 (9H, m), 1.64 (13H, m). The acid was converted to the N-methyl-D-glucamine salt and lyophilised from water/dioxan. Found: C, 60.04; H, 8.44; N, 7.69%. $C_{37}H_{56}N_4O_9$.2.3 mols H$_2$O requires: C, 59.84; H, 8.23; N, 7.54%.

EXAMPLE 230

3-{[5-(Adamantan-1-yloxymethyl)-2-cyclohept-4-enyl-1H-imidazole-4-carbonyl]-amino}-benzoic Acid 5-(Adamantan-1-yloxymethyl)-2-cyclohept-4-enyl-1H-imidazole-4-carboxylic acid benzyl ester was prepared according to the procedure of Example 216, steps a, b, c, d with the modification that cyclohept-4-enecarboxaldehyde (D. F. Murray et al. *J. Org Chem.* 1986, 51, 1) was used in step d instead of cyclohexanecarboxaldehyde. The benzyl ester was hydrolysed according to the procedure of Example 211, step b and the resulting 5-(adamantan-1-yloxymethyl)-2-cyclohept-4-enyl-1H-imidazole-4-carboxylic acid was reacted with 3-amino-benzoic acid methyl ester according to the procedure of Example 20, step d to afford 3-{[5-(adamantan-1-yloxymethyl)-2-cyclohept-4-enyl-1H-imidazole-4-carbonyl]-amino}-benzoic acid methyl ester. The methyl ester was hydrolysed according to the procedure of Example 36, step d to afford the title compound. $^1$H NMR (300 MHz, d$_6$-DMSO) 12.90 (1H, br s), 12.40 (1H, br s), 9.87 (1H, br s), 8.44 (1H, s), 7.93 (1H, d), 7.63 (1H, d), 7.42 (1H, t), 5.81 (2H, m), 4.79 (2H, s), 3.04 (1H, m), 2.30 (2H, m), 2.11 (5H, m), 1.96 (2H, m), 1.76–1.53 (14H, m). The acid was converted to the N-methyl-D-glucamine salt and lyophilised from water/dioxan. Found: C, 59.69; H, 7.90; N, 7.88%. $C_{36}H_{52}N_4O_9$.2.1 mols H$_2$O requires: C, 59.81; H, 7.84; N, 7.75%.

EXAMPLE 231

(3-{[5-(Adamantan-1-yloxymethyl)-2-cyclohet-4-enyl-1H-imidazole-4-carbonyl]-amino}-phenyl)-acetic Acid 5-(Adamantan-1-yloxymethyl)-2-cyclohept-4-enyl-1H-imidazole-4-carboxylic acid benzyl ester was prepared according to the procedure of Example 216, steps a, b, c, d with the modification that cyclohept-4-enecarboxaldehyde (D. F. Murray et al. *J. Org. Chem.* 1986, 51, 1) was used in step d instead of cyclohexanecarboxaldehyde. The benzyl ester was hydrolysed according to the procedure of Example 211, step b and the resulting 5-(adamantan-1-yloxymethyl)-2-cyclohept4-enyl-1H-imidazole4-carboxylic acid was reacted with (3-amino-phenyl)-acetic acid benzyl ester according to the procedure of Example 20, step d to afford (3-{[5-(adamantan-1-yloxymethyl)-2-cyclohept-4-enyl-1H-imidazole-4-carbonyl]-amino}-phenyl)-acetic acid benzyl ester. The benzyl ester was hydrolysed according to the procedure of Example 211, step b to afford the title compound. $^1$H NMR (300 MHz, d$_6$-DMSO) 12.25 (2H, br m), 9.45 (1H, br s), 7.62 (2H, m), 7.24 (1H, t), 6.94 (1H, d), 5.82 (2H, br s), 4.78 (2H, s), 3.53 (2H, s), 3.03 (1H, m), 2.30 (2H, m), 2.13 (5H, m), 1.94 (2H, m), 1.76–1.58 (14H, m). The acid was converted to the N-methyl-D-glucamine salt and lyophilised from water/dioxan. Found: C, 60.40; H, 8.07; N, 7.72%. $C_{37}H_{54}N_4O_9$.2.1 mols H$_2$O requires: C, 60.38; H, 7.96; N, 7.61%.

EXAMPLE 232

3-{[5-(Adamantan-1-yloxymethyl)-2-bicyclo[2.2.1]hept-7-yl-1H-imidazole-4-carbonyl]-amino}-benzoic Acid The title compound was prepared according to the procedure of Example 216, with the modification that bicyclo[2.2.1]hepta-2,5-diene-7-carbaldehyde (G. W. Klumpp et al. *Tetrahedron*, 1981, 37, 187) was used in step d instead of cyclohexanecarboxaldehyde. $^1$H NMR (300 MHz, d$_6$-DMSO) 12.90 (1H, br s), 12.18 (1H, br s), 9.59 (1H, s), 8.42 (1H, s), 7.93 (1H, d), 7.61 (1H, d), 7.42 (1H, t), 4.79 (2H, br s), 2.76 (1H, s), 2.63 (2H, s), 2.09 (3H, br s), 1.76–1.53 (16H, m), 1.27 (2H, d), 1.18 (2H, d). The acid was converted to the N-methyl-D-glucamine salt and lyophilised from water/dioxan. Found: C, 59.87; H, 8.14; N, 7.45%. $C_{36}H_{52}N_4O_9$.2.2 mols H$_2$O requires: C, 59.98; H, 7.83; N, 7.77%.

EXAMPLE 233

3-{[5-(Adamantan-1-yloxymethyl)-2-(tetrahydro-pyran-4-yl)-1H-imidazole-4-carbonyl]-amino}-benzoic Acid The title compound was prepared according to the procedure of Example 216, with the modification that tetrahydro-pyran-4-carbaldehyde (R. K. Anderson, P. C. Chapman et al. *J. Antibiotics* 1993, 46, 331) was used in step d instead of cyclohexanecarboxaldehyde. $^1$H NMR (300 MHz, d$_6$-DMSO) 9.82 (1H, br s), 8.44 (1H, s), 7.94 (1H, d), 7.62 (1H, d), 7.43 (1H, t), 4.80 (2H, s), 3.92 (2H, m), 3.41 (2H, m), 3.00 (1H, m), 2.11 (3H, s), 1.81 (10H, m), 1.58 (6H, m). The acid was converted to the N-methyl-D-glucamine salt and lyophilised from water/dioxan. Found: C, 56.42; H, 7.95; N, 7.62%. $C_{34}H_{50}N_4O_{10}$.3.0 mols H$_2$O requires: C, 56.03; H, 7.75; N, 7.69%.

EXAMPLE 234

(±)-endo-3-{[5-(Adamantan-1-yloxymethyl)-2-bicyclo[2.2.1]hept-5-en-2-yl-1H-imidazole-4-carbonyl]-amino}-benzoic Acid (±)-endo-5-(Adamantan-1-yloxymethyl)-2-bicyclo[2.2.1]hept-5-en-2-yl-1H-imidazole-4-carboxylic acid benzyl ester was prepared according to the procedure of Example 216, steps a, b, c and d with the modification that (±)-5-norbornene-2-carboxaldehyde was used in step d instead of cyclohexanecarboxaldehyde. The benzyl ester was hydrolysed according to the procedure of Example 211, step b and the resulting (±)-endo-5-(adamantan-1-yloxymethyl)-2-bicyclo[2.2.1]hept-5-en-2-yl-1H-imidazole-4-carboxylic acid was reacted with 3-amino-benzoic acid methyl ester according to the procedure of Example 20, step d to afford (±)-endo-3-{[5-(adamantan-1-yloxymethyl)-2-bicyclo[2.2.2]hept-5-en-2-yl-1H-imidazole-4-carbonyl]-amino}-benzoic acid methyl ester. The methyl ester was hydrolysed according to the procedure of Example 211, step b to afford the title compound. $^1$H NMR (300 MHz, d$_4$-MeOH) 8.32 (1H, s), 7.77 (2H, d), 7.38 (1H, t), 6.29 (1H, dd), 5.79 (1H, dd), 4.86 (2H, s), 3.46 (1H, m), 3.28 (1H, br s), 2.98 (1H, br s), 2.17 (4H, m), 1.86 (6H, m), 1.67 (6H, m), 1.49 (3H, m). The acid was converted to the N-methyl-D-glucamine salt and lyophilised from water/dioxan. Found: C, 58.69; H, 7.88; N, 7.46%. $C_{36}H_{50}N_4O_9$.3.1 mols H$_2$O requires: C, 58.52; H, 7.67; N, 7.58%.

EXAMPLE 235 endo-3-{[5-(Adamantan-1-yloxymethyl)-2-((1S,2S)-bicyclo[2.2.1]hept-5-en-2-yl)-1H-imidazole-4-carbonyl]-amino}-benzoic Acid endo-5-(Adamantan-1-yloxymethyl)-2-((1S,2S)-bicyclo[2.2.1]hept-5-en-2-yl)-1H-imidazole-4-carboxylic acid benzyl ester was prepared according to the procedure of Example 216, steps a, b, c and d with the modification that (1S,2S)-bicyclo[2.2.1]hept-5-en-2-carbaldehyde (prepared from (1S,2S)-bicyclo[2.2.1]hept-5-en-2-carboxylic acid (G. Helmchen et al. *Tetrahedron Letters* 1985, 26, 3095)) was used instead of cyclohexanecarboxaldehyde. The benzyl ester was hydrolysed according to the procedure of Example 211, step b and the resulting endo-5-(adamantan-1-yloxymethyl)-2-((1S,2S)-bicyclo[2.2.1]hept-5-en-2-yl)-1H-imidazole-4-carboxylic acid was reacted with 3-amino-benzoic acid methyl ester according to the procedure of Example 20, step d to afford endo-3-{[5-(adamantan-1-yloxymethyl)-2-((1S,2S)-bicyclo[2.2.2]hept-5en-2-yl)-1H-imidazole-4-carbonyl]-amino}-benzoic acid methyl ester. The methyl ester was hydrolysed according to the procedure of Example 211, step b to afford the title compound. $[\alpha]_D^{27}$ −97.4° (c=0.76, MeOH) $^1$H NMR (300 MHz, d$_4$-MeOH) 8.32 (1H, s), 7.77 (2H, d), 7.38 (1H, t), 6.29 (1H, dd), 5.79 (1H, dd), 4.86 (2H, s), 3.46 (1H, m), 3.28 (1H, br s), 2.98 (1H, br s), 2.17 (4H, m), 1.86 (6H, m), 1.67 (6H, m), 1.49 (3H, m). The acid was converted to the N-methyl-D-glucamine salt and lyophilised from water/dioxan. Found: C, 58.66; H, 7.66; N, 7.38%. $C_{36}H_{50}N_4O_9$.3.1 mols H$_2$O requires: C, 58.52; H, 7.67; N, 7.58%.

EXAMPLE 236 endo-3-{[5-(Adamantan-1-yloxymethyl)-2-((1R,2R)-bicyclo[2.2.1]hept-5-en-2-yl-1H-imidazole-4-carbonyl]-amino}-benzoic Acid endo-5-(Adamantan-1-yloxymethyl)-2-((1R,2R)-bicyclo[2.2.1]hept-5-en-2-yl)-1H-imidazole-4-carboxylic acid benzyl ester was prepared according to the procedure of Example 216, steps a, b, c and d with the modification that (1R,2R)-bicyclo[2.2.1]hept-5-en-2-carbaldehyde (prepared from (1R,2R)-bicyclo[2.2.1]hept-5-en-2-carboxylic acid (G. Helmchen et al. *Tetrahedron Letters* 1985, 26, 3095)) was used instead of cyclohexanecarboxaldehyde. The benzyl ester was hydrolysed according to the procedure of Example 211, step b and the resulting endo-5-(adamantan-1-yloxymethyl)-2-((1R,2R)-bicyclo[2.2.1]hept-5-en-2-yl)-1H-imidazole-4-carboxylic acid was reacted with 3-aminobenzoic acid methyl ester according to the procedure of Example 20, step d to afford endo-3-{[5-(adamantan-1-yloxymethyl)-2-((1R,2R)-bicyclo[2.2.2]hept-5-en-2-yl)-1H-imidazole-4-carbonyl]-amino}-benzoic acid methyl ester. The methyl ester was hydrolysed according to the procedure of Example 211, step b to afford the title compound. $[\alpha]_D^{26}$ +97.3° (c=0.74, MeOH) $^1$H NMR (300 MHz, d$_4$-MeOH) 8.32 (1H, s), 7.77 (2H, d), 7.38 (1H, t), 6.29 (1H, dd), 5.79 (1H, dd), 4.86 (2H, s), 3.46 (1H, m), 3.28 (1H, br s), 2.98 (1H, br s), 2.17 (4H, m), 1.86 (6H, m), 1.67 (6H, m), 1.49 (3H, m). The acid was converted to the N-methyl-D-glucamine salt and lyophilised from water/dioxan. Found: C, 60.94; H, 7.64; N, 7.84%. $C_{36}H_{50}N_4O_9$.1.6 mols $H_2O$ requires: C, 60.84; H, 7.53; N, 7.88%.

EXAMPLE 237

3-{[5-(2-Adamantan-1-yl-ethyl)-2-o-tolyl-1H-imidazole-4-carbonyl]-amino}-4-chloro-benzoic Acid The title compound was prepared according to the procedure of Example 102, with the modification that 3-amino-4-chloro-benzoic acid methyl ester hydrochloride was used in step a instead of D,L-α-phenylglycine methyl ester hydrochloride. $^1$H NMR (300 MHz, d$_6$-DMSO) 12.50 (1H, br s), 7.98 (1H, d), 7.71 (1H, d), 7.54–7.28 (6H, m), 2.85 (2H, br s), 2.47 (3H, s), 1.98 (3H, s), 1.69–1.34 (14H, m). The acid was converted to the N-methyl-D-glucamine salt and lyophilised from water/dioxan. Found: C, 60.42; H, 6.88; N, 7.56%. $C_{37}H_{49}ClN_4O_8$.1.1 mol $H_2O$ requires: C, 60.58; H, 7.04; N, 7.64%.

EXAMPLE 238

3-{[5-(2-Adamantan-1-yl-ethyl)-2-o-tolyl-1H-imidazole-4-carbonyl]-amino}-4-fluoro-benzoic Acid The title compound was prepared according to the procedure of Example 102, with the modification that 3-amino-4-fluoro-benzoic acid methyl ester (prepared in two steps from 4-fluoro-3-nitrobenzoic acid ) was used in step a instead of D,L-α-phenylglycine methyl ester hydrochloride. $^1$H NMR (300 MHz, d$_6$-DMSO) 7.98 (1H, d), 7.72 (1H, d), 7.59–7.51 (3H, m), 7.42 (3H, m), 2.95 (2H, m), 2.39 (3H, s), 1.95 (3H, s), 1.73–1.42 (14H, m). The acid was converted to the N-methyl-D-glucamine salt and lyophilised from water/dioxan. Found: C, 57.69; H, 7.30; N, 7.08%. $C_{37}H_{49}FN_4O_8$.4.0 mols $H_2O$ requires: C, 57.80; H, 7.47; N, 7.29%.

EXAMPLE 239

3-{[5-(2-Adamantan-1-yl-ethyl)-2-o-tolyl-1H-imidazole-4-carbonyl]-amino}-4-methyl-benzoic Acid The title compound was prepared according to the procedure of Example 102, with the modification that 3-amino-4-methyl-benzoic acid methyl ester (prepared in two steps from 4-methyl-3-nitrobenzoic acid ) was used in step a instead of D,L-α-phenylglycine methyl ester hydrochloride. $^1$H NMR (300 MHz, d$_6$-DMSO) 12.80 (1H, br s), 9.53 (1H, br s), 8.65 (1H, br s), 7.63 (2H, m), 7.34 (4H, m), 2.99 (2H, m) 2.60 (3H, s), 2.54 (3H, s), 1.95 (3H, s), 1.69–1.45 (14H, m). The acid was converted to the N-methyl-D-glucamine salt and lyophilised from water/dioxan. Found: C, 63.76; H, 7.80; N, 7.82%. $C_{38}H_{52}N_4O_8$.1.3 mol $H_2O$ requires: C, 63.79; H, 7.68; N, 7.83%.

EXAMPLE 240

3-{[5-(2-Adamantan-1-yl-ethyl)-2-o-tolyl-1H-imidazole-4-carbonyl]-amino}-2,6-dimethyl-benzoic Acid Step a. 3-{[5-(2-Adamantan-1-yl-ethyl)-2-o-tolyl-1H-imidazole-4-carbonyl]-amino}-2,6-dimethyl-benzoic Acid Methyl Ester 5-(2-Adamantan-1-yl-ethyl)-2-o-tolyl-1H-imidazole4-carboxylic acid (Example 93) (374 mg, 1.00 mmol) was reacted with 3-amino-2,6-dimethyl-benzoic acid methyl ester (prepared from 2,6-dimethyl-benzoic acid by nitration, esterification and reduction) (179 mg, 1.00 mmol) according to the procedure of Example 20, step d. The crude product was purified by flash chromatography (silica, hexane/ethyl acetate 2:1) to afford colourless foam (344 mg, 64%). $^1$H NMR (300 MHz, CDCl$_3$) 9.32 (1H, br s), 9.22 (1H, br s), 8.12 (1H, d), 7.55 (1H, d), 7.29 (3H, m), 7.08 (1H, d), 3.92 (3H, s), 3.12 (2H, m) 2.63 (3H, s), 2.28 (6H, s), 1.97 (3H, s), 1.74–1.44 (14H, m).

Step b

Boron tribromide (1M solution in DCM) (3.00 ml, 3.00 mmol) was added dropwise to an ice cooled solution of the product of step a (326 mg, 0.61 mmol) in DCM (3 ml) and the mixture was stirred at this temperature for 1 h. Water (50 ml) was slowly added and the product was extracted with chloroform (50 ml). The organic phase was washed with brine (50 ml), dried (MgSO$_4$) and the solvent was evaporated. The crude product was purified by flash column chromatography (silica, DCM/MeOH, 7:1) to afford the title compound as a white solid (69 mg, 22%). $^1$H NMR (300 MHz, d$_6$-DMSO) 12.58 (1H, br s), 9.30 (1H, br s), 7.82 (1H, d), 7.63 (1H, m), 7.30 (3H, m), 7.02 (1H, d), 2.95 (2H, m) 2.58 (3H, s), 2.22 (3H, s), 2.18 (3H, s), 1.94 (3H, br s), 1.66–1.40 (14H, m). The acid was converted to the N-methyl-D-glucamine salt and lyophilised from water/dioxan. Found: C, 61.60; H, 7.91; N, 7.59%. $C_{39}H_{54}N_4O_8$.3.0 mols $H_2O$ requires: C, 61.56; H, 7.95; N, 7.36%.

EXAMPLE 241

5-{[5-(2-Adamantan-1-yl-ethyl)-2-o-tolyl-1H-imidazole-4-carbonyl]-amino}-2-amino-benzoic Acid Dihydrochloride Step a. 5-{[5-(2-Adamantan-1-yl-ethyl)-2-o-tolyl-1H-imidazole-4-carbonyl]-amino}-2-tert-butoxycarbonyl-amino-benzoic Acid The acid was prepared according to the procedure of Example 102, with the modification that 5-amino-2-tert-butoxycarbonylamino-benzoic acid methyl ester (prepared from 2-amino-5-nitrobenzoic acid by esterification, BOC-protection, and reduction) was used in step a instead of D,L-α-phenylglycine methyl ester hydrochloride. $^1$H NMR (300 MHz, d$_6$-DMSO) 12.56 (1H, br s), 12.44 (1H, br s), 9.75 (1H, br s), 8.29 (1H, m), 8.07 (1H, m), 7.72–7.59 (2H, m), 7.32–7.25 (3H, m), 2.96 (2H, m), 2.56 (3H, s), 1.94 (3H, s), 1.70–1.40 (23H, m).

Step b

Hydrochloric acid (2 ml of 4M solution in dioxan) was added to a solution of the product of step a (395 mg, 0.66 mmol) in chloroform (4 ml). The resultant suspension was stirred at room temperature for 16 h, diluted with chloroform (40 ml) and the solvent was evaporated. The residue was triturated with diethyl ether to afford white solid (270 mg, 72%). $^1$H NMR (300 MHz, $d_6$-DMSO/$D_2O$) 8.17 (1H, d), 7.68–7.39 (5H, m), 6.91 (1H, d), 3.00 (2H, m), 2.46 (3H, s), 1.92 (3H, br s), 1.68–1.41 (14H, m). Found: C, 56.04; H, 7.00; N, 8.63%. $C_{30}H_{36}Cl_2N_4O_3 \cdot 4.0$ mols $H_2O$ requires: C, 55.99; H, 6.89; N, 8.71%.

EXAMPLE 242

5-{[5-(2-Adamantan-1-yl-ethyl)-2-o-tolyl-1H-imidazole-4-carbonyl]-amino}-2-dimethylamino-benzoic Acid Step a. 5-Amino-2-dimethylamino-benzoic Acid Methyl Ester 2-Amino-5-nitro-benzoic acid was esterified with hydrochloric acid/methanol, then 2-tert-butoxycarbonylamino-5-nitro-benzoic acid methyl ester was prepared. Alkylation (cesium carbonate, iodomethane), then removal of the tert-butoxycarbonyl protecting group (trifluoroacetic acid) afforded 2-methylamino-5-nitro-benzoic acid methyl ester. Alkylation (sodium hydride, iodomethane), then catalytic hydrogenation of the nitro group afforded 5-amino-2-dimethylamino-benzoic acid methyl ester. $^1$H NMR (300 MHz, $CDCl_3$) 7.06–6.97 (2H, m), 6.77 (1H, m), 3.90 (3H, s), 4.00–3.50 (2H, br s), 2.78 (6H, s).

Step b. 5-{[5-(2-Adamantan-1-yl-ethyl)-2-o-tolyl-1H-imidazole-4-carbonyl]-amino}-2-dimethylamino-benzoic Acid Methyl Ester 5-(2-Adamantan-1-yl-ethyl)-2-o-tolyl-1H-imidazole-4-carboxylic acid (Example 93) (364 mg, 1.00 mmol) was reacted with the product of step a (266 mg, 1.37 mmol) according to the procedure of Example 20, step d to afford white solid after purification by flash chromatography (silica, hexane/ethyl acetate 2:1) (399 mg, 74%). $^1$H NMR (300 MHz, $CDCl_3$) 9.15 (1H, br s), 9.07 (1H, br s), 7.92 (1H, d), 7.79 91H, dd), 7.56 (1H, d), 7.30 (3H, m), 6.99 (1H, d), 3.90 (3H, s), 3.14 (2H, m), 2.82 (6H, s), 2.59 (3H, s), 1.98 (3H, br s), 1.74–1.44 (14H, m).

Step c

A solution of the product of step b (395 mg, 0.73 mmol) and lithium hydroxide (153 mg, 3.65 mmol) in water (4 ml) and THF (4 ml) was heated at reflux for 24 h. The mixture was allowed to cool and pH=7 buffer (50 ml) was added. The product was extracted with chloroform (2×40 ml), the combined organic phases were dried ($MgSO_4$) and the solvent was evaporated to afford white solid (384 mg, 100%). $^1$H NMR (300 MHz, $d_6$-DMSO) 12.51 (1H, br s), 9.80 (1H, s), 8.52 (1H, d), 7.99 (1H, dd), 7.72 (1H, d), 7.59 (1H, d), 7.30 (3H, m), 2.96 (2H, m), 2.81 (6H, s), 2.54 (3H, s), 1.95 (3H, br s), 1.75–1.46 (14H, m). Found: C, 66.18; H, 7.69; N, 9.64%. $C_{32}H_{38}N_4O_3 \cdot 3.0$ mols $H_2O$ requires: C, 66.18; H, 7.64; N, 9.65%.

EXAMPLE 243

3-{[5-(2-Adamantan-1-yl-ethyl)-2-o-tolyl-1H-imidazole-4-carbonyl]-amino}-5-trifluoromethyl-benzoic Acid 5-(2-Adamantan-1-yl-ethyl)-2-o-tolyl-1H-imidazole-4-carboxylic acid (Example 93) was converted to the title compound according to the procedure of Example 20, steps d and e, with the modification that 3-amino-5-trifluoromethyl-benzoic acid benzyl ester (prepared in two steps from 3-nitro-5-trifluoromethyl-benzoic acid) was used in step d instead 5-amino-isophthalic acid dibenzyl ester. $^1$H NMR (300 MHz, $d_6$-DMSO) 12.65 (1H, br s), 9.97 (1H, br s), 8.62 (1H, s), 8.34 (1H, s), 7.88 (1H, s), 7.60 (1H, m), 7.29 (1H, m), 3.00 (2H, m) 2.56 (3H, s), 1.94 (3H, s), 1.66–1.41 (14H, m). The acid was converted to the N-methyl-D-glucamine salt and lyophilised from water/dioxan. Found: C, 56.99; H, 6.81; N, 6.98%. $C_{38}H_{49}F_3N_4O_8 \cdot 3.0$ mol $H_2O$ requires: C, 56.99; H, 6.92; N, 7.00%.

EXAMPLE 244

5-{[5-(2-Adamantan-1-yl-ethyl)-2-o-tolyl-1H-imidazole-4-carbonyl]-amino}-2-methoxy-benzoic Acid 5-(2-Adamantan-1-yl-ethyl)-2-o-tolyl-1H-imidazole-4-carboxylic acid (Example 93) was converted to the title compound according to the procedure of Example 20, steps d and e, with the modification that 5-amino-2-methoxy-benzoic acid benzyl ester (prepared in three steps from o-anisic acid) was used in step d instead 5-amino-isophthalic acid dibenzyl ester. $^1$H NMR (300 MHz, $d_6$-DMSO) 12.50 (1H, br s), 9.55 (1H, br s), 8.11 (1H, d), 7.81 (1H, dd), 7.59 (1H, d), 7.30 (3H, m), 7.07 (1H, d), 3.78 (3H, s), 2.98 (2H, m) 2.54 (3H, s), 1.95 (3H, s), 1.71–1.40 (14H, m). The acid was converted to the N-methyl-D-glucamine salt and lyophilised from water/dioxan. Found: C, 59.80; H, 7.65; N, 7.55%. $C_{38}H_{52}N_4O_9 \cdot 3.0$ mol $H_2O$ requires: C, 59.83; H, 7.66; N, 7.34%.

EXAMPLE 245

5-{[5-(2-Adamantan-1-yl-ethyl)-2-o-tolyl-1H-imidazole-4-carbonyl]-amino}-2-chloro-benzoic Acid The tile compound was prepared according to the procedure of Example 102, with the modification that 5-amino-2-chloro-benzoic acid methyl ester hydrochloride was used in step a instead of D,L-α-phenylglycine methyl ester hydrochloride. $^1$H NMR (300 MHz, $d_6$-DMSO) 13.5 (1H, br s), 12.50 (1H, br s), 9.87 (1H, s), 8.34 (1H, d), 7.94 (1H, dd), 7.58 (1H, d), 7.47 (1H, d), 7.31 (3H, m), 2.98 (2H, m), 2.53 (3H, s), 1.95 (3H, br s), 1.66–1.40 (14H, m). The acid was converted to the N-methyl-D-glucamine salt and lyophilised from water/dioxan. Found: C, 59.97; H, 7.14; N, 7.60%. $C_{37}H_{49}ClN_4O_8 \cdot 1.5$ mol $H_2O$ requires: C, 60.03; H, 7.08; N, 7.57%.

EXAMPLE 246

5-{[5-(2-Adamantan-1-yl-ethyl)-2-o-tolyl-1H-imidazole-4-carbonyl]-amino}-2-bromo-benzoic Acid The title compound was prepared according to the procedure of Example 102, with the modification that 5-amino-2-bromo-benzoic acid methyl ester (prepared in steps from 2-bromo-5-nitro-benzoic acid) was used in step a instead of D,L-α-phenylglycine methyl ester hydrochloride. 1H NMR (300 MHz, $d_6$-DMSO) 13.5–12.80 (2H, br s), 9.97 (1H, br s), 8.29 (1H, d), 7.87 (1H, dd), 7.60 (2H, m), 7.32 (3H, m), 2.98 (2H, m), 2.53 (3H, s), 1.95 (3H, s), 1.66–1.44 (14H, m). The acid was converted to the N-methyl-D-glucamine salt and lyophilised from water/dioxan. Found: C, 56.48; H, 6.78; N, 7.09%. $C_{37}H_{49}BrN_4O_8 \cdot 1.5$ mol $H_2O$ requires: C, 56.63; H, 6.68; N, 7.14%.

EXAMPLE 247

3-{[5-(2-Adamantan-1-yl-ethyl)-2-o-tolyl-1H-imidazole-4-carbonyl]-amino}-5-methyl-benzoic Acid Step a. 3-{[5-(2-Adamantan-1-yl-ethyl)-2-o-tolyl-1H-imidazole-4-carbonyl]-amino}-5-methyl-benzoic Acid Ethyl Ester 4-Bromo-3-methyl-benzoic acid was esterified, then nitrated to afford 4-bromo-3-methyl-5-nitro-benzoic acid ethyl ester. Catalytic hydrogenation afforded 3-amino-5-methyl-benzoic acid ethyl ester, which was reacted with 5-(2-adamantan-1-yl-ethyl)-2-o-tolyl-1H-imidazole-4-carboxylic acid (Example 3) according to the procedure of Example 20, step d to afford white solid after flash column chromatography (silica, hexane/ethyl acetate 3:1). $^1$H NMR (300 MHz, CDCl$_3$) 9.23 (1H, br s), 9.11 (1H, br s), 8.03 (1H, s), 7.90 (1H, s), 7.57 (2H, m), 7.36–7.27 (3H, m), 4.36 (2H, q), 3.16 (2H, m), 2.60 (3H, s), 2.42 (3H, s), 2.00 (3H, br s), 1.68–1.38 (17H, m).

Step b

A solution of the product of step a (360 mg, 0.68 mmol) and potassium hydroxide (152 mg, 2.71 mmol) in ethanol (6 ml) and water (1 ml) was heated at reflux for 40 min. Hydrochloric acid (2M, 2 ml) was added and the reaction mixture was diluted with ethyl acetate (40 ml). The organic phase was washed with water (30 ml), brine (30 ml), dried (MgSO$_4$) and the solvent was evaporated to afford the title compound as a white solid (350 mg, 100%). $^1$H NMR (300 MHz, d$_6$-DMSO) 13.00 (1H, br s), 10.10 (1H, br s), 8.25 (1H, s), 7.80 (1H, s), 7.64 (1H, d), 7.48–7.33 (4H, m), 3.01 (2H, m), 2.53 (3H, s), 2.35 (3H, s), 1.95 (3H, br s), 1.67–1.42 (14H, m). The acid was converted to the N-methyl-D-glucamine salt and lyophilised from water/dioxan. Found: C, 62.64; H, 7.75; N, 7.39%. C$_{38}$H$_{52}$N$_4$O$_8$.2.0 mol H$_2$O requires: C, 62.62; H, 7.74; N, 7.69%.

EXAMPLE 248

3-{[5-(2-Adamantan-1-yl-ethyl)-2-o-tolyl-1H-imidazole-4-carbonyl]-amino}-2,6-difluoro-benzoic Acid 2,6-Difluoro-3-nitro-benzoic acid ethyl ester (K. Soon Kim et al. *J. Med. Chem.* 1993, 36, 2335) was hydrogenated to afford 3-amino-2,6-difluoro-benzoic acid ethyl ester. This was reacted with 5-(2-adamantan-1-yl-ethyl)-2-o-tolyl-1H-imidazole-4-carboxylic acid (Example 93) according to the procedure of Example 20, step d to afford 3-{[5-(2-adamantan-1-yl-ethyl)-2-o-tolyl-1H-imidazole-4-carbonyl]-amino}-2,6-difluoro-benzoic acid ethyl ester. The ester was hydrolysed according to the procedure of Example 247, step b to afford the title compound. $^1$H NMR (300 MHz, d$_6$-DMSO) 14.00 (1H, br s), 12.60 (1H, br s), 9.48 (1H, s), 8.20 (1H, m), 7.61 (1H, m), 7.34–7.16 (4H, m), 2.95 (2H, m), 2.56 (3H, s), 1.94 (3H, br s), 1.66–1.39 (14H, m). The acid was converted to the N-methyl-D-glucamine salt and lyophilised from water/dioxan. Found: C, 61.88; H, 6.86; N, 7.59%. C$_{37}$H$_{48}$F$_2$N$_4$O$_8$ requires: C, 62.17; H, 6.77; N, 7.84%.

EXAMPLE 249

3-{[5-(2-Adamantan-1-yl-ethyl)-1-carboxymethyl-2-o-tolyl-1H-imidazole-4-carbonyl]-amino}-benzoic Acid Trifluoroacetic Acid Salt Step a. 5-(2-Adamantan-1-yl-ethyl)-1-tert-butoxycarbonylmethyl-2-o-tolyl-1H-imidazole-4-carboxylic acid benzyl ester and 5-(2-adamantan-1-yl-ethyl)-3-tert-butoxycarbonylmethyl-2-o-tolyl-3H-imidazole-4-carboxylic Acid Benzyl Ester To an ice cooled soluiton of 5-(2-adamantan-1-yl-ethyl)-2-o-tolyl-1H-imidazole-4-carboxylic acid benzyl ester (prepared according to the procedure of Example 70, step a, using o-tolualdehyde instead of 2-dimethylamino-benzaldehyde) (1.00 g, 2.20 mol) in DMF (10 ml) was added sodium hydride (60% dispersoin in oil) (132 mg, 3.30 mmol). The cooling bath was removed and the reaction mixture was stirred at room temperature for 15 min. The mixture was cooled to 0° C. and tert-butyl bromoacetate (0.34 ml, 2.30 mmol) was added. The reaction mixture was stirred at room temperature for 16 h, quenched with water (50 ml), and the products were extracted with ethyl acetate (50 ml). The organic phase was washed with brine (2×40 ml), dried (MgSO$_4$) and the solvent was evaporated. The products were separated by flash column chromatography (silica, hexane/ethyl acetate 2:1). The high R$_f$ product (400 mg, 32%) was identified as 5-(2-adamantan-1-yl-ethyl)-3-tert-butoxycarbonylmethyl-2-o-tolyl-3H-imidazole-4-carboxylic acid benzyl ester, whilst the low R$_f$ material (450 mg, 36%) was the isomeric 5-(2-adamantan-1-yl-ethyl)-1-tert-butoxycarbonylmethyl-2-o-tolyl-1H-imidazole-4-carboxylic acid benzyl ester. $^1$H NMR (300 MHz, CDCl$_3$) of the high R$_f$ material 7.46–7.23 (9H, m), 5.30 (2H, s), 4.66 (2H, s), 2.85 (2H, m), 2.19 (3H, s), 1.88–1.39 (26H, m). $^1$H NMR (300 MHz, CDCl$_3$) of the low R$_f$ material 7.48–7.25 (9H, m), 5.37 (2H, s), 4.28 (2H, s), 2.84 (2H, m), 2.19 (3H, s), 1.95–1.24 (26H, m).

Step b. 5-(2-Adamantan-1-yl-ethyl)-1-tert-butoxycarbonylmethyl-2-o-tolyl-1H-imidazole-4-carboxylic Acid 5-(2-Adamantan-1-yl-ethyl)-1-tert-butoxycarbonylmethyl-2-o-tolyl-1H-imidazole-4-carboxylic acid benzyl ester (step a, low R$_f$ product) (442 mg, 0.78 mmol) was hydrogenolysed according to the procedure of Example 1, step e to afford colourless foam (342 mg, 92%). $^1$H NMR (300 MHz, CDCl$_3$) 7.40–7.19 (4H, m), 4.45 (2H, s), 2.83 (2H, m), 2.10 (3H, s), 1.94 (3H, br s), 1.71–1.51 (12H, m), 131–1.24 (11H, m).

Step c. 3-{[5-(2-Adamantan-1-yl-ethyl)-1-tert-butoxycarbonylmethyl-2-o-tolyl-1H-imidazole-4-carbonyl]-amino}-benzoic Acid Benzyl Ester The product of step b (324 mg, 0.68 mmol) was reacted with 3-amino-benzoic acid benzyl ester (154 mg, 0.68 mmol) according to the procedure of Example 20, step d to afford colourless foam (284 mg, 61%). $^1$H NMR (300 MHz, CDCl$_3$) 9.21 (1H, s), 8.16 (2H, m), 7.80–7.77 (1H, m), 7.48–7.27 (10H, m), 5.36 (2H, s), 4.33 (2H, s), 3.02 (2H, m), 2.24 (3H, s), 2.01 (3H, br s), 1.77–1.37 (23H, m).

Step d. 3-{[5-(2-Adamantan-1-yl-ethyl)-1-tert-butoxycarbonylmethyl-2-o-tolyl-1H-imidazole-4-carbonyl]-amino}-benzoic Acid The product of step c (273 mg, 0.40 mmol) was hydrogenolysed according to the procedure of Example 1, step e to afford white solid (223 mg, 93%). $^1$H NMR (300 MHz, d$_6$-DMSO) 13.00–12.00 (1H, br s), 9.90 (1H, s), 8.52 (1H, s), 7.93 (1H, m), 7.68 (1H, d), 7.45–7.25 (5H, m), 4.49 (2H, s), 2.94 (2H, m), 2.17 (3H, s), 1.96 (3H, br s), 1.72–1.55 (12H, m), 1.31 (11H, m).

Step e

A solution of the product of step d (217 mg, 0.36 mmol) in trifluoroacetic acid was stirred at room temperature for 16 h. The trifluoroacetic acid was removed in vacuum, the residue was dissolved in chloroform (15 ml) and the solvent was evaporated to afford the triflouoroacetic acid salt. $^1$H NMR (300 MHz, d$_6$-DMSO) 9.91 (1H, s), 8.52 (1H, d), 7.96 (1H, d), 7.63 (1H, d), 7.45–7.27 (5H, m), 5.00 (2H, br s), 2.93 (2H, m), 2.17 (3H, s), 1.96 (3H, br s), 1.71–1.54 (12H, m), 1.31 (2H, m). Found: C, 62.33; H, 5.73; N, 6.27%. C$_{34}$H$_{36}$F$_3$N$_3$O$_7$ requires: C, 62.28; H, 5.53; N, 6.41%.

EXAMPLE 250

3-{[5-(2-Adamantan-1-yl-ethyl)-1-ethoxycarbonylmethyl-2-o-tolyl-1H-imidazole-4-carbonyl]-amino}-benzoic Acid The title compound was prepared using the same procedure as in Example 249, steps a, b, c and d, with the modification that ethyl bromoacetate was used in step a instead of tert-butyl bromoacetate. $_1$H NMR (300 MHz, d$_6$-DMSO) 9.91 (1H, s), 8.52 (1H, s), 7.95 (1H, d), 7.63 (1H, d), 7.44–7.26 (5H, m), 4.62 (2H, s), 4.09 (2H, q), 2.93 (2H, m), 2.17 (3H, s), 1.95 (3H, br s), 1.71–1.54 (12H, m), 1.29 (2H, m), 1.11 (3H, t). The acid was converted to the N-methyl-D-glucamine salt and lyophilised from water/dioxan. Found: C, 61.58; H, 7.67; N, 6.89%. C$_{41}$H$_{56}$N$_4$O$_{10}$.2.0 mols H$_2$O requires: C, 61.48; H, 7.55; N, 7.00%.

EXAMPLE 251

3-{[5-(2-Adamantan-1-yl-ethyl)-1-benzyl-2-o-tolyl-1H-imidazole-4-carbonyl]-amino}-benzoic Acid 5-(2-Adamantan-1-yl-ethyl)-1-benzyl-2-o-tolyl-1H-imidazole-4-carboxylic acid was prepared according to the procedure of Example 73, steps a and b, with the modification that benzyl-bromide was used in step a instead of iodomethane. This acid was reacted with 3-amino-benzoic acid methyl ester hydrochloride according to the procedure of Example 102, step a. The methyl ester was hydrolyzed using the same procedure as in Example 247, step b to afford the title compound. $^1$H NMR (300 MHz, d$_6$-DMSO) 12.80 (1H, br s), 9.93 (1H, br s), 8.52 (1H, s), 7.93 (1H, m), 7.61 (1H, m), 7.43–7.24 (8H, m), 6.89 (2H, m), 5.03 (2H, s), 2.83 (2H, m), 2.12 (3H, s), 1.90 (3H, s), 1.66–1.53 (6H, m), 1.39 (6H, s), 1.13 (2H, m). The acid was converted to the N-methyl-D-glucamine salt and lyophilised from water/dioxan. Found: C, 65.59; H, 7.47; N, 7.14%. C$_{44}$H$_{56}$N$_4$O$_8$.2.0 mol H$_2$O requires: C, 65.65; H, 7.51; N, 6.96%.

EXAMPLE 252

3-{[5-(2-Adamantan-1-yl-ethyl)-2-cyclohexyl-1H-imidazole-4-carbonyl]-amino}-4-methylbenzoic Acid 5-(2-Adamantan-1-yl-ethyl)-2-cyclohexyl-1H-imidazole-4-carboxylic acid was prepared according to the procedure of Example 70, steps a and b, with the modification that cyclohexanecarboxaldehyde was used in step a instead of 2-dimethylamino-benzaldehyde. This acid was reacted with 3-amino-4-methyl-benzoic acid methyl ester according to the procedure of Example 20, step d. The methyl ester was hydrolyzed using the same procedure as in Example 247, step b to afford the title compound. $^1$H NMR (300 MHz, d$_6$-DMSO) 14.00 (1H, br s), 10.41 (1H, br s), 7.98 (1H, br s), 7.74 (1H, d), 7.41 (1H, d), 2.95 (3H, m), 2.49 (3H, s), 2.04–1.25 (25H, m). The acid was converted to the N-methyl-D-glucamine salt. Found: C, 58.71; H, 8.51; N, 7.21%. C$_{37}$H$_{56}$N$_4$O$_8$.4.0 mol H$_2$O requires: C, 58.71; H, 8.52; N, 7.40%.

EXAMPLE 253

3-{[5-(2-Adamantan-1-yl-ethyl)-2-cyclohexyl-1H-imidazole-4-carbonyl]-amino}-2-methyl-benzoic Acid 5-(2-Adamantan-1-yl-ethyl)-2-cyclohexyl-1H-imidazole-4-carboxylic acid (Example 252) was reacted with 3-amino-2-methyl-benzoic acid benzyl ester (prepared in two steps from 2-methyl-3-nitro-benzoic acid) according to the procedure of Example 20, step d. The benzyl ester was hydrogenated using the same procedure as in Example 1, step c to afford the title compound. $^1$H NMR (300 MHz, d$_6$-DMSO) 13.00 (1H, br s), 11.95 (1H, br s), 9.31 (1H, br s), 8.01 (1H, d), 7.49 (1H, d), 7.24 (1H, m), 2.85 (2H, m), 2.60 (1H, m), 2.39 (3H, s), 1.93–1.24 (27H, m). The acid was converted to the N-methyl-D-glucamine salt and lyophilised from water/dioxan. Found: C, 62.84; H, 8.55; N, 7.80%. C$_{37}$H$_{56}$N$_4$O$_8$.1.0 mol H$_2$O requires: C, 63.23; H, 8.32; N, 7.97%.

EXAMPLE 254

5-{[5-(2-Adamantan-1-yl-ethyl)-2-cyclohexyl-1H-imidazole-4-carbonyl]-amino}-2-fluoro-benzoic Acid 5-(2-Adamantan-1-yl-ethyl)-2-cyclohexyl-1H-imidazole-4-carboxylic acid (Example 252) was reacted with 5-amino-2-fluoro-benzoic acid methyl ester according to the procedure of Example 20, step d. The methyl ester was hydrolysed using the same procedure as in Example 36, step d to afford the title compound. $^1$H NMR (300 MHz, d$_6$-DMSO) 10.79 (1H, br s), 8.32 (1H, dd), 7.97 (1H, m), 7.32 (1H, m), 2.91 (3H, m), 1.98–1.34 (27H, m). The acid was converted to the N-methyl-D-glucamine salt and lyophilised from water/dioxan. Found: C, 56.04; H, 8.48; N, 7.28%. C$_{36}$H$_{53}$FN$_4$O$_8$.4.5 mols H$_2$O requires: C, 56.16; H, 8.12; N, 7.28%.

EXAMPLE 255

(±)-2-(3-{[5-(2-Adamantan-1-yl-ethyl)-2-cyclohexyl-1H-imidazole-4-carbonyl]-amino}-phenyl)-propionic Acid 5-(2-Adamantan-1-yl-ethyl)-2-cyclohexyl-1H-imidazole-4-carboxylic acid (Example 252) was reacted with (±)-2-(3-amino-phenyl)-propionic acid ethyl ester (S. Mutti et al. *Synth. Comm.* 1997, 27, 425) according to the procedure of Example 20, step d. The ethyl ester was hydrolysed using the same procedure as in Example 247, step b to afford the title compound. $^1$H NMR (300 MHz, d$_6$-DMSO) 12.20 (2H, br s), 9.44 (1H, s), 7.64 (2H, m), 7.23 (1H, m), 6.96 (1H, d), 3.61 (1H, m), 2.86 (2H, m), 2.60 (1H, m), 1.98–1.19 (30H, m). The acid was converted to the N-methyl-D-glucamine salt and lyophilised from water/dioxan. Found: C, 62.88; H, 8.66; N, 7.68%. C$_{38}$H$_{58}$N$_4$O$_8$.1.5 mols H$_2$O requires: C, 62.87; H, 8.47; N, 7.72%.

EXAMPLE 256

2-(3-{[5-(2-Adamantan-1-yl-ethyl)-2-cyclohexyl-1H-imidazole-4-carbonyl]-amino}-phenyl)-2-methyl-propionic Acid 5-(2-Adamantan-1-yl-ethyl)-2-cyclohexyl-1H-imidazole-4-carboxylic acid (Example 252) was reacted with 2-(3-amino-phenyl)-2-methyl-propionic acid ethyl ester (prepared from 2-(4-chloro-phenyl)-2-methyl-propionic acid using Mutti's procedure (S. Mutti et al. *Synth. Comm.* 1997, 27, 425)) according to the procedure of Example 20, step d. The ethyl ester was hydrolysed using the same procedure as in Example 247, step b to afford the title compound. $^1$H NMR (300 MHz, d$_6$-DMSO) 10.52 (1H, br s), 7.70 (2H, m), 7.32 (1H, m), 7.12 (1H, d), 2.93 (3H, m), 1.98–1.35 (33H, m). The acid was converted to the N-methyl-D-glucamine salt and lyophilised from water/dioxan. Found: C, 63.89; H, 8.61; N, 7.77%; C$_{39}$H$_{60}$N$_4$O$_8$.1.0 mol H$_2$O requires: C, 64.09; H, 8.55; N, 7.67%.

EXAMPLE 257

1-(3-{[5-(2-Adamantan-1-yl-ethyl)-2-cyclohexyl-1H-imidazole-4-carbonyl]-amino}-phenyl)-cyclopentanecarboxylic Acid 5-(2-Adamantan-1-yl-ethyl)-2-cyclohexyl-1H-imidazole-4-carboxylic acid (Example 252) was reacted with 1-(3-amino-phenyl)-1-cyclopentanecarboxylic acid ethyl ester (prepared from 1-(4-chloro-phenyl)-1-cyclopentanecarboxylic acid using Mutti's procedure (S. Mutti et al. *Synth. Comm.* 1997, 27, 425)) according to the procedure of Example 20, step d. The ethyl ester was hydrolysed using the same procedure as in Example 247, step b to afford the title compound. $^1$H NMR (300 MHz, d$_6$-DMSO) 12.00 (1H, br s), 9.29 (1H, br s), 7.63 (2H, m), 7.16 (1H, m), 7.02 (1H, d), 2.85 (2H, m), 2.49 (3H, m), 1.98–1.34 (33H, m). The acid was converted to the N-methyl-D-glucamine salt and lyophilised from water/dioxan. Found: C, 62.88; H, 8.79; N, 7.07%. C$_{41}$H$_{62}$N$_4$O$_8$.2.5 mols H$_2$O requires: C, 62.81; H, 8.61; N, 7.15%.

EXAMPLE 258

3-(3-{[5-(2-Adamantan-1-yl-ethyl)-2-cyclohexyl-1H-imidazole-4-carbonyl]-amino}-phenyl)-propionic Acid Trifluoroacetic Acid Salt The title compound was prepared according to the procedure of Example 97, with the modification that 5-(2-adamantan-1-yl-ethyl)-2-cyclohexyl-1H-imidazole-4-carboxylic acid (Example 252) was used in step a instead of 5-(2-adamantan-1-yl-ethyl)-2-o-tolyl-1H-imidazole-4-carboxylic acid. $^1$H NMR (300 MHz, d$_6$-DMSO) 13.50–13.00 (1H, br s), 9.86 (1H, br s), 7.51 (2H, m), 7.26 (1H, t), 6.99 (1H, d), 2.81 (5H, m), 2.54 (2H, m), 1.93–1.33 (27H, m). Found: C, 63.79; H, 6.98; N, 6.67%. C$_{33}$H$_{42}$F$_3$N$_3$O$_5$ requires: C, 64.17; H, 6.85; N, 6.80%.

EXAMPLE 259 trans-3-(3-{[5-(2-Adamantan-1-yl-ethyl)-2-cyclohexyl-1H-imidazole-4-carbonyl]-amino}-phenyl)-acrylic Acid 5-(2-Adamantan-1-yl-ethyl)-2-cyclohexyl-1H-imidazole-4-carboxylic acid (Example 252) was reacted with 3-(3-amino-phenyl)-acrylic acid methyl ester (prepared in two steps from 3-nitro-benzaldehyde) according to the procedure of Example 20, step d. The methyl ester was hydrolysed using the same procedure as in Example 36, step d to afford the title compound. $^1$H NMR (300 MHz, d$_6$-DMSO) 12.00 (1H, br s), 9.55 (1H, br s), 8.00 (1H, s), 7.86 (1H, m), 7.57 (1H, d), 7.36 (2H, m), 6.50 (1H, d), 2.89 (2H, m), 2.68 (1H, m), 1.94 (5H, br s), 1.80–1.51 (17H, m), 1.39–1.19 (5H, m). The acid was converted to the N-methyl-D-glucamine salt and lyophilised from water/dioxan. Found: C, 60.52; H, 8.50; N, 7.59%. C$_{38}$H$_{56}$N$_4$O$_8$.3.0 mols H$_2$O requires: C, 60.78; H, 8.32; N, 7.46%.

EXAMPLE 260

(±)-(3-{[5-(2-Adamantan-1-yl-ethyl)-2-cyclohexyl-1H-imidazole-4-carbonyl]-amino}-phenyl)-2-hydroxy-propionic Acid Step a. (±)-3-(3-Amino-phenyl)-2-hydroxy-propionic Acid Tert-butyl Ester Sodium hydride (60% dispersion in oil) (1.32 g, 33.0 mmol) was added to a solution of 3-nitro-benzaldehyde (4.53 g, 30.0 mmol) and tert-butyl-bromoacetate (4.87 ml, 33.0 mmol) in DMF (100 ml). The resulting suspension was heated at 65° C. for 2 h, cooled, then quenched with water (10 ml). The mixture was diluted with ethyl acetate (100 ml), the organic phase was washed with water (150 ml), brine (2×150 ml), dried (MgSO$_4$) and the solvent was evaporated. The residue was dissolved in dioxan (50 ml) and hydrogenated over palladium on charcoal (10%, 1.00 g) for 24 h. The catalyst was removed by filtration and the solvent was evaporated. The crude product was purified by flash column chromatography (silica, hexane/ethyl acetate 1:1) to afford colourless oil (2.95 g, 41%). $^1$H NMR (300 MHz, CDCl$_3$) 7.07 (1H, m), 6.60 (3H, m), 4.30 (1H, dd), 3.61 (2H, br s), 3.00 (1H, dd), 2.85 (2H, m), 1.46 (9H, s).

Step b. (±)-Acetoxy-3-(3-amino-phenyl)-propionic Acid tert-butyl Ester

Acetic anhydride (1.60 ml, 16.9 mmol) was added to a stirred solution of the product of step a (2.94 g, 12.4 mmol), triethylamine (2.59 ml, 18.6 mmol) and 4-dimethylaminopyridine (DMAP) (cat.) in DCM (40 ml). The reaction mixture was stirred for 16 h, washed with 10% aqueous citric acid (50 ml), saturated sodium bicarbonate (50 ml), then the organic phase was dried (MgSO$_4$) and the solvent was evaporated. The crude product was purified by flash column chromatography (silica, hexane/ethyl acetate 1:1) to afford yellow oil (549 mg, 16%). $^1$H NMR (300 MHz, CDCl$_3$) 7.07 (1H, m), 6.60 (3H, m), 5.07 (1H, m), 3.62 (2H, br s), 3.08–2.93 (21H, m), 2.09 (3H, s), 1.42 (9H, s).

Step c. (±)-3-(3-{[5-(2-Adamantan-1-yl-ethyl)-2-cyclohexyl-1H-imidazole-4-carbonyl]-amino}-phenyl)-2-acetoxy-propionic Acid tert-butyl Ester 5-(2-Adamantan-1-yl-ethyl)-2-cyclohexyl-1H-imidazole-4-carboxylic acid (Example 252) (690 mg, 1.94 mmol) was reacted with the product of step b (540 mg, 1.94 mmol) according to the procedure of Example 20, step d to afford colourless foam after purification by flash chromatography (silica, hexane/ethyl acetate 2:1) (287 mg, 24%). $^1$H NMR (300 MHz, CDCl$_3$) 9.04 (1H, br s), 8.63 (1H, br s), 7.60 (2H, m), 7.25 (1H, m), 6.97 (1H, d), 5.11 (1H, m), 3.17–3.03 (4H, m), 2.80 (1H, m), 2.10–1.27 (399H, m).

Step d. (±)-3-(3-{[5-(2-Adamantan-1-yl-ethyl)-2-cyclohexyl-1H-imidazole-4-carbonyl]-amino}-phenyl)-2-hydroxy-propionic Acid tert-butyl Ester A solution of the product of step c (282 mg, 0.46 mmol) and potassium carbonate (96 mg, 0.70 mmol) in methanol (3 ml) and water (0.3 ml) was stirred at room temperature for 3 h. The reaction was quenched with 10% aqueous citric acid (1 ml), then diluted with ethyl acetate (20 ml). The organic phase was washed with water (20 ml), brine (20 ml), dried (MgSO$_4$) and the solvent was evaporated. The residue was purified by flash chromatography (silica, hexane/ethyl acetate 2:1) to afford colourless foam (167 mg, 63%). $^1$H NMR (300 MHz, CDCl$_3$) 9.05 (1H, br s), 8.62 (1H, br s), 7.60 (2H, m), 7.25 (1H, m), 6.98 (1H, d), 4.34 (1H, m), 3.13–3.02 (4H, m), 2.93 (1H, m), 2.85 (1H, d), 2.68 (1H, m), 2.05–1.35 (36H, m).

Step e

The product of step d (161 mg, 0.28 mmol) was deprotected according to the procedure of Example 249, step e. The crude product (173 mg, 98%) was crystallised from methanol/water to afford the acid as a white solid (34 mg, 20%). $^1$H NMR (300 MHz, d$_6$-DMSO/D$_2$O) 7.51 (2H, m), 7.15 (1H, m), 6.91 (1H, d), 3.72 (1H, dd), 3.00–2.49 (5H, m), 1.91–1.06 (27H, m). Found: C, 68.54; H, 7.52; N, 7.74%. C$_{31}$H$_{41}$N$_3$O$_4$.0.29 mol CF$_3$COOH requires: C, 68.62; H, 7.53; N, 7.60%.

EXAMPLE 261

(±)-(3-{[5-(2-Adamantan-1-yl-ethyl)-2-cyclohexyl-1H-imidazole-4-carbonyl]-amino}-phenyl)-amino-acetic Acid di(trifluoroacetic Acid) Salt (±)-tert-Butoxycarbonylamino-(3-nitro-phenyl)-acetic acid methyl ester (WO 97/09335) was hydrogenated to afford (±)-(3-amino-phenyl)-tert-butoxycarbonylamino-acetic acid methyl ester. This was reacted with 5-(2-adamantan-1-yl-ethyl)-2-cyclohexyl-1H-imidazole-4-carboxylic acid (Example 252) according to the procedure of Example 20, step d. The methyl ester was hydrolysed using the same procedure as in Example 36, step d. The tert-butoxycarbonyl protecting group was removed using the same procedure as in Example 249, step e to afford the title compound as the di(trifluoroacetic acid) salt. $^1$H NMR (300 MHz, d$_6$-DMSO) 7.96 (1H, s), 7.70 (1H, d), 7.42 (1H, m), 7.20 (1H, d), 5.11(1H, s), 2.89 (3H, m), 1.93–1.28 (27H, m). Found: C, 53.14; H, 6.01; N, 7.13%. C$_{34}$H$_{42}$F$_6$N$_4$O$_7$.2.0 mols H$_2$O requires: C, 53.12; H, 6.03; N, 7.29%.

EXAMPLE 262

(3-{[5-(2-Adamantan-1-yl-ethyl)-2-cyclohexyl-1H-imidazole-4-carbonyl]-amino}-benzenesulfonylamino)-acetic Acid 3-Nitro-benzenesulfonyl chloride was reacted with glycine benzyl ester and the resulting (3-nitro-benzensulfonylamino)-acetic acid benzyl ester was reduced with tin chloride to afford (3-amino-benzenesulfonylamino)-acetic acid benzyl ester. This was reacted with 5-(2-adamantan-1-yl-ethyl)-2-cyclohexyl-1H-imidazole-4-carboxylic acid (Example 252) according to the procedure of Example 20, step d. The benzyl ester was hydrolysed using the same procedure as in Example 1, step e to afford the title compound. $^1$H NMR (300 MHz, d$_6$-DMSO) 12.00 (1H, br s), 9.71 (1H, br s), 8.35 (1H, s), 7.96 (2H, m), 7.45 (2H, m), 3.57 (2H, s), 2.88 (2H, m), 2.60 (1H, m), 1.94–1.32 (27H, m). The acid was converted to the N-methyl-D-glucamine salt and lyophilised from water/dioxan. Found: C, 55.50; H, 7.88; N, 8.83%. C$_{37}$H$_{57}$N$_5$O$_{10}$.2.0 mols H$_2$O requires: C, 55.55; H, 7.69; N, 8.75%.

EXAMPLE 263

(3-{[5-(2-Adamantan-1-yl-ethyl)-2-cyclohexyl-1H-imidazole-4-carbonyl]-amino}-benzoylamino)-acetic Acid 3-Nitro-benzoic acid was reacted with glycine methyl hydrochloride and the resulting (3-nitro-benzoylamino)-acetic acid methyl ester was hydrogenated to afford (3-amino-benzoylamino)-acetic acid methyl ester. This was reacted with 5-(2-adamantan-1-yl-ethyl)-2-cyclohexyl-1H-imidazole-4-carboxylic acid (Example 252) according to the procedure of Example 20, step d. The methyl ester was hydrolysed using the same procedure as in Example 36, step d to afford the title compound. $^1$H NMR (300 MHz, d$_6$-DMSO) 10.54 (1H, br s), 8.80 (1H, t), 8.25 (1H, s), 7.91 (1H, d), 7.61 (1H, d), 7.45 (1H, d), 3.92 (2H, m), 2.93 (3H, m), 1.98–1.33 (27H, m). The acid was converted to the N-methyl-D-glucamine salt and lyophilised from water/dioxan. Found: C, 57.22; H, 8.30; N, 8.81%. C$_{38}$H$_{57}$N$_5$O$_9$.4.0 mols H$_2$O requires: C, 57.06; H, 8.19; N, 8.75%.

EXAMPLE 264

(±)-Acetylamino-(3-{[5-(2-adamantan-1-yl-ethyl)-2-cyclohexyl-1H-imidazole-4-carbonyl]-amino}-phenyl)-acetic Acid (±)-Acetylamino-(3-amino-phenyl)-acetic acid methyl ester was prepared from (±)-tert-butoxycarbonylamino-(3-nitro-phenyl)-acetic acid methyl ester (WO 97/09335). This was reacted with 5-(2-adamantan-1-yl-ethyl)-2-cyclohexyl-1H-imidazole-4-carboxylic acid (Example 252) according to the procedure of Example 20, step d. The methyl ester was hydrolysed using the same procedure as in Example 36, step d to afford the title compound. $^1$H NMR (300 MHz, d$_6$-DMSO) 12.80 (1H, br s), 10.00 (1H, br s), 8.59 (1H, d), 7.74 (2H, m), 7.32 (1H, t), 7.09 (1H, d), 5.28 (1H, m), 2.88 (3H, m), 1.98–1.33 (30H, m). The acid was converted to the N-methyl-D-glucamine salt and lyophilised from water/dioxan. Found: C, 57.24; H, 8.43; N, 8.47%. C$_{39}$H$_{59}$N$_5$O$_9$.4.0 mols H$_2$O requires: C, 57.55; H, 8.30; N, 8.60%.

EXAMPLE 265

(±)-2-Acetylamino-3-(3-{[5-(2-adamantan-1-yl-ethyl)-2-cyclohexyl-1H-imidazole-4-carbonyl]-amino}-phenyl)-propionic Acid (±)-2-Acetylamino-3-(3-amino-phenyl)-acetic acid methyl ester (T. Lowary et al. *J. Org. Chem.* 1998, 63, 9657) was reacted with 5-(2-adamantan-1-yl-ethyl)-2-cyclohexyl-1H-imidazole-4-carboxylic acid (Example 252) according to the procedure of Example 20, step d. The methyl ester was hydrolysed using the same procedure as in Example 36, step d to afford the title compound. $^1$H NMR (300 MHz, d$_6$-DMSO) 12.80 (1H, br s), 9.42 (1H, br s), 8.16 (1H, br d), 7.59 (2H, m), 7.21 (1H, t), 6.92 (1H, d), 4.40 (1H, m), 3.01 (4H, m), 2.68 (1H, m), 1.94–1.20 (30H, m). The acid was converted to the N-methyl-D-glucamine salt and lyophilised from water/dioxan. Found: C, 58.04; H, 8.40; N, 8.37%. C$_{40}$H$_{61}$N$_5$O$_9$.4.0 mols H$_2$O requires: C, 58.02; H, 8.40; N, 8.46%.

EXAMPLE 266

[(3-{[5-(2-Adamantan-1-yl-ethyl)-2-cyclohexyl-1H-imidazole-4-carbonyl]-amino}-benzoyl)-methyl-amino]-acetic Acid 3-Nitro-benzoic acid was reacted with sarcosine ethyl hydrochloride and the resulting [(3-nitro-benzoyl)-methyl-amino]-acetic acid ethyl ester was hydrogenated to afford [(3-amino-benzoyl)-methyl-amino]-acetic acid ethyl ester. This was reacted with 5-(2-adamantan-1-yl-ethyl)-2- cyclohexyl-1H-imidazole-4-carboxylic acid (Example 252) according to the procedure of Example 20, step d. The ethyl ester was hydrolysed using the same procedure as in Example 247, step b to afford the title compound. $^1$H NMR (300 MHz, d$_6$-DMSO) 10.79 (1H, br s), 7.83 (2H, m), 7.44 (1H, m), 7.14 and 7.01 (1H, 2×m), 4.15 and 3.97 (2H, 2×s), 2.94 (6H, m), 2.03–1.25 (27H, m). The acid was converted to the N-methyl-D-glucamine salt and lyophilised from water/dioxan. Found: C, 60.14; H, 8.24; N, 8.97%. C$_{39}$H$_{59}$N$_5$O$_9$.2.0 mols H$_2$O requires: C, 60.21; H, 8.16, N 9.00%.

EXAMPLE 267

N-(3-{[5-(2-Adamantan-1-yl-ethyl)-2-cyclohexyl-1H-imidazole-4-carbonyl]-amino}-phenyl)-malonamic Acid 3-Nitroaniline was reacted with methyl malonyl chloride to afford N-(3-nitro-phenyl)-malonamic acid methyl ester. Hydrogenation afforded N-(3-amino-phenyl)-malonamic acid methyl ester, which was reacted with 5-(2-adamantan-1-yl-ethyl)-2-cyclohexyl-1H-imidazole-4-carboxylic acid (Example 252) according to the procedure of Example 20, step d. The methyl ester was hydrolysed using the same procedure as in Example 247, step b to afford the title compound. $^1$H NMR (300 MHz, d$_6$-DMSO) 10.30 (1H, br s), 10.20 (1H, br s), 8.06 (1H, s), 7.40 (2H, m), 7.27 (1H, t), 3.36 (2H, s), 2.92 (3H, m), 1.98–1.34 (27H, m). The acid was converted to the N-methyl-D-glucamine salt and lyophilised from water/dioxan. Found: C, 57.04; H, 8.30; N, 8.49%. C$_{38}$H$_{57}$N$_5$O$_9$.4.0 mols H$_2$O requires: C, 57.06; H, 8.19; N, 8.75%.

EXAMPLE 268

3-{[5-(2-Adamantan-1-yl-ethyl)-2-cyclohexyl-1H-imidazole-4-carbonyl]-amino}-benzenesulfonic Acid Oxalyl chloride (147 μl, 1.69 mmol) was added to an ice cooled suspension of 5-(2-adamantan-1-yl-ethyl)-2-cyclohexyl-1H-imidazole-4-carboxylic acid (Example 252) (500 mg, 1.40 mmol) in DCM (8 ml), followed by two drops of DMF. The mixture was stirred at room temperature for 1 h, then the solvent was evaporated. The residue was suspended in THF (8 ml), and tretaed sequentially with metanilic acid (346 mg, 2.00 mmol), N,N-diisopropylethylamine (348 μl, 2.00 mmol) and 4-dimethylaminopyridine (DMAP) (cat). The suspension was stirred at room temperature for 120 h. Water (30 ml), ethyl acetate (30 ml) and methanol (2 ml) were added and the mixture was stirred for 1 h. The solid was filtered and dried to afford the title compound (294 mg, 41%). $^1$H NMR (300 MHz, d$_6$-DMSO) 10.10 (1H, br s), 7.92 (1H, br s), 7.67 (1H, m), 7.34 (2H, m), 2.98–2.86 (3H, m), 2.02–1.34 (27H, m). The acid was converted to the N-methyl-D-glucamine salt and lyophilised from water/dioxan. Found: C, 57.87; H, 7.73; N, 7.74%. C$_{35}$H$_{54}$N$_5$O$_9$S.1.0 mol H$_2$O requires: C, 57.99; H, 7.79; N, 7.73%.

EXAMPLE 269

3-(5-{[5-(2-Adamantan-1-yl-ethyl)-2-cyclohexyl-1H-imidazole-4-carbonyl]-amino}-2-chloro-phenyl)-acrylic Acid 3-(5-Amino-2-chloro-phenyl)-acrylic acid methyl ester (prepared in two steps from 2-chloro-5-nitro-benzaldehyde) was reacted with 5-(2-adamantan-1-yl-ethyl)-2-cyclohexyl-1H-imidazole-4-carboxylic acid (Example 252) according to the procedure of Example 20, step d. The methyl ester was hydrolysed using the same procedure as in Example 36, step d to afford the title compound. $^1$H NMR (300 MHz, d$_6$-DMSO) 10.80 (1H, br s), 8.25 (1H, d), 7.96 (1H, d), 7.87 (1H, d), 7.55 (1H, d), 6.44 (1H, d), 2.94 (3H, m), 1.98–1.33 (27H, m). The acid was converted to the N-methyl-D-glucamine salt and lyophilised from water/dioxan. Found: C, 55.45; H, 7.91; N, 6.97%. C$_{38}$H$_{55}$ClN$_4$O$_8$.5.0 mols H$_2$O requires: C, 55.57; H, 7.98; N, 6.82%.

EXAMPLE 270

(3-{[5-(2-Adamantan-1-yl-ethyl)-2-cyclohexyl-1H-imidazole-4-carbonyl]-amino}-2,6-difluoro-phenyl)-acetic Acid (2,6-Difluoro-phenyl)-acetic acid was esterified, the ester was nitrated and the nitro group was hydrogenated to afford (3-amino-2,6-difluoro-phenyl)-acetic acid ethyl ester. This was reacted with 5-(2-adamantan-1-yl-ethyl)-2-cyclohexyl-1H-imidazole-4-carboxylic acid (Example 252) according to the procedure of Example 20, step d. The ethyl ester was hydrolysed using the same procedure as in Example 247, step b to afford the title compound. $^1$H NMR (300 MHz, d$_6$-DMSO) 10.10 (1H, br s), 7.68 (1H, br m), 7.13 (1H, t), 3.68 (2H, s), 2.90 (3H, m), 2.01–1.34 (27H, m). The acid was converted to the N-methyl-D-glucamine salt and lyophilised from water/dioxan. Found: C, 56.07; H, 8.01; N, 6.99%. C$_{37}$H$_{54}$F$_2$N$_4$O$_8$.4.0 mols H$_2$O requires: C, 56.05; H, 7.88; N, 7.07%.

EXAMPLE 271

3-(5-{[5-(2-Adamantan-1-yl-ethyl)-2-cyclohexyl-1H-imidazole-4-carbonyl]-amino)-2-chloro-phenyl)-propionic Acid 3-(5-Amino-2-chloro-phenyl)-acrylic acid methyl ester (prepared in two steps from 2-chloro-5-nitro-benzaldehyde) was reduced with aluminium amalgam to produce 3-(5-amino-2-chloro-phenyl)-propionic acid methyl ester. This was reacted with 5-(2-adamantan-1-yl-ethyl)-2-cyclohexyl-1H-imidazole-4-carboxylic acid (Example 252) according to the procedure of Example 20, step d. The methyl ester was hydrolysed using the same procedure as in Example 36, step d to afford the title compound. $^1$H NMR (300 MHz, d$_6$-DMSO) 14.00 (1H, br s), 10.70 (1H, br s), 7.71 (2H, m), 7.42 (1H, d), 2.90 (5H, m), 2.54 (2H, m), 1.98–1.50 (27H, m). The acid was converted to the N-methyl-D-glucamine salt and lyophilised from water/dioxan. Found: C, 57.86; H, 8.02; N, 6.81%. C$_{38}$H$_{57}$ClN$_4$O$_8$.3.0 mols H$_2$O requires: C, 57.97; H, 8.07; N, 7.12%.

EXAMPLE 272

(S)-2-(3-{[5-(2-Adamantan-1-yl-ethyl)-2-cyclohexyl-1H-imidazole-4-carbonyl]-amino}-benzoylamino)-propionic Acid 3-Nitrobenzoyl chloride was reacted with L-alanine benzyl ester, then reduced with aluminium amalgam to produce (S)-2-(3-amino-phenyl)-propionic acid benzyl ester. This was reacted with 5-(2-adamantan-1-yl-ethyl)-2-cyclohexyl-1H-imidazole-4-carboxylic acid (Example 252) according to the procedure of Example 20, step d. The benzyl ester was hydrogenolysed using the same procedure as in Example 1, step e to afford the title compound. $^1$H NMR (300 MHz, d$_6$-DMSO) 11.96 (1H, br s), 9.46 (1H, br s), 8.57 (1H, br d), 8.16 (1H, s), 7.95 (1H, m), 7.54 (1H, d), 7.40–7.35 (1H, m), 4.40 (1H, m), 2.87 (2H, m), 2.63 (1H, m), 1.94–1.32 (30H, m). The acid was converted to the N-methyl-D-glucamine salt and lyophilised from water/dioxan. Found: C, 58.89; H, 8.28; N, 8.97%. $C_{39}H_{59}N_4O_9$.3.0 mols $H_2O$ requires: C, 58.85; H, 8.23; N, 8.86%.

EXAMPLE 273

(R)-2-(3-{[5-(2-Adamantan-1-yl-ethyl)-2-cyclohexyl-1H-imidazole-4-carbonyl]-amino}-benzoylamino)-propionic Acid 3-Nitrobenzoyl chloride was reacted with D-alanine benzyl ester, then reduced with tin chloride to produce (R)-2-(3-amino-phenyl)-propionic acid benzyl ester. This was reacted with 5-(2-adamantan-1-yl-ethyl)-2-cyclohexyl-1H-imidazole-4-carboxylic acid (Example 252) according to the procedure of Example 20, step d. The benzyl ester was hydrogenolysed using the same procedure as in Example 1, step e to afford the title compound. $^1$H NMR (300 MHz, $d_6$-DMSO) 11.96 (1H, br s), 9.46 (1H, br s), 8.57 (1H, br d), 8.16 (1H, s), 7.96 (1H, d), 7.54 (1H, d), 7.40–7.35 (1H, m), 4.41 (1H, m), 2.87 (2H, m), 2.63 (1H, m), 1.94–1.32 (30H, m). The acid was converted to the N-methyl-D-glucamine salt and lyophilised from water/dioxan. Found: C, 60.15; H, 8.33; N, 9.04%. $C_{39}H_{59}N_5O_9$.2.0 mols $H_2O$ requires: C, 60.21; H, 8.16; N, 9.00%.

EXAMPLE 274

(3-{[5-(2-Adamantan-1-yl-ethyl)-2-cyclohexyl-1H-imidazole-4-carbonyl]-amino}-phenylamino)-acetic Acid 3-Nitrophenylisocyanate was reacted with tert-butanol to form (3-nitro-phenyl)-carbamic acid tert-butyl ester. This was reacted with benzyl 2-bromoacetate, then the tert-butyloxycarbonyl group was removed and the resulting (3-nitro-phenylamino)-acetic acid benzyl ester was reduced with aluminium amalgam to afford (3-amino-phenylamino)-acetic acid benzyl ester. This was reacted with 5-(2-adamantan-1-yl-ethyl)-2-cyclohexyl-1H-imidazole-4-carboxylic acid (Example 252) according to the procedure of Example 20, step d. The benzyl ester was hydrogenolysed using the same procedure as in Example 1, step e to afford the title compound. $^1$H NMR (300 MHz, $d_6$-DMSO/$D_2O$) 7.02–6.86 (3H, m), 6.23 (1H, d), 3.55 (2H, s), 2.83 (2H, m), 2.61 (1H, m), 1.88–1.19 (27H, m). The acid was converted to the N-methyl-D-glucamine salt and lyophilised from water/dioxan. Found: C, 59.09; H, 8.60; N, 9.41%. $C_{37}H_{57}N_5O_8$.3.0 mols $H_2O$ requires: C, 58.95; H, 8.42; N, 9.29%.

EXAMPLE 275

3-{2-[5-(2-Adamantan-1-yl-ethyl)-1-methyl-2-o-tolyl-1H-imidazol-4-yl]-vinyl}-benzoic Acid Step a. [5-(2-Adamantan-1-yl-ethyl)-1-methyl-2-o-tolyl-1H-imidazol-4-yl]-methanol Lithium aluminium hydride (355 mg, 9.34 mmol) was added in small portions to an ice cooled solution of 5-(2-adamantan-1-yl-ethyl)-1-methyl-2-o-tolyl-1H-imidazole-4-carboxylic acid ethyl ester (Example 73, step a) (1.83 g, 4.67 mmol) in THF (20 ml). The suspension was allowed to warm to room temperature and stirred for 2 h. The reaction mixture was quenched sequentially with water (360 µl), sodium hydroxide (2M, 360 µl) and water (3×360 µl), diluted with ethyl acetate (50 ml) and treated with magnesium sulfate. The suspension was filtered through celite, the solid residues were washed with ethyl acetate (20 ml) and chloroform (100 ml) and the filtrate was evaporated to afford white solid (2.15 g). $^1$H NMR (300 MHz, $d_6$-DMSO/$D_2O$) 7.34–7.24 (4H, m), 4.60 (2H, s), 3.32 (3H, s), 2.61 (2H, m), 2.40 (1H, br s), 2.20 (3H, s), 2.01 (3H, br s), 1.78–1.58 (12H, m), 1.32 (2H, m).

Step b. 5-(2-Adamantan-1-yl-ethyl)-1-methyl-2-o-tolyl-1H-imidazole-4-carbaldehyde A mixture of the product of step a (2.14 g, 5.87 mmol) and manganese(IV) oxide (5.10 g, 58.7 mmol) in dioxan (60 ml) was heated at reflux for 2.5 h. The suspension was allowed to cool and then filtered through celite. The solid residue was washed with chloroform (180 ml) and the filtrate was evaporated to afford the aldehyde (1.23 g,72%). $^1$H NMR (300 MHz, $CDCl_3$) 9.98 (1H, s), 7.42–7.27 (4H, m), 3.37 (3H, s), 2.99 (2H, m) 2.21 (3H, s), 2.02 (3H, br s), 1.78–1.62 (12H, m), 1.36 (2H, m).

Step c. 3-{2-[5-(2-Adamantan-1-yl-ethyl)-1-methyl-2-o-tolyl-1H-imidazol-4-yl]-vinyl}-benzoic acid methyl Ester Sodium hydride (60% dispersion in oil) (122 mg, 3.05 mmol) was added to an ice cooled suspension of 3-methoxycarbonyl-benzyl-triphenylphosphonium bromide (1.25 g, 2.54 mmol) in THF (5 ml). The yellow suspension was stirred at room temperature for 10 min, cooled to 0° C. and the solution of the product of step b (7686 mg, 2.12 mmol) in THF (5 ml) was added. The suspension was allowed to warm to room temperature and stirred for 72 h. Water (2 ml), then ethyl acetate (40 ml) were added. The organic phase was washed with water (30 ml), brine (30 ml), dried ($MgSO_4$) and the solvent was evaporated. The crude product was purified by flash column chromatography (silica, hexane/ethyl acetate 5:2) to afford the product as 2:1 mixture of trans/cis isomers (778 mg, 74%).

Step d

The product of step c (741 mg, 1.50 mmol) was hydrolysed according to the procedure of Example 36, step d to afford the title compound as 1:1 mixture of cis/trans isomers (740 mg, 100%). $^1$H NMR (300 MHz, $d_6$-DMSO) (1:1 mixture of cis/trans isomers.) 8.09–6.55 (10H, m), 3.52 and 3.49 (3H, 2×s), 2.90 and 2.49 (2H, 2×m), 2.26 and 2.16 (3H, 2×m), 1.95 (3H, m), 1.69–1.16 (14H, m). The acid was converted to the N-methyl-D-glucamine salt and lyophilised from water/dioxan. Found: C, 61.74; H, 8.43; N, 5.49%. $C_{39}H_{53}N_3O_7$.4.5 mols $H_2O$ requires: C, 61.89; H, 8.26; N, 5.55%.

EXAMPLE 276

3-{2-[5-(2-Adamantan-1-yl-ethyl)-3-methyl-2-o-tolyl-3H-imidazol-4-yl]-vinyl}-benzoic Acid The title compound was prepared according to the procedure of Example 275, with the modification that 5-(2-adamantan-1-yl-ethyl)-3-methyl-2-o-tolyl-3H-imidazole-4-carboxylic acid ethyl ester (Example 73, step a) was used in step a instead of 5-(2-adamantan-1-yl-ethyl)-1-methyl-2-o-tolyl-1H-imidazole4-carboxylic acid ethyl ester. $^1$H NMR (300 MHz, $d_6$-DMSO) complex, mixture of cis/trans isomers. The acid was converted to the N-methyl-D-glucamine salt and lyophilised from water/dioxan. Found: C, 62.67; H, 8.29; N, 5.70%. $C_{39}H_{53}N_3O_7.4.0$ mols $H_2O$ requires: C, 62.63; H, 8.22; N, 5.62%.

EXAMPLE 277

3-{2-[5-(2-Adamantan-1-yl-ethyl)-3-methyl-2-o-tolyl-3H-imidazol-4-yl]-ethyl}-benzoic Acid 3-{2-[5-(2-Adamantan-1-yl-ethyl)-3-methyl-2-o-tolyl-3H-imidazol-4-yl]-vinyl}-benzoic acid (Example 276) (200 mg, 0.42 mmol) was hydrogenated according of the procedure of Example 1, step e to afford the title compound (171 mg, 86%). $^1$H NMR (300 MHz, $d_6$-DMSO) 14.20 (1H, br s), 7.81 (1H, m), 7.75 (1H, br s), 6.61 (1H, m), 7.54–7.40 (5H, m), 3.51 (3H, s), 3.02 (4H, m), 2.15 (5H, m), 1.90 (3H, br s), 1.68–1.55 (6H, m), 1.35 (6H, m), 0.93 (2H, m). The acid was converted to the N-methyl-D-glucamine salt and lyophilised from water/dioxan. Found: C, 61.09; H, 8.49; N, 5.62%. $C_{39}H_{55}N_3O_7.5.0$ mols $H_2O$ requires: C, 61.00; H, 8.53; N, 5.47%.

EXAMPLE 278

3-{2-[5-(2-Adamantan-1-yl-ethyl)-1-methyl-2-o-tolyl-1H-imidazol-4-yl]-ethyl}-benzoic Acid 3-{2-[5-(2-Adamantan-1-yl-ethyl)-1-methyl-2-o-tolyl-1H-imidazol-4-yl]-vinyl}-benzoic acid (Example 275) (422 mg, 0.88 mmol) was hydrogenated according of the procedure of Example 1, step e to afford the title compound (399 mg, 94%). $^1$H NMR (300 MHz, $d_6$-DMSO) 14.80 (1H, br s), 7.77 (2H, m), 7.64–7.37 (6H, m), 3.41 (3H, s), 3.01 (4H, m), 2.39 (2H, m), 2.17 (3H, s), 1.92 (3H, s), 1.69–1.57 (6H, m), 1.41 (6H, m) 1.00 (2H, m). The acid was converted to the N-methyl-D-glucamine salt and lyophilised from water/dioxan. Found: C, 62.45; H, 8.69; N, 5.77%. $C_{39}H_{55}N_3O_7.4.0$ mols $H_2O$ requires: C, 62.46; H, 8.47; N, 5.60%.

EXAMPLE 279

3-{[5-(2-Adamantan-1-yl-ethyl)-1-methyl-2-o-tolyl-1H-imidazol-4-ylmethyl]-amino}-benzoic Acid Step a. 3-{[5-(2-Adamantan-1-yl-ethyl)-1-methyl-2-o-tolyl-1H-imidazol-4-ylmethyl]-amino}-benzoic Acid Benzyl Ester To a solution of 5-(2-adamantan-1-yl-ethyl)-1-methyl-2-o-tolyl-1H-imidazole-4-carbaldehyde (Example 275, step b) (500 mg, 1.38 mmol) and 3-amino-benzoic acid benzyl ester (313 mg, 1.38 mmol) in 1,2-dichloroethane (5 ml) were added sodium triacetoxyborohydride (409 mg, 1.93 mmol) and then acetic acid (79 μl, 1.38 mmol). The suspension was stirred at room temperature for 2 h, then saturated sodium bicarbonate (40 ml) was added. The product was extracted with ethyl acetate (40 ml), the organic phase was washed with brine (40 ml), dried (MgSO$_4$) and the filtrate was evaporated. The residue was purified by flash column chromatography (silica, hexane/ethyl acetate 1:1) to afford the product (725 mg, 92%). $^1$H NMR (300 MHz, CDCl$_3$) 7.44–7.23 (12H, m), 6.91 (1H, m), 5.36 (2H, s), 4.50 (1H, br s), 4.24 (2H, s), 3.33 (3H, s), 2.61 (2H, m), 2.20 (3H, s), 2.00 (3H, br s), 1.77–1.57 (12H, m), 1.31 (2H, m).

Step b

The product of step a (714 mg, 1.24 mmol) was hydrogenolysed according to the procedure of Example 1, step e to afford the title compound (600 mg, 100%). $^1$H NMR (300 MHz, $d_6$-DMSO) 7.35–7.08 (7H, m), 6.91 (1H, m), 4.11 (2H, br s), 3.27 (3H, s), 2.58 (2H, m), 2.14 (3H, s), 1.92 (3H, br s), 1.69–1.51 (12H, m), 1.20 (2H, m). The acid was converted to the N-methyl-D-glucamine salt and lyophilised from water/dioxan. Found: C, 63.93; H, 8.33; N, 7.80%. $C_{38}H_{54}N_4O_7.2.0$ mols $H_2O$ requires: C, 63.84; H, 8.18; N, 7.84%.

EXAMPLE 280

3-{2-[5-(2-Adamantan-1-yl-ethyl)-2-o-tolyl-1H-imidazol-4-yl]-ethyl}-benzoic Acid 5-(2-Adamantan-1-yl-ethyl)-1-benzyl-2-o-tolyl-1H-imidazole-4-carboxylic acid ethyl ester was prepared according to the procedure of Example 73, step a, with the modification that benzyl-bromide was used instead of iodomethane. This was converted to 3-{2-[5-(2-adamantan-1-yl-ethyl)-1-benzyl-2-o-tolyl-1H-imidazol-4-yl]-vinyl}-benzoic acid methyl ester using essentially the same procedure as in Example 275, steps a, b and c. This product was hydrogenolysed according to the procedure of Example 1, step e to afford 3-{2-[5-(2-adamantan-1-yl-ethyl)-2-o-tolyl-1H-imidazol-4-yl]-ethyl}-benzoic acid methyl ester. The methyl ester was hydrolysed according to the procedure of Example 36, step d to afford the title compound. $^1$H NMR (300 MHz, $d_6$-DMSO) 7.74 (2H, m), 7.50 (1H, m), 7.37–7.21 (5H, m), 2.95 (2H, m), 2.75 (2H, m), 2.50 (3H, s), 2.20 (2H, m), 1.90 (3H, s), 1.67–1.56 (6H, m), 1.38 (6H, br s), 0.96 (2H, m). The acid was converted to the N-methyl-D-glucamine salt and lyophilised from water/dioxan. Found: C, 65.43; H, 8.24; N, 5.80%. $C_{38}H_{53}N_3O_7.2.0$ mols $H_2O$ requires: C, 65.21; H, 8.21; N, 6.00%.

EXAMPLE 281

5-(2-Adamantan-1-yl-ethyl)-2-o-tolyl-1H-imidazole-4-carboxylic Acid 3-carboxy-phenyl Ester Step a. 5-(2-Adamantan-1-yl-ethyl)-2-o-tolyl-1H-imidazole-4-carboxylic Acid 3-benzyloxycarbonyl-phenyl Ester A solution of 5-(2-adamantan-1-yl-ethyl)-2-o-tolyl-1H-imidazole-4-carboxylic acid (Example 93) (57 mg, 0.16 mmol) and 1,1'-carbonyldiimidazole(25 mg, 0.16 mmol) in DMF (0.5 ml) was stirred at room temperature for 30 min. 3-Benzyloxycarbonyl-phenol (36 mg, 0.16 mmol) was added and the mixture was stirred at 115° C. for 16 h, then cooled to room temperature. Water (5 ml) was added and the mixture was extracted with ethyl acetate (3×5 ml). The combined extracts were washed with brine, dried (MgSO$_4$) and the solvent was evaporated. The crude product was purified by flash chromatography (silica, DCM/ethyl acetate 9:1) to afford colourless foam (15 mg, 17%). $^1$H NMR (300 MHz, CDCl$_3$) 7.97 (1H, m), 7.91 (1H, m), 7.39 (4H, m), 5.37 (2H, s), 3.01 (2H, m), 2.52 (3H, s), 1.94 (3H, br s), 1.66 (6H, m), 1.54 (8H, m).

Step b

The product of step a (15 mg, 0.03 mmol) was hydrogenolysed according to the procedure of Example 1, step a to afford the title compound (12 mg, 90%). $^1$H NMR (300 MHz, $d_4$-MeOH) 7.95 (1H, m), 7.88 (1H, m), 7.41 (6H, m), 3.05 (2H, m), 2.45 (3H, s), 1.95 (3H, br s), 1.71 (6H, m), 1.61 (6H, m), 1.52 (2H, m). The acid was converted to the N-methyl-D-glucamine salt and lyophilised from water/dioxan. Found: C, 60.43; H, 7.52; N, 5.73%. $C_{37}H_{49}N_3O_9.3.1$ mols $H_2O$ requires: C, 60.47; H, 7.56; N, 5.72%.

EXAMPLE 282

5-(2-Adamantan-1-yl-ethyl)-2-cyclohexyl-1H-imidazole-4-carboxylic Acid 3-carboxy-phenyl Ester The title compound was prepared according to the procedure given in Example 281, with the modification that 5-(2-adamantan-1-yl-ethyl)-2-cyclohexyl-1H-imidazole-4-carboxylic acid (Example 252) was used in step a instead of 5-(2-adamantan-1-yl-ethyl)-2-o-tolyl-1H-imidazole-4-carboxylic acid. $^1$H NMR (300 MHz, $d_4$-MeOH) 7.94 (1H, dt), 7.84 (1H, t), 7.55 (1H, t), 7.46 (1H, ddd), 2.94 (2H, m), 2.77 (1H, m) 1.94 (7H, m), 1.70 (8H, m), 1.58 (7H, m), 1.42 (5H, m). The acid was converted to the N-methyl-D-glucamine salt and lyophilised from water/dioxan. Found: C, 61.32; H, 8.34; N, 5.87%. $C_{36}H_{53}N_3O_9$.1.9 mols $H_2O$ requires: C, 61.21; H, 8.11; N, 5.95%.

EXAMPLE 283

3-(4-{[5-(2-Adamantan-1-yl-ethyl)-2-cyclohexyl-1H-imidazole-4-carbonyl]-amino}-phenyl)-propionic Acid 3-(4-Amino-phenyl)-propionic acid acid benzyl ester (prepared in two steps from 4-nitrocinnamic acid) was reacted with 5-(2-adamantan-1-yl-ethyl)-2-cyclohexyl-1H-imidazole-4-carboxylic acid (Example 252) according to the procedure of Example 20, step d. The benzyl ester was hydrogenolysed using the same procedure as in Example 1, step e to afford the title compound. $^1$H NMR (300 MHz, $d_6$-DMSO) 12.00 (1H, br s), 9.28 (1H, br s), 7.63 (1H, d), 7.14 (1H, d), 2.86 (2H, m), 2.76 (2H, t), 2.64 (1H, m), 2.62 (2H, m), 2.49 (2H, m), 1.93–1.30 (27H, m). The acid was converted to the N-methyl-D-glucamine salt and lyophilised from water/dioxan. Found: C, 60.77; H, 8.69; N, 7.49%; $C_{38}H_{58}N_4O_8$.3.0 $H_2O$ requires: C, 60.62; H, 8.57; N, 7.44%.

EXAMPLE 284

3-(3-{[5-(2-Adamantan-1-yl-ethyl)-2-cyclohexyl-1H-imidazole-4-carbonyl]-amino}-2,6-difluoro-phenyl)-propionic Acid 2,6-Difluorocinnamic acid was esterified, then hydrogenated to afford 3-(2,6-difluoro-phenyl)-propionic acid ethyl ester. This was nitrated and the nitro group was hydrogenated to afford 3-(3-amino-2,6-difluoro-phenyl)-propionic acid ethyl ester. This was reacted with 5-(2-adamantan-1-yl-ethyl)-2-cyclohexyl-1H-imidazole-4-carboxylic acid (Example 252) according to the procedure of Example 20, step d. The ethyl ester was hydrolysed using the same procedure as in Example 247, step b to afford the title compound. $^1$H NMR (300 MHz, $d_6$-DMSO) 12.20 (1H, br s), 12.00 (1H, br s), 9.27 (1H, br s), 8.06 (1H, br m), 7.03 (1H, m), 2.86 (4H, m), 2.60 (1H, m), 2.51 (2H, m), 1.93–1.31 (27H, m). The acid was converted to the N-methyl-D-glucamine salt and lyophilised from water/dioxan. Found: C, 59.04; H, 8.00; N, 7.33%; $C_{38}H_{56}F_2N_4O_8$.2.0 $H_2O$ requires: C, 59.20; H, 7.85; N, 7.27%.

EXAMPLE 285

(S)-1-(3-{[5-(2-Adamantan-1-yl-ethyl)-2-cyclohexyl-1H-imidazole-4-carbonyl]-amino}-benzoyl)-pyrrolidine-2-carboxylic Acid 3-Nitrobenzoyl chloride was reacted with L-proline tert-butyl ester hydrochloride, then hydrogenated to produce (S)-1-(3-amino-phenyl)-pyrrolidin-2-carboxylic acid tert-butyl ester. This was reacted with 5-(2-adamantan-1-yl-ethyl)-2-cyclohexyl-1H-imidazole-4-carboxylic acid (Example 252) according to the procedure of Example 20, step d. The tert-butyl ester was deprotected by treating the chloroform solution of the ester with 4.0 M solution of hydrogen chloride in dioxan to afford the title compound as the hydrochloride salt. $^1$H NMR (300 MHz, $d_6$-DMSO) (mixture of tautomers) 14.10 (1H, br s), 10.95 (1H, br m), 8.00 and 7.79 (1H, 2×m), 7.88 (1H, m), 7.41 (1H, m), 7.26 and 7.11 (1H, 2×), 4.43 (1H, m), 4.12 (1H, m), 3.48 (1H,m), 2.97 (3H, m), 2.28–1.29 (31H, m). Found: C, 64.88; H, 7.78; N, 8.92%; $C_{34}H_{45}ClN_4O_4$.1.0 mol $H_2O$ requires: C, 65.11; H, 7.55; N, 8.93%.

EXAMPLE 286

5-(Adamantan-1-yloxymethyl)-2-cyclohexyl-1H-imidazole-4-carboxylic Acid (3-hydroxycarbamoyl-phenyl)-amide Step a. 5-(Adamantan-1-yloxymethyl)-2-cyclohexyl-1H-imidazole-4-carboxylic Acid (3-benzyloxycarbamoyl-phenyl)-amide 3-{[5-(Adamantan-1-yloxymethyl)-2-cyclohexyl-1H-imidazole-4-carbonyl]-amino}-benzoic acid (Example 216) (910 mg, 1.90 mmol) was reacted with O-benzylhydroxylamine hydrochloride (455 mg, 2.85 mmol) in the presence of triethylamine (0.40 ml, 2.85 mmol) according to the procedure of Example 20, step d. The crude material was purified by flash column chromatography (silica, DCM/methanol 95:5) to afford a colourless foam (910 mg, 84%). $^1$H NMR (300MHz, $CDCl_3$) 9.25 (1H, br s), 9.06 (1H, s), 8.64 (1H, s), 8.01 (1H, s), 7.84 (1H, m), 7.41 (6H, m), 5.06 (2H, s), 4.98 and 4.81 (2H, 2×s), 2.72 (1H, m), 2.19 (3H, br s), 2.07 (2H, m), 1.90–1.36 (20H, m).

Step b

The product of step a (900 mg, 1.58 mmol) was deprotected using the same procedure as in Example 1, step e. The crude product was purified by flash column chromatography (silica, DCM/methanol 95:5) to afford an off-white solid. $^1$H NMR (300 MHz, $d_6$-DMSO) 12.16 (1H, br s), 11.12 (1H, br s), 9.57 (1H, s), 8.98 (1H, br s), 8.15 (1H, s), 7.88 (1H, d), 7.36 (2H, m), 4.79 (2H, s), 2.68 (1H, m), 2.11 (3H, br s), 1.90 (2H, m), 1.76 (8H, m), 1.59 (8H, m), 1.39–1.20 (4H, m). The hydroxamic acid was converted to the N-methyl-D-glucamine salt and lyophilised from water/dioxan. Found: C, 58.34; H, 8.23; N 9.54%; $C_{35}H_{53}N_5O_9$.1.9 $H_2O$ requires: C, 58.21; H, 7.93; N, 9.70%.

EXAMPLE 287

5-(Adamantan-1-yloxymethyl)-2-cyclohexyl-1H-imidazole-4-carboxylic Acid (3-hydroxycarbamoylmethyl-phenyl)-amide The title compound was prepared according to the procedure of Example 286, with the modification that (3-{[5-(adamantan-1-yloxymethyl)-2-cyclohexyl-1H-imidazole-4-carbonyl]-amino}-phenyl)-acetic acid (Example 219) was used in step a instead of 3-{[5-(adamantan-1-yloxymethyl)-2-cyclohexyl -1H-imidazole-4-carbonyl]-amino}-benzoic acid. $^1$H NMR (300 MHz, $d_6$-DMSO) 12.15 (1H, s), 10.62 (1H, s), 9.37 (1H, s), 8.80 (1H, s), 7.68 (1H, s), 7.58 (1H, d), 7.21 (1H, t), 6.94 (1H, d), 4.79 (2H, s), 3.25 (2H, s), 2.69 (1H, m), 2.11 (3H, br s), 1.90 (2H, m), 1.75 (8H, m), 1.55

(8H, m), 1.30 (4H, m). The hydroxamic acid was converted to the N-methyl-D-glucamine salt and lyophilised from water/dioxan. Found: C, 59.81; H, 8.06; N, 9.68%; $C_{36}H_{55}N_5O_9 \cdot 1.1H_2O$ requires: C, 59.87; H, 7.99; N, 9.70%.

EXAMPLE 288

3-{[5-(Adamantan-1-yloxymethyl)-2-bicyclo[2.2.1]hepta-2,5-dien-7-yl-1H-imidazole-4-carbonyl]-amino}-benzoic Acid 5-(Adamantan-1-yloxymethyl)-2-bicyclo[2.2.1]hepta-2,5-dien-7-yl-1H-imidazole4-carboxylic acid benzyl ester was prepared according to the procedure of Example 216, steps a, b, c and d with the modification that norbornadiene-7-carboxaldehyde (J. Stapersma and G. W. Klumpp *Tetrahedron*, 1981, 37, 187) was used in step d instead of cyclohexanecarboxaldehyde. The benzyl ester was hydrolysed according to the procedure of Example 211, step b and the resulting 5-(adamantan-1-yloxymethyl)-2-bicyclo[2.2.1]hepta-2,5-dien-7-yl-1H-imidazole-4-carboxylic acid was reacted with 3-amino-benzoic acid benzyl ester according to the procedure of Example 20, step d to afford 3-{[5-(adamantan-1-yloxymethyl)-2-bicyclo[2.2.1]hepta-2,5-dien-7-yl-1H-imidazole-4-carbonyl]-amino}-benzoic acid benzyl ester. The benzyl ester was hydrolysed according to the procedure of Example 211, step b and the crude product was purified by flash column chromatography (silica, DCM/methanol 95:5 ) to afford the title compound. $^1$H NMR (300 MHz, $d_6$-DMSO) 12.10 (1H, br s), 9.65 (1H, br s), 8.42 (1H, br s), 7.92 (1H, d), 7.62 (1H, d), 7.41 (1H, t), 6.90 (2H, s), 6.59 (2H, s), 4.75 (2H, s), 4.06 (2H, s), 3.47 (1H, s), 2.10 (3H, br s), 1.75 (6H, s), 1.58 (6H, m). The acid was converted to the N-methyl-D-glucamine salt and lyophilised from water/dioxan. Found: C, 58.71; H, 7.44; N, 7.50%. $C_{36}H_{48}N_4O_9 \cdot 3.0$ mols $H_2O$ requires: C, 58.84; H, 7.41; N, 7.62%.

EXAMPLE 289 endo-5-{[5-(Adamantan-1-yloxymethyl)-2-((1S,2S)-bicyclo[2.2.1]hept-5-en-2-yl)-1H-imidazole-4-carbonyl]-amino}-2-methyl-benzoic Acid endo-5-(Adamantan-1-yloxymethyl)-2-((1S,2S)-bicyclo[2.2.1]hept-5-en-2-yl)-1H-imidazole-4-carboxylic acid (Example 235) was reacted with 5-amino-2-methyl-benzoic acid benzyl ester according to the procedure of Example 20, step d to afford endo-5-{[5-(adamantan-1-yloxymethyl)-2-((1S,2S)-bicyclo[2.2.1]hept-5-en-2-yl)-1H-imidazole-4-carbonyl]-amino}-2-methyl-benzoic acid benzyl ester. The benzyl ester was hydrolysed according to the procedure of Example 211, step b to afford the title compound. $[\alpha]_D^{29}$ −66.23° (c=0.77, DMF). $^1$H NMR (300 MHz, $d_6$-DMSO) 12.80 (1H, br s), 12.03 (1H, s), 9.45 (1H, s), 8.26 (1H, d), 7.77 (1H, dd), 7.20 (1H, d), 6.18 (1H, dd), 5.75 (1H, d), 4.81 (1H, d), 4.73 (1H, d), 3.35 (2H, m), 2.91 (1H, br m), 2.46 (3H, s), 2.03 (4H, m), 1.75 (6H, m), 1.58 (7H, m), 1.38 (2H, s). The acid was converted to the N-methyl-D-glucamine salt and lyophilised from water/dioxan. Found: C, 61.02; H, 7.69; N, 7.58%; $C_{37}H_{52}N_4O_9 \cdot 1.8$ $H_2O$ requires: C, 60.98; H, 7.68; N, 7.69%.

EXAMPLE 290 endo-5-{[5-(Adamantan-1-yloxymethyl)-2-((1R,2R)-bicyclo[2.2.1]hept-5-en-2-yl)-1H-imidazole-4-carbonyl]-amino}-2-methyl-benzoic Acid endo-5-(Adamantan-1-yloxymethyl)-2-((1R,2R)-bicyclo[2.2.1]hept-5-en-2-yl)-1H-imidazole-4-carboxylic acid (Example 236) was reacted with 5-amino-2-methyl-benzoic acid benzyl ester according to the procedure of Example 20, step d to afford endo-5-{[5-(adamantan-1-yloxymethyl)-2-((1R,2R)-bicyclo[2.2.1]hept-5-en-2-yl)-1H-imidazole-4-carbonyl]-amino}-2-methyl-benzoic acid benzyl ester. The benzyl ester was hydrolysed according to the procedure of Example 211, step b to afford the title compound. $[\alpha]_D^{29}$ +84.0° (c=0.75, DMF). $^1$H NMR (300 MHz, $d_4$-MeOH) 8.13 (1H, d), 7.85 (1H, dd), 7.32 (1H, m), 6.45 (1H, dd), 5.85 (1H, dd), 4.87 (2H, s), 3.60 (1H, m), 3.37 (1H, br m), 3.12 (1H, br m), 2.58 (3H, s), 2.36 (1H, m), 2.20 (3H, br s), 1.90 (6H, m), 1.66 (7H, m), 1.54 (2H, m). The acid was converted to the N-methyl-D-glucamine salt and lyophilised from water/dioxan. Found: C, 58.82; H, 7,52; N, 7.38%; $C_{37}H_{52}N_4O_9 \cdot 1.8$ $H_2O$ .0.7 mol HCl requires: C, 58.88; H, 7.52; N, 7.42%.

EXAMPLE 291 endo-3-{[5-(Adamantan-1-yloxymethyl)-2-((1S,2S)-bicyclo[2.2.1]hept-2-yl)-1H-imidazole-4-carbonyl]-amino}-benzoic Acid endo-5-(Adamantan-1-yloxymethyl)-2-((1S,2S)-bicyclo[2.2.1]hept-5-en-2-yl)-1H-imidazole-4-carboxylic acid (Example 235) was reacted with 3-amino-benzoic acid benzyl ester according to the procedure of Example 20, step d to afford endo-5-{[5-(adamantan-1-yloxymethyl)-2-((1S,2S)-bicyclo[2.2.1]hept-5-en-2-yl)-1H-imidazole-4-carbonyl]-amino}-benzoic acid benzyl ester. The benzyl ester was hydrogenolysed according to the procedure of Example 1, step e to afford the title compound. $[\alpha]_D^{29}$ −14.3° (c=0.63, DMF). $^1$H NMR (300 MHz, $d_6$-DMSO) 11.20 (1H, br s), 8.45 (1H, s), 8.01 (1H, d), 7.69 (1H, d), 7.49 (1H, t), 4.92 (2H, dd), 2.74(1H, m), 2.34 (1H, m), 2.11 (4H, m), 1.85 (1H, m), 1.77 (6H, m), 1.62–1.20 (12H, m), 0.92 (1H, m). The acid was converted to the N-methyl-D-glucamine salt and lyophilised from water/dioxan.

EXAMPLE 292 endo-3-{[5-(Adamantan-1-yloxymethyl)-2-((1R,2R)-bicyclo[2.2.1]hept-2-yl)-1H-imidazole-4-carbonyl]-amino}-benzoic Acid endo-5-(Adamantan-1-yloxymethyl)-2-((1R,2R)-bicyclo[2.2.1]hept-5-en-2-yl)-1H-imidazole-4-carboxylic acid (Example 236) was reacted with 3-amino-benzoic acid benzyl ester according to the procedure of Example 20, step d to afford endo-3-{[5-(adamantan-1-yloxymethyl)-2-((1R,2R)-bicyclo [2.2.1]hept-5-en-2-yl)-1H-imidazole-4-carbonyl]-amino}-benzoic acid benzyl ester. The benzyl ester was hydrogenolysed according to the procedure of Example 1, step e to afford the title compound. $[\alpha]_D^{29}$ +9.8° (c=0.61, DMF). $^1$H NMR (300 MHz, $d_6$-DMSO) 11.20 (1H, br s), 8.45 (1H, s), 8.01 (1H, d), 7.69 (1H, d), 7.49 (11H, t), 4.92 (2H, dd), 2.74(11H, m), 2.34 (1H, m), 2.11 (4H, m), 1.85 (1H, m), 1.77 (6H, m), 1.62–1.20 (12H, m), 0.92 (1H, m). The acid was converted to the N-methyl-D-glucamine salt and lyophilised from water/dioxan. Found: C, 58.46; H, 7.94; N, 7.81%; $C_{36}H_{52}N_4O_9 \cdot 2.9$ $H_2O$ requires: C, 58.66; H, 7.90; N, 7.60%.

EXAMPLE 293

5-{[5-(Adamantan-1-yloxymethyl)-2-bicyclo[2.2.1]hept-7-yl-1H-imidazole-4-carbonyl]-amino}-2-methyl-benzoic Acid The title compound was prepared according to the procedure of Example 216, with the modification that bicyclo

[2.2.1]hepta-2,5-diene-7-carbaldehyde (G. W. Klumpp et al. *Tetrahedron* 1981, 37, 187) was used in step d instead of cyclohexanecarboxaldehyde and 5-amino-2-methyl-benzoic acid benzyl ester replaced 3-amino-benzoic acid benzyl ester in step f. $^1$H NMR (300 MHz, d$_6$-DMSO) 12.15 (1H, br s), 9.48 (1H, br s), 8.23 (1H, br s), 7.76 (1H, dd), 7.21 (1H, d), 4.77 (2H, s), 2.74 (1H, s), 2.62 (2H, s), 2.45 (3H, s), 2.09 (3H, br s), 1.75–1.52 (16H, m), 1.26 (2H, d), 1.17 (2H, d). The acid was converted to the N-methyl-D-glucamine salt and lyophilised from water/dioxan. Found: C, 60.47; H, 7.94; N, 7.50%; $C_{37}H_{54}N_4O_9$.2.0 H$_2$O requires: C, 60.47; H, 7.96; N, 7.62%.

EXAMPLE 294 exo-3-([5-(Adamantan-1-yloxymethyl)-2-((1S,2R)-bicyclo[2.2.1]hept-5-en-2-yl)-1H-imidazole-4-carbonyl]-amino}-benzoic Acid exo-5-(Adamantan-1-yloxymethyl)-2-((1S,2R)-bicyclo[2.2.1]hept-5-en-2-yl)-1H-imidazole-4-carboxylic acid benzyl ester was isolated as a minor product from the preparation and purification of endo-5-(adamantan-1-yloxymethyl)-2-((1S,2S)-bicyclo[2.2.1]hept-5-en-2-yl)-1H-imidazole-4-carboxylic acid benzyl ester (Example 235). This exo-isomer was converted to the title compound following the same procedure as in Example 235. $[\alpha]_D^{29}$ −7.3° (c=0.82, DMF). $^1$H NMR (300 MHz, d$_4$MeOH) 8.35 (1H, t), 7.94 (1H, ddd), 7.76 (1H, dt), 7.46 (1H, t), 6.23 (2H, m), 4.90 (2H, s), 3.01 (2H, m), 2.76 (1H, ddd), 2.18 (4H, m), 1.90 (6H, d), 1.69 (7H, m), 1.58 (1H, ddd), 1.45 (1H, m). The acid was converted to the N-methyl-D-glucamine salt and lyophilised from water/dioxan. Found: C, 61.85; H, 7.58; N, 8.09%; $C_{36}H_{50}N_4O_9$.0.9 H$_2$O requires: C, 61.84; H, 7.47; N, 8.01%.

EXAMPLE 295 exo-3-{[5-(Adamantan-1-yloxymethyl)-2-((1R,2S)-bicyclo[2.2.1]hept-5-en-2-yl)-1H-imidazole-4-carbonyl]-amino}-benzoic Acid exo-5-(Adamantan-1-yloxymethyl)-2-((1R,2S)-bicyclo[2.2.1]hept-5-en-2-yl)-1H-imidazole-4-carboxylic acid benzyl ester was isolated as a minor product from the preparation and purification of endo-5-(adamantan-1-yloxymethyl)-2-((1R,2R)-bicyclo[2.2.1]hept-5-en-2-yl)-1H-imidazole-4-carboxylic acid benzyl ester (Example 236). This exo-isomer was converted to the title compound following the same procedure as in Example 236. $[\alpha]_D^{29}$ +7.8° (c=0.77, DMF). $^1$H NMR (300 MHz, d$_4$MeOH) 8.32 (1H, t), 7.97 (1H, dd), 7.81 (1H, d), 7.48 (1H, t), 6.27 (2H, s), 4.91 (2H, s), 3.08 (2H, d), 2.86 (1H, dd), 2.18 (4H, m), 1.91 (6H, d), 1.71 (8H, m), 1.51 (1H, m). The acid was converted to the N-methyl-D-glucamine salt and lyophilised from water/dioxan. Found: C, 60.05; H, 7.42; N, 7.93%; $C_{36}H_{50}N_4O_9$.0.9 H$_2$O requires: C, 60.30; H, 7.16; N, 7.81%.

EXAMPLE 296

5-{[5-(Adamantan-1-yloxymethyl)-2-cycloheptyl-1H-imidazole-4-carbonyl]-amino}-2-methyl-benzoic Acid The title compound was prepared according to the procedure of Example 216, with the modification that cycloheptanecarboxaldehyde was used in step d instead of cyclohexanecarboxaldehyde and 5-amino-2-methyl-benzoic acid benzyl ester replaced 3-amino-benzoic acid benzyl ester in step f. $^1$H NMR (300 MHz, d$_6$-DMSO) 12.40 (1H, br s), 12.11 (1H, br s), 9.55 (1H, s), 8.30 (1H, s), 7.76 (1H, d), 7.20 (1H, d), 4.78 (2H, s), 2.87 (1H, m), 2.45 (3H, s), 2.10–1.47 (27H, m). The acid was converted to the N-methyl-D-glucamine salt and lyophilised from water/dioxan. Found: C, 60.38; H, 8.36; N, 7.51%; $C_{37}H_{56}N_4O_9$.2.0 H$_2$O requires: C, 60.31; H, 8.21; N, 7.60%.

EXAMPLE 297

3-{[5-(Adamantan-1-yloxymethyl)-2-cyclooctyl-1H-imidazole-4-carbonyl]-amino}-benzoic Acid The title compound was prepared according to the procedure of Example 216, with the modification that cyclooctanecarboxaldehyde (prepared from cyclooctanone according to the procedure given in Example 205, steps a and b) was used in step d instead of cyclohexanecarboxaldehyde. $^1$H NMR (300 MHz, d$_6$-DMSO) 12.40 (1H, br s), 12.10 (1H, br s), 9.70 (1H, br s), 8.45 (1H, s), 7.91 (1H, d), 7.61 (1H, d), 7.41 (1H, t), 4.99 (2H, s), 2.95 (1H, m), 2.10–1.58 (29H, m). The acid was converted to the N-methyl-D-glucamine salt and lyophilised from water/dioxan. Found: C, 61.14; H, 8.41; N, 7.53%; $C_{37}H_{56}N_4O_9$.2.5 H$_2$O requires: C, 61.05; H, 8.17; N, 7.70%.

EXAMPLE 298

5-{[5-(Adamantan-1-yloxymethyl)-2-cyclooctyl-1H-imidazole-4-carbonyl]-amino}-2-methyl-benzoic Acid The title compound was prepared according to the procedure of Example 216, with the modification that cyclooctanecarboxaldehyde (prepared from cyclooctanone according to the procedure given in Example 205, steps a and b) was used in step d instead of cyclohexanecarboxaldehyde and 5-amino-2-methyl-benzoic acid benzyl ester replaced 3-amino-benzoic acid benzyl ester in step f. $^1$H NMR (300 MHz, d$_6$-DMSO) 12.40 (1H, br s), 12.10 (1H, br s), 9.55 (1H, br s), 8.29 (1H, s), 7.78 (1H, d), 7.20 (1H, d), 4.78 (2H, s), 2.96 (1H, m), 2.45 (3H, s), 2.10–1.53 (29H, m). The acid was converted to the N-methyl-D-glucamine salt and lyophilised from water/dioxan. Found: C, 61.55; H, 8.31; N, 7.60%; $C_{38}H_{58}N_4O_9$.1.5 H$_2$O requires: C, 61.52; H, 8.28; N, 7.55%.

EXAMPLE 299

5-{[5-(Adamantan-1-yloxymethyl)-2-cyclohexyl-1H-imidazole-4-carbonyl]-amino}-2-fluoro-benzoic Acid 5-{[5-(Adamantan-1-yloxymethyl)-2-cyclohexyl-1H-imidazole-4-carbonyl]-amino}-2-fluoro-benzoic acid methyl ester was prepared according to the procedure of Example 216, steps a, b, c, d, e and f with the modification that 5-amino-2-fluoro-benzoic acid methyl ester replaced 3-amino-benzoic acid benzyl ester in step f. Deprotection was carried out following essentially the procedure of Example 36, step d to afford the title compound. $^1$H NMR (300 MHz, d$_6$-DMSO) 10.00 (1H, br s), 8.34 (1H, m), 7.94 (1H, m), 7.27 (1H, t), 4.79 (2H, s), 2.76 (1H, m), 2.11 (3H, br s), 1.90 (2H, m), 1.76–1.53 (16H, m), 1.35–1.27 (4H, m). The acid was converted to the N-methyl-D-glucamine salt and lyophilised from water/dioxan. Found: C, 56.20; H, 7.82; N, 7.59%; $C_{35}H_{51}FN_4O_9$.3.0 H$_2$O requires: C, 56.44; H, 7.71; N, 7.52%.

EXAMPLE 300

5-{[5-(Adamantan-1-yloxymethyl)-2-bicyclo[2.2.2]oct-1-yl-1H-imidazole-4-carbonyl]-amino}-2-methyl-benzoic Acid The title compound was prepared according to the procedure of Example 216, with the modification that bicyclo

[2.2.2]oct-1-yl-carbaldehyde (prepared by pyridinium chlorochromate oxidation of bicyclo[2.2.2]oct-1-yl-methanol (C. A. Grob, M. Ohta, E. Renk and A. Weiss, *Helv. Chim. Acta* 1958, 41, 1191)) was used in step d instead of cyclohexanecarboxaldehyde and 5-amino-2-methyl-benzoic acid benzyl ester replaced 3-amino-benzoic acid benzyl ester in step f. $^1$H NMR (300 MHz, $d_6$-DMSO) 12.05 (1H, br s), 9.48 (1H, br s), 8.22 (1H, br s), 7.76 (1H, dd), 7.21 (1H, d), 4.76 (2H, s), 2.45 (3H, s), 2.08 (3H, br s), 1.88–1.73 (12H, m), 1.62–1.51 (13H, m). The acid was converted to the N-methyl-D-glucamine salt and lyophilised from water/dioxan. Found: C, 60.69; H, 8.29; N, 7.28%; $C_{38}H_{56}N_4O_9$.2.0 $H_2$requires: C, 60.94; H, 8.08; N, 7.48%.

EXAMPLE 301

5-{[5-(Adamantan-1-yloxymethyl)-2-bicyclo[2.2.2]oct-2-en-1-yl-1H-imidazole-4-carbonyl]-amino}-2-methyl-benzoic Acid The title compound was prepared according to the procedure of Example 225, with the modification that 5-amino-2-methyl-benzoic acid benzyl ester replaced 3-amino-benzoic acid benzyl ester. $^1$H NMR (300 MHz, $d_6$-DMSO) 12.75 (1H, br s), 12.29 (1H, br s), 9.59 (1H, br s), 8.28(1H, br s), 7.80 (1H, d), 7.22 (1H, d), 6.72 (1H, d), 6.38 (1H, t), 4.80 (2H, s), 2.62 (1H, br s), 2.46 (3H, s), 2.10 (3H, br s), 1.96 (2H, t), 1.77 (6H, s), 1.68–1.54 (8H, m), 1.47–1.30 (4H, m). The acid was converted to the N-methyl-D-glucamine salt and lyophilised from water/dioxan. Found: C, 61.19; H, 7.98; N, 7.58%; $C_{38}H_{54}N_4O_9$.2.0 $H_2O$ requires: C, 61.11; H, 7.83; N, 7.50%.

EXAMPLE 302

3-{[5-(Adamantan-1-yloxymethyl)-2-(4-pentyl-bicyclo[2.2.2]oct-1-yl)-1H-imidazole-4-carbonyl]-amino}-benzoic Acid The title compound was prepared according to the procedure of Example 216, with the modification that 4-pentyl-bicyclo[2.2.2]oct-1-yl-carbaldehyde (prepared in two steps from 4-pentyl-bicyclo[2.2.2]oct-1-yl-carboxylic acid) was used in step d instead of cyclohexanecarboxaldehyde. $^1$H NMR (300 MHz, $d_6$-DMSO) 12.07 (1H, br s), 9.58 (1H, br s), 8.41 (1H, s), 7.91 (1H, d), 7.62 (1H, d), 7.41 (1H, t), 4.77 (2H, s), 2.10 (3H, br s), 1.85–1.22 (32H, m), 0.85 (3H, t). The acid was converted to the N-methyl-D-glucamine salt and lyophilised from water/dioxan. Found: C, 63.16; H, 8.64; N, 7.18%; $C_{42}H_{64}N_4O_9$.1.5 $H_2O$ requires: C, 63.32; H, 8.49; N, 7.03%.

EXAMPLE 303

3-{[5-(Adamantan-1-yloxymethyl)-2-(1-methyl-cyclohexyl)-1H-imidazole-4-carbonyl]-amino}-benzoic Acid The title compound was prepared according to the procedure of Example 216, with the modification that 1-methyl-cyclohexanecarboxaldehyde (prepared in two steps from 1-methyl-1-cyclohexanecarboxylic acid) was used in step d instead of cyclohexanecarboxaldehyde. $^1$H NMR (300 MHz, $d_6$-DMSO) 13.00 (1H, br s), 12.40 (1H, br s), 9.80 (1H, br s), 8.38 (1H, s), 7.95 (1H, d), 7.64 (1H, d), 7.44 (1H, t), 4.80 (2H, s), 2.17 (2H, m), 2.10 (3H, s), 1.76 (6H, s), 1.62–1.34 (14H, m), 1.25 (3H, s). The acid was converted to the N-methyl-D-glucamine salt and lyophilised from water/dioxan.

EXAMPLE 304

3-{[5-(Adamantan-1-yloxymethyl)-2-o-tolyl-1H-imidazole-4-carbonyl]-amino}-benzoic Acid The title compound was prepared according to the procedure of Example 216, with the modification that o-tolualdehyde was used in step d instead of cyclohexanecarboxaldehyde. $^1$H NMR (300 MHz, $d_6$-DMSO) 12.80 (1H, br s), 12.75 (1H, s), 9.86 (1H, s), 8.50 (1H, s), 7.96 (1H, d), 7.62 (2H, m), 7.40 (1H, m), 7.30 (3H, m), 4.90 (2H, s), 2.52 (3H, s), 2.12 (3H, s), 1.79 (6H, s), 1.59 (6H, m). The acid converted to the N-methyl-D-glucamine salt and lyophilised from water/dioxan. Found: C, 61.00; H, 7.41; N, 8.00%; $C_{36}H_{48}N_4O_9$.1.6 $H_2O$ requires: C, 60.96; H, 7.27; N, 7.90%.

EXAMPLE 305

5-{[5-(Adamantan-1-yloxymethyl)-2-o-tolyl-1H-imidazole-4-carbonyl]-amino}-2-methyl-benzoic Acid The title compound was prepared according to the procedure of Example 216, with the modification that o-tolualdehyde was used in step d instead of cyclohexanecarboxaldehyde and 5-amino-2-methyl-benzoic acid benzyl ester replaced 3-amino-benzoic acid benzyl ester in step f. $^1$H NMR (300 MHz, $d_6$-DMSO) 12.70 (1H, br s), 9.77 (1H, s), 8.30 (1H, s), 7.79 (1H, m), 7.58 (1H, d), 7.31 (3H, m), 7.22 (1H, d), 4.89 (2H, s), 2.52 (3H, s), 2.47 (3H, s), 2.11 (3H, br s), 1.79 (6H, s), 1.59 (6H, s). The acid was converted to the N-methyl-D-glucamine salt and lyophilised from water/dioxan. Found: C, 60.85; H, 7.67; N, 7.73%; $C_{37}H_{50}N_4O_9$.2.0 $H_2O$ requires: C, 60.76; H, 7.45; N, 7.66%.

EXAMPLE 306

3-{[5-(Adamantan-1-yloxymethyl)-2-(2-cyano-phenyl)-1H-imidazole-4-carbonyl]-amino}-benzoic Acid The title compound was prepared according to the procedure of Example 216, with the modification that 2-cyano-benzaldehyde was used in step d instead of cyclohexanecarboxaldehyde. $^1$H NMR (300 MHz, $d_6$-DMSO) 13.25 (2H, br s), 9.80 (1H, br s), 8.41 (1H, s), 8.04 (1H, d), 7.97 (1H, d), 7.85 (2H, m), 7.63 (2H, m), 7.46 (1H, t), 4.91 (2H, s), 2.12 (3H, s), 1.80 (6H, s), 1.59 (6H, m). The acid was converted to the N-methyl-D-glucamine salt and lyophilised from water/dioxan.

EXAMPLE 307

3-{[5-(Adamantan-1-yloxymethyl)-2-(2-chloro-phenyl)-1H-imidazole-4-carbonyl]-amino}-benzoic Acid 5-(Adamantan-1-yloxymethyl)-2-(2-chloro-phenyl)-1H-imidazole-4-carboxylic acid benzyl ester was prepared according to the procedure of Example 216, steps a, b, c and d with the modification that 2-chloro-benzaldehyde was used in step d instead of cyclohexanecarboxaldehyde. The benzyl ester was hydrolysed according to the procedure of Example 211, step b and the resulting 5-(adamantan-1-yloxymethyl)-2-(2-chloro-phenyl)-1H-imidazole-4-carboxylic acid was reacted with 3-amino-benzoic acid methyl ester according to the procedure of Example 20, step d to afford 3-{[5-(adamantan-1-yloxymethyl)-2-(2-chloro-phenyl)-1H-imidazole-4-carbonyl]-amino}-benzoic acid methyl ester. The methyl ester was hydrolysed according to the procedure of Example 36, step d to afford the title compound. $^1$H NMR (300 MHz, d$_6$-DMSO) 12.82 (2H, br s), 9.96 (1H, s), 8.51 (1H, s), 7.94 (1H, d), 7.73 (1H, dd), 7.61 (2H, m), 7.45 (3H, m), 4.90 (2H, s), 2.11 (3H, s), 1.79 (6H, s), 1.59 (6H, s). The acid was converted to the N-methyl-D-glucamine salt and lyophilised from water/dioxan.

EXAMPLE 308

3-{[5-(Adamantan-1-yloxymethyl)-2-cyclohexyl-3-hydroxy-3H-imidazole-4-carbonyl]-amino}-benzoic Acid Step a. 5-[2-(Adamantan-1-yloxy)-1-hydroxy-ethylidene]-2,2-dimethyl-[1,3]dioxane-4,6-dione A mixture of (adamantan-1-yloxy)-acetic acid (Example 216, step a) (32.3 g, 0.153 mol) and 1,1'-carbonyl-diimidazole (27.6 g, 0.17 mol) in anhydrous DCM (600 ml) was stirred at 0° C. for 15 min, then at room temperature for 75 min. The mixture was concentrated in vacuo (~300 ml) and the solution was added dropwise over 20 min to a solution of 2,2-dimethyl-1,3-dioxan-4,6-dione (22.1 g, 0.153 mol) and pyridine (30 ml, 0.371 mol) in anhydrous DCM (450 ml) at 0° C. under argon. The mixture was allowed to warm to room temperature and stirred for 16 h. The solution was washed with 2M HCl (2×500 ml), brine (500 ml) and dried (MgSO$_4$). Filtration and evaporation gave the product as a white solid, which was washed with hexane, isolated by filtration and dried (50.1 g, 97%). $^1$H NMR (300MHz, CDCl$_3$) 4.92 (2H, s), 2.19 (3H, br s), 1.82 (6H, s), 1.74 (6H, s), 1.64 (6H, m).

Step b. 5-[4-(Adamantan-1-yloxy)-3-oxo-butyrylamino]-benzoic Acid Benzyl Ester

A mixture of the product of step a (3.36 g, 10.0 mmol), 3-amino-benzoic acid benzyl ester (3.41 g, 15 mmol) and DMAP (cat.) in toluene (50 ml) was heated under argon at reflux for 16 h. The mixture was allowed to cool to room temperature, diluted with ethyl acetate (50 ml), washed successively with 1M HCl (50 ml), sat. sodium bicarbonate (75 ml), brine (75 ml) and dried (MgSO$_4$). Filtration and evaporation of the solvent gave the crude product as a red oil, which was purified by flash column chromatography (silica, DCM/ethyl acetate 9:1). The product was obtained as a yellow oil (2.14 g, 46%). $^1$H NMR (300 MHz, CDCl$_3$) 9.19 (1H, br s), 8.06 (1H, s), 7.95 (1H, d), 7.83 (1H, d), 7.40 (6H, m), 5.37 (2H, s), 4.14 (2H, s), 3.74 (2H, s), 2.19 (3H, br s), 1.78 (6H, s), 1.65 (6H, m).

Step c. 3-[4-(Adamantan-1-yloxy)-2-hydroxyimino-3-oxo-butyrylamino]-benzoic Acid Benzyl Ester To a solution of the product of step b (2.10 g, 4.55 mmol) in acetic acid (20 ml) and THF (20 ml) was added water (2 ml). The mixture was cooled to 5° C. and an aqueous solution (3 ml) of sodium nitrite (0.41 g, 5.92 mmol) was added dropwise while maintaining the temperature below 10° C. Upon completion of the addition, the reaction mixture was allowed to warm to room temperature and stirred for 1 h. The THF and acetic acid were removed in vacuo and the solution was partitioned between water (100 ml) and ethyl acetate (100 ml). 1M NaOH was added until pH 8 was reached, the layers were separated, and the aqueous layer was washed with ethyl acetate (20 ml). The combined organic layers were washed with brine (100 ml), dried (MgSO$_4$) and the solvent was evaporated to yield a yellow oil (2.13 g, 96%). The crude product was purified by flash column chromatography (silica, DCM/ethyl acetate 95:5) to afford a yellow foam (1.29 g, 58%). $^1$H NMR (300 MHz, CDCl$_3$) 11.04 (1H, br s), 8.23 (1H, s), 7.94 (1H, d), 7.86 (1H, d), 7.50–7.36 (6H, m), 5.39 (2H, s), 4.82 (2H, s), 2.20 (3H, br s), 1.81 (6H, s), 1.65 (6H, m).

Step d. 3-{[5-(Adamantan-1-yloxymethyl)-2-cyclohexyl-3-hydroxy-3H-imidazole-4-carbonyl]-amino}-benzoic Acid Benzyl Ester A mixture of 3-[4-(adamantan-1-yloxy)-2-hydroxyimino-3-oxo-butyrylamino]-benzoic acid benzyl ester (1.16 g, 2.36 mmol), ammonium acetate (3.64 g, 47.2 mmol) and cyclohexane carboxaldehyde (0.38 ml, 3.14 mmol) in acetic acid (30 ml) was heated at 80° C. under argon for 2 h. The mixture was cooled to room temperature and concentrated to remove most of the acetic acid. The residue was dissolved in ethyl acetate (50 ml) and neutralised with sat. sodium bicarbonate. The aqueous phase was extracted with ethyl acetate (30 ml), the combined organic phases were washed with brine (50 ml), dried (MgSO$_4$) and the solvent was evaporated. The crude product was purified by flash column chromatography (silica, DCM/MeOH 95:5) to afford yellow foam (990 mg, 72%). $^1$H NMR (300MHz, CDCl$_3$) (mixture of rotamers) 13.30 and 9.12 (1H, 2×br s), 13.08 and 10.89 (1H, 2×s), 8.28 and 8.17 (1H, 2×s), 8.10–7.80 (2H, 4×d), 7.40 (6H, m), 5.38 and 5.37 (2H, 2×s), 4.97 and 4.79 (2H, 2×s), 3.27 and 2.92 (1H, 2×m), 2.20 and 2.14 (3H, 2×br s), 1.94–1.34 (22H, m).

Step e

The product of step d (660 mg, 1.13 mmol) was hydrogenolysed according to the procedure of Example 1, step e to afford the title compound as a white solid (540 mg, 98%). $^1$H NMR (300 MHz, d$_6$-DMSO) 13.98 (1H, br s), 12.97 (2H, br s), 8.29 (1H, s), 7.76 (1H, d), 7.65 (1H, d), 7.45 (1H, t), 4.80 (2H, s), 3.12 (1H, m), 2.11 (3H, br s), 1.76–1.57 (18H, m), 1.34–1.19 (4H, m). The acid was converted to the N-methyl-D-glucamine salt and lyophilised from water/dioxan. Found: C, 58.20; H, 7.99; N, 7.79%; C$_{35}$H$_{52}$N$_4$O$_{10}$.1.9 H$_2$O requires: C, 58.11; H, 7.78; N, 7.75%.

EXAMPLE 309

3-{[5-(Adamantan-1-ylmethoxymethyl)-2-cyclohexyl-1H-imidazole-4-carbonyl]-amino}-benzoic Acid Step a. (Adamantan-1-ylmethyoxy)-acetic Acid A solution of 1-adamantanemethanol (3.11 g, 18.7 mmol) in dry DMF (50 ml) was added to a suspension of sodium hydride (60% dispersion in oil, 1.55 g, 38.6 mmol) in DMF (20 ml). The mixture was warmed to 80° C. for 1 h, cooled to room temperature and a solution of chloroacetic acid (1.86 g, 19.6 mmol) in DMF (25 ml) was added dropwise. The mixture was heated at 80° C. for 17 h. On cooling, the mixture was poured into water (100 ml), extracted with ethyl acetate (2×80 ml), and the extracts were washed with 5%KHSO$_4$ (150 ml), brine (150 ml) and dried (MgSO$_4$). Filtration and evaporation of the solvent gave a white solid which was washed with diethyl ether and water, isolated by filtration and dried in vacuo at 50° C. The product was obtained as a white fluffy solid (1.61 g, 38%). $^1$H NMR (300 MHz, CDCl$_3$) 4.08 (2H, s), 3.14 (2H, s), 2.00 (3H, br s), 1.70 (6H, q), 1.57 (6H, br s).

Step b

The product of step a was converted to the title compound according to the procedure of Example 216, steps b, c, d, e, f and g. $^1$H NMR (300 MHz, d$_6$-DMSO) 12.25 (1H, br s), 9.75 (1H, s), 8.49 (1H, s), 7.92 (1H, d), 7.61 (1H, d), 7.42 (1H, t), 4.76 (2H, s), 3.00 (2H, s), 2.75 (1H, m), 1.89–1.25 (25H, m). The acid was converted to the N-methyl-D-glucamine salt and lyophilised from water/dioxan.

EXAMPLE 310

5-{[5-(Adamantan-1-ylmethoxymethyl)-2-cyclohexyl-1H-imidazole-4-carbonyl]-amino}-2-methyl-benzoic Acid (Adamantan-1-ylmethyoxy)-acetic acid (Example 310) was converted to the title compound according to the procedure of Example 216, steps b, c, d, e, f and g, with the modification that 5-amino-2-methyl-benzoic acid benzyl ester was used in step f instead of 3-amino-benzoic acid benzyl ester. $^1$H NMR (300 MHz, d$_6$-DMSO) 12.30 (1H, br s), 9.63 (1H, s), 8.31 (1H, s), 7.79 (1H, d), 7.21 (1H, d), 4.74 (2H, s), 2.99 (2H, s), 2.70 (1H, m), 2.46 (3H, s), 1.92–1.24 (25H, m). The acid was converted to the N-methyl-D-glucamine salt and lyophilised from water/dioxan.

EXAMPLE 311

3-{[5-(Adamantan-1-yloxymethyl)-2-(2,6-dichloro-phenyl)-1H-imidazole-4-carbonyl]-amino}-benzoic Acid 5-(Adamantan-1-yloxymethyl)-2-(2,6-dichloro-phenyl)-1H-imidazole-4-carboxylic acid benzyl ester was prepared according to the procedure of Example 216, steps a, b, c and d with the modification that 2,6-dichloro-benzaldehyde was used in step d instead of cyclohexanecarboxaldehyde. The benzyl ester was hydrolysed according to the procedure of Example 211, step b and the resulting 5-(adamantan-1-yloxymethyl)-2-(2,6-dichloro-phenyl)-1H-imidazole-4-carboxylic acid was reacted with 3-amino-benzoic acid methyl ester according to the procedure of Example 20, step d to afford 3-{[5-(adamantan-1-yloxymethyl)-2-(2,6-dichloro-phenyl)-1H-imidazole-4-carbonyl]-amino}-benzoic acid methyl ester. The methyl ester was hydrolysed according to the procedure of Example 36, step d to afford the title compound. $^1$H NMR (300 MHz, d$_6$-DMSO) 12.87 (2H, s), 10.00 (1H, s), 8.58 (1H, s), 7.94 (1H, d), 7.58 (4H, m), 7.39 (1H, t), 4.93 (2H, s), 2.11 (3H, s), 1.79 (6H, s), 1.58 (6H, s). The acid was converted to the N-methyl-D-glucamine salt and lyophilised from water/dioxan.

EXAMPLE 312

3-{[5-(Adamantan-1-yloxymethyl)-2-(2,4,6-trimethyl-phenyl)-3-hydroxy-3H-imidazole-4-carbonyl]-amino}-benzoic Acid The title compound was prepared using essentially the same procedure as in Example 308, with the modification that 2,4,6-trimethylbenzaldehyde was used in step d instead of cyclohexanecarboxaldehyde. $^1$H NMR (300 MHz, d$_6$-DMSO) 13.87 (1H, br s), 8.22 (1H, s), 7.76 (1H, d), 7.58 (1H, d), 7.38 (1H, t), 6.91 (2H, s), 4.76 (2H, s), 2.28 (3H, s), 2.09 (3H, s), 2.06 (6H, s), 1.77 (6H, s), 1.57 (6H, s). The acid was converted to the N-methyl-D-glucamine salt and lyophilised from water/dioxan.

EXAMPLE 313

3-{[5-(Adamantan-1-yloxymethyl)-2-(2,6-dichloro-phenyl)-3-hydroxy-3H-imidazole-4-carbonyl]-amino}-benzoic Acid 3-{[5-(Adamantan-1-yloxymethyl)-2-(2,6-dichloro-phenyl)-3-hydroxy-3H-imidazole-4-carbonyl]-amino}-benzoic acid benzyl ester was prepared using essentially the same procedure as in Example 308, steps a, b, c and d with the modification that 2,6-dichloro-benzaldehyde was used in step d instead of cyclohexanecarboxaldehyde. The benzyl ester was hydrolysed using the same procedure as in Example 211, step b to afford the title compound. $^1$H NMR (300 MHz, d$_6$-DMSO) 13.57 (1H, br s), 13.48 (1H, br s), 12.98 (1H, br s), 8.33 (1H, s), 7.67 (5H, m), 7.47 (1H, t), 4.94 (2H, br s), 2.11 (3H, s), 1.79 (6H, s), 1.58 (6H, m). The acid was converted to the N-methyl-D-glucamine salt and lyophilised from water/dioxan.

EXAMPLE 314

3-{[5-(Adamantan-1-yloxymethyl)-2-bicyclo[2.2.2]oct-1-yl-3-hydroxy-3H-imidazole-4-carbonyl]-amino}-benzoic Acid The title compound was prepared using essentially the same procedure as in Example 308, with the modification that bicyclo[2.2.2]oct-1-yl-carbaldehyde (prepared by pyridinium chlorochromate oxidation of bicyclo[2.2.2]oct-1-yl-methanol (C. A. Grob, M. Ohta, E. Renk and A. Weiss *Helv. Chim. Acta* 1958, 41, 1191)) was used in step d instead of cyclohexanecarboxaldehyde. $^1$H NMR (300 MHz, d$_6$-DMSO) 13.58 (1H, br s), 12.90 (2H, br s), 8.28 (1H, s), 7.79 (1H, d), 7.66 (1H, d), 7.46 (1H, t), 4.73 (2H, s), 2.10 (3H, s), 2.02 (6H, br s), 1.75 (6H, s), 1.57–1.48 (13H, m). The acid was converted to the N-methyl-D-glucamine salt and lyophilised from water/dioxan.

The compounds of the examples were tested for binding at the CCK$_B$ receptor in mouse cortical membranes by means of a radioligand binding assay. The procedure was as follows:

The whole brains from male mice (CD1 22–25 g; Charles River) were removed and placed in ice-cold buffer (pH 7.2 @ 21±3°) of the following composition (mM); 10 HEPES, 130 NaCl, 4.7 KCl, 5 MgCl$_2$, 1 EDTA and containing 0.25 gl$^{-1}$ bacitracin. The cortex was dissected, weighed and homogenised in 40 ml ice-cold buffer using a Teflon-in-glass homogeniser. The homogenate was centrifuged at 39800 g for 20 min at 40, the supernatant discarded and the pellet resuspended by homogenisation in fresh buffer. The homogenate was recentrifuged (39800 g, 20 min @ 4°) and the final pellet was resuspended in HEPES buffer to give a tissue concentration of 20 mg ml$^{-1}$ (original wet weight).

The membranes (400 ml) were incubated for 150 min at 21±3° in a final volume of 0.5 ml with HEPES buffer containing [$^{125}$I]-CCK$_8$(S) (0.05 ml; 200 pM NEN 2200 Ci mmol$^{-1}$) and competing compound. Total and non-specific binding of [$^{125}$I]-CCK$_8$(S) were defined using 0.05 ml of buffer and 0.05 ml of 10 mM L-365260 respectively. The assay was terminated by rapid filtration through pre-soaked Whatman GF/B filters using a Brandell Cell Harvester. The filters were washed (3×3 ml) with ice-cold 50 mM Tris-HCl (pH 7.4 @ 4° C.) and bound radioactivity determined by counting (1 min) in a gamma-counter.

The compounds of the examples were also tested for gastrin antagonist activity in an immature rat stomach assay. The procedure was as follows:

The oesophagus of immature rats (33–50 g, ca. 21 days old) was ligated at the level of the cardiac sphincter and the duodenal sphincter was cannulated. The stomach was excised and flushed with ca. 1 ml of unbuffered physiological saline solution. The fundus was punctured and cannulated. A further 4–5 ml of unbuffered solution was flushed through the stomach to ensure the preparation was not leaking. The stomach was lowered into a jacketed organ bath containing 40 ml of buffered solution containing $3\times10^{-8}$ M 5-methylfurmethide, maintained at 37° and gassed vigorously with 95% $O_2$/5% $CO_2$. The stomach was continuously perfused at a rate of 1 ml min$^{-1}$ with unbuffered solution gassed with 100% $O_2$ with the perfusate passing over an internally referenced pH-electrode fixed 12 cm above the stomach.

After 120 min of stabilisation the drugs were added directly to the serosal solution in the organ bath and after a further 60 min cumulative pentagastrin dose-response curves were started. Changes in acid secretion were monitored and the curves analysed according to Black et al., Br. J. Pharmacol., 1985, 86, 581.

The results obtained from the gastrin and CCK assays are set out in Table 1.

TABLE 1

| Example No | $CCK_B$ $pK_i$ | Gastrin $pK_b$ |
|---|---|---|
| 1 | 6.72 | 6.33 |
| 2 | 7.31 | |
| 3 | 5.84 | |
| 4 | 7.06 | 5.79 |
| 5 | 6.64 | |
| 6 | 6.08 | |
| 7 | 6.19 | |
| 8 | 5.99 | |
| 9 | 5.88 | |
| 10 | 5.52 | |
| 11 | 7.06 | 5.79 |
| 12 | 5.95 | 6.00 |
| 13 | 6.44 | 6.21 |
| 14 | 5.88 | |
| 15 | 6.74 | |
| 16 | 6.14 | |
| 17 | 6.68 | |
| 18 | 6.64 | |
| 19 | 6.35 | |
| 20 | 6.60 | |
| 21 | 6.09 | |
| 22 | 5.39 | |
| 23 | 5.91 | |
| 24 | 6.00 | 6.32 |
| 25 | 7.16 | |
| 26 | 5.83 | 6.39 |
| 27 | 5.45 | |
| 28 | 5.91 | |
| 29 | 5.83 | |
| 30 | 5.97 | |
| 31 | 5.78 | |
| 32 | 5.32 | |
| 33 | 5.73 | |
| 34 | 5.80 | |
| 35 | 5.41 | |
| 36 | 5.50 | |
| 37 | 6.68 | 5.90 |
| 38 | 5.95 | |
| 39 | 5.69 | |
| 40 | 6.03 | 6.69 |
| 41 | 5.36 | |
| 42 | 5.82 | 7.30 |
| 43 | 6.07 | 7.20 |
| 44 | 6.92 | |
| 45 | 6.3 | |
| 46 | 6.19 | 5.60 |
| 47 | 6.60 | 6.63 |
| 48 | 6.57 | |
| 49 | 6.74 | |
| 50 | 6.48 | 7.58 |
| 51 | 5.58 | |
| 52 | 5.59 | |
| 53 | 5.78 | |
| 54 | 6.51 | 6.09 |
| 55 | 6.19 | 6.64 |
| 56 | 6.62 | 7.74 |

TABLE 1-continued

| Example No | $CCK_B$ $pK_i$ | Gastrin $pK_b$ |
|---|---|---|
| 57 | 6.92 | 7.23 |
| 58 | 6.10 | 7.64 |
| 59 | 6.60 | 7.24 |
| 60 | 6.85 | 8.11 |
| 61 | 6.83 | 7.50 |
| 62 | 6.41 | 5.92 |
| 63 | 5.96 | 5.79 |
| 64 | 5.86 | |
| 65 | 7.25 | 7.00 |
| 66 | 6.70 | 7.26 |
| 67 | 7.08 | 8.00 |
| 68 | 6.33 | |
| 69 | 6.40 | 7.05 |
| 70 | 6.61 | |
| 71 | 6.73 | 6.10 |
| 72 | 6.53 | 5.91 |
| 73 | 6.38 | 8.18 |
| 74 | 6.49 | 7.59 |
| 75 | 6.70 | 6.58 |
| 76 | 7.60 | 8.31 |
| 77 | 5.00 | |
| 78 | 6.73 | 7.68 |
| 79 | 7.93 | 8.27 |
| 80 | 7.17 | 7.96 |
| 81 | 6.57 | 7.28 |
| 82 | 7.88 | |
| 83 | 8.65 | |
| 84 | 8.99 | 6.79 |
| 85 | 6.32 | |
| 86 | 5.99 | 6.13 |
| 87 | 5.57 | 5.93 |
| 88 | 5.18 | |
| 89 | 6.17 | 7.70 |
| 90 | 5.16 | |
| 91 | 5.42 | |
| 92 | 5.99 | 6.80 |
| 93 | 5.60 | |
| 94 | 5.27 | |
| 95 | 5.60 | |
| 96 | 6.78 | 7.91 |
| 97 | 8.17 | 6.30 |
| 98 | 7.60 | |
| 99 | 6.73 | |
| 100 | 6.93 | |
| 101 | 6.43 | |
| 102 | 6.11 | |
| 103 | 6.58 | 6.18 |
| 104 | 6.89 | 7.37 |
| 105 | 7.33 | 7.06 |
| 106 | 8.23 | 8.20 |
| 107 | | 7.65 |
| 108 | 5.63 | 5.81 |
| 109 | 7.35 | |
| 110 | 6.47 | 5.98 |
| 111 | 7.04 | 7.38 |
| 112 | 7.34 | 8.03 |
| 113 | 8.14 | 8.26 |
| 114 | 7.50 | 8.65 |
| 115 | 7.59 | 8.20 |
| 116 | 7.87 | 8.67 |
| 117 | 7.44 | 8.44 |
| 118 | 6.11 | |
| 119 | 6.55 | |
| 120 | 5.81 | |
| 121 | 5.62 | |
| 122 | 5.99 | 5.52 |
| 123 | 6.69 | |
| 124 | 7.2 | 7.81 |
| 125 | 6.98 | 8.64 |
| 126 | 7.66 | 7.80 |
| 127 | 5.77 | |
| 128 | 5.67 | |
| 129 | 6.66 | 6.42 |
| 130 | 8.02 | |
| 131 | 6.39 | 6.47 |
| 132 | 7.37 | 8.09 |
| 133 | 6.85 | 7.92 |

TABLE 1-continued

| Example No | CCK$_B$ pK$_i$ | Gastrin pK$_b$ |
|---|---|---|
| 135 | 8.21 | 7.65 |
| 136 | 5.38 | 6.83 |
| 137 | 6.49 | 8.29 |
| 138 | 7.3 | 7.59 |
| 139 | | 7.80 |
| 140 | | 7.54 |
| 141 | | 7.21 |
| 142 | | 6.75 |
| 143 | 6.72 | 7.22 |
| 144 | 6.36 | 7.85 |
| 145 | 6.58 | |
| 146 | 6.82 | 7.29 |
| 147 | 6.04 | |
| 148 | 6.99 | 7.27 |
| 149 | 8.27 | |
| 150 | 6.84 | 6.19 |
| 151 | 8.20 | 7.66 |
| 152 | 7.98 | 7.94 |
| 153 | 8.31 | 7.24 |
| 154 | 7.61 | 8.06 |
| 155 | 8.54 | 8.49 |
| 156 | | 7.20 |
| 157 | | 6.66 |
| 158 | 6.12 | 6.98 |
| 159 | 7.91 | 6.50 |
| 160 | | 6.04 |
| 161 | 7.41 | 7.09 |
| 162 | 5.78 | |
| 165 | 5.74 | 6.91 |
| 166 | 6.87 | 7.89 |
| 167 | 7.55 | 7.86 |
| 168 | 6.61 | 7.19 |
| 169 | 6.88 | 7.12 |
| 170 | 5.84 | |
| 171 | 6.85 | 7.41 |
| 172 | 7.67 | 8.43 |
| 173 | 8.21 | 8.32 |
| 174 | 6.60 | 6.69 |
| 175 | | 8.53 |
| 176 | | 8.18 |
| 177 | 6.22 | 6.82 |
| 178 | 6.61 | 6.78 |
| 179 | 7.39 | 7.33 |
| 180 | 5.73 | |
| 181 | 6.17 | |
| 182 | | 7.29 |
| 183 | | 7.37 |
| 184 | | 7.15 |
| 185 | 6.34 | 6.81 |
| 186 | 6.81 | 7.96 |
| 187 | 7.22 | 7.12 |
| 188 | 7.59 | 8.11 |
| 189 | | 7.21 |
| 190 | 6.76 | 8.38 |
| 191 | 7.54 | 7.17 |
| 192 | 7.18 | 6.85 |
| 193 | 7.24 | 7.69 |
| 194 | 6.8 | 6.28 |
| 195 | 7.37 | 8.18 |
| 196 | 7.42 | 8.15 |
| 197 | 6.11 | 7.15 |
| 198 | 8.06 | 8.09 |
| 199 | 7.75 | 8.79 |
| 200 | 8.42 | 9.05 |
| 201 | 8.06 | 8.31 |
| 202 | 6.95 | 7.54 |
| 203 | | 7.93 |
| 204 | | 8.24 |
| 205 | 7.32 | 8.08 |
| 206 | | 6.58 |
| 207 | | 7.16 |
| 208 | | 8.46 |
| 209 | 8.68 | 8.96 |
| 210 | | 6.89 |
| 211 | 8.64 | 8.59 |
| 212 | | 8.61 |
| 213 | | 7.12 |
| 214 | | 7.99 |
| 215 | | 6.44 |
| 216 | 7.90 | 9.06 |
| 217 | 8.40 | 8.40 |
| 218 | | 6.83 |
| 219 | | 7.16 |
| 220 | 8.53 | 9.33 |
| 221 | | 9.15 |
| 222 | | 7.69 |
| 223 | | 9.11 |
| 224 | | 7.74 |
| 225 | | 9.18 |
| 226 | | 7.87 |
| 227 | | 7.28 |
| 228 | | 9.14 |
| 229 | | 7.45 |
| 230 | | 8.21 |
| 231 | | 7.49 |
| 232 | | 8.86 |
| 233 | | 7.15 |
| 234 | | 8.71 |
| 235 | | 8.52 |
| 236 | | 8.98 |
| 237 | 5.12 | |
| 238 | 5.23 | |
| 239 | 5.7 | |
| 240 | 7.58 | |
| 241 | 7.22 | 5.33 |
| 242 | 6.49 | 6.13 |
| 243 | 6.27 | |
| 244 | 6.74 | |
| 245 | 8.19 | 6.62 |
| 246 | 8.44 | 6.08 |
| 247 | 6.52 | |
| 248 | 7.59 | |
| 250 | | 6.73 |
| 252 | 6.77 | 6.58 |
| 253 | 7.26 | 7.19 |
| 254 | 7.9 | 7.93 |
| 255 | 8.85 | 6.75 |
| 256 | | 6.15 |
| 258 | | 6.69 |
| 259 | | 7.15 |
| 260 | | 7.01 |
| 262 | | 6.65 |
| 263 | | 7.12 |
| 264 | | 6.06 |
| 265 | | 6.83 |
| 266 | | 7.72 |
| 267 | | 6.95 |
| 268 | | 6.65 |
| 269 | | 6.03 |
| 270 | | 6.71 |
| 271 | | 6.45 |
| 272 | | 6.73 |
| 273 | | 7.31 |
| 276 | | 5.93 |
| 277 | | 6.00 |
| 278 | | 7.19 |
| 279 | | 6.84 |
| 280 | | 5.74 |
| 281 | | 5.68 |
| 282 | | 6.15 |
| 283 | | 5.94 |
| 284 | | 7.01 |
| 285 | | 6.00 |
| 286 | | 7.57 |
| 287 | | 7.04 |
| 288 | | 7.88 |
| 289 | | 8.74 |
| 290 | | 8.55 |
| 291 | | 9.12 |
| 292 | | 8.57 |
| 293 | | 8.52 |
| 294 | | 8.43 |
| 295 | | 8.61 |
| 296 | | 8.68 |

TABLE 1-continued

| Example No | CCK$_B$ pK$_i$ | Gastrin pK$_b$ |
|---|---|---|
| 297 | | 9.07 |
| 298 | | 8.71 |
| 299 | | 7.69 |
| 300 | | 8.52 |
| 301 | | 8.58 |
| 302 | | 6.23 |
| 303 | | 7.93 |
| 304 | | 7.62 |
| 305 | | 8.00 |
| 306 | | 7.23 |
| 308 | | 7.73 |
| 309 | | 7.61 |
| 310 | | 6.94 |
| 311 | | 8.06 |
| 312 | | 7.46 |
| 313 | | 7.73 |
| 314 | | 8.20 |

The compounds of certain examples were also tested in a CCK$_A$ binding assay as follows:

The pancreatata were removed from male guineau-pigs (200–300 g; Dunkin Hartley) and placed in ice-cold HEPES buffer (pH 7.2 @ 21±3° C.). The pancreatata were homogenised in 40 ml ice-cold HEPES buffer using a polytron (Brinkmann, PT10, setting 10) 4×1 second. The homogenate was centrifuged at 39,800 g for 15 min at 4° C. The supernatant was discarded and the pellet re-suspended using a Teflon-in-glass homogeniser in 20 volumes of fresh buffer and re-centrifuged as above. The final pellet was re-suspended using a Teflon-in-glass homogeniser to a tissue concentration of 1 mg.ml$^{-1}$ (original weight), and filtered through a 500 μm pore-size Nytex mesh.

The membranes (400 μl; containing 0.375 μM PD134, 308) were incubated for 150 minutes at 21±3° C. in a final volume of 0.5 ml with HEPES buffer containing [$^{125}$I]-CCK$_8$ (S) (50 μl; 200 pM) and competing compound. Total and non-specific binding of [$^{125}$I]-CCK$_8$ (S) were defined using 50 μl of buffer and 50 μ of 100 nM L-364,718 respectively. The assay was terminated by rapid filtration through pre-soaked Whatman GF/B filters using a Brandell Cell Harvetser. The filters were washed (3×3 ml) with ice-cold 50 mM Tris HCl (pH 7.4 @ 4° C.) and bound radioactivity was determined by counting (1 min) in a gamma counter.

The results obtained are set out in Table 2.

TABLE 2

| Example | CCK$_A$ pK$_i$ |
|---|---|
| 76 | 6.2 |
| 155 | 6.9 |
| 200 | 6.6 |
| 211 | 7.0 |
| 216 | 6.3 |
| 219 | 6.3 |
| 221 | 6.1 |
| 224 | 6.2 |
| 235 | 5.6 |
| 236 | 6.1 |

What is claimed is:

1. A compound of the formula (I)

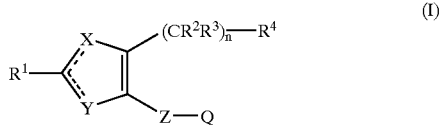

wherein

X and Y are independently =N—, —N(R$^5$)— (R$^5$ being selected from H, Me, Et, Pr, Bn, —OH and —CH$_2$COOR$^6$, wherein R$^6$ represents H, Me, Et, Pr or Bn), n is from 1 to 4;

R$^1$ is H or C$_1$ to C$_{15}$ hydrocarbyl wherein up to three C atoms may optionally be replaced by N, O or S atoms and up to three H atoms may optionally be replaced by halogen atoms;

R$^2$ is selected from H, Me, Et, Pr and OH, each R$^2$ being independently selected from H, Me, Et, Pr and OH when n is greater than 1;

R$^3$ (when n is 1) is selected from H, Me, Et and Pr; or (when n is greater than 1) each R$^3$ is independently selected from H, Me, Et and Pr, or two R$^3$ groups on neighbouring carbon atoms are linked to form a C$_3$ to C$_6$ carbocylic ring, or two R$^3$ groups are absent from neighbouring carbon atoms which are linked by a double bond; or R$^2$ and R$^3$ on the same carbon atom together represent an =O group;

R$^4$ is C$_1$ to C$_{15}$ hydrocarbyl wherein up to two C atoms may optionally be replaced by N, O or S atoms and up to two H atoms may optionally be replaced by halogen atoms;

Z is (NR$^7$)$_a$—CO—(NR$^8$)$_b$— (wherein a is 0 or 1, b is 0 or 1, and R$^7$ and R$^8$ are independently selected from the groups recited above for R$^6$), —CO—NR$^7$—CH$_2$—CO—NR$^8$—, —CO—O—, —CH$_2$—CH$_2$—, —CH=CH—, —CH$_2$—NR$^8$— or a bond;

Q is —R$^9$V, or

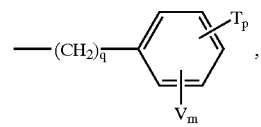

(wherein R$^9$ is —CH$_2$—; —CH$_2$—CH$_2$—; or

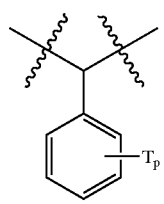

or R$^9$ and R$^8$, together with the nitrogen atom to which R$^8$ is attached, form a pyrrolidine ring which is substituted by V;

V is —CO—NH—SO$_2$—Ph, —SO$_2$—NH—CO—Ph, —CH$_2$OH, or a group of the formula —R$^{10}$U, (wherein U is —COOH, tetrazolyl, —CONHOH— or —SO$_3$H; and R$^{10}$ is a bond; C$_1$ to C$_6$ hydrocarbylene, optionally substituted by hydroxy, amino or acetamido; —O—(C$_1$ to C$_3$ alkylene)—; —SO$_2$NR$^{11}$—CHR$^{12}$—;

—CO—NR$^{11}$—CHR$^{12}$—, R$^{11}$ and R$^{12}$ being independently selected from H and methyl; or —NH—(CO)$_c$—CH$_2$—, c being 0 or 1);

T is C$_1$ to C$_6$ hydrocarbyl, —NR$^6$R$^7$ (wherein R$^6$ and R$^7$ are as defined above), —OMe, —OH, —CH$_2$OH, halogen or trihalomethyl;

m is 1 or 2;

p is from 0 to 3; and q is from 0 to 2, with the proviso that q is 1 or 2 when Z is a bond);

or a pharmaceutically acceptable salt thereof.

2. A compound according to claim 1 wherein Q is

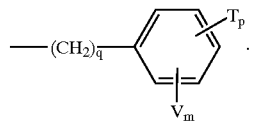

3. A compound according to claim 2 wherein Q is

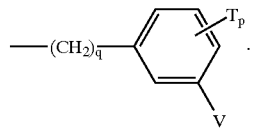

4. A compound according to claim 1 wherein R$^1$ is C$_1$ to C$_{12}$ independently =N—, =CH—, —NH—, —NOH— or —NMe—.

5. A compound according to claim 1 wherein X is —NH— and Y is =CH—, or Y is —NH— and X is =CH—.

6. A compound according to claim 1 wherein X is —NH— or —NOH— and Y is =N— or wherein X is =N— and Y is —NH— or —NOH.

7. A compound according to claim 1 wherein R$^1$ is C$_1$ to C$_{12}$ hydrocarbyl, wherein one C atom may optionally be replaced by N or O and up to three H atoms may optionally be replaced by F, Cl or Br.

8. A compound according to claim 1 wherein R$^1$ is C$_3$ to C$_{12}$ alicyclic; phenyl, optionally substituted with OMe, NMe$_2$, CF$_3$, Me, F, Cl, Br or I; or C$_1$ to C$_8$ alkyl.

9. A compound according to claim 1 wherein Z is —CO—NH—.

10. A compound according to claim 1 wherein p is 0 or 1, and q is 0.

11. A compound according to claim 1 wherein T is C$_1$ to C$_6$ hydrocarbyl or halo.

12. A compound according to claim 1 wherein V is —CO$_2$H, —CH$_2$CO$_2$H or tetrazolyl.

13. A compound according to claim 1 wherein R$^2$ and R$^3$ are H, and n is from 1 to 3.

14. A compound according to claim 1 wherein R$^2$ and R$^3$ together form an =O group, and n is 1.

15. A compound according to claim 13 wherein R$^4$ is C$_3$ to C$_{12}$ carbocyclic.

16. A compound according to claim 13 wherein R$^4$ is —NH—R$^{13}$ or —OR$^{13}$, in which R$^{13}$ is C$_3$ to C$_{12}$ carbocyclic.

17. A compound according to claim 1 wherein R$^5$ is selected from H, Me, Et, Pr and Bn; Z is —(NR$^7$)$_a$—CO(NR$^8$)$_b$—, —CO—NH—CH$_2$—CO—NH— or a bond; Q is

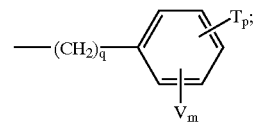

V is CO—NH—SO$_2$—Ph, —SO$_2$—NH—CO—Ph, —OCH$_2$COOH, tetrazolyl or CH$_2$)$_s$COOH, wherein s is from 0 to 2; and T is C$_1$ to C$_6$ hydrocarbyl, —NR$^6$R$^7$, —OMe, —OH, —CH$_2$OH or halogen.

18. A compound according to claim 1 wherein R$^5$ is selected from H, Me, Et, Pr and Bn; Z is —NR$^7$)$_a$—CO—(NR$^8$)$_b$—, Q is —(CH$_2$)$_r$COOH, wherein r is from 1 to 3; and T is C$_1$ to C$_6$ hydrocarbyl, —NR$^6$R$^7$, —OMe, —OH, —CH$_2$OH or halogen.

19. A compound according to claim 1 wherein R$^5$ is selected from H, Me, Et, Pr and Bn; —Z—Q is

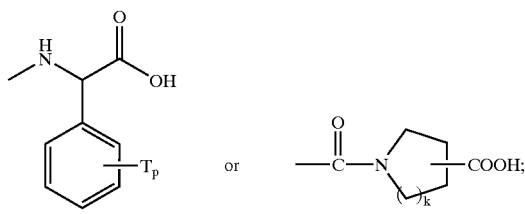

k is 1 or 2; and T is C$_1$ to C$_6$ hydrocarbyl, —NR$^6$R$^7$, —OMe, —OH, —CH$_2$OH or halogen.

20. A compound which is degraded in vivo to yield a compound according to claim 1.

21. A pharmaceutical composition comprising a compound according to claim 1 together with a pharmaceutically acceptable diluent or carrier.

22. A compound according to claim 15 wherein R$^{13}$ is adamantyl, cycloheptyl, cyclohexyl or phenyl.

23. A compound according to claim 16, wherein R$^{13}$ is adamantyl, cycloheptyl, cyclohexyl or phenyl.

* * * * *